US012690903B2

(12) United States Patent　(10) Patent No.: US 12,690,903 B2

Lundquist et al.　(45) Date of Patent: Jul. 28, 2026

(54) COMBINED INTRAMEDULLARY - EXTRAMEDULLARY BONE STABILIZATION AND ALIGNMENT SYSTEM

(71) Applicants:Andrew D Lundquist, Edina, MN (US); Jonathan Fisher, Sandpoint, ID (US)

(72) Inventors: Andrew D Lundquist, Edina, MN (US); Jonathan Fisher, Sandpoint, ID (US)

( * ) Notice: Subject to any disclaimer, the term of this patent is extended or adjusted under 35 U.S.C. 154(b) by 196 days.

(21) Appl. No.: 18/199,971

(22) Filed: May 21, 2023

(65) Prior Publication Data

US 2024/0058041 A1　Feb. 22, 2024

Related U.S. Application Data

(63) Continuation-in-part of application No. 16/726,592, filed on Dec. 24, 2019, now Pat. No. 12,059,182, which is a continuation of application No. 15/418,130, filed on Jan. 27, 2017, now Pat. No. 10,517,655, which is a continuation-in-part of application No. 14/733,451, filed on Jun. 8, 2015, now Pat. No. 10,226,292.

(51) Int. Cl.
| | |
|---|---|
| *A61B 17/80* | (2006.01) |
| *A61B 17/17* | (2006.01) |
| *A61B 17/72* | (2006.01) |
| *A61B 17/88* | (2006.01) |

(52) U.S. Cl.
CPC ...... *A61B 17/7291* (2013.01); *A61B 17/1728* (2013.01); *A61B 17/7233* (2013.01); *A61B 17/8061* (2013.01); *A61B 17/809* (2013.01); *A61B 17/8897* (2013.01)

(58) Field of Classification Search
CPC ............ A61B 17/1725; A61B 17/1728; A61B 17/1775; A61B 17/7233; A61B 17/7283; A61B 17/7291; A61B 17/8061; A61B 17/164; A61B 17/1682
See application file for complete search history.

(56) References Cited

U.S. PATENT DOCUMENTS

| | | | | |
|---|---|---|---|---|
| 2009/0036931 A1* | 2/2009 | Pech | .................. | A61B 17/7291 606/62 |
| 2015/0073414 A1* | 3/2015 | Rogachefsky | ..... | A61B 17/1725 606/64 |

* cited by examiner

*Primary Examiner* — Samuel S Hanna

(74) *Attorney, Agent, or Firm* — Wells St. John P.S.

(57)　ABSTRACT

Disclosed is a combined intramedullary and extramedullary bone stabilization and alignment system, which includes both methods and apparatuses for the alignment and stabilization of a first bone or piece of bone to a second bone or piece of bone. Embodiments of the system may include an implant device which has an elongated framework within the intramedullary portion and an extramedullary portion which are cannulated. The cannulated aspect of the framework includes a wire aperture through both the intramedullary portion and the extramedullary portion.

4 Claims, 106 Drawing Sheets

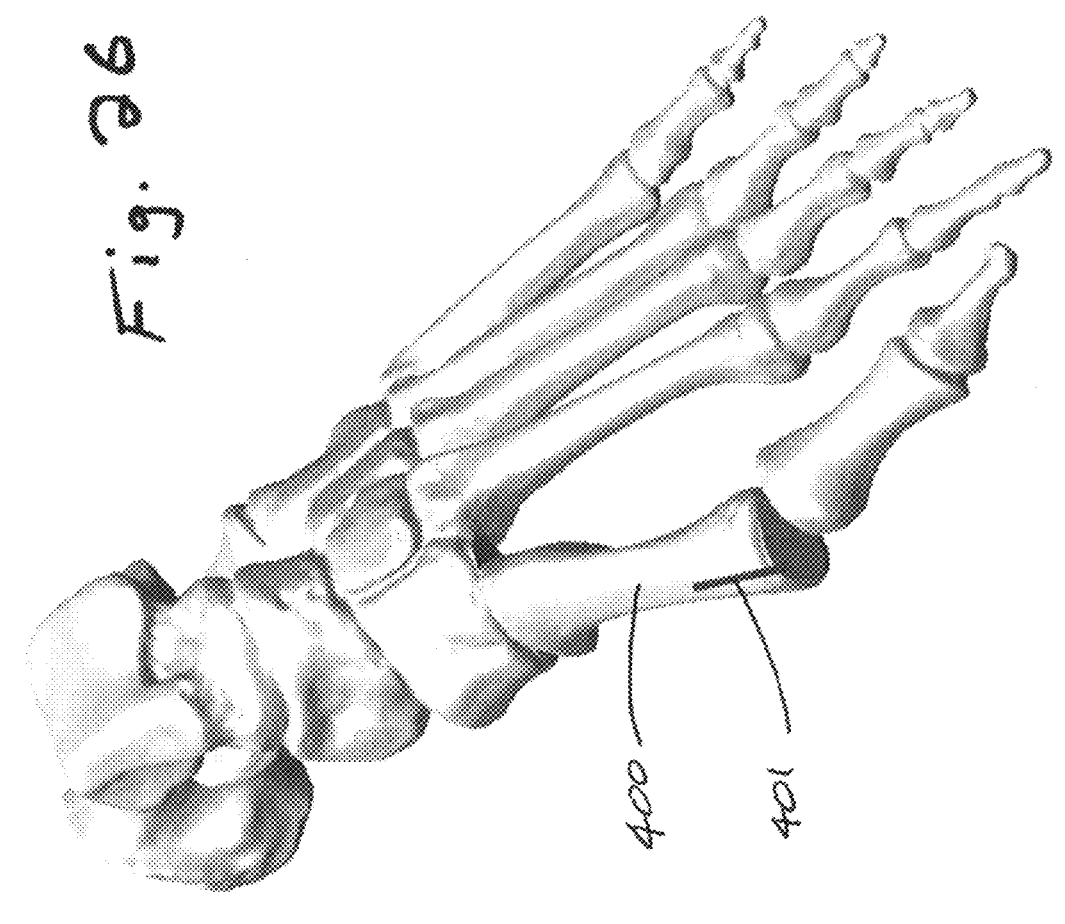

Incision and Exposure

- Patient is positioned in supine

- Intraoperative fluoroscopy is highly recommended

- A dorsal medial or medial longitudinal incision of 1.5 cm to 2.0 cm is made overlying the first metatarsal head (approximated by the red line)

- The neurovascular bundle is isolated and protected

- The first metatarsal phalangeal joint capsule is incised according to the surgeon's preference to expose the first metatarsal medial eminence

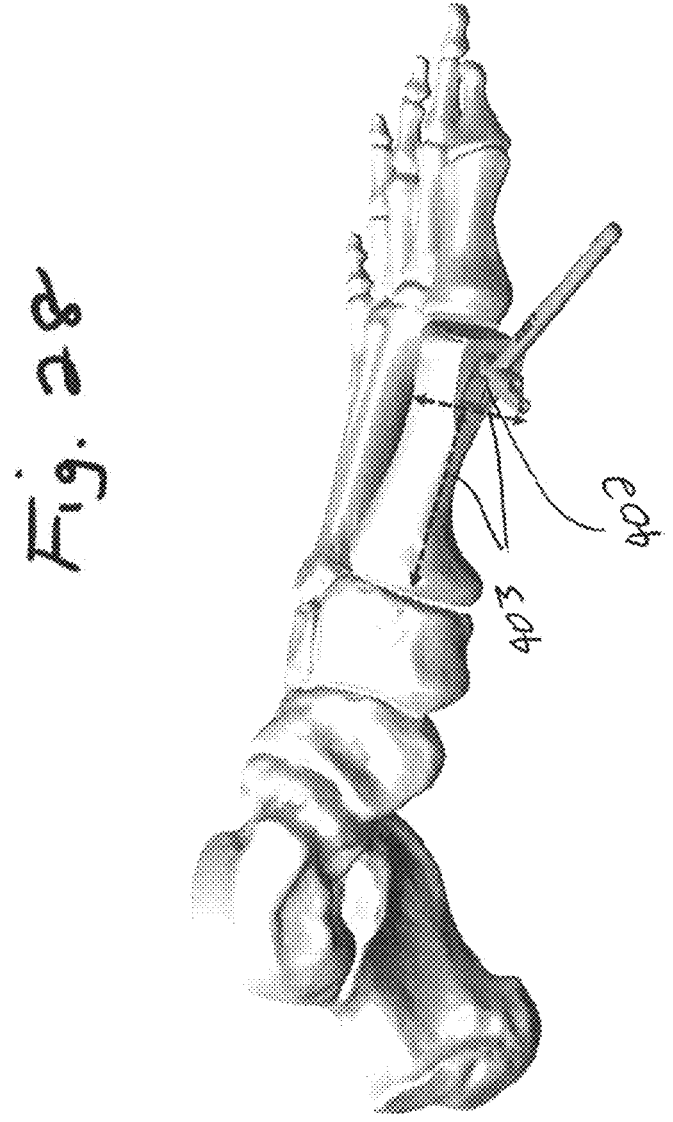

Fig. 2a

Step 2a: Template
(Template Positioning)

- The osteotomy location is at the level of the surgical neck at the metaphyseal/diaphyseal junction. Specifically, this is just proximal to the sesamoids and the vascular bundle to the inferior metatarsal head

- The face of the medial bunion template is seated flush with the surface of the medial eminence resection

- The proximal face of the medial bunion template is rotated such that it is oriented perpendicular to the longitudinal axis of the metatarsal shaft. Note the proximal face of the template represents the location of the cutting guide surface for the osteotomy

- The template is then positioned superior/inferior to best fit in the area of the resected medial eminence

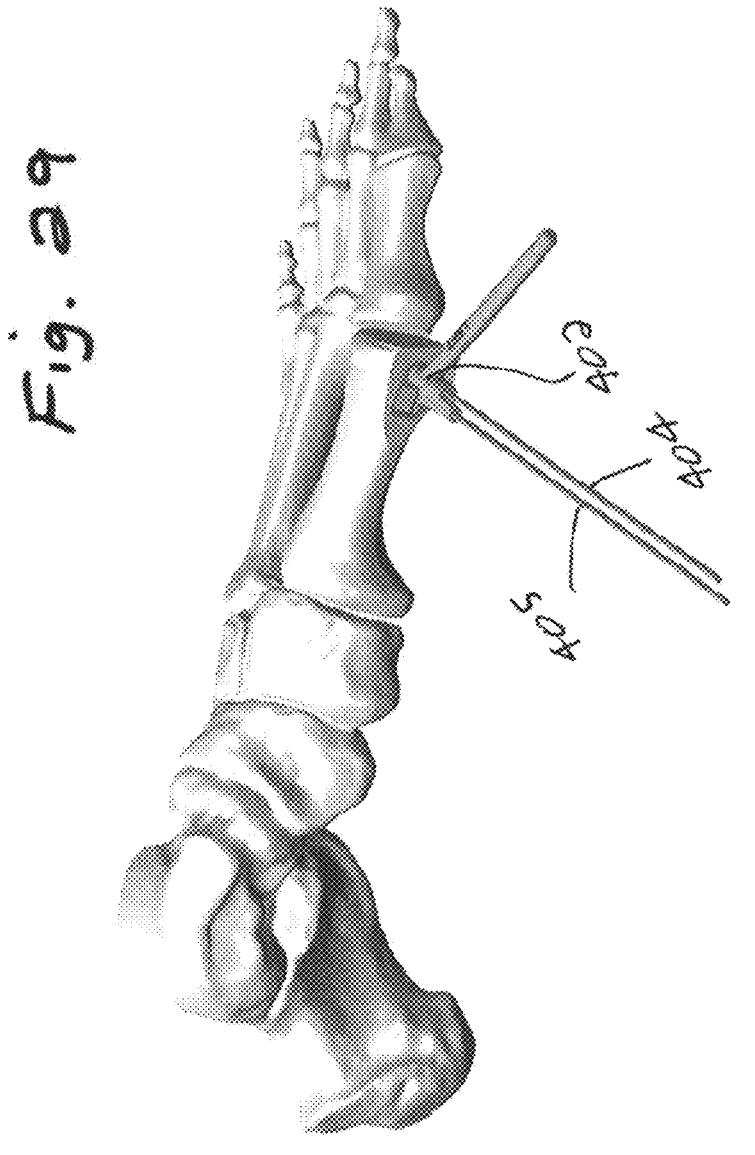

Fig. 29

Step 2b: Template
(Template Fixation and
Burr Area Demarcation)

- The media bunion template is stabilized in the proper position by inserting a ø1.6mm k-wire into each hole of the template

- The k-wire holes may be used for screw fixation in subsequent steps to fixate the plate to the metatarsal head. However, if other screw hole positions are later desired, those positions can be chosen despite this step in the procedure Step 3:
Burning the Distal
1st Metatarsal

• Use a power burr or rongeur
to remove approximately
5mm x 5mm of bone in the
area of the mark

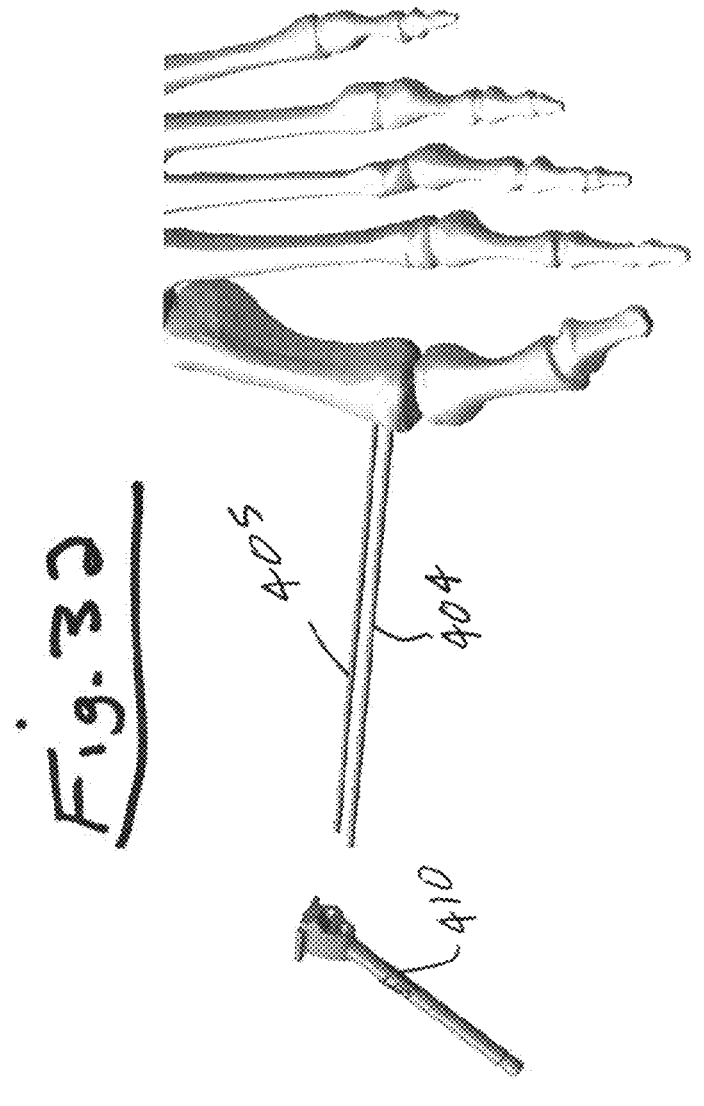

Fig. 33

Step 4a:
Place Osteotomy
Guide

- Use the osteotomy guide to assess if enough bone has been removed during the burring step. There is a prominence on the guide that mimics a similar feature that sits on the plate implant.

- Place the guide over the k-wires that were placed in step 2.

- Seat the guide up against the face of the resected medial eminence.

- If the guide can be seated flush with the resection, then the amount of bone removal during the burring step is adequate.

- If the guide cannot be seated flush, then additional bone removal may be necessary. Repeat bone removal from step 3 to remove interferences until the osteotomy guide can be seated flush on the resection plane of the medial eminence.

Step 6:
Preparation for Broaching
the 1ˢᵗ Metatarsal Canal

- Use a wire driver to remove the
  ø1.6mm k-wires from the
  metatarsal head

- This will give clearance for the
  broach to penetrate the canal of
  the first metatarsal Step 7a:
Broaching the 1ˢᵗ Metatarsal Canal

- Use the broach to displace the metatarsal head laterally and insert the broach into the metatarsal canal

- The proper orientation of the broach can be confirmed when the letter M marked on the broach faces medially

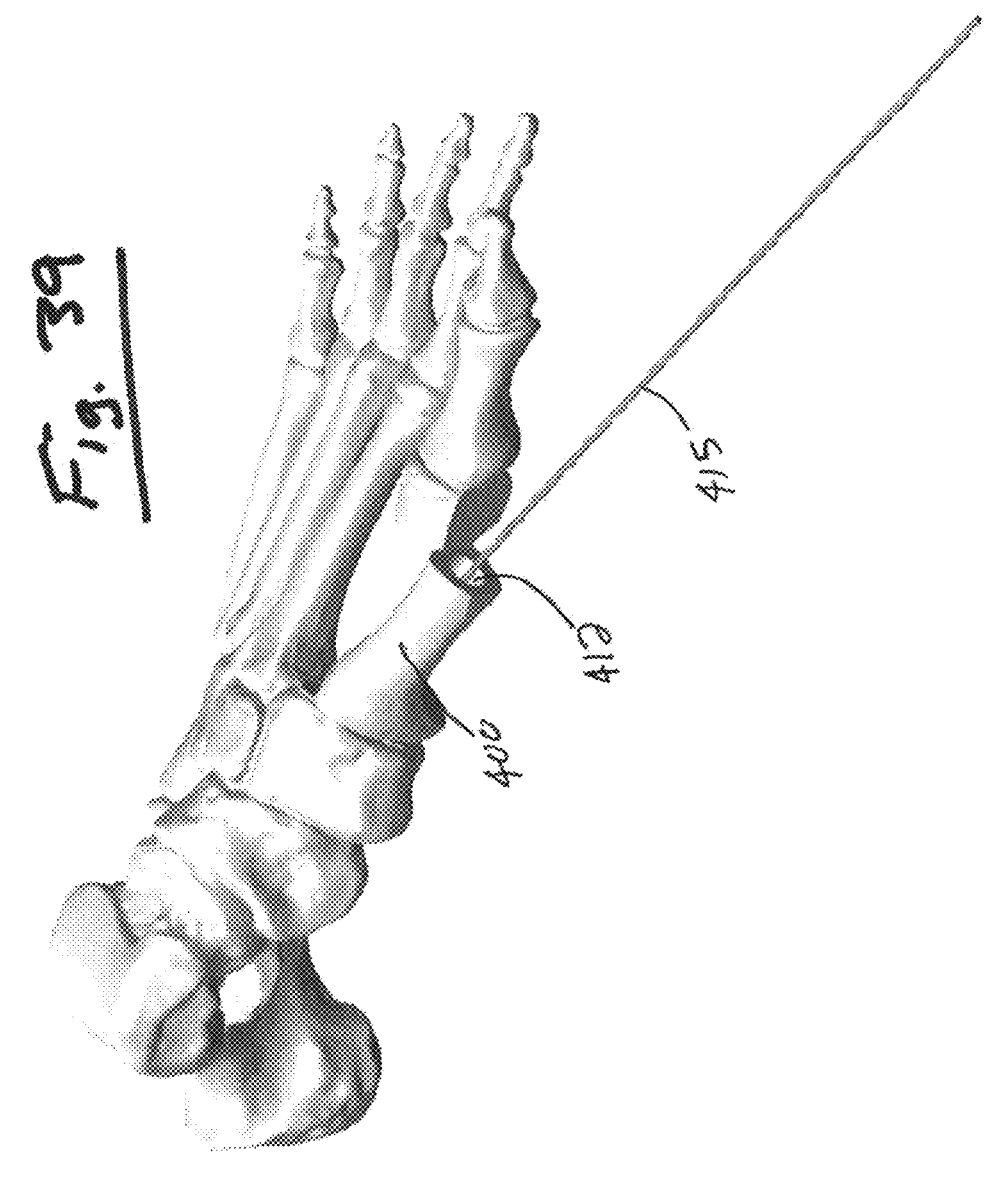
*Fig. 39*
Step 8b:
K-Wire Placement
• Remove the broach from the metatarsal canal leaving the ø1.6mm k-wire in place
• With the wire in position, the shaft is now ready to receive the medial bunion plate

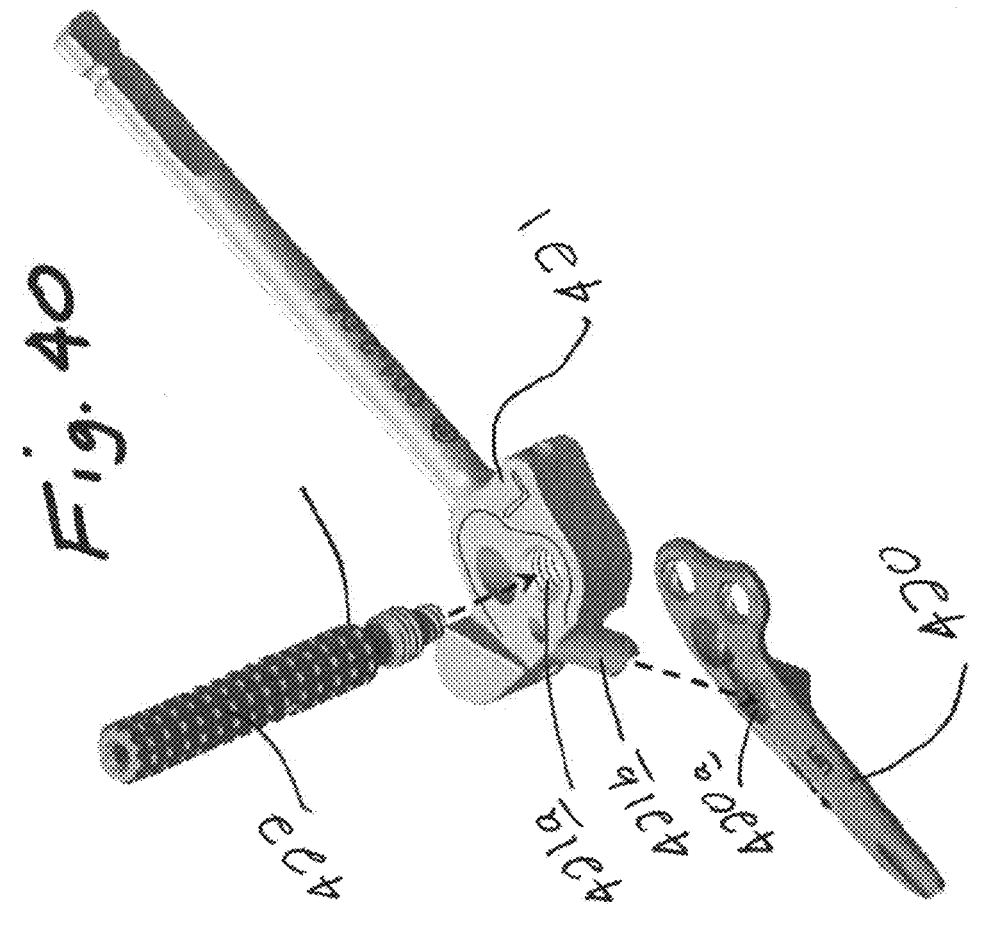

*Fig. 40*

Step 9a:
Assemble Plate to Inserter

- The medial plate has one size each for left and right cases. Remove the proper plate from the implant caddy.

- Assemble the medial button inserter to the plate by placing the proximal dome of the inserter into the proximal oblique hole of the plate.

- Thread the distal tower into the threaded hole of the inserter until the threads at the tip of the tower engage the threaded interior hole of the plate.

- The plate is now securely fastened to the inserter.

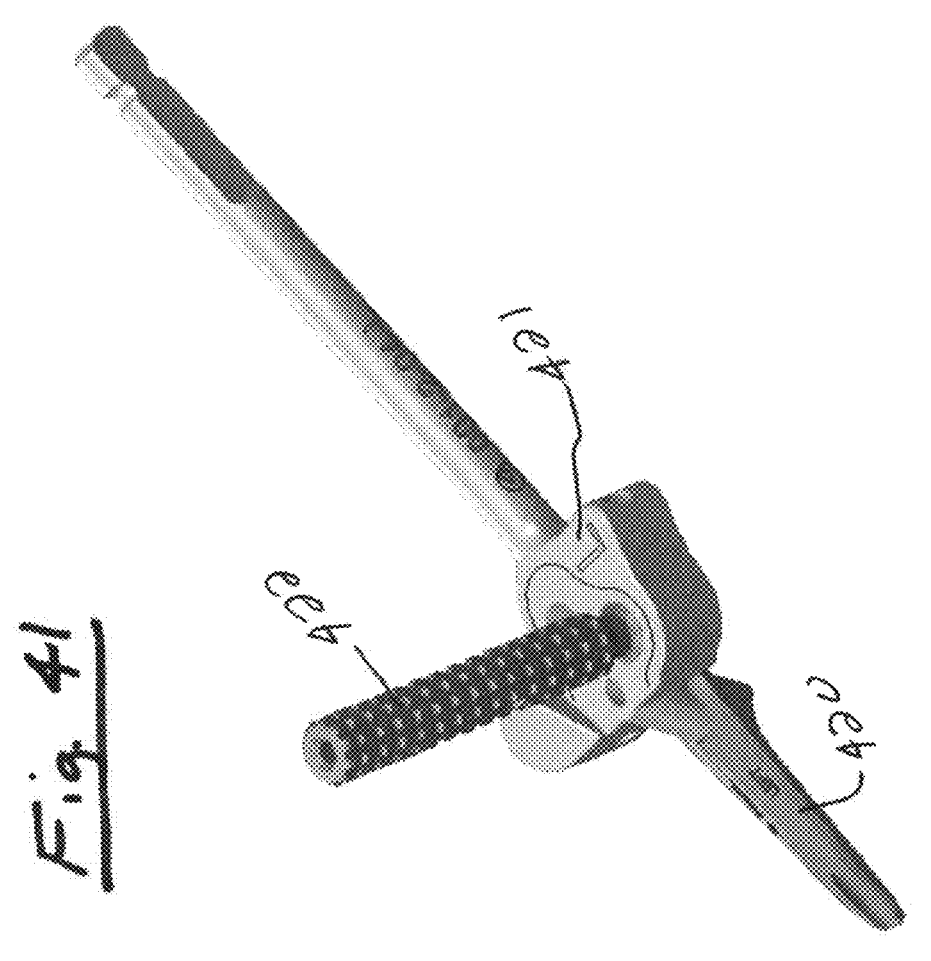
*Fig. 41*
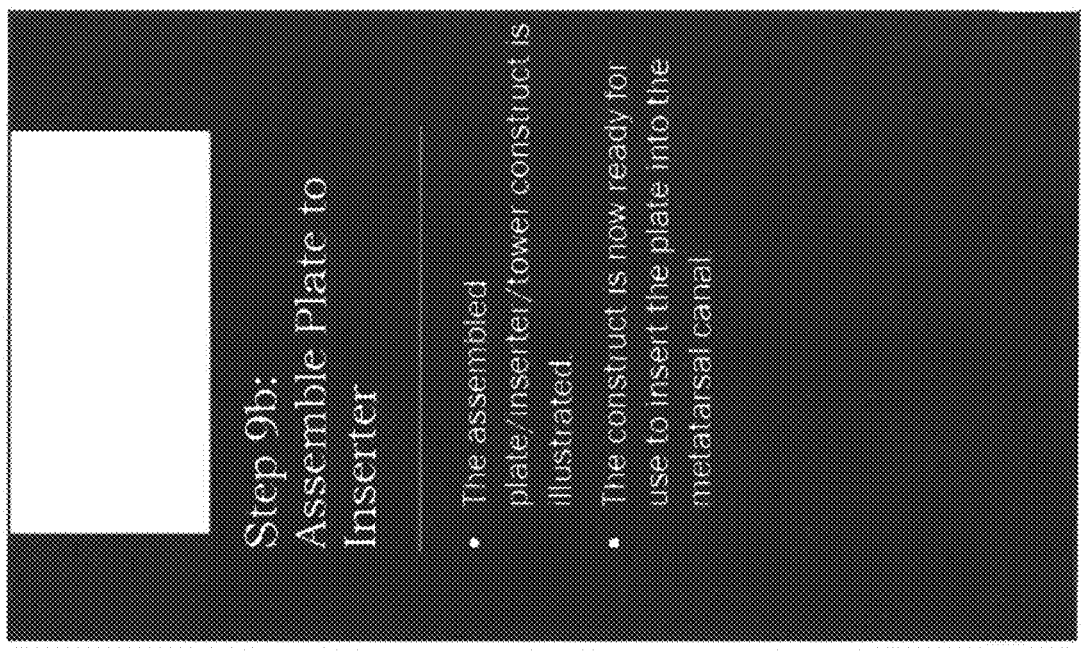

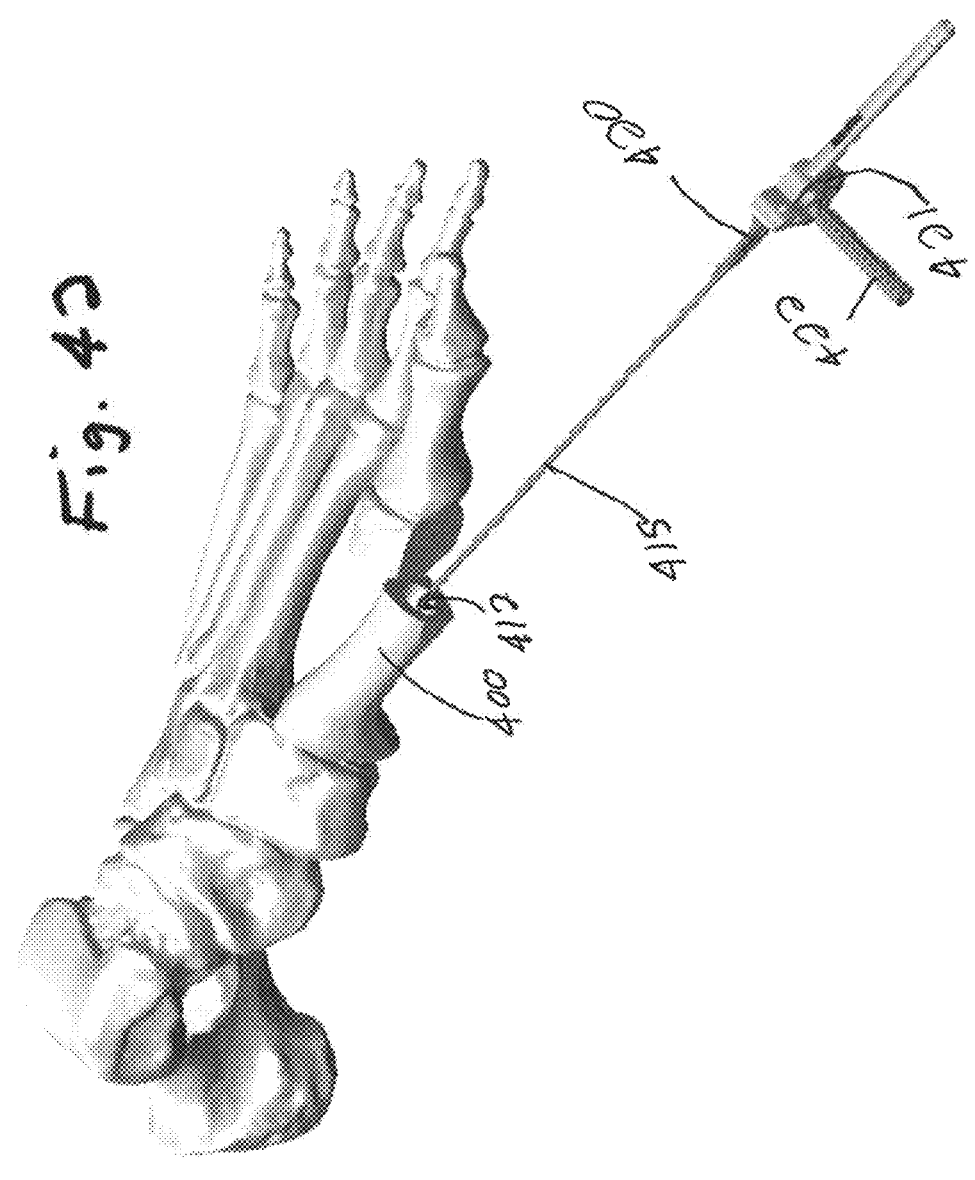
Fig. 42
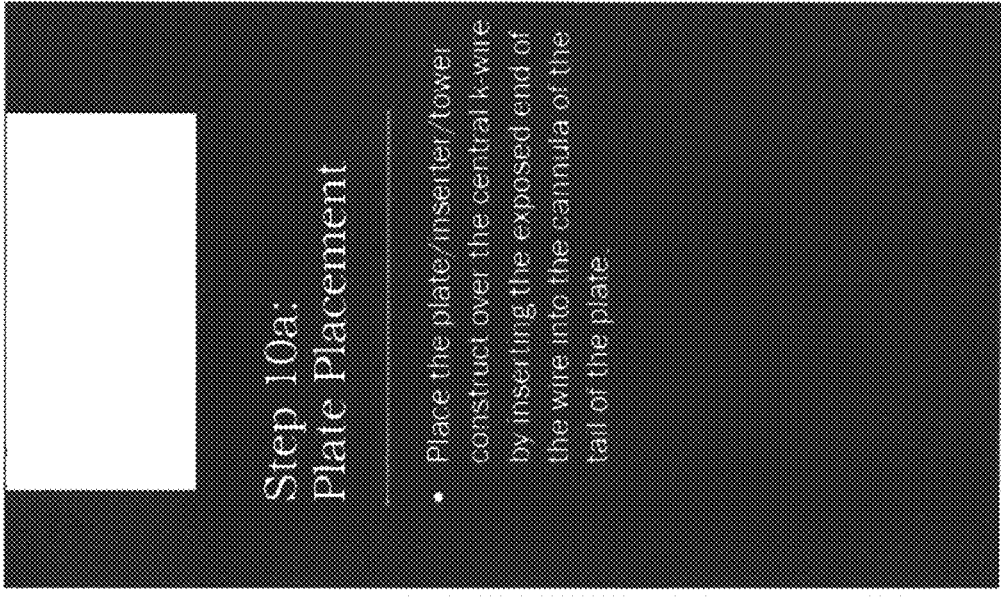

Step 10b:
Plate Placement

• Insert the plate/inserter/tower construct over the k-wire and into the metatarsal canal until the inserter bottoms out on the plane of the osteotomy

• Orient the construct such that the exposed lateral face of the plate is in contact with the resection plane of the medial eminence of the metatarsal head

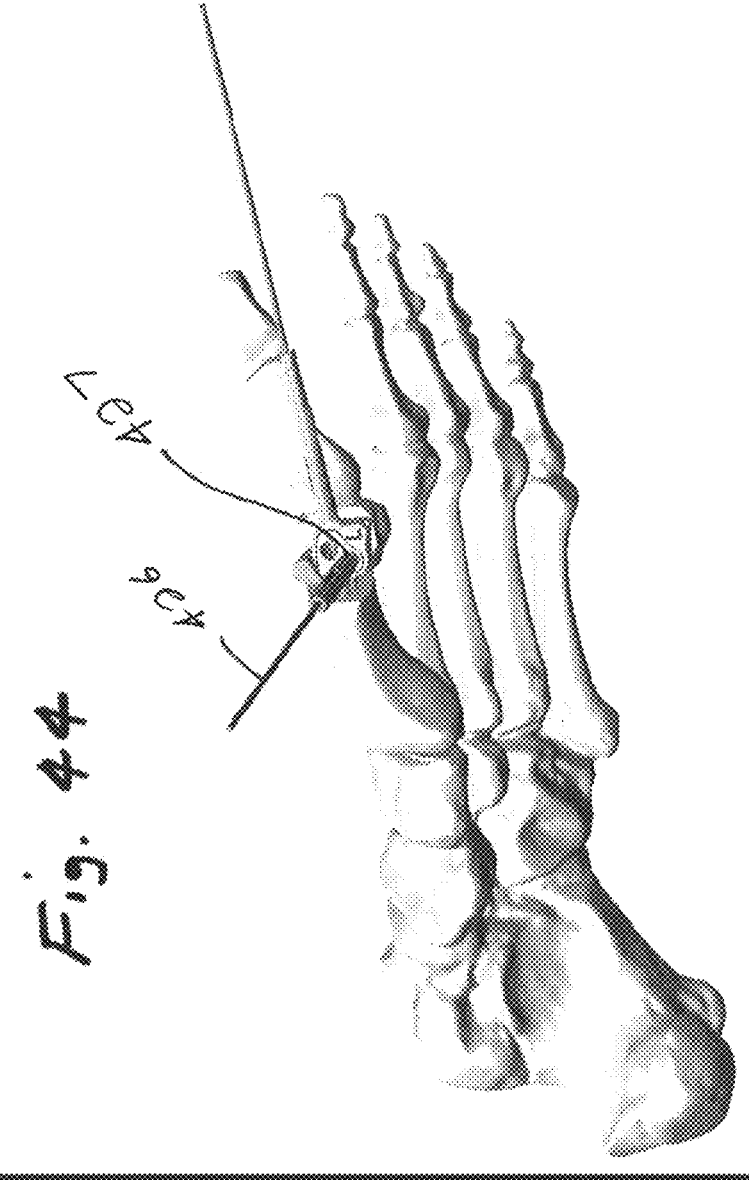

Step 11a:
Distal Inferior Screw

- The optimum position of the plate is achieved on the metatarsal head and confirmed under visualization and image intensification

- The distal inferior hole from step 2 can be aligned with the distal inferior plate hole and a ø1.6mm k-wire is inserted. If there is difficulty aligning with the previously prepared hole or a different position is desired, the ø1.6mm k-wire can be placed in that new location.

*Fig. 44*

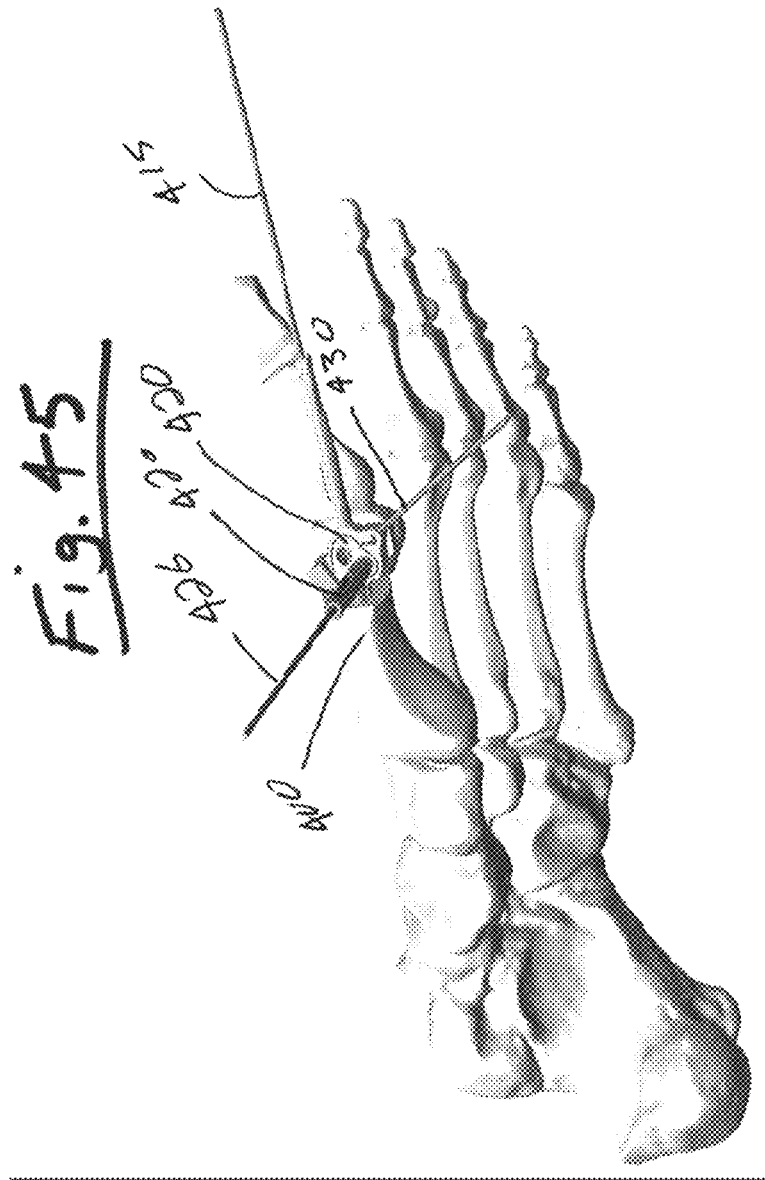

*Fig. 45*

Step 11b:
Distal Inferior Screw

- With the k-wire in place through the distal tower, plate, and into the metatarsal head, insert a Ø1.6mm k-wire through the inferior anti-rotation hole of the inserter until contact with the dorsolateral cortex of the metatarsal head is achieved

- This will capture the metatarsal head to the plate/inserter/tower construct and allow for translation and rotational correction of the metatarsal head relative to the metatarsal shaft

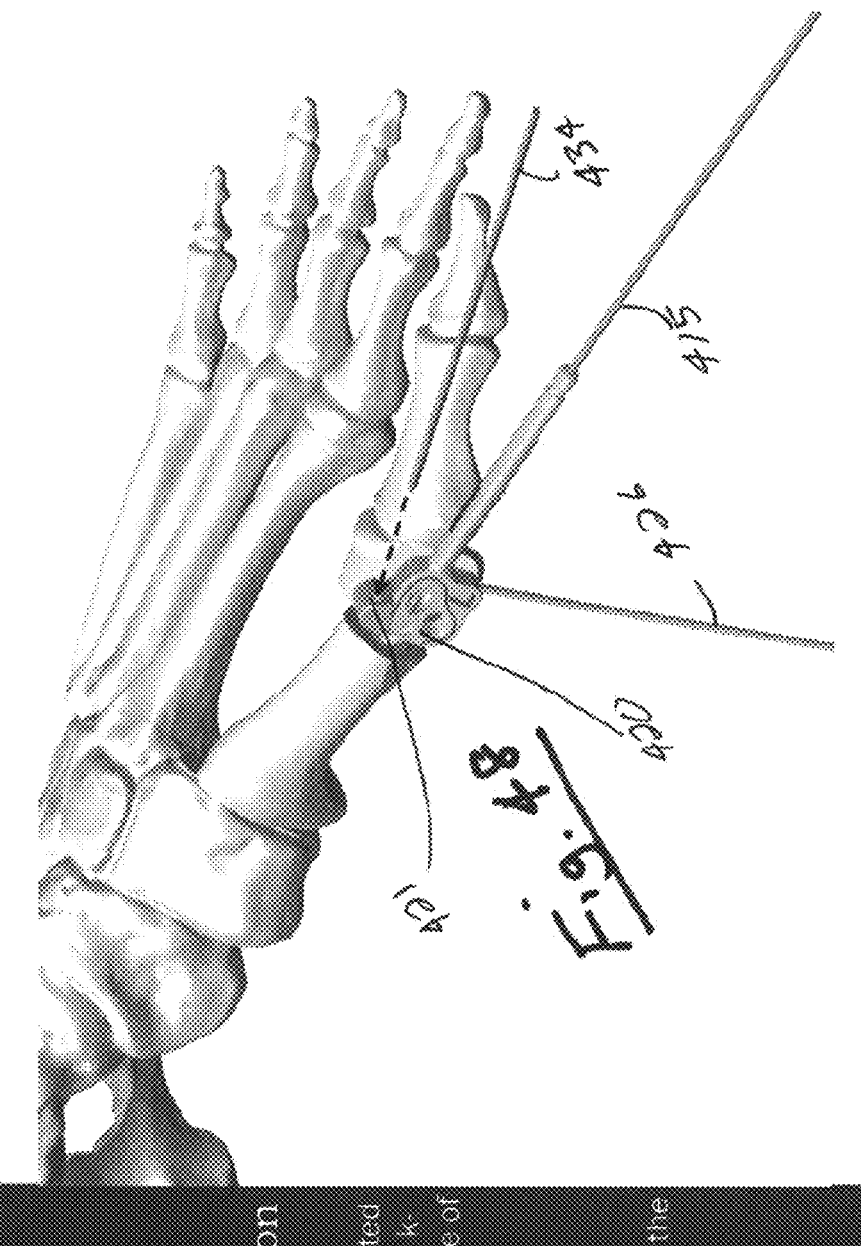

Step 13a:
Compress Metatarsal Head
to Metatarsal Shaft

- Once the metatarsal head is stabilized in the corrected position, remove the central 0.9 or 1.6mm k-wire from the construct

- Removal of the central k-wire provides access to place the distal oblique screw through the insertor and plate into the metatarsal shaft

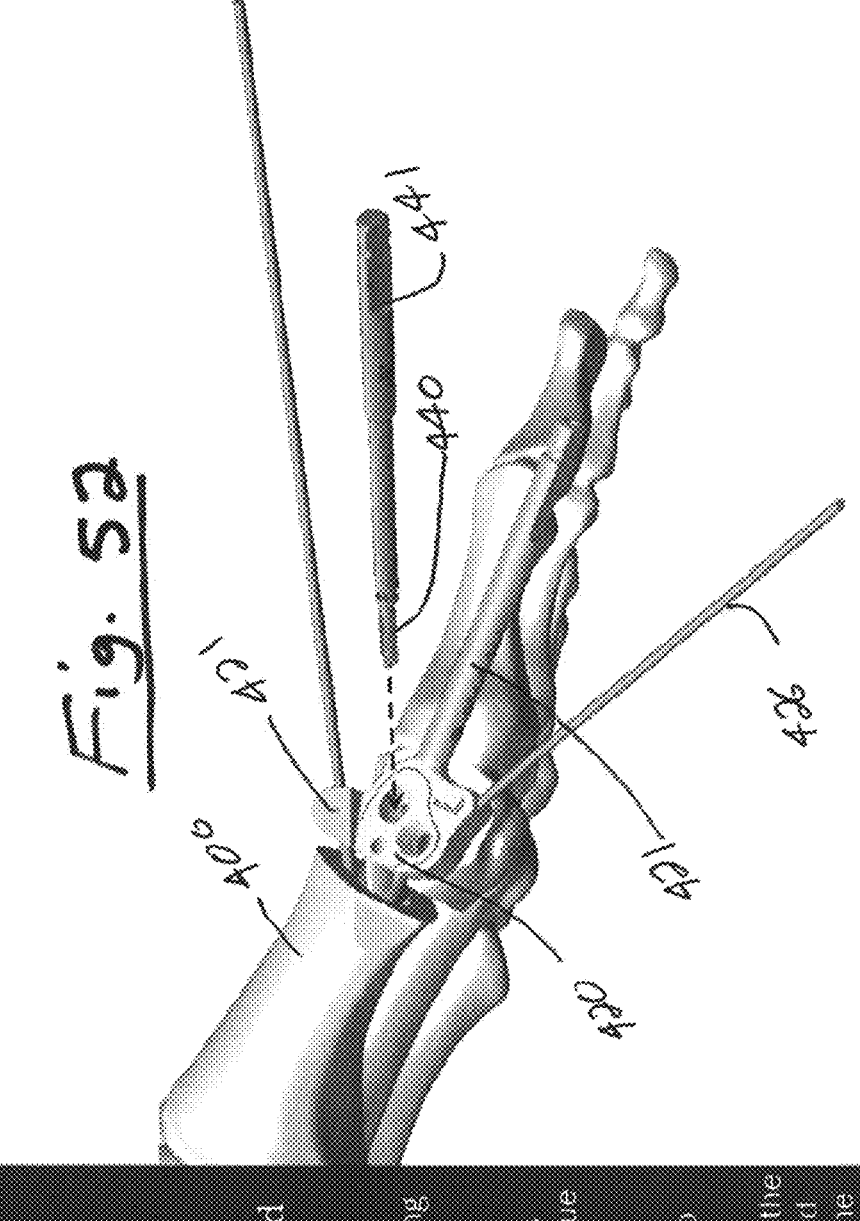

*Fig. 52*

Step 13d:
Compress Metarsal Head
to Metarsal Shaft

- Remove a ø2.4mm non-locking screw of the identified length from the implant caddy
- Note only non-locking screws are compatible with the oblique screw holes of the plate
- The scale on the side of the implant caddy may be used to verify screw length
- Use a T5 screwdriver to drive the screw through the inserter and plate, and into the cortex of the metatarsal shaft but do not fully seat and tighten at this step Step 14:
Remove Inserter and
Wires

- Remove the remaining k-wire
  and separate the inserter from
  the plate
- The plate is now secured and
  compressed to the metatarsal
  head
- The metatarsal head is now
  compressed to the metatarsal
  shaft via the plate and distal
  oblique screw in the corrected
  position Step 15b:
Distal Superior Screw

- Remove the distal tower and the k-wire
- Use the depth gauge to measure screw length
- Remove a locking or non-locking screw of the measured length from the implant caddy. The scale on the side of the caddy can be used to verify the proper screw length was selected
- Use a T6 screwdriver to fully seat the screw in place

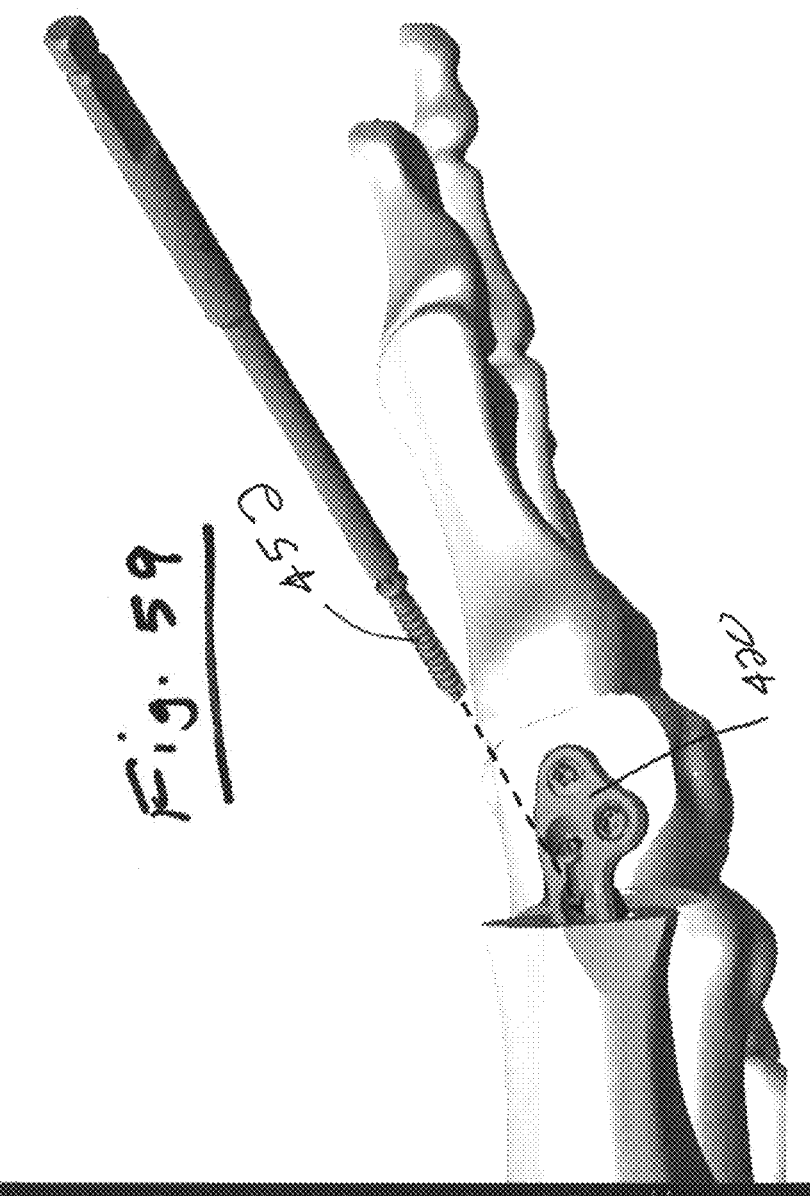

Step 16b:
Proximal Oblique Screw

- Remove the proximal tower and the k-wire (or drill)
- Use the depth gauge to measure proper screw length
- Remove a 2.4mm non-locking screw of the identified length from the implant caddy. The scale on the side of the caddy may be used to verify proper screw length. Note: only non-locking screws are compatible with the proximal oblique screw hole
- Use a T6 screwdriver to fully seat the screw through the plate and through the lateral cortex of the metatarsal shaft

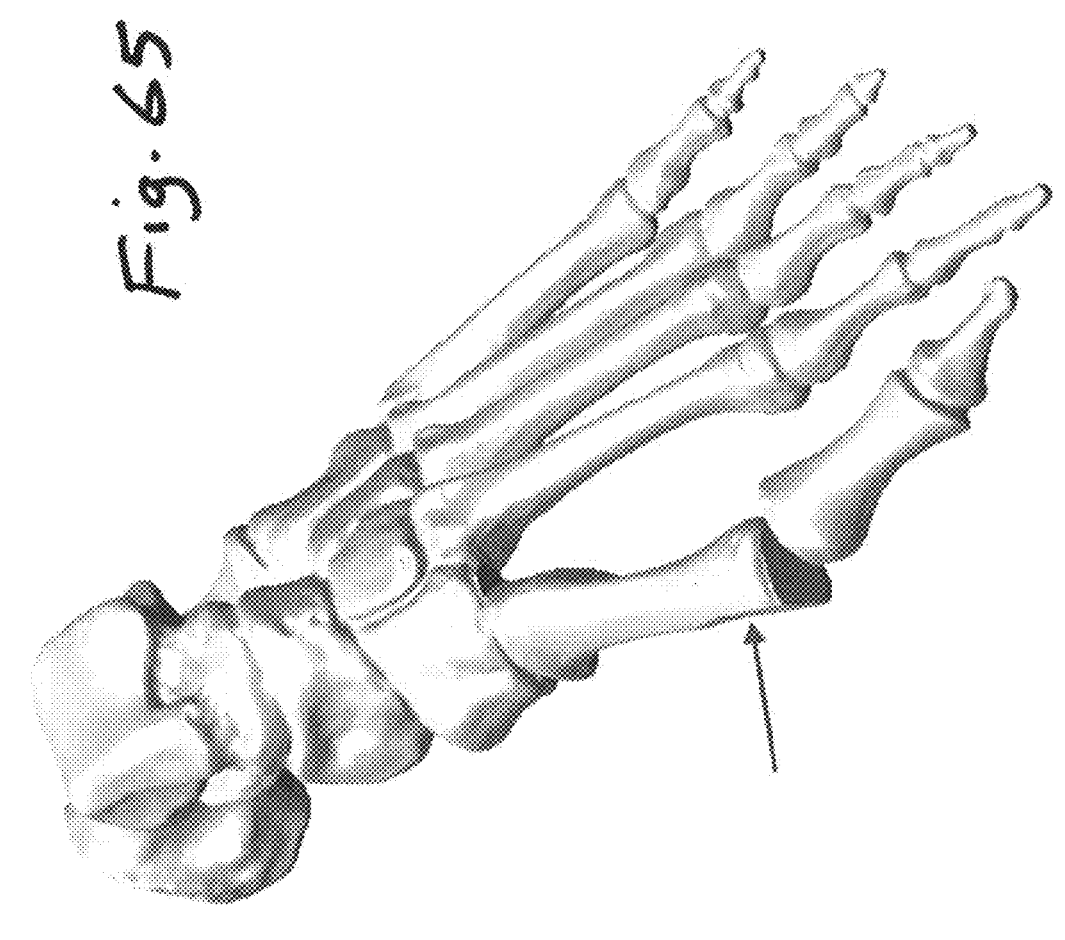

Fig. 65

Optional Step for Dorsal
Bunion Plate:
Medial Eminence Resection and
Optional Lateral Release

• Resection of the medial eminence
  may be performed if desired

• At the surgeon's discretion a
  lateral soft tissue release can be
  performed either percutaneously,
  through a second incision overlying
  the first intermetatarsal space, or
  through a medial transarticular
  approach. Transect horizontally the
  lateral metatarsal sesamoid
  suspensory ligament and release
  the lateral part of the conjoined
  adductor tendon. The lateral
  collateral ligament is respected to
  prevent iatrogenic hallux varus

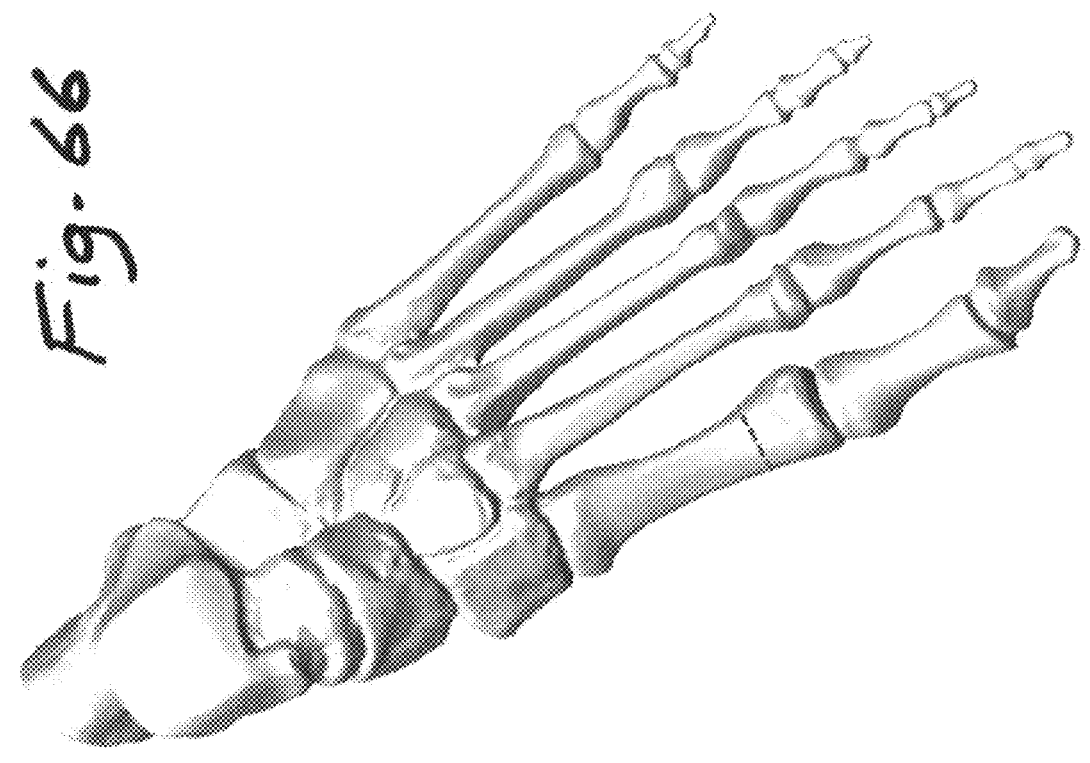

*Fig. 66*

Step 1:
Transverse Osteotomy

- The ideal osteotomy location is at the level of the surgical neck, at the metaphyseal-diaphyseal junction. Specifically, this is just proximal to the sesamoids and the vascular bundle to the interior metatarsal head.

- Use a sagittal blade to perform the osteotomy. Ensure that proper retraction is used to protect the extensor tendons and soft tissue structures during the osteotomy.

- The obliquity of the osteotomy, in the horizontal plane can have a lengthening or shortening effect.

- The osteotomy should be positioned to provide the correction necessary for the patient case.

- If the osteotomy is angled distally, the result will be a lengthened metatarsal.

- If the osteotomy is angled proximal, the result will be a shortened metatarsal.

Step 2b:
Broaching the 1ˢᵗ
Metatarsal Canal

- Insert the broach into the metatarsal canal until the positive stop on the broach contacts the level of the osteotomy
- This will ensure that the plate can be fully inserted into the metatarsal canal without impedance Step 3a:
K-Wire Placement

- Once the broach is fully seated, insert a 9" long ø1.6mm k-wire through the cannulation of the handle and through the broach

- Insert the k-wire until cortical contact is made to anchor the wire in place

- Care should be taken not to penetrate the wire through the proximal end of the metatarsal and into the metatarso-cuneiform joint

Step 3b:
K-Wire Placement

- Remove the broach from the metatarsal canal leaving the Ø1.6mm k-wire in place

- With the wire in position the shaft is now ready to receive the hallux limitus plate or the dorsal bunion plate

- Proceed to Step 4 for hallux limitus plates

- Proceed to Step 12 for dorsal bunion plates

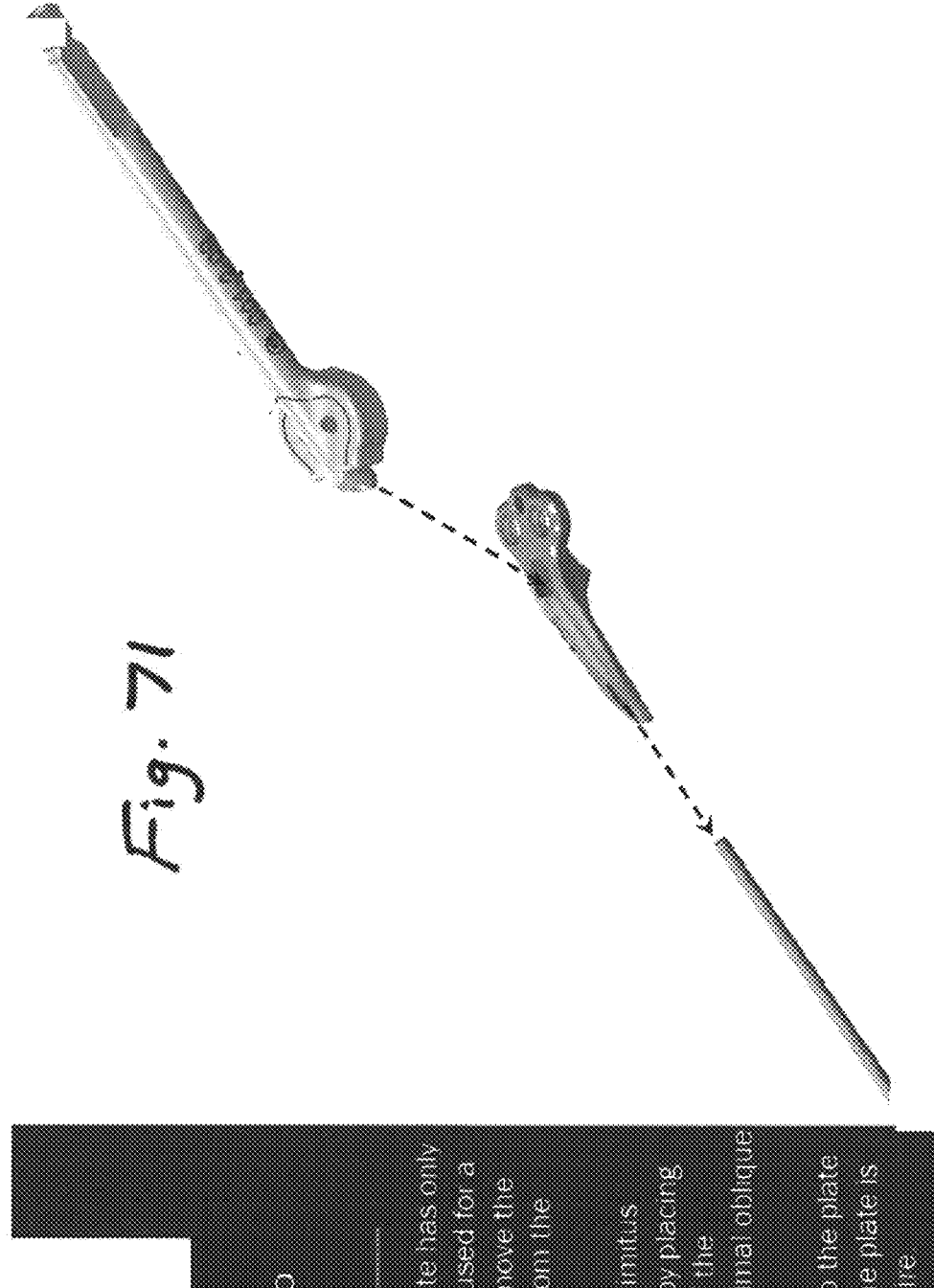

*Fig. 71*

Step 4a:
Assemble Plate to
Inserter

• The hallux limitus plate has only one size and can be used for a left or right case. Remove the hallux limitus plate from the implant caddy

• Assemble the hallux limitus inserter to the plate by placing the proximal dome of the inserter into the proximal oblique hole of the plate

• Secure the inserter to the plate with your hands as the plate is inserted onto the k-wire

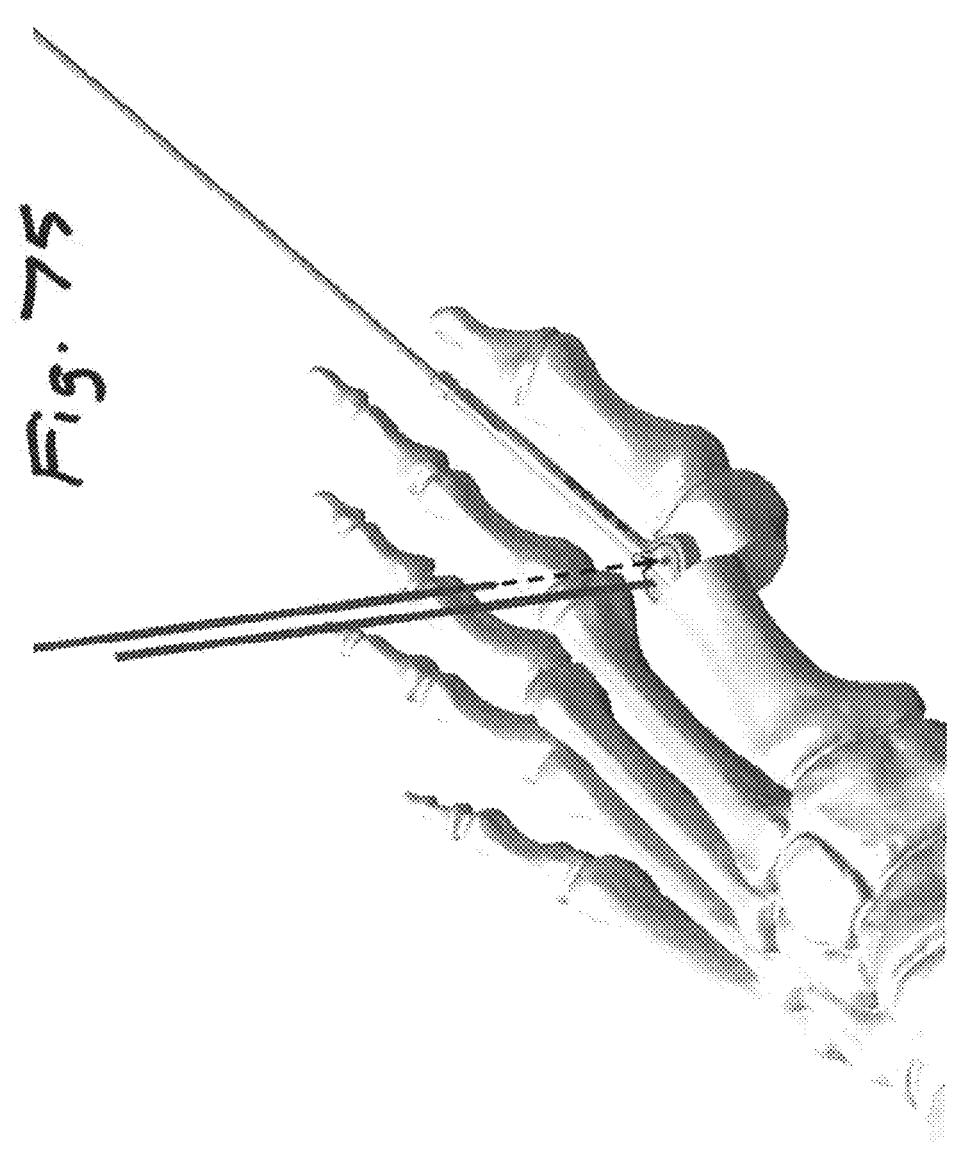
*Fig. 75*
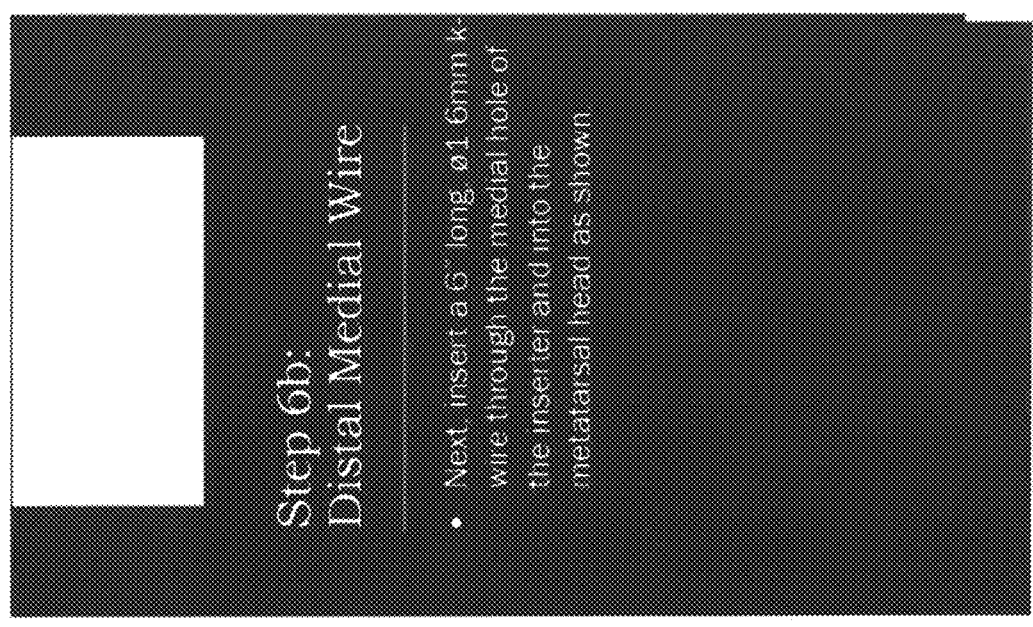
Step 6b:
Distal Medial Wire
- Next insert a 6" long, ø1.6mm K-
  wire through the medial hole of
  the inserter and into the
  metatarsal head as shown Step 7a:
Remove Central K-Wire and Inserter

• Remove the central 0" long ø1.6mm k-wire from the construct

• Remove the inserter while leaving the 6" long k-wires in place

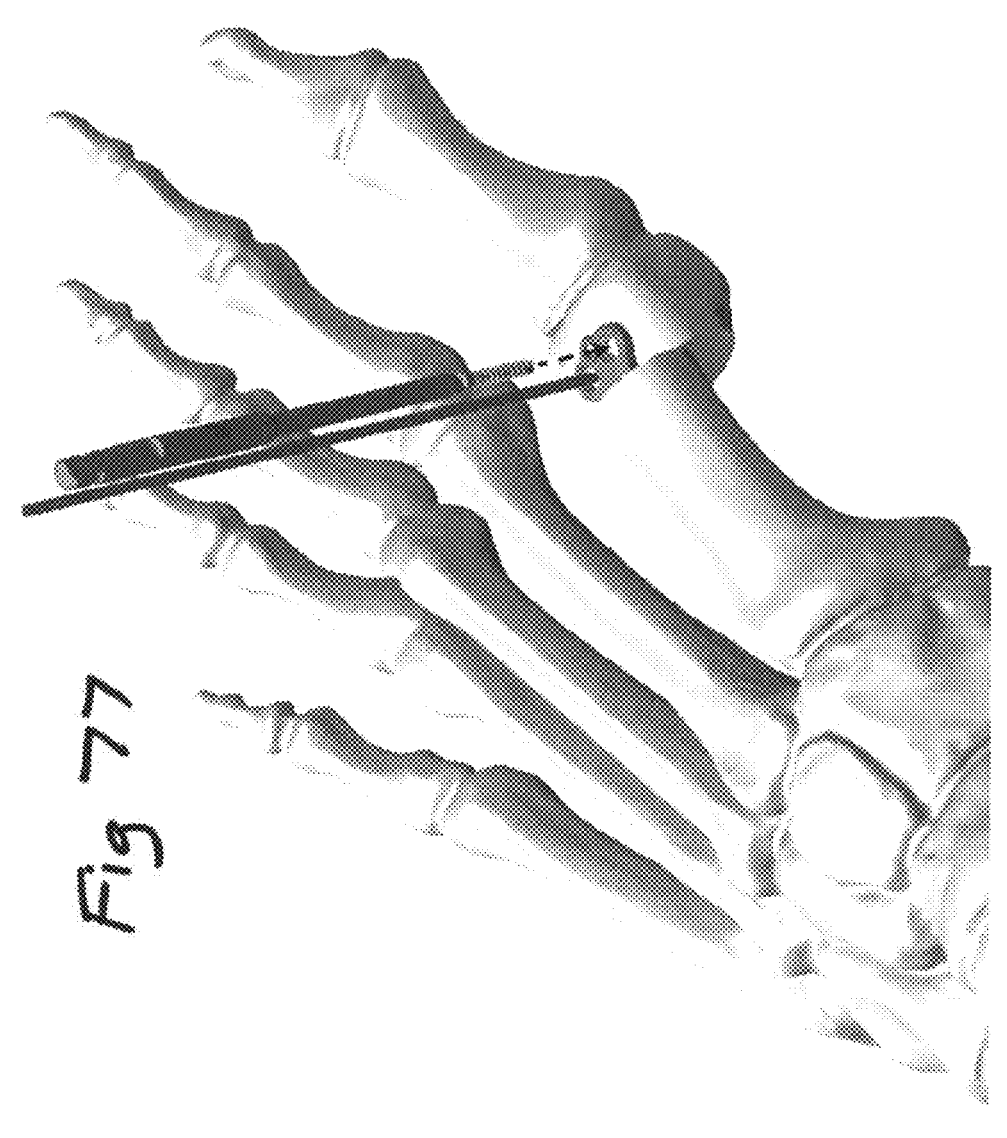

Fig 77

Step 8a:
Distal Medial Screw

- Remove the medial k-wire
- Use the depth gauge through the plate to measure the appropriate screw length
- Remove a 2.4mm non locking screw of appropriate length from the screw caddy.
- The scale on the side of the caddy can be used to verify the proper screw length was selected
- A non-locking screw should be used for the first screw in the metatarsal head so that compression of the plate to the metatarsal head can be achieved
- Use a T6 screwdriver to drive the screw through the plate into the metatarsal head until the screw is fully seated

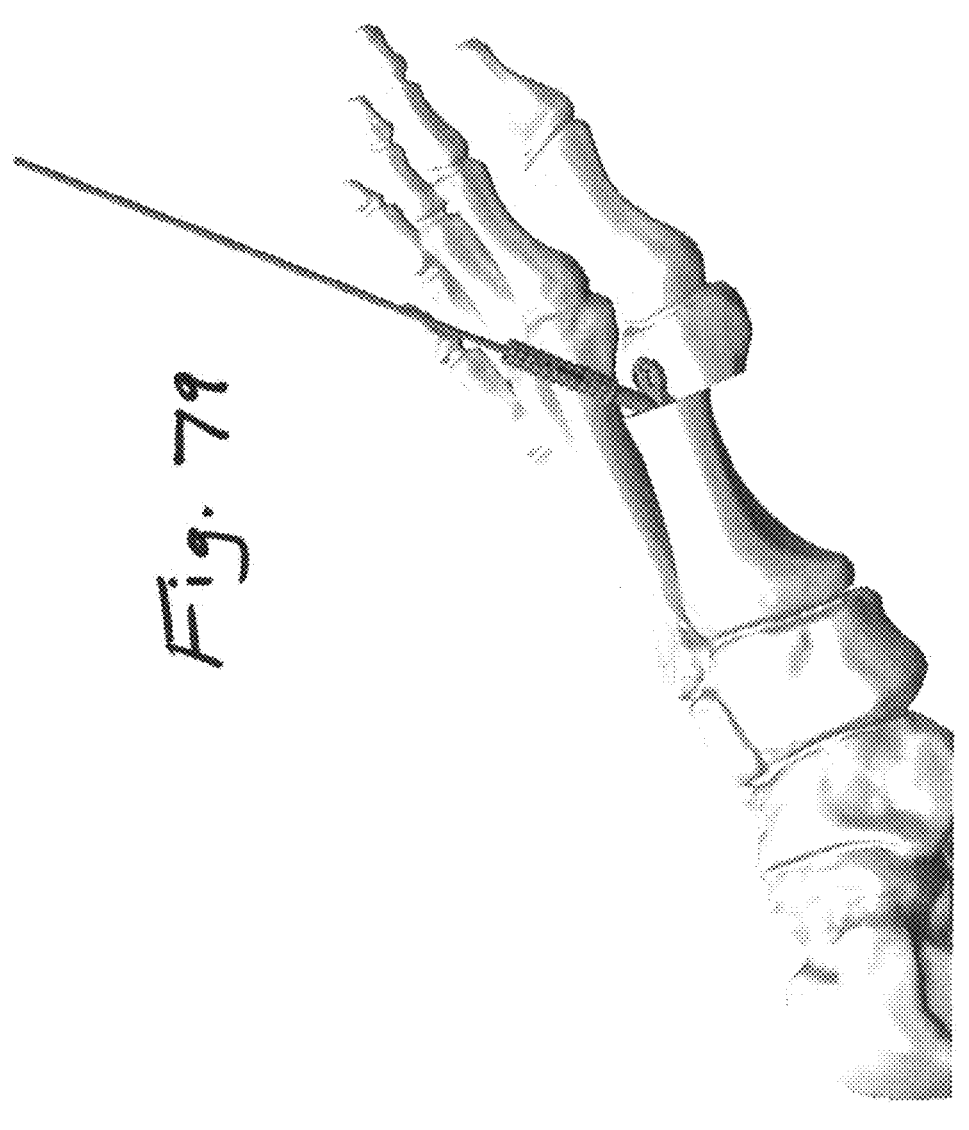

*Fig. 7a*

Step 10a:
Oblique Screw

- Insert the proximal tower through the oblique hole of the hallux limbus plate and snap into place

- Under fluoroscopy, drive a 6 long ø1.6mm k-wire through the proximal tower and into the inferior cortex of the metatarsal shaft

- Remove the k-wire and the proximal tower

- Use the depth gauge to measure proper screw length that will engage to the inferior cortex 11a: Final Hallux Limitus Placement

- Under discretion of the surgeon, the medial non-locking screw may be explanted and replaced with a locking screw of the same length. This step is not a requirement.

- Check the final positioning of the plate and screws with A/P, Sesamoid Axial, and Lateral Fluoroscopy

- Close the incisions with sutures of the surgeon's preference

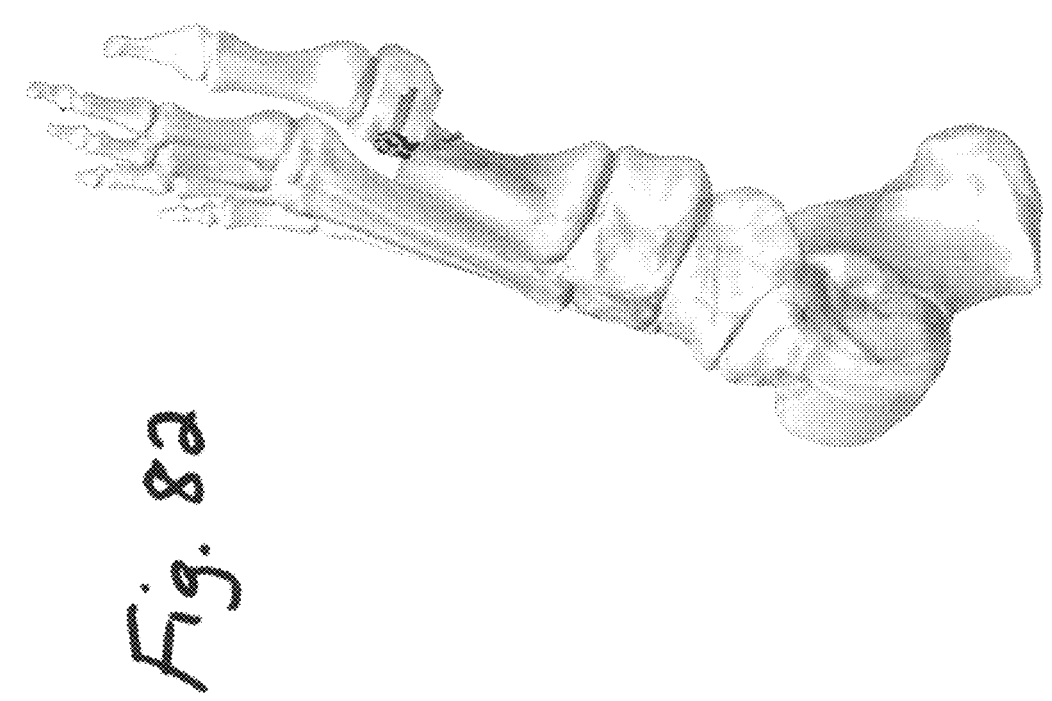
*Fig. 82*
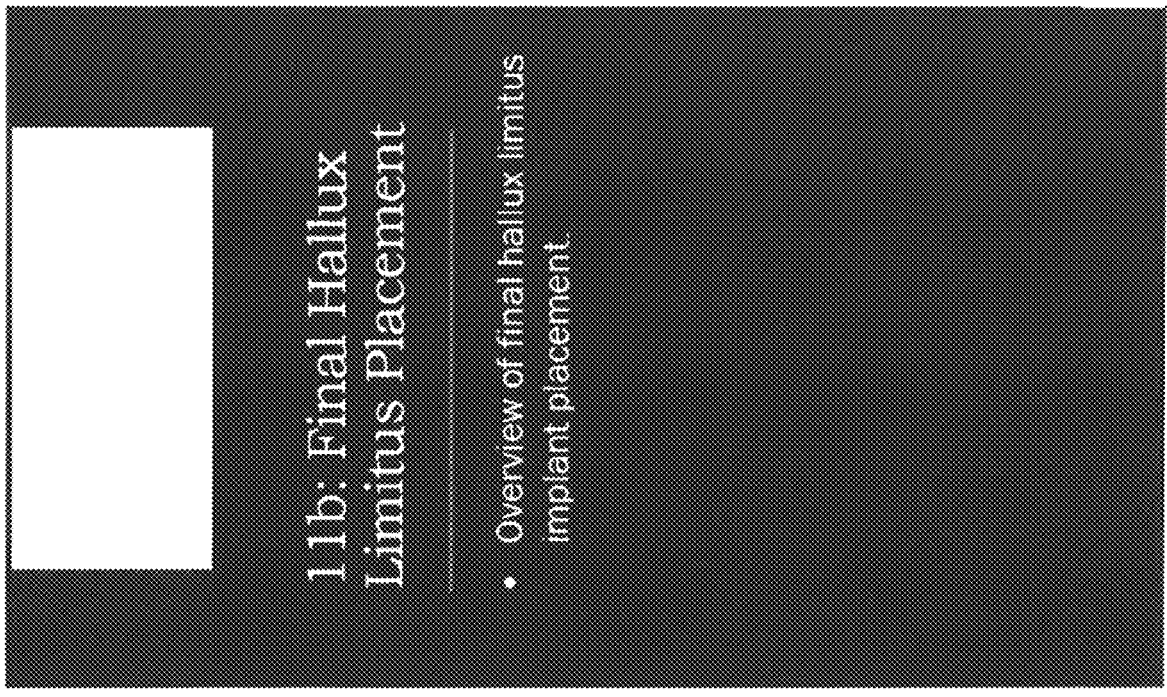

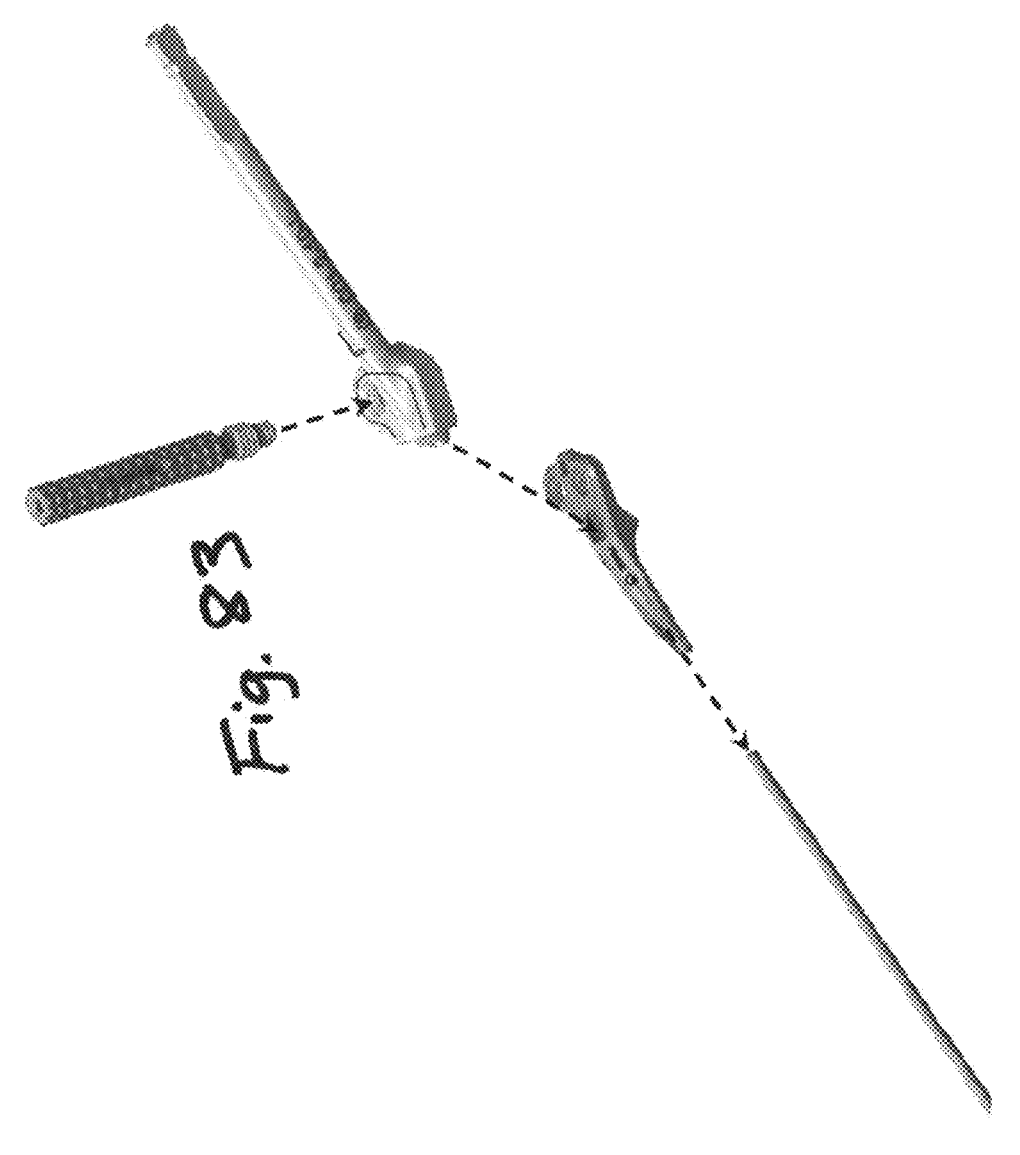

Fig. 83

Step 12a:
Assemble Plate to
Inserter

- The dorsal bunion plate has one size each for left and right cases. Remove the proper plate from the implant caddy.

- Assemble the dorsal bunion inserter to the plate by placing the proximal dome of the inserter into the oblique hole of the plate

- Thread the distal tower into the threaded hole of the inserter until the threads at the tip of the tower engage the threaded inferior hole of the plate

- The plate is now securely fastened to the inserter

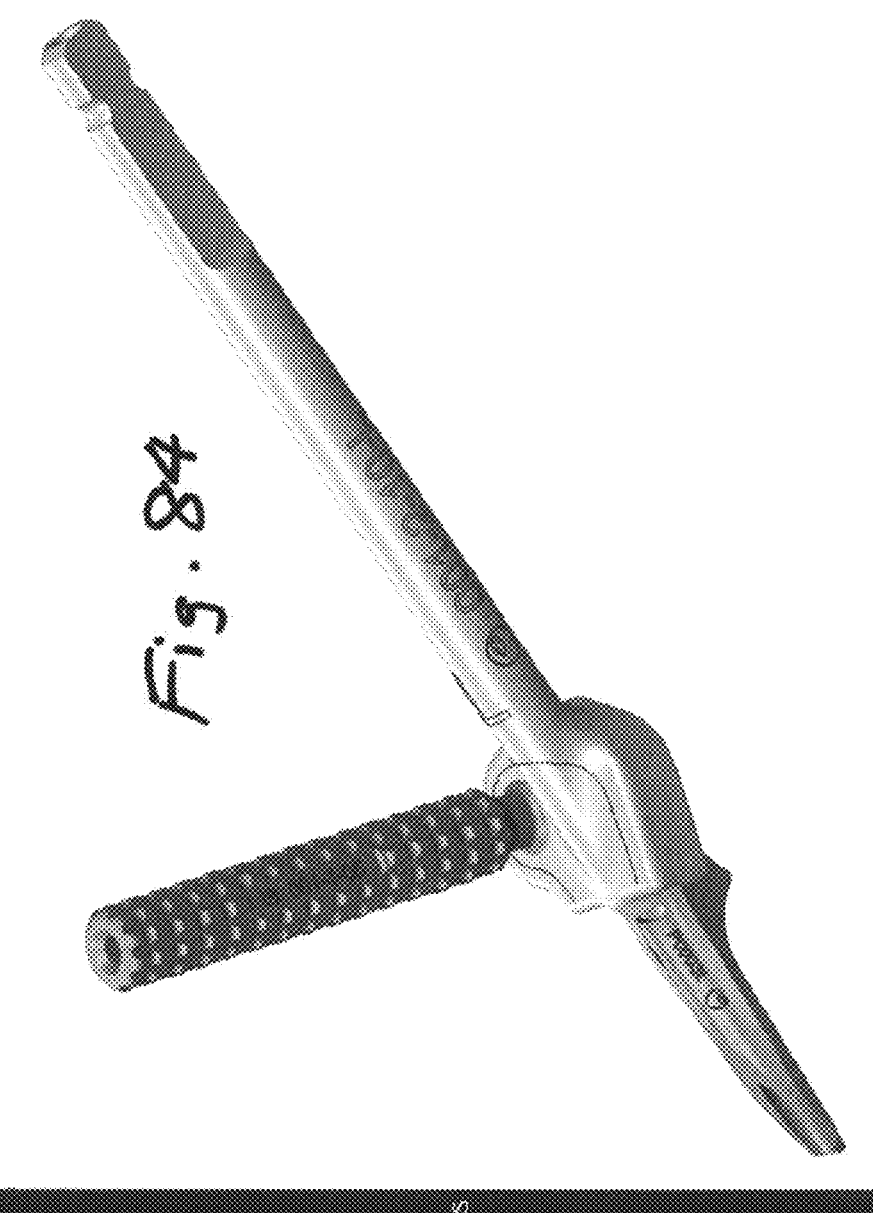
Fig. 84
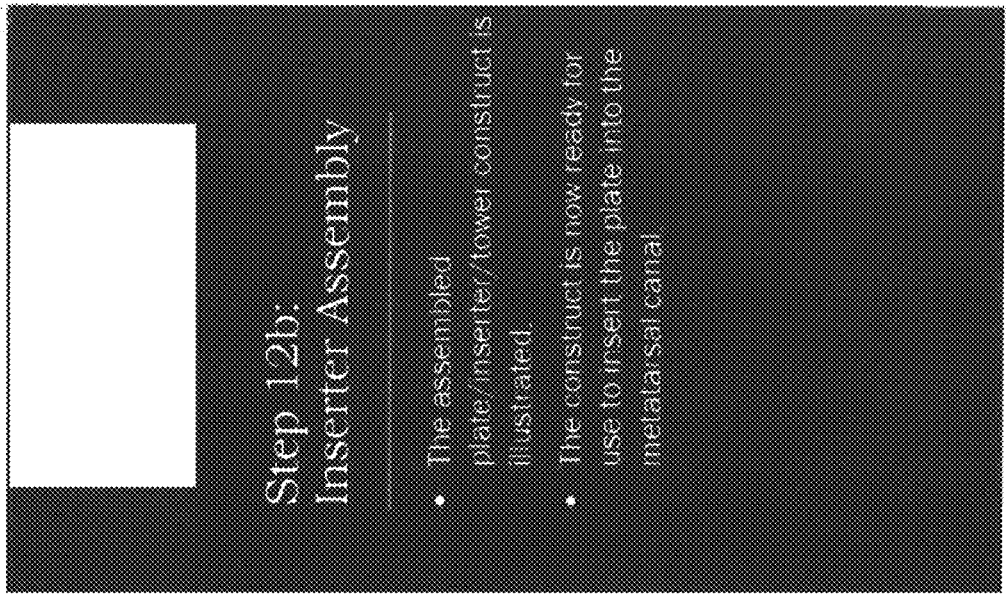
Step 12b:
Inserter Assembly
- The assembled plate/inserter/tower construct is illustrated.
- The construct is now ready for use to insert the plate into the metatarsal canal Step 15a:
Distal Medial Screw

• Remove the central 9" long, ø1.6mm K-wire from the construct

• Remove the inserter

Step 15b:
Distal Medial Screw

- Assemble the distal tower by threading into the medial hole of the dorsal bunion plate.

- Insert a 6 long ø1.6mm k-wire through the tower and into the metatarsal head to the desired depth as guided under fluoroscopy.

- Remove the distal tower and k-wire.

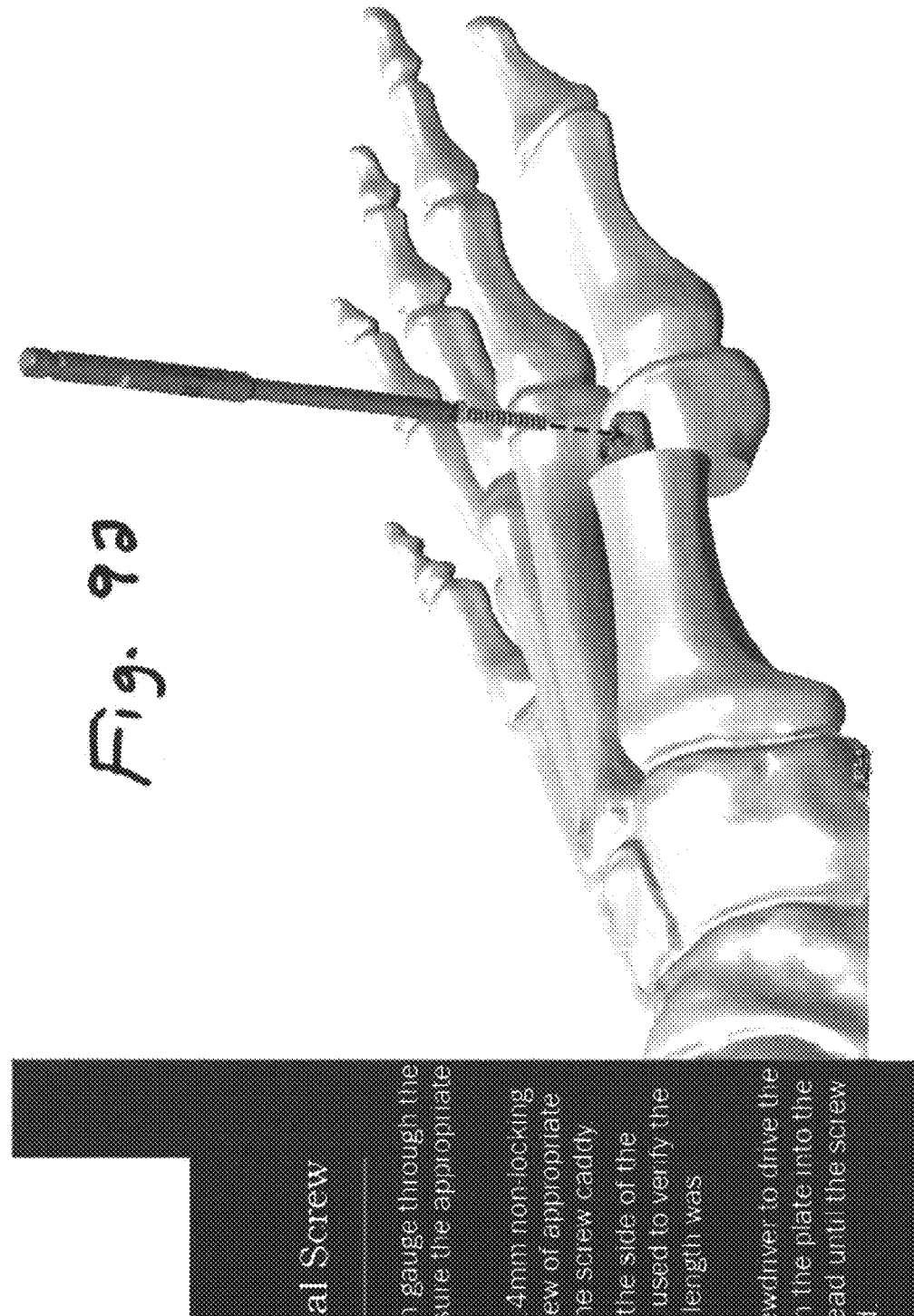

*Fig. 93*

Step 15c:
Distal Medial Screw

- Use the depth gauge through the plate to measure the appropriate screw length
- Remove a ⌀2.4mm non-locking or locking screw of appropriate length from the screw caddy
- The scale on the side of the caddy can be used to verify the proper screw length was selected
- Use a T6 screwdriver to drive the screw through the plate into the metatarsal head until the screw is fully seated

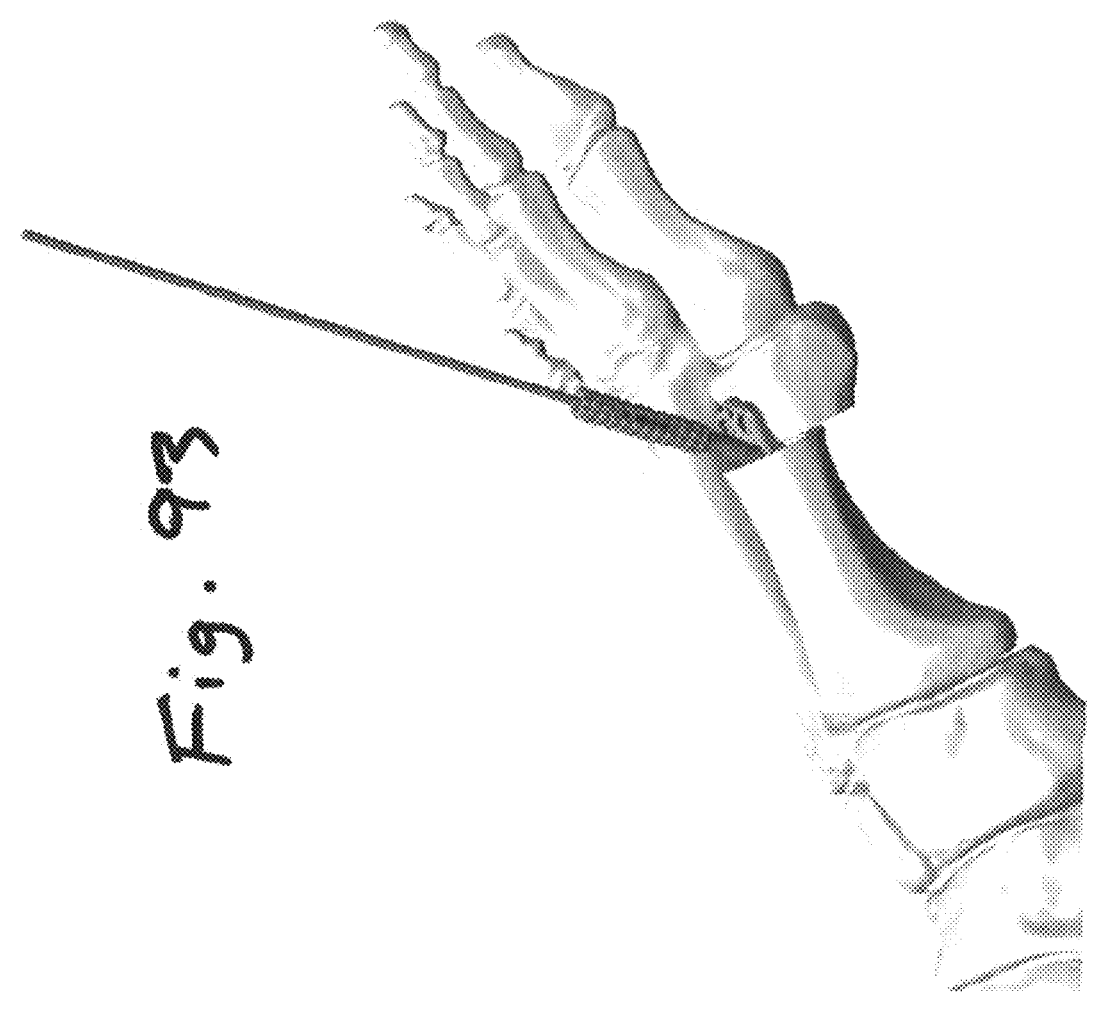

Fig. 93

Step 16a:
Oblique Screw

- Insert the proximal tower though the oblique hole of the dorsal bunion plate and snap into place

- Under fluoroscopy, drive a 6" long ⌀1.6mm k-wire though the proximal tower and into the inferior cortex of the metatarsal shaft

- Remove the k-wire and the proximal tower

- Use the depth gauge to measure proper screw length that will engage to the inferior cortex

Step 16b:
Oblique Screw

- Remove a ⌀2.4mm non-locking screw of the identified length from the implant caddy

- Note only non-locking screws are compatible with the oblique screw hole of the plate

- The scale on the side of the implant caddy may be used to verify screw length

- Use a T6 screwdriver to drive the screw through the plate and into the cortex of the metatarsal shaft

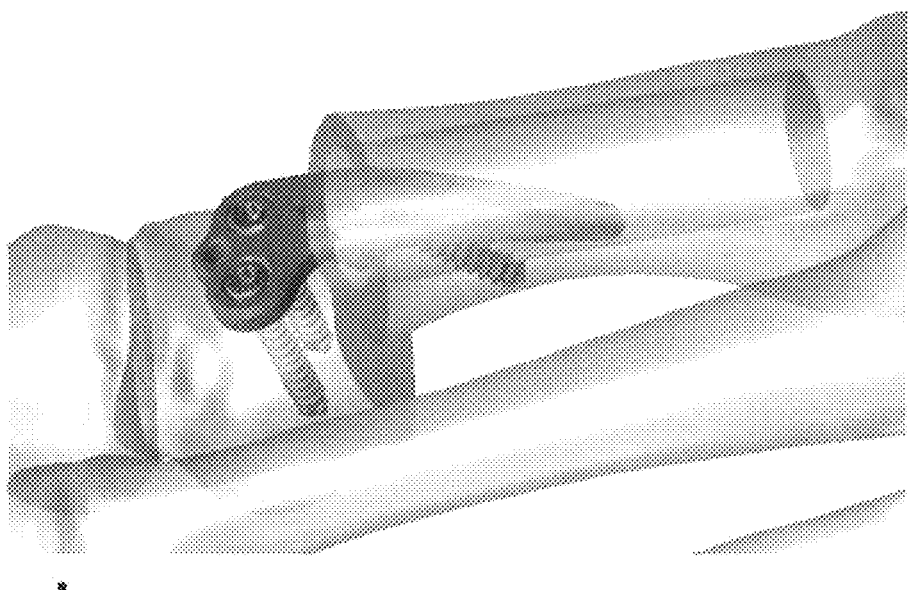
Fig 95
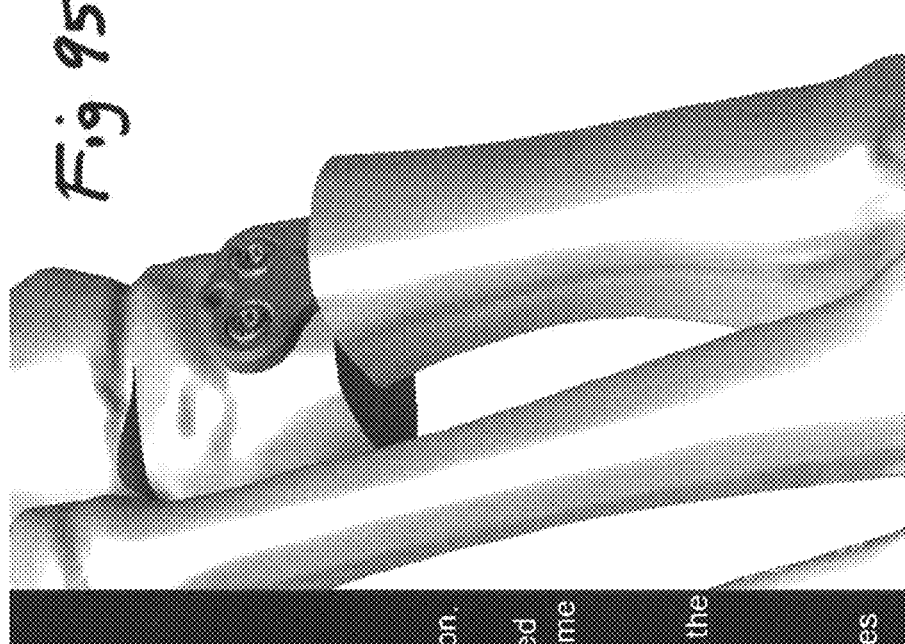
17a:
Final Dorsal Bunion Placement
- Under discretion of the surgeon the medial non-locking screw may be explanted and replaced with a locking screw of the same length. This step is not a requirement.
- Check the final positioning of the plate and screws with A/P, Sesamoid Axial, and Lateral Fluoroscopy.
- Close the incisions with sutures of the surgeon's preference.

Fig. 96
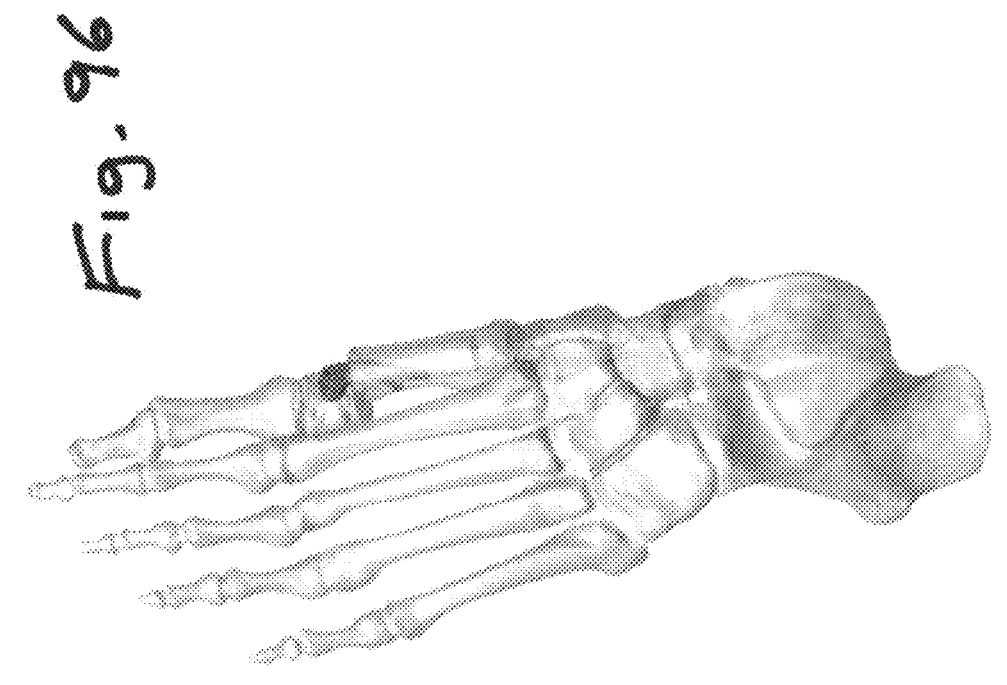
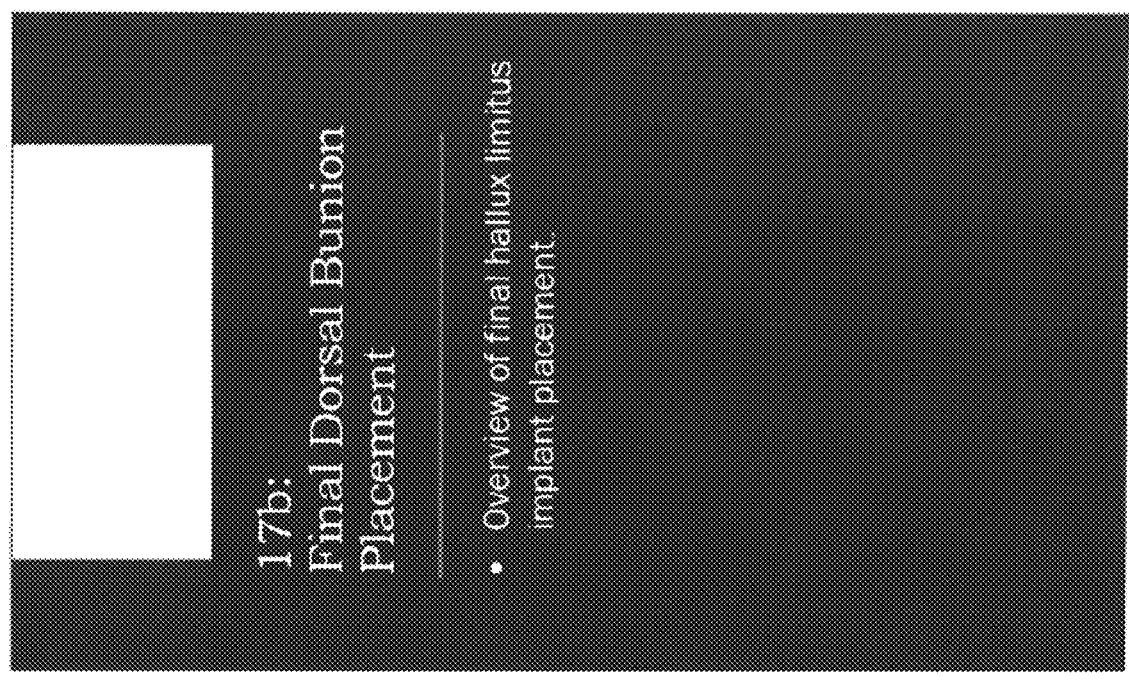
17b:
Final Dorsal Bunion Placement
• Overview of final hallux limitus implant placement.

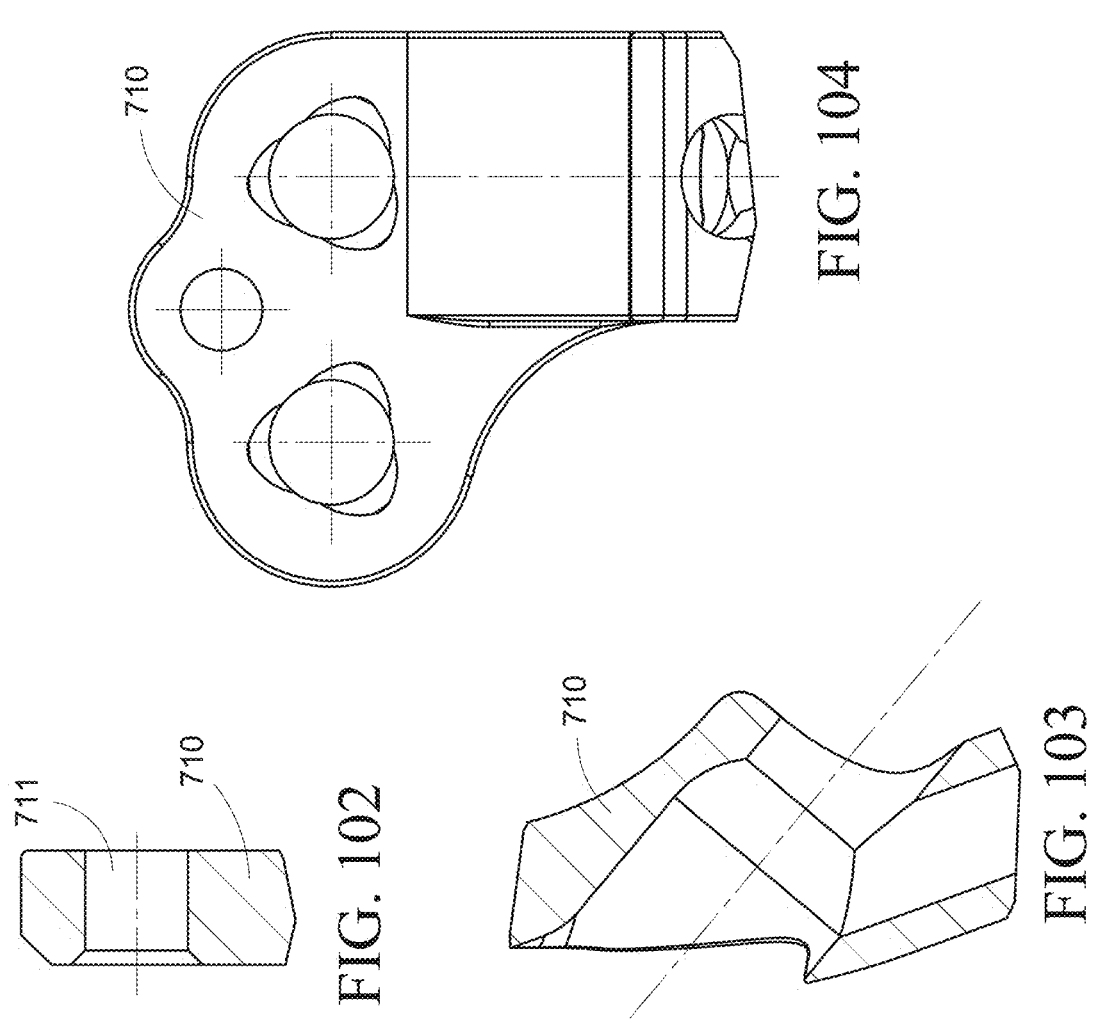
FIG. 104
FIG. 102
FIG. 103
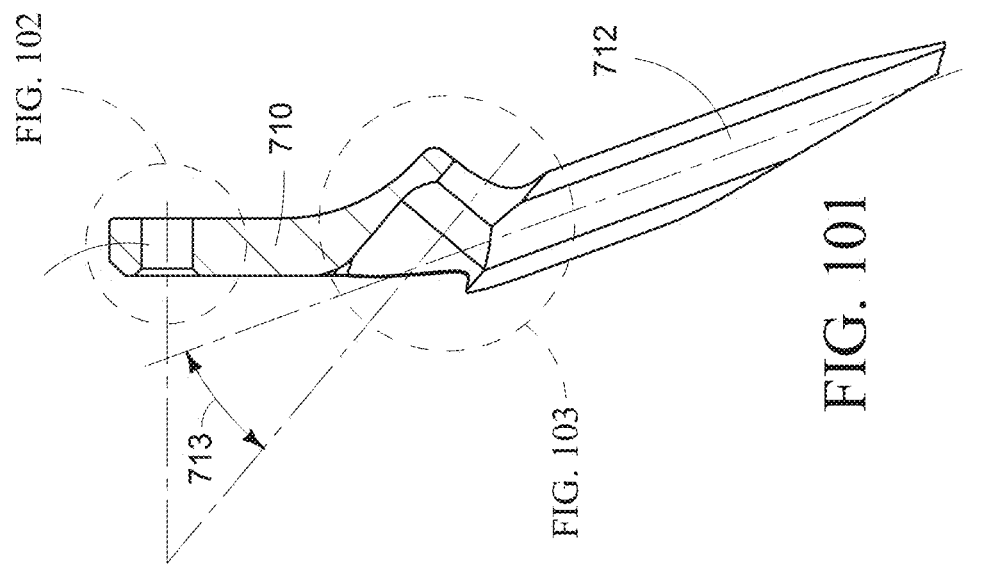
FIG. 101

735

735

735

735

117

117

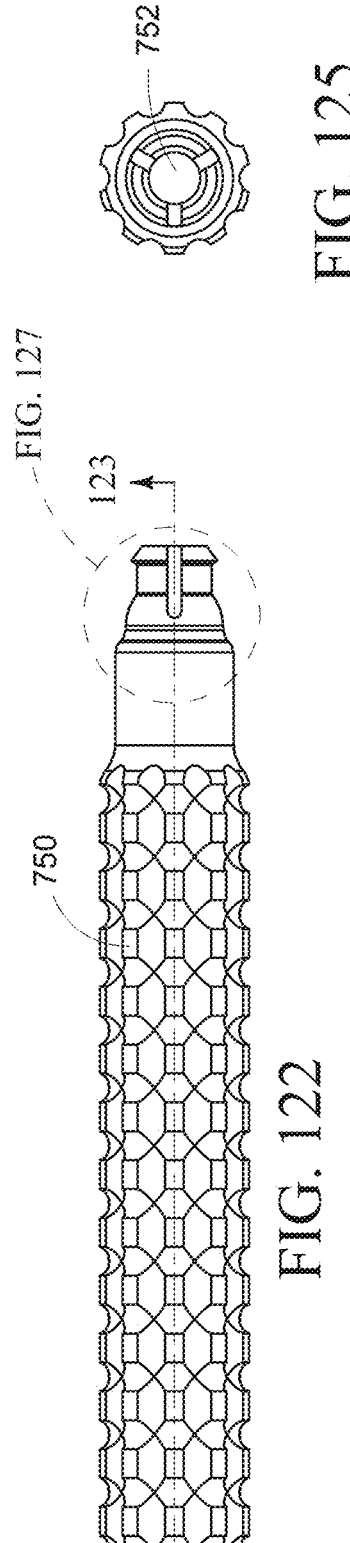
FIG. 122
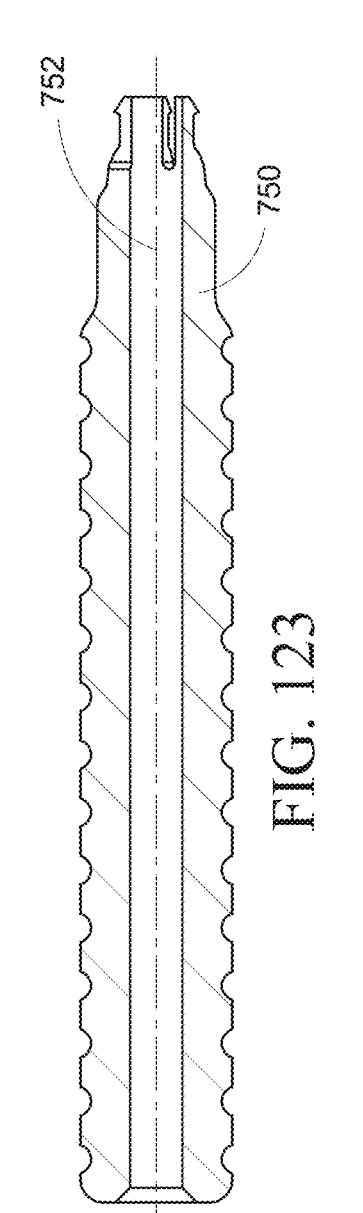
FIG. 123
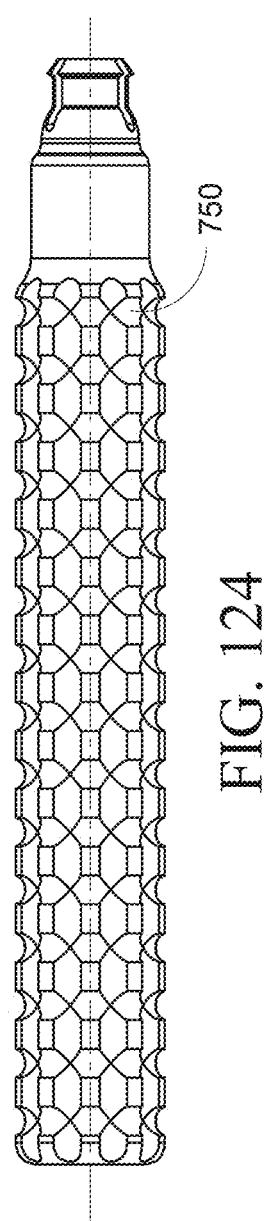
FIG. 124
FIG. 125

COMBINED INTRAMEDULLARY - EXTRAMEDULLARY BONE STABILIZATION AND ALIGNMENT SYSTEM

CROSS REFERENCE TO RELATED APPLICATION

This application claims the benefit of U.S. patent application Ser. No. 16/726,592, filed Dec. 24, 2019, which claims the benefit of U.S. Pat. No. 10,517,655, filed Jan. 27, 2017, which claims the benefit of U.S. patent Ser. No. 10/226,292, filed Jun. 8, 2015.

TECHNICAL FIELD

This invention pertains to a combined intramedullary and extramedullary stabilization and alignment system for use on the bones and joints of mammals.

BACKGROUND OF THE INVENTION

For many years numerous surgical procedures have been performed to stabilize and align (or re-align) parts of the skeletal structure of mammals. These surgeries include the alignment of existing joints as well as the fusion or attachment of one part of a bone to another part of a bone that have been separated surgically or otherwise. A surgical osteotomy for example is a procedure where a bone is cut to change the alignment (lengthen, shorten or otherwise change).

Bunion and/or hallux valgus surgeries are examples of applications for some embodiments of this invention wherein a bone is surgically cut or separated into two pieces or portions (osteotomy), and then surgically fixed back together in a more desired multi-planar and/or rotational alignment and stabilization. "Hallux" is used as another name for a person's big toe, and generally includes two bones or "phalanges" and valgus generally refers to a deformation of a bone or joint. The term "hallux valgus" typically refers to a deviation of the big or great toe toward the inside portion or fibular border of the foot.

An example of this type of surgical procedure relates to bunion surgery, which may also be referred to as a bunionectomy or a surgical procedure to correct or relieve a bunion. A bunion is a distortion or enlargement of a joint in the big toe which causes the big toe to curve outwardly toward the other toes in the foot. The metatarsal bone protrudes medially and can rotate externally (see FIG. 1).

In a typical foot the first intermetatarsal angle is in the five to ten degree range (generally under fifteen degrees), whereas in a foot with metatarsus primus varus, the first intermetatarsal angle may be greater than fifteen degrees and can increase to twenty degrees or more. The "first" intermetatarsal angle is the angle between the first and second metatarsal bones. A metatarsus primus varus is a condition in which the first metatarsal bone has an increased angle away from the second metatarsal bone and some rotational distortion.

Some estimate there are approximately two-hundred thousand to four-hundred thousand bunion or Hallux Valgus (HV) surgical procedures performed every year. Metatarsus primus generally occurs along with bunion and hallux valgus.

The difficulties with some of the prior art surgical procedures are multiple and many modifications of the basic procedure have been proposed and explored. However, despite the years of attempts to modify the bunionectomy, there is still a relatively high rate of patient dissatisfaction with bunion and hallux valgus types of surgeries.

In the bunion surgery example the deformity most often addressed by the surgical procedure is the increase in the angle between the first and second metatarsals, an example of which is illustrated in FIG. 1 (angle 93). The view of the deformity shown in FIG. 1 only shows one plane of deformation whereas in most bunion conditions the patient has deformity in multiple planes and some further include rotational deformity (angle 94, FIG. 1). In the prior art these deformity angles may be referred to as the first intermetatarsal angle ("IMA") and the second intermetatarsal angle, with the first intermetatarsal angle being the angle between the first and the second metatarsal bones.

It is believed that in many bunion surgeries the failure to recognize and/or solve the frontal plan rotation deformation for example, results in less than desirable surgical results. The prospects for a successful surgical procedure are further limited by the difficulties associated with the imprecise nature of being able to more precisely view and align the two part/portions of the bones or portions/parts/pieces of bones being fixed together (or the joint being re-aligned).

Only a few of the existing surgical procedures or systems address both the translational and rotational deformity issues. One of the most common surgical procedures used to address the translational and rotational deformity issues is referred to as a Lapidus Bunionectomy, in which the first metatarsal is fixed to the medial cuneiform. Unfortunately the Lapidus Bunionectomy has historically had a four to six week non-weight bearing postoperative healing period.

Despite the longstanding and recognized need for an improved system to address the various deformities and/or issues typically associated with skeletal or bone misalignment and/or deformity in mammals, there is still a need for an improved system.

Aspects of this invention such as the cannulated aspect of the implant device have an advantage of providing the surgeon an additional alignment tool for use during the surgery in combination with what is referred to as a wire or "K-wire". The term K-wire is used broadly in the surgical field to refer to a wire or pin that may have numerous deviations (sharpened portions, threaded portions, various or varying thicknesses, etc). K-wires were originally referred to as Kirschner wires because Martin Kirschner was originally credited with the introduction of the wires into surgery in the early 1900's.

In surgeries, K-wires may be conveniently used for temporary or permanent fixation. In some applications K-wires may first be inserted into one part or portion of the bone or joint, and then the intramedullary and extramedullary portions of one embodiment of the invention can be slid over the K-wire to achieve more consistent improved alignment of the device. This will lead to more consistent desired (or improved) alignment of the joint and/or fusion.

There are substantial opportunities in these types of surgeries for improvement in the precise placement and fixation of the metatarsal head, to meet two objectives of the surgery, namely the centering of the metatarsal head over the sesamoid, and the angular alignment or rotational adjustment to reduce the angle between the first and second metatarsals.

Generally, after the implant device is attached to the metatarsal head it is oftentimes desirable, but not very feasible under current technology, to make micro-adjustments to manipulate or move the metatarsal head laterally or rotationally/angularly. Embodiments and aspects of this invention provide the surgeon with the ability to make these lateral and rotational micro-adjustments to, for example, center the metatarsal head over the sesamoid or the sesamoid apparatus and to make the desired rotational or angular adjustment. At this stage of the surgery an axial view of the sesamoid may provide the surgeon the image to allow the surgeon to accurately see how much rotation or angular adjustment may be needed in order to micro adjust the metatarsal head into as near to the exact position as can be accomplished. The current technology heretofore has not provided a sufficient ability (or any ability) to make such micro-adjustments, including using the sesamoid at axial view.

Aspects of this embodiment provide a new and novel ability to make post-attachment adjustments to position the metatarsal head, by providing a system which allows the surgeon to make post plate attachment adjustments to position the metatarsal head laterally and rotationally/angularly.

It is therefore an object of aspects or embodiments of this invention to provide a system and tool whereby post attachment adjustments (including micro adjustments) can be made to finally position or fixate the metatarsal head laterally and rotationally/angularly more accurately.

It is a further object of some embodiments of this invention to provide an adjustment tool, integral with or separate from the drill and/or wire guide or template, is attachable and detachable to and from the implant device, to provide for the post metatarsal head attachment adjustment of the position (such as lateral position) and the angular position of the metatarsal head.

It is therefore an object of some embodiments of this invention to provide an improved stabilization and/or alignment system which may be used to address bone and joint alignment issues generally, and which may include foot related bunion and unwanted metatarsal deformations.

It is a further object of this invention to provide such system which provides an improved alignment tool during the surgical procedure, such as by providing a cannulated intramedullary portion that is disposed to be inserted into a bone over the wire or k-wire as a guide. It is a further object to provide such a system wherein the extramedullary portion is also cannulated.

Other objects, features, and advantages of this invention will appear from the specification, claims, and accompanying drawings which form a part hereof. In carrying out the objects of this invention, it is to be understood that its essential features are susceptible to change in design and structural arrangement, with only one practical and preferred embodiment being illustrated in the accompanying drawings, as required.

BRIEF DESCRIPTION OF THE DRAWINGS

Preferred embodiments of the invention are described below with reference to the following accompanying drawings.

FIG. 5 is a top skeletal schematic representation of bones in a typical human foot, illustrating an example of an implant device contemplated by embodiments of this invention, wherein a drill guide or template is used to align the drilling of a transverse fastener aperture through the fastener aperture in the intramedullary portion of the implant, for the later insertion of a screw there-through;

FIG. 13 is top skeletal schematic representation of bones in a typical human foot, illustrating an example of an angled implant device (such as shown in FIG. 12) contemplated by embodiments of this invention, wherein a drill guide or template is used to align the drilling of a transverse fastener aperture through the fastener aperture in the intramedullary portion of the implant, for the later insertion of a screw there-through;

FIGS. 26-63 illustrate and describe one example of an embodiment of this invention regarding a system applicable to a medial bunion apparatus and procedure;

FIGS. 64-96 illustrate one example of an embodiment of this invention regarding a system applicable to a Hallux Limitus-Dorsal bunion apparatus and procedure; and FIGS. 97-144 illustrate examples of apparatus and devices that may be utilized in embodiments of the system (s) described herein, as further described below.

DETAILED DESCRIPTION OF THE PREFERRED EMBODIMENTS

Many of the fastening, connection, manufacturing and other means and components utilized in this invention are widely known and used in the field of the invention described, and their exact nature or type is not necessary for an understanding and use of the invention by a person skilled in the art or science; therefore, they will not be discussed in significant detail. Furthermore, the various components shown or described herein for any specific application of this invention can be varied or altered as anticipated by this invention and the practice of a specific application or embodiment of any element may already be widely known or used in the art or by persons skilled in the art or science; therefore, each will not be discussed in significant detail.

The terms "a", "an", and "the" as used in the claims herein are used in conformance with long-standing claim drafting practice and not in a limiting way. Unless specifically set forth herein, the terms "a", "an", and "the" are not limited to one of such elements, but instead mean "at least one".

Although the embodiments of this invention as applied to certain foot surgeries is primarily discussed to describe the invention, it will be noted by those of ordinary skill in the industry that the methods and apparatuses disclosed in this invention may be utilized in other bone related applications. For example, while the application discussed is a metatarsal osteotomy, it may be applied to osteotomies on other bones or pieces/parts of bones as well. Aspects of this invention may also be used to stabilize or fix two different bones together, including two bones comprising a joint. Still further embodiments of this invention may be utilized in fixing, stabilizing and/or aligning two portions/parts/pieces of bones, all within the contemplation of embodiments of this invention.

Figure 1:
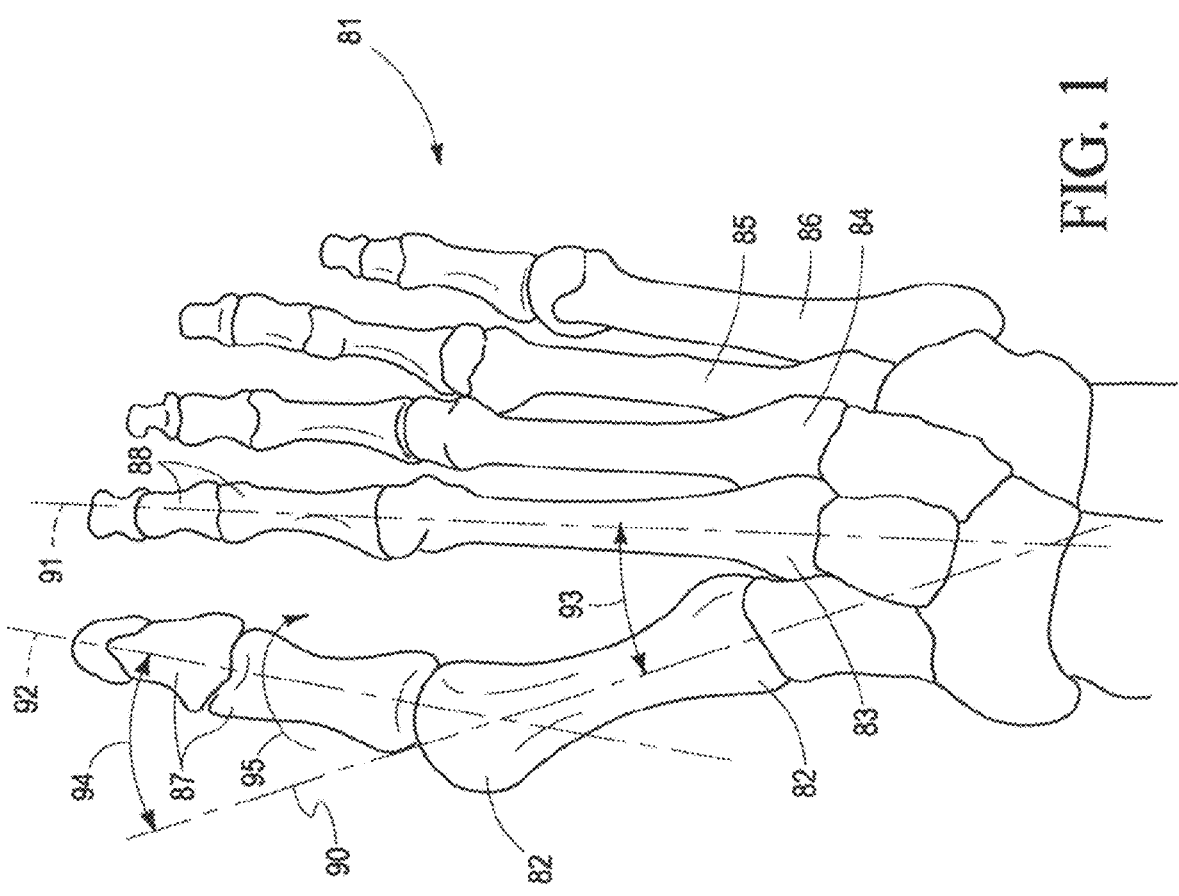
FIG. 1 is a top view of bones in a typical human foot illustrating bunion and metatarsal issues.

FIG. 1 is a top view of bones in a typical human foot 81 illustrating bunion and metatarsal issues. FIG. 1 shows first metatarsal bone 82, second metatarsal bone 83, third metatarsal bone 84, fourth metatarsal bone 85 and fifth metatarsal bone 86 of foot 81. FIG. 1 also shows the pair of first phalange bones 87 and second pair of phalange bones 88 for the second or middle toe.

FIG. 1 illustrates the approximate center line 90 of the first metatarsal bone 82 as item 90, the approximate center line 92 for the phalange bones 87 for the first toe and the approximate center line 91 for the second metatarsal bone 83. Angle 93 would represent the first intermetatarsal angle ("IMA") and angle 94 would represent an amount that the phalanges rotated relative to the first metatarsal bone 82, while arrow 95 may be indicative of further rotation of that portion of the big toe.

Figure 2:
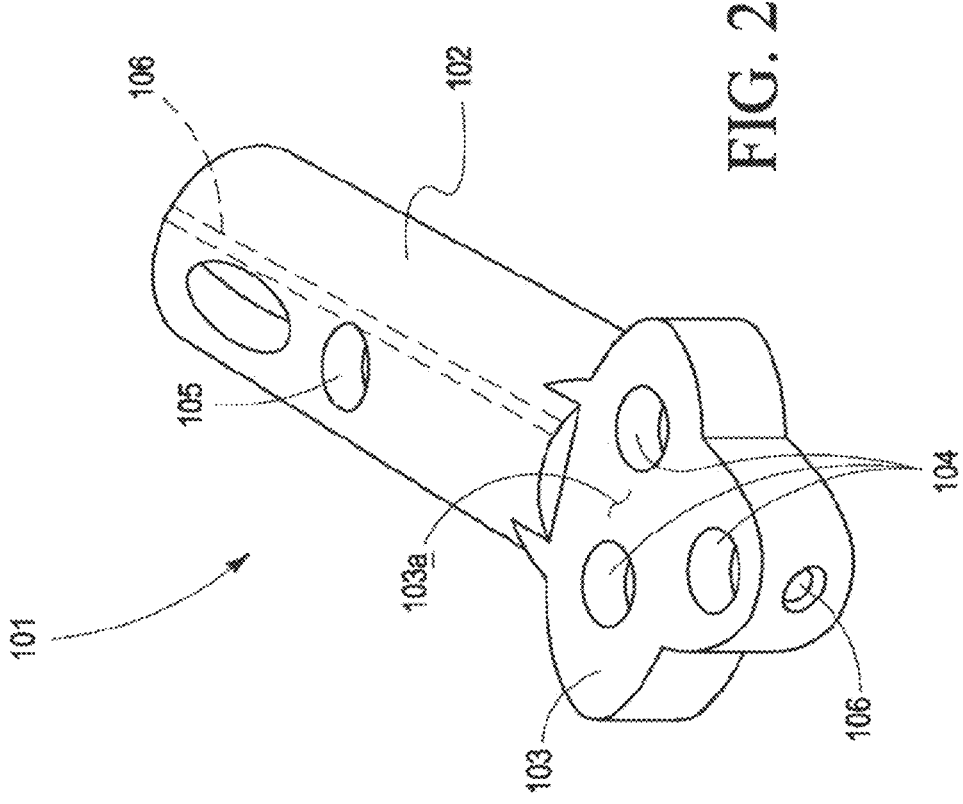
FIG. 2 is a perspective view of an example of one embodiment of an implant device contemplated by this invention.

FIG. 2 is a perspective view of an example of one embodiment of an implant device 101 contemplated by this invention, illustrating the framework with the intramedullary portion 102, extramedullary portion 103, and the K-wire aperture 106 through both the intramedullary portion 102 and the extramedullary portion 103.

FIG. 2 further illustrates fastener apertures 104, and an abutment surface 103a which, in some embodiments of this invention, may be configured for abutment with a portion of the second piece of the metatarsal bone to which it is intended to be fastened. The intramedullary portion 102 also includes transverse aperture 105.

In some embodiments of this invention, the intramedullary portion of the apparatus may be partially or fully inserted into the center or medulla portion of the bone, first bone or first section or piece of the bone.

In this application the term plate as used is not limited to any particular geometric shape such as a flat bodied portion, but instead is broader than that and may include different and other shapes and configurations.

Figure 3:
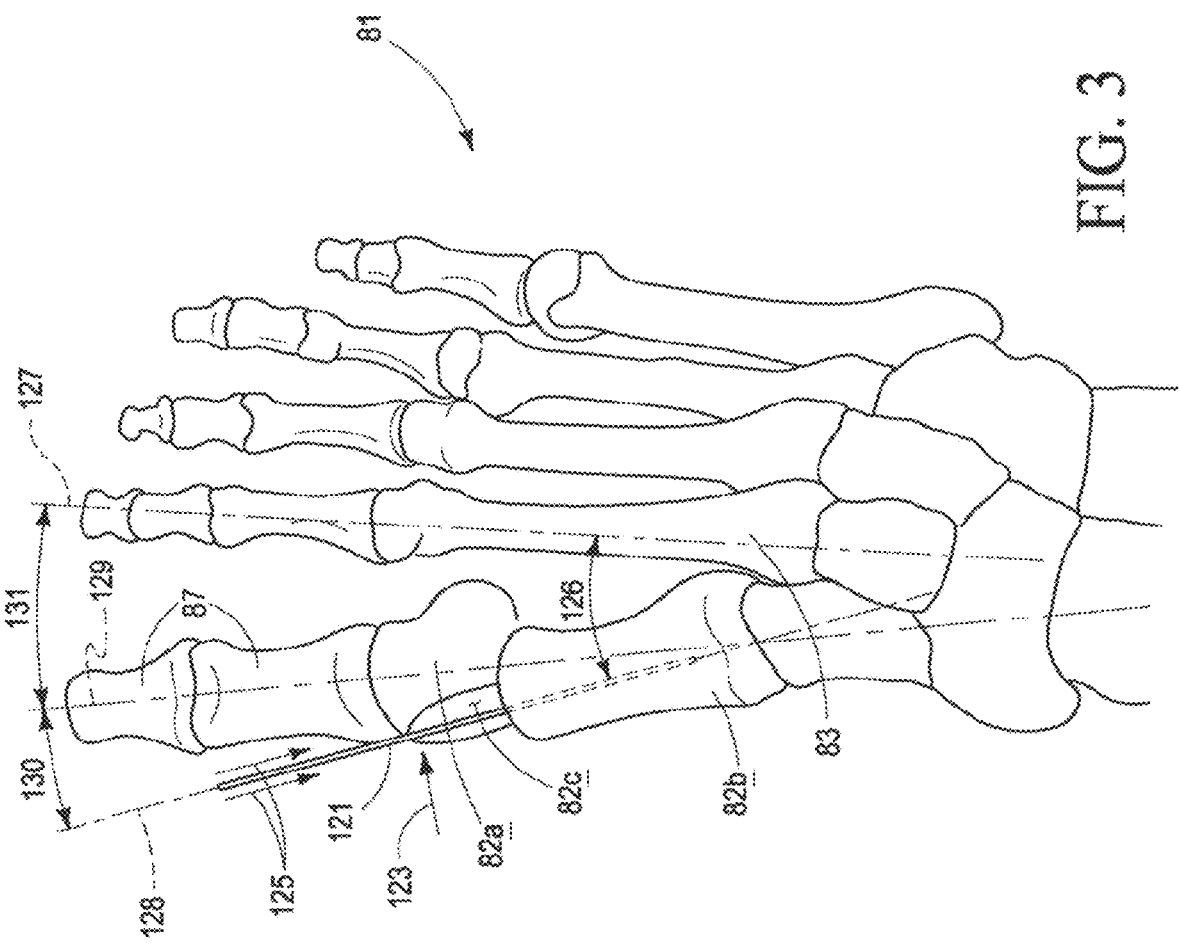
FIG. 3 is a top skeletal schematic view of bones in a typical human foot illustrating a first metatarsal bone that has been cut or severed transversely and a K-wire inserted into a first piece of the first metatarsal bone.

FIG. 3 is a top skeletal schematic view of bones in a typical human foot 81 illustrating a first metatarsal bone 82 (shown in FIG. 1) having been transversely cut and a K-wire 121 inserted into a first piece 82b of the first metatarsal bone. FIG. 3 also illustrates first intermetatarsal angle 126 between the approximate center line of the first metatarsal bone and the approximate centerline 127 of the second metatarsal bone 83.

FIG. 3 shows a second piece 82a of the first metatarsal bone 82 (shown in FIG. 1) which has been cut, sawed or severed from first piece 82b of the first metatarsal bone as part of the surgical procedure. The second piece 82a of the metatarsal bone also includes surface 82c, which may have been prepared or reformed by cutting, sawing and/or grinding to provide an interface surface for the implant device (shown in other figures) to abut, fasten to and otherwise interact with.

Once the first metatarsal bone 82 (shown in FIG. 1) has been cut or sawed into a first bone piece 82b and a second bone piece 82a of the first metatarsal bone, and the desired surface area 82c has been cut into the second piece 82a of the first metatarsal bone, the second piece 82a of the first metatarsal bone 82 may be moved toward the second metatarsal bone 83 as illustrated by arrow 123.

The second piece 82a of the first metatarsal bone 82 shown in FIG. 3 would be relocated (represented by arrow 123) to a location which would produce the desired or preferred alignment of the big toe or Halux. Once the second piece 82a of the first metatarsal bone 82 is placed at the desired angular and alignment location, the K-wire 121 may be implanted, inserted or forced (arrows 125) into the first piece 82b of the first metatarsal bone 82 at a desired angle to enable the implant device (item 99, FIG. 4) to be inserted over the K-wire 121 and provide the desired angle for the big toe or Hallux.

FIG. 3 further illustrates a new center line 129 for the big toe, which is angle 130 from the prior center line 128 of the first metatarsal bone 82, and now only angle 131 offset from the centerline 127 of the second metatarsal bone 83.

In the embodiments which make use of a K-wire, this may eliminate the need to drill a hole through the bone but instead the K-wire can be more efficiently inserted through other known means with less or minimal negative effects to the bone of the patient. It will be appreciated by those of ordinary skill in the art that while a K-wire is referred to herein, this invention is not so limited as it includes a pin, wire, thin rod or other similar alignment component.

It will further be appreciated that the insertion of the K-wire into, for example, the first metatarsal piece may be accomplished in any one of a number of different ways known in the art, such as forced insertion, screwing or through the use of tools, all within the contemplation of this invention and with no one in particular being required to practice this invention.

In the prior art situations in which a K-wire is used for temporary alignment of the two pieces of bone, the wire must be removed before a fixation device may be removed. The removal of the K-wire makes it much more difficult to consistently get as precise of an alignment as desired for the resulting fixed bone sections. In embodiments of this invention and because of the wire aperture or cannulated feature of this invention, the K-wire or wire aperture can be slid over the K-wire to position, align and guide the implant device to its desired and aligned location. During the alignment process the surgical area (and the alignment and position) of the K-wire can be readily seen through use of x-ray device to further assist in more precisely obtaining the desired angles.

Figure 4:
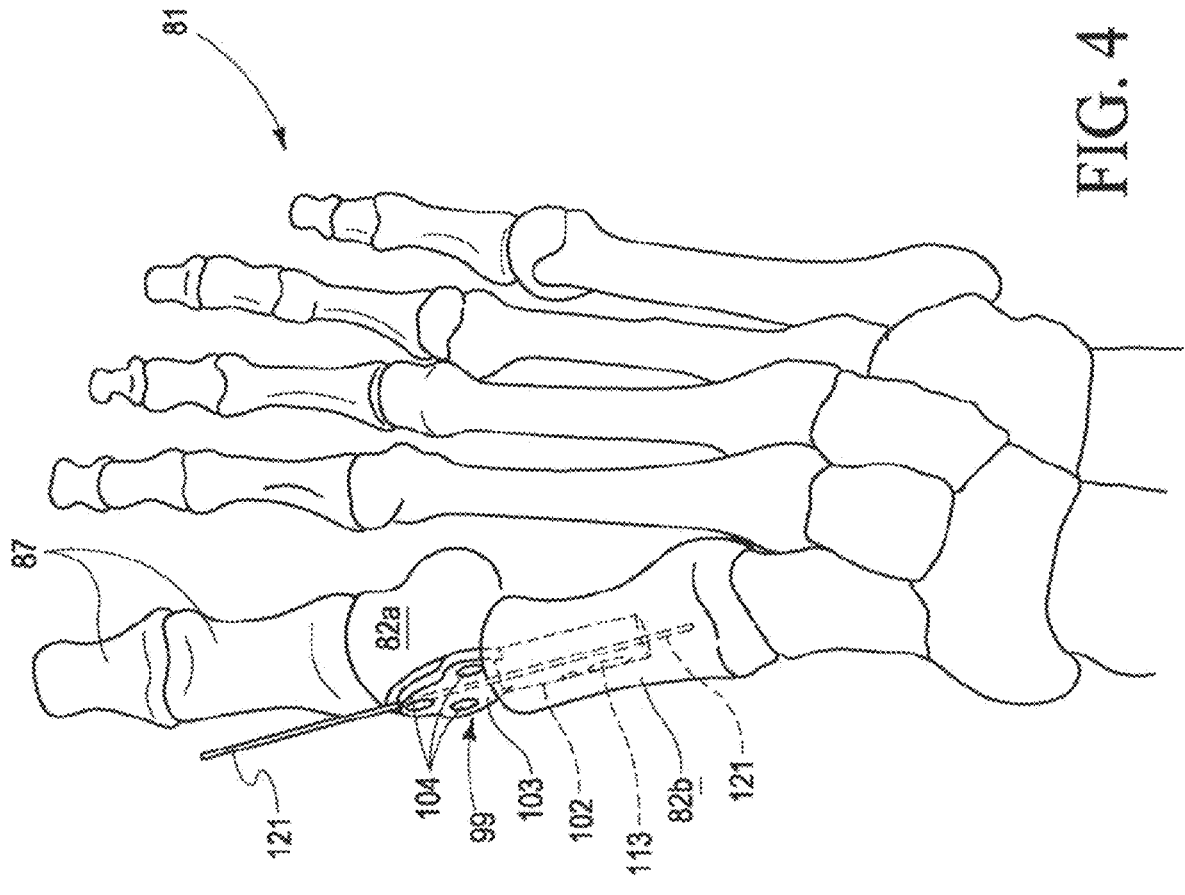
FIG. 4 is a top skeletal schematic representation of bones in a typical human foot, illustrating an example of an implant device contemplated by embodiments of this invention, with the intramedullary portion inserted over the K-wire and into the first piece of the first metatarsal bone piece and abutting or alongside the second metatarsal bone piece.

FIG. 4 is a top skeletal schematic representation of bones in a typical human foot 81, illustrating an example of an implant device 99 contemplated by some embodiments of this invention, with the intramedullary portion 102 inserted over the K-wire 121 and into the first piece 82b of the first metatarsal bone, and the extramedullary portion 103 of the implant device 99 abutting or alongside the prepared surface (shown as item 82c in FIG. 3) in the second piece 82a of the first metatarsal bone 82. FIG. 4 further shows a transverse screw aperture 99 for the transverse insertion of a screw through the bone and the intramedullary portion 102.

FIG. 4 shows how the K-wire 121 serves as an initial alignment aid and then as the guide inserting or implanting the intramedullary portion 102 at the desired angle. It will be appreciated by those of ordinary skill in the art, the benefits and advantages of utilizing the K-wire 121 for the alignment or re-alignment. Current practice requires the surgeon under more difficult circumstances to more roughly estimate the alignment when inserting plates and other devices that are currently used as part of these types of surgeries.

Figure 5:
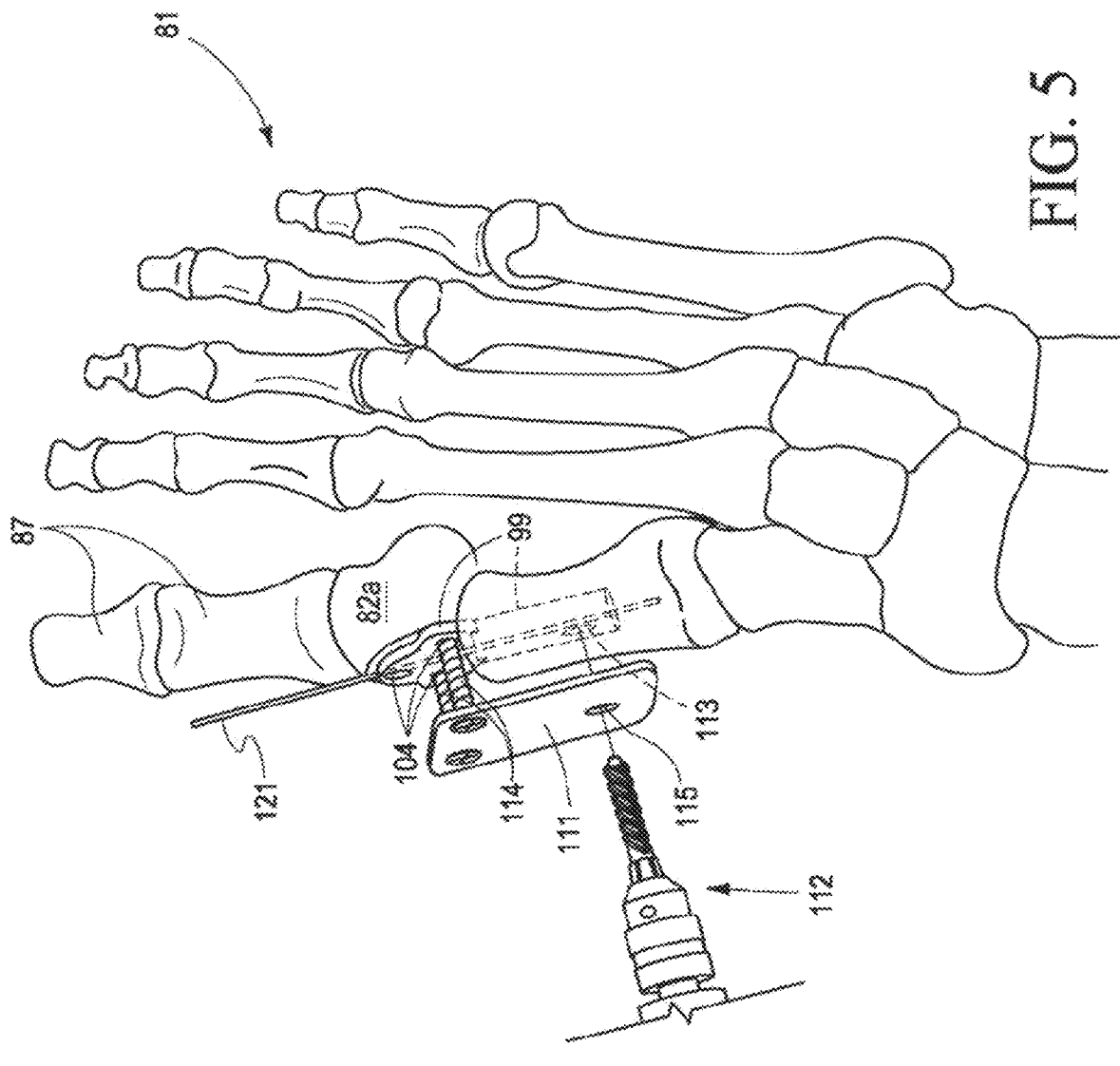
Figure 6:
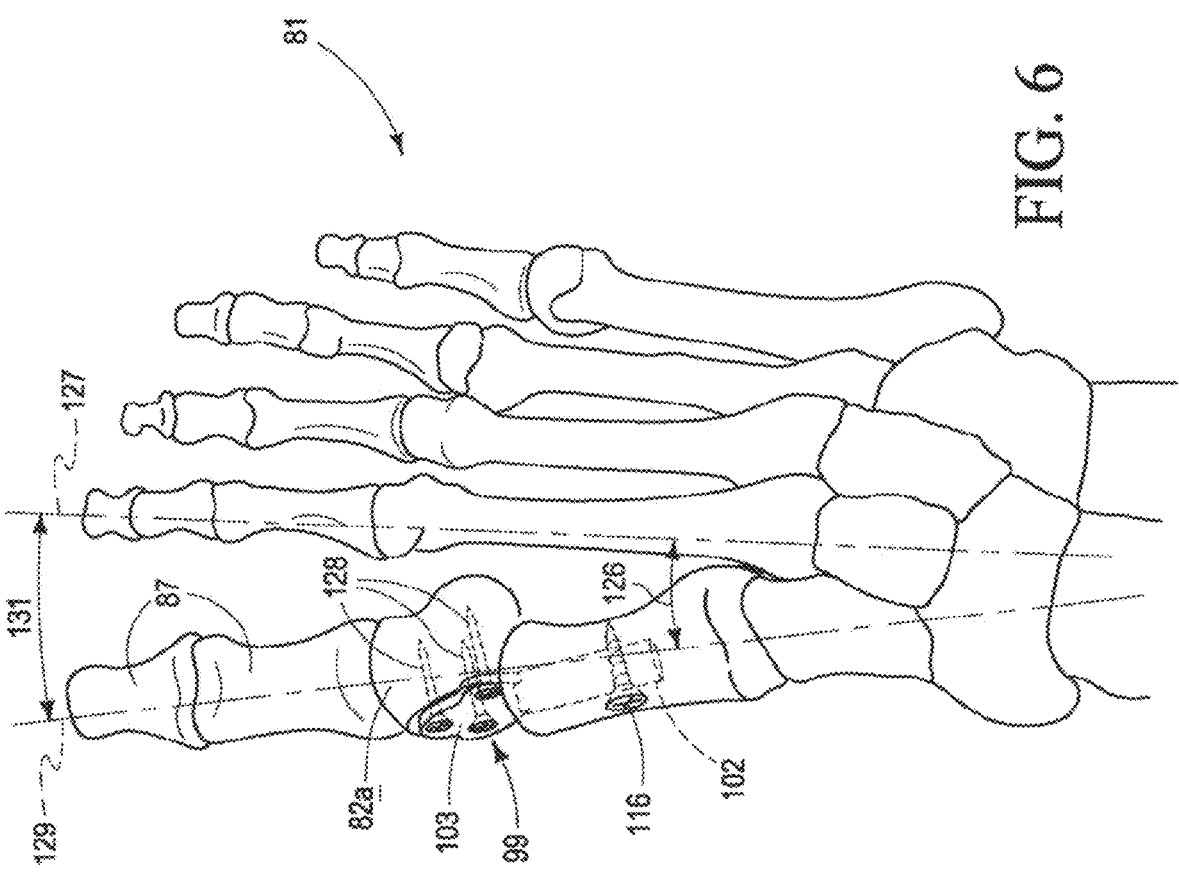
FIG. 6 is a top skeletal schematic representation of bones as shown in FIG. 4, and further illustrating bone fasteners secured within the second piece of the first metatarsal bone.

FIG. 5 is a top skeletal schematic representation of bones in a typical human foot, illustrating an example of an implant device 99 contemplated by embodiments of this invention, wherein a drill guide or template 111 is used to align the transverse drilling of a pilot hole through the bone and through a transverse screw aperture 113 in the intramedullary portion of the implant device 99, for the later insertion of a screw (as shown in FIG. 6). The drill guide 111 is a template to provide sufficient guidance and alignment of the drill 112 through drill hole 115 in the drill guide such that the hole drilled through the bone aligns with the transverse screw or fastener aperture 113 in the intramedullary portion of the implant device. While the alignment example shown in FIG. 5 illustrates the use of two screws 114 which fix the drill guide 111 relative to the implant device 99, other alignment mechanisms or tools may be utilized within the contemplation of embodiments of this invention, with no one being required to practice this invention.

FIG. 6 is a top skeletal schematic representation of the foot 81 as shown in FIG. 4, and further illustrates bone fasteners 128 (screws in the example of the embodiment shown) that have been placed through the fastener apertures 104 (shown in FIG. 4) in the extra-medullary portion 103 of the implant device 99 and secured or fastened within the second piece 82a of the first metatarsal bone. Bone fastener 116, a screw in this example, is shown transversely screwed into the bone through the screw aperture in the intramedullary portion 102 of the implant device 99. FIG. 6 also shows phalange bones 87 of the big toe, as well as the new angle 131 between the new centerline 129 of the big toe and the centerline 127 of the second toe.

It will be noted and appreciated by those of ordinary skill in the art that this invention is not limited to any one particular bone fastener, but instead any one of a number of known and to be discovered bone fasteners may be utilized within the contemplation of this invention, such as without limitation, bone screws, bone nails and the like.

Figure 7:
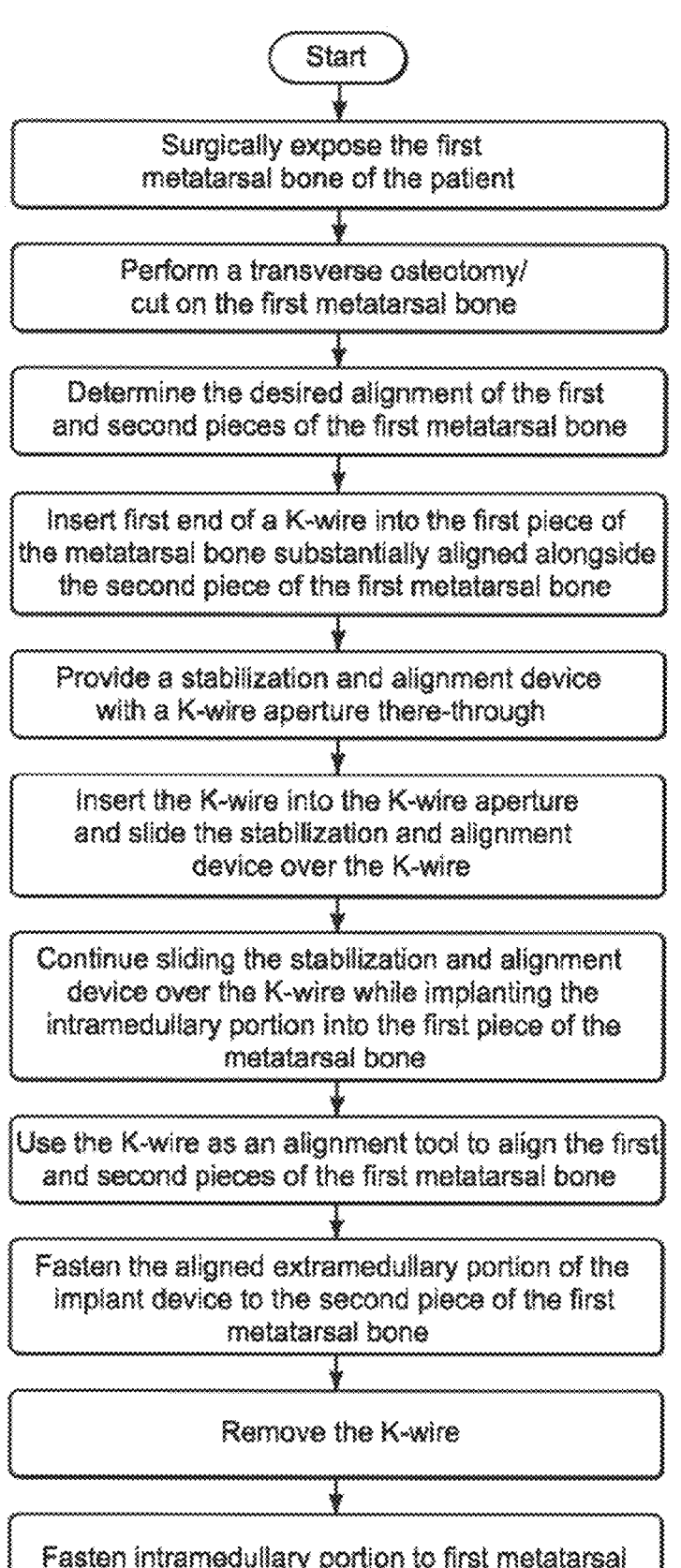
FIG. 7 is a box diagram flow chart of an example of a method or process contemplated by embodiments of this invention.

FIG. 7 is a box diagram flow chart of an example of a method or process contemplated by embodiments of this invention. The first step in FIG. 7 is the beginning of a surgery in which the patient's tissue must be parted in order to expose the first metatarsal bone of the patient's foot to provide sufficient vision and clearance for the remaining steps of the surgical alignment and stabilization process, as well as the installation of the implant device.

The next step involves the transverse cutting, sawing or severing of the first metatarsal bone of the patient into at least a first piece and a second piece. Then the second piece of the first metatarsal bone is placed into the desired alignment with the first piece of the first metatarsal bone for the desired angular result, as shown in FIG. 3.

There is an intermediate elective next step that may be and is preferably performed, and that is preparing a surface on the second piece of the first metatarsal bone to better receive and interact with the extramedullary portion of the implant device. It is preferred to create a flat surface on the second piece of the first metatarsal bone to provide a surface or interface to which the extramedullary portion of the implant device can be fastened. The surface may be prepared by grinding or cutting tools or in other ways customary in the trade.

The first end of a wire may then be inserted or implanted within the first piece of the first metatarsal bone, aligning the second end of the wire substantially alongside the second piece of the first metatarsal bone surface to which the extramedullary portion of the implant device will be fastened or attached. It is without limitation at this approximate stage that the benefits of utilizing a wire for alignment combined with a cannulated implant device can be achieved. The wire may be utilized through x-rays or visual observation to obtain the desired alignment of not only the first and second pieces of the first metatarsal bone, but also the general alignment of the toe in question which would also include the phalange bones.

Once the first piece and the second piece of the first metatarsal bone are aligned and the wire is inserted into the first piece with the desired alignment, an embodiment of an implant device may be provided.

An implant device is provided which may include an elongated framework which includes the intramedullary portion and the extramedullary portion, the extramedullary portion including at least one fastener aperture disposed to receive one or more bone fasteners to affix the extramedullary portion of the implant device to the second piece of the first metatarsal bone. Embodiments of the implant device are cannulated in that those embodiments have a contiguous wire aperture through both the intramedullary portion and the extramedullary portion of its framework. This allows the implant device to receive the wire in the wire aperture and slide down the second end of the wire with the intramedullary portion first. However, in other embodiments the wire aperture may provide interaction with the wire through a non-contiguous and/or intermittent wire aperture that extends partially or wholly throughout the length of the intramedullary portion.

Once the intramedullary portion reaches the location on the first piece of the first metatarsal bone where the wire protrudes, it can be forced or implanted into the first metatarsal bone with the already implanted portion of the wire serving as its directional guide and thereby aligning the implant device.

Once the intramedullary portion of the implant device is inserted or implanted into the first piece of the first metatarsal bone to the desired depth, the extramedullary portion of the implant device should be positioned alongside and/or abutting the desired surface of the second piece of the first metatarsal bone (with the second end of the wire protruding through the top of the wire aperture in the extramedullary portion of the implant device).

Fasteners may be placed through the fastener apertures in the extramedullary portion transversely to fasten the extramedullary portion to the second piece of the first metatarsal bone. It will be appreciated by those of ordinary skill in the art that any one of a number of different types of fasteners may be utilized to attach, fasten or secure the extramedullary portion of the implant device to the second piece of the first metatarsal bone, with no one particular being required to practice this invention. A preferred fastening mechanism is the use of bone screws or bone nails.

Once the proper alignment of the implant device has been achieved, the wire may be removed, although it does not have to be removed to practice this invention.

Figure 8:
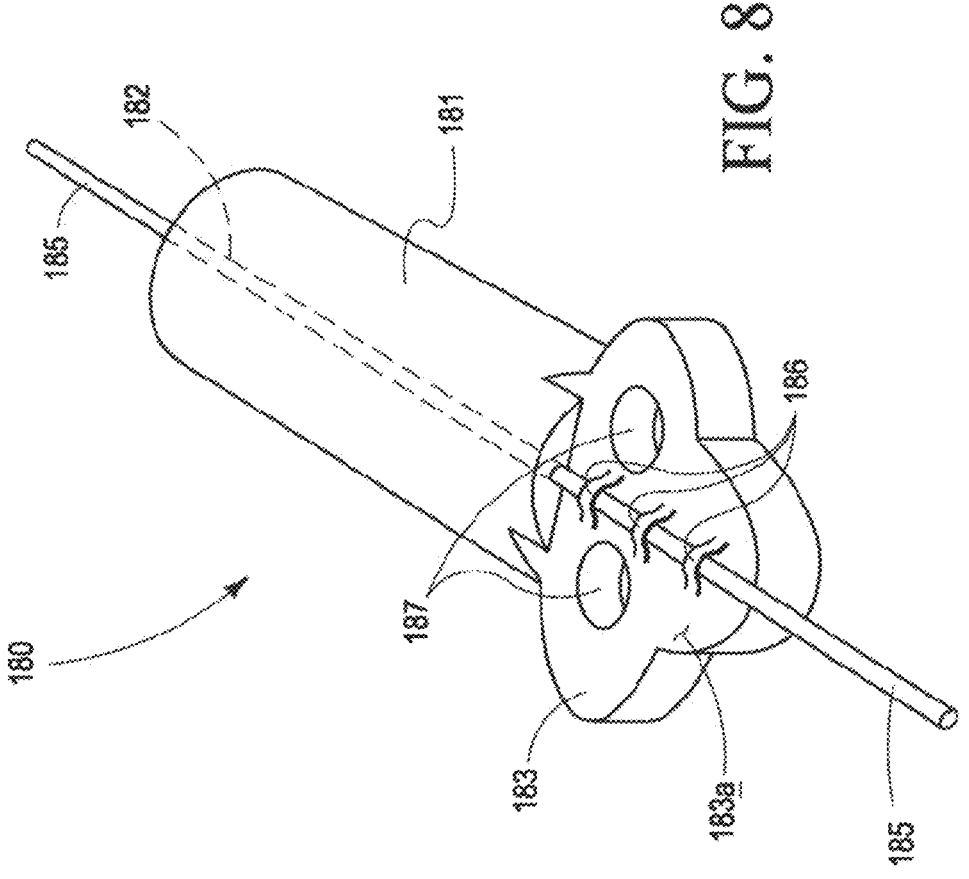
FIG. 8 is a perspective view of another example of another embodiment of an implant device contemplated by this invention.

FIG. 8 is a perspective view of another example of another embodiment of an implant device 180 contemplated by this invention. FIG. 8 illustrates implant device 180, intramedullary portion 181 of the implant device framework, as well as the extramedullary portion 183 of the implant device framework or body. The intramedullary portion 181 includes a wire or wire aperture 182 therethrough configured to receive and combine with wire 185 to provide alignment for the implant device via the wire 185.

Bone fastener apertures 187 through extramedullary portion 183 provide the aperture through which fasteners may be inserted transversely to then fasten the extramedullary portion 183 to a bone or piece of bone. FIG. 8 also illustrates that the wire aperture need not be fully closed, but must provide an appropriate aperture clearance or tolerance so that the wire 185 can combine with the wire aperture in the implant device to precisely align the implant device and assist in the alignment of the bones or pieces of bones that are being aligned or realigned as they are being fixed or stabilized by the implant device. FIG. 8 shows three guides 186 or bridges on the surface 183a of the extramedullary portion 183 and through which the wire 185 (which may also be referred to as a pin or K-wire) is inserted.

While FIG. 8 shows the intramedullary portion 181 without any transverse screw apertures, it should be noted that this embodiment may also be provided with transverse screw or other fastening apertures as shown in other figures, with this invention not being limited to any one such configuration.

Figure 9:
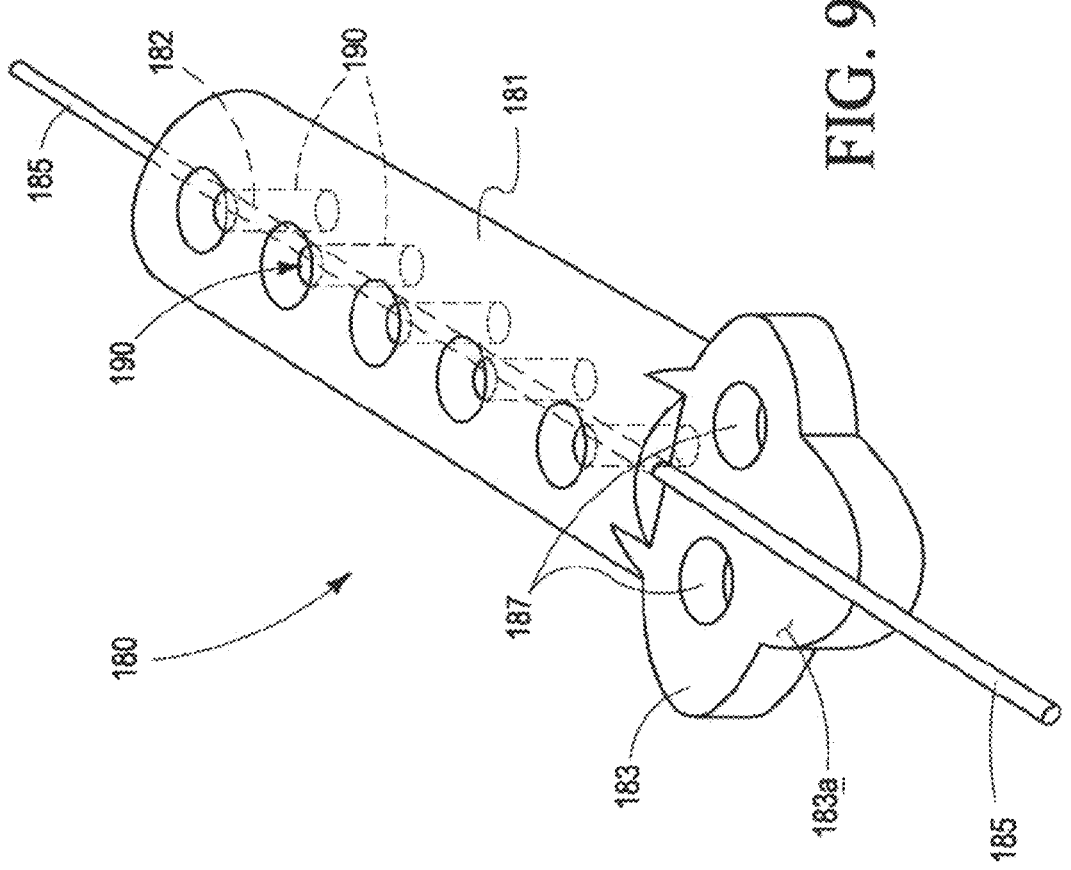
FIG. 9 is a perspective view of another example of an embodiment of an implant device contemplated by this invention wherein the k-wire aperture is only through the intramedullary portion of the implant device.

FIG. 9 is a perspective view of another example of an embodiment of an implant device 180 contemplated by this invention wherein the k-wire aperture 182 only extends through the intramedullary portion 181 of the implant device 180 and does not also extend through the extramedullary portion 183 as shown in other figures herein. The k-wire 185 in this example of an embodiment instead abuts or is adjacent to the surface 183a of the extramedullary portion 183.

FIG. 9 illustrates transverse apertures 190 (for fasteners or screws) through the intramedullary portion 181. The transverse apertures 190 may be normal or perpendicular to the axis of the intramedullary portion (or to the k-wire), or one or more of the transverse apertures may also be at an angle to facilitate for example the angles between the extramedullary portion and intramedullary portion illustrated in FIG. 11, FIG. 12 or FIG. 13, as examples. FIG. 9 also shows fastener apertures 187 in the extramedullary portion 183.

It should also be noted that there may be multiple transverse apertures in the intramedullary portion 181 of the implant device 180, with a first transverse aperture being at a dissimilar angle to a second transverse aperture, to achieve desired results according to the particular application of the invention.

Figures 10, 10A, 10B, 11:
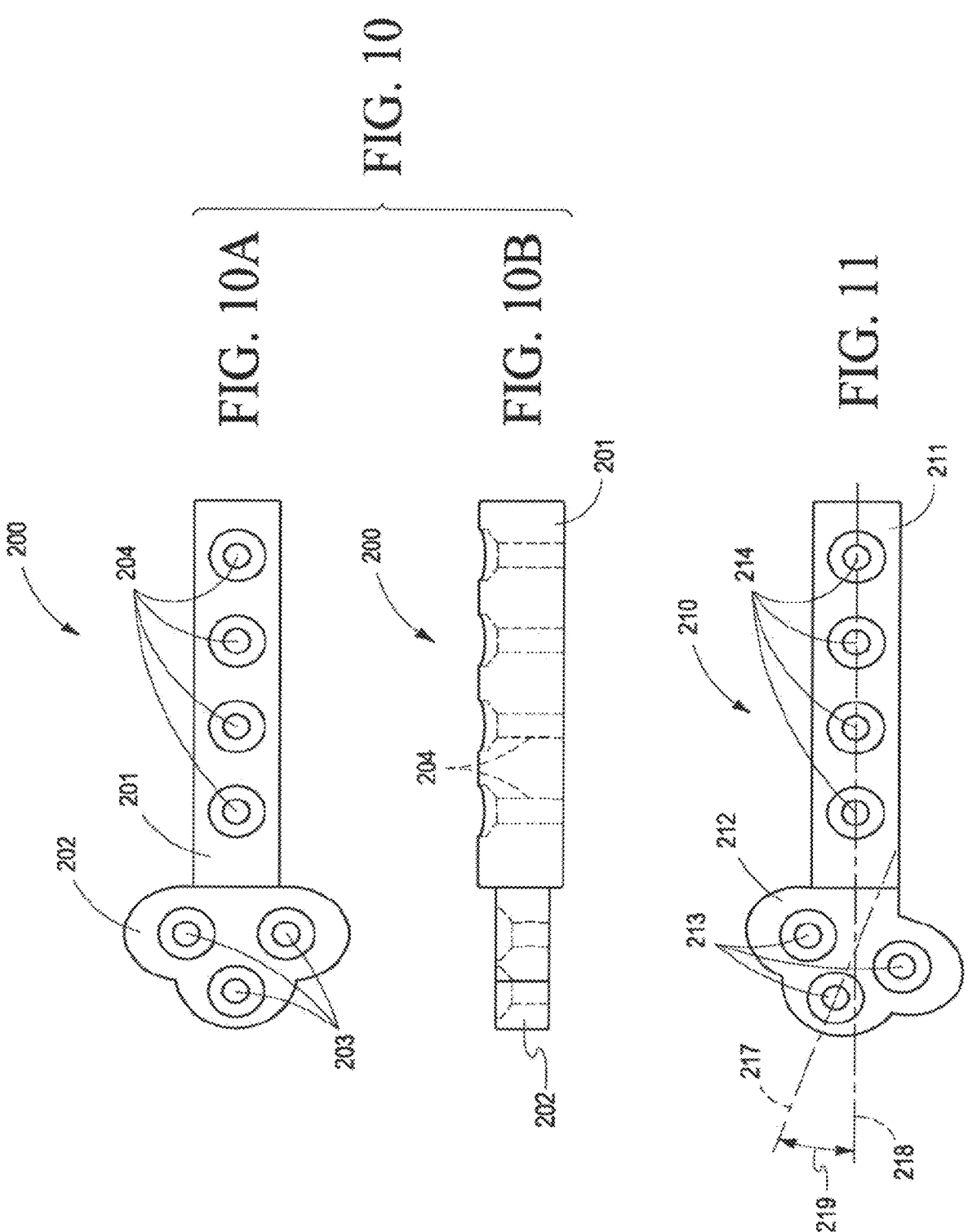
FIG. 10 constitutes FIGS. 10A and 10B, which are different views of another embodiment of an implant device contemplated by embodiments of this invention.
FIG. 10A is top view and FIG. 10B is an elevation view of an example of another embodiment of an implant device contemplated by this invention.
FIG. 11 is a top view of an example of an embodiment of this invention wherein the intramedullary portion of the implant device is at an angle relative to the extramedullary portion.

FIG. 10 constitutes FIGS. 10A and 10B, which are different views of another embodiment of an implant device 200 contemplated by embodiments of this invention as described below relative to the description of FIGS. 10A and 10B.

Figure 13:
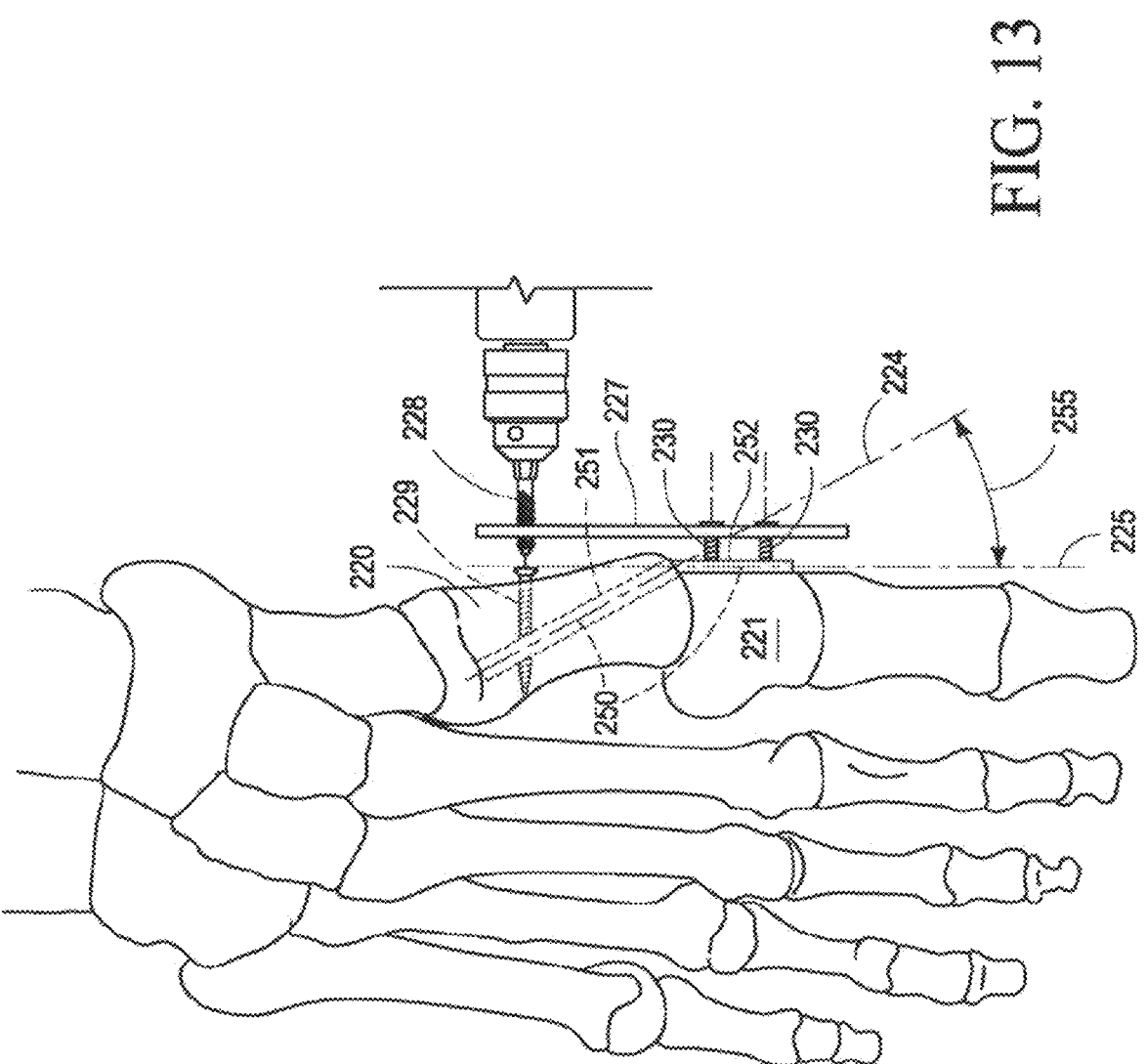

FIG. 10A is a top view and FIG. 10B is an elevation view of an example of another embodiment of an implant device 200 contemplated by this invention, illustrating extramedullary portion 202 with transverse apertures 203 (which may be used as fastener apertures as shown in FIG. 6, and/or as a means to attach a drill guide or template as shown in FIGS. 5 & 13, all within the contemplation of this invention), intramedullary portion 201 with a plurality of transverse fastener apertures 204.

FIG. 11 is a top view of an example of an embodiment of an implant device 210 contemplated by this invention, wherein the intramedullary portion 211 of the implant device 210 is at an angle 219 relative to the extramedullary portion 212. FIG. 11 shows extramedullary portion 212 with transverse apertures 213 (which may be used as fastener apertures as shown in FIG. 6, and/or as a means to attach a drill guide or template as shown in FIGS. 5 & 13, all within the contemplation of this invention), intramedullary portion 211 with a plurality of transverse fastener apertures 214. The angle 219 in this embodiment is the angle between the centerline or axis 218 of the intramedullary portion 211 and the angle of the centerline of the fastener apertures 213 and/or of the extramedullary portion 212. It may be desirable for some patient conditions to impart an angle such as angle 219 between the different parts of the metatarsal bone.

Figure 12:
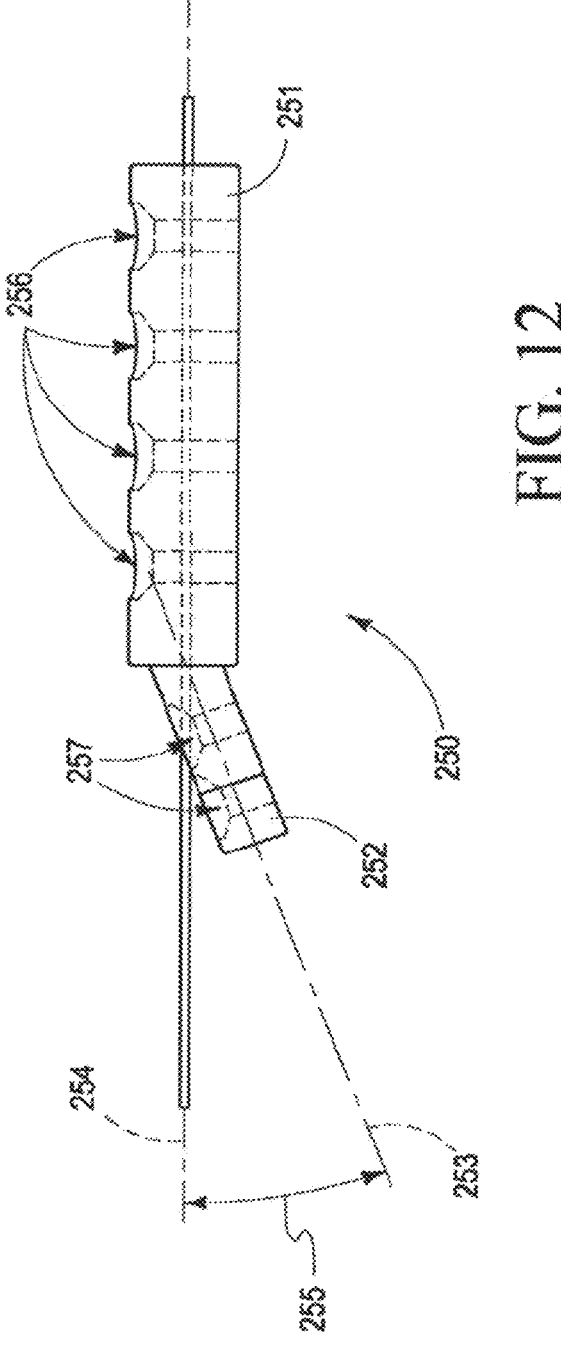
FIG. 12 is an elevation view of an example of another embodiment of an implant device contemplated by this invention, wherein the intramedullary portion of the implant device is at an angle relative to the extramedullary portion of the implant, only in a different plane than that illustrated in FIG. 11.

FIG. 12 is an elevation view of an example of another embodiment of an implant device 250 contemplated by this invention, wherein the intramedullary portion 251 of the implant device 250 is at an angle 255 relative to the extramedullary portion 252 of the implant 250, but the angle is in a different plane than the angle in FIG. 11. FIG. 12 illustrates extramedullary portion 252 with transverse apertures 257 (which may be used as fastener apertures as shown in FIG. 6, and/or as a means to attach a drill guide or template as shown in FIGS. 5 & 13, all within the contemplation of this invention), intramedullary portion 251 with a plurality of transverse fastener apertures 256. The angle 255 in this embodiment is the angle between the centerline or axis 254 of the intramedullary portion 251 and the downward angle of the centerline of the extramedullary portion 252. It may be desirable for some patient conditions to impart an angle, such as angle 255, between the different parts of the metatarsal bone (as shown in FIG. 13).

It should be noted that the particular angle desired may vary from patient to patient, and may be determined in advance of surgery, or altered during the course of the surgery to adapt to the angle of the bones and cuts made in or on the bones, all within the contemplation of embodiments of this invention. Known bending methods and devices may be utilized to bend or alter the angle such as shown as angle 255 in FIGS. 12 & 13.

FIG. 13 is top skeletal schematic representation of bones in a typical human foot, illustrating an example of an embodiment of an implant device 250 (one example of which is shown in FIG. 12) contemplated by embodiments of this invention, wherein a drill guide 227 or template is used to align the drilling of a hole to facilitate the insertion of a fastener 229 (a screw in this example) through the bone 220 and through the transverse fastener aperture in the intramedullary portion 251 of the implant device 250. This process may be practiced in a similar manner to that process described above regarding FIG. 5.

The drill guide 227 is a template to provide sufficient guidance and alignment of the drill 228 through the bone and through a fastener aperture in the screw (examples of which are shown in FIG. 12) such that the hole drilled through the bone aligns with the screw aperture in the intramedullary portion of the implant device. FIG. 13 shows the angle 255 between a centerline 224 of the intramedullary portion 251 and a centerline 225 of the extramedullary portion 252. Drill alignment guide 227 is shown fixed to the extramedullary portion 252 via screws 230, to secure the drill guide 227 in place to facilitate the drilling of a hole through the bone that aligns with the transverse fastener aperture (shown in other figures) in the intramedullary portion 251 of the implant 250. In this case the screws will be inserted at an angle to the intramedullary portion. The drill configuration is shown for illustration purposes only as there would not be drilling after the screw 229 is inserted, and is further not to scale—but instead the pilot hole for the screw would be drilled to the sizing, depth and configuration desired.

It will be noted and appreciated by those of ordinary skill in the art that the K-wire aperture or wire aperture may, but need not, be a fully enclosed uninterrupted aperture through both the intramedullary portion and the extramedullary portion of the implant device framework. The wire aperture or cannulated feature may also be dis-continuous in that there may be interruptions or breaks in the aperture so along as the wire is consistently located and surrounded to allow the wire to be used as an alignment device or mechanism for the implant device. The wire aperture therefore may be a less than complete slit through which the wire may be inserted and retained for the alignment purposes stated herein.

It should be noted that while the drawings and general description are directed toward the metatarsal bone in a foot, the implant device and method described herein may equally be used in other applications, with no one particular application being required to practice this invention.

Figure 14:
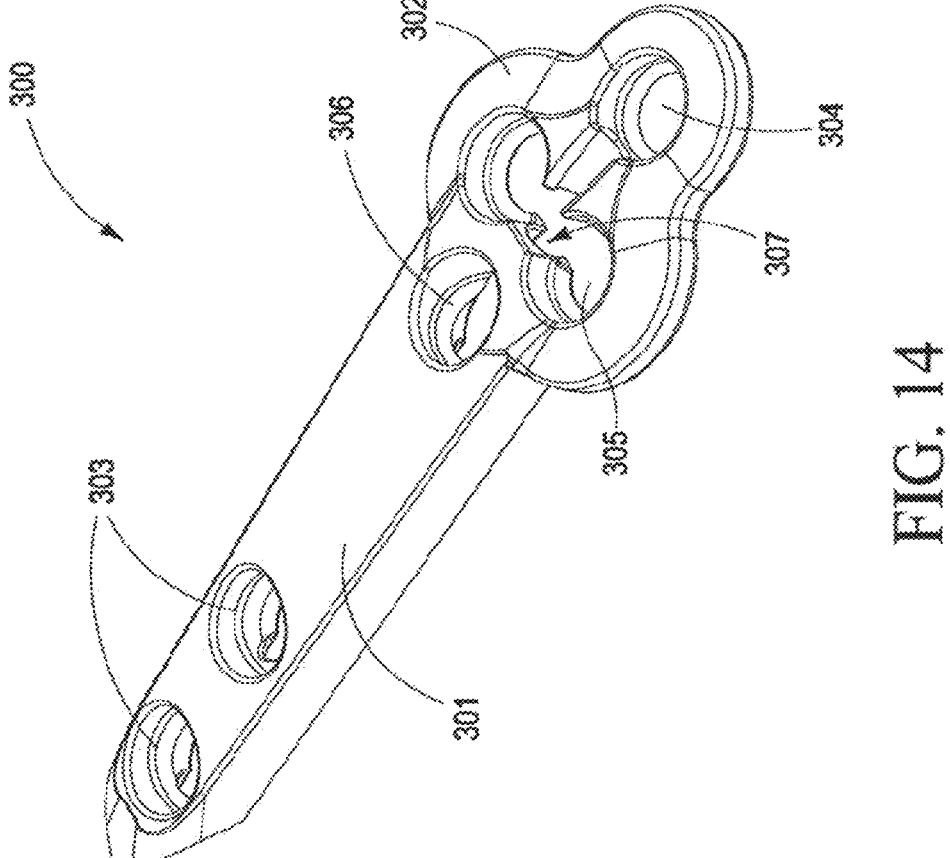
FIG. 14 is a perspective view of another example of an implant device contemplated by some embodiments of this invention.

FIG. 14 is a perspective view of another example of an implant device 300 contemplated by some embodiments of this invention, transverse fastener apertures 303 & 306, intramedullary portion 301, extramedullary portion 302, wire apertures 307, extramedullary fastener apertures 304 & 305.

Figures 15, 16:
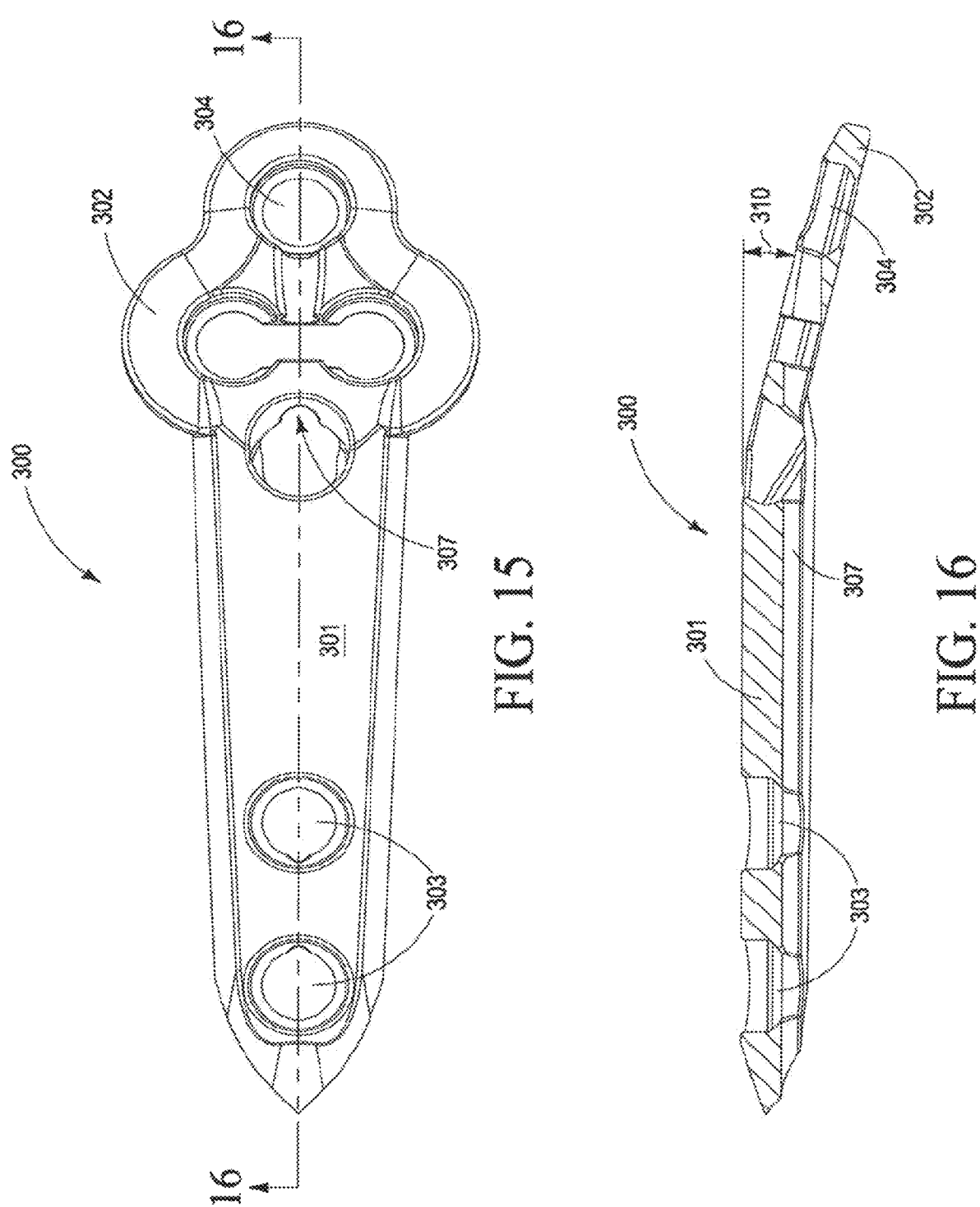
FIG. 15 is a top view of the example of the implant device illustrated in FIG. 14.
FIG. 16 is a front view of the example of the implant device illustrated in FIG. 14.

FIG. 15 is a top view of the example of the implant device 300 illustrated in FIG. 14, illustrating intramedullary portion 301 and extramedullary portion 302. Like numbered items referenced in prior figures may not be repeated herein.

FIG. 16 is a front view of the example of the implant device 300 illustrated in FIG. 14, showing transverse fastener apertures 303 in the intramedullary portion 301 and transverse fastener aperture 304 in the extramedullary portion, the extramedullary portion 302 being at angle 310 relative to the axis of intramedullary portion 301. Like numbered items referenced in prior figures may not be repeated herein.

Figure 17:
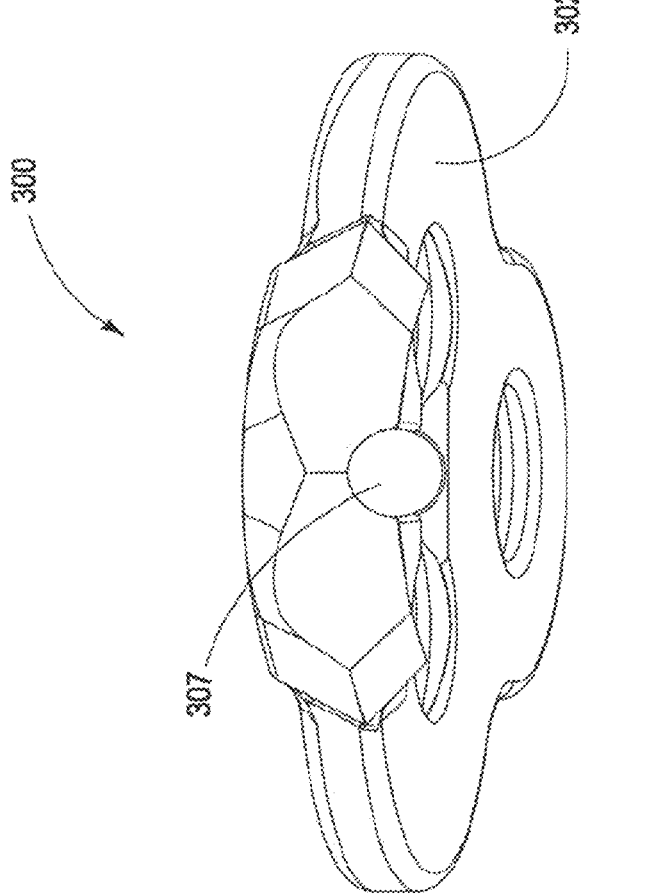
FIG. 17 is an end view of the example of the implant device illustrated in FIG. 14.

FIG. 17 is an end view of the example of the implant device 300 illustrated in FIG. 14, showing wire aperture 307 and extramedullary portion 302. A guide wire or K-wire may be utilized to position and or angle where the extramedullary portion is inserted into the metatarsal bone, and then the intramedullary portion may be inserted into the bone over the guide wire, and thereby positioned as guided by wire aperture 307. Like numbered items referenced in prior figures may not be repeated herein.

Figures 18, 19:
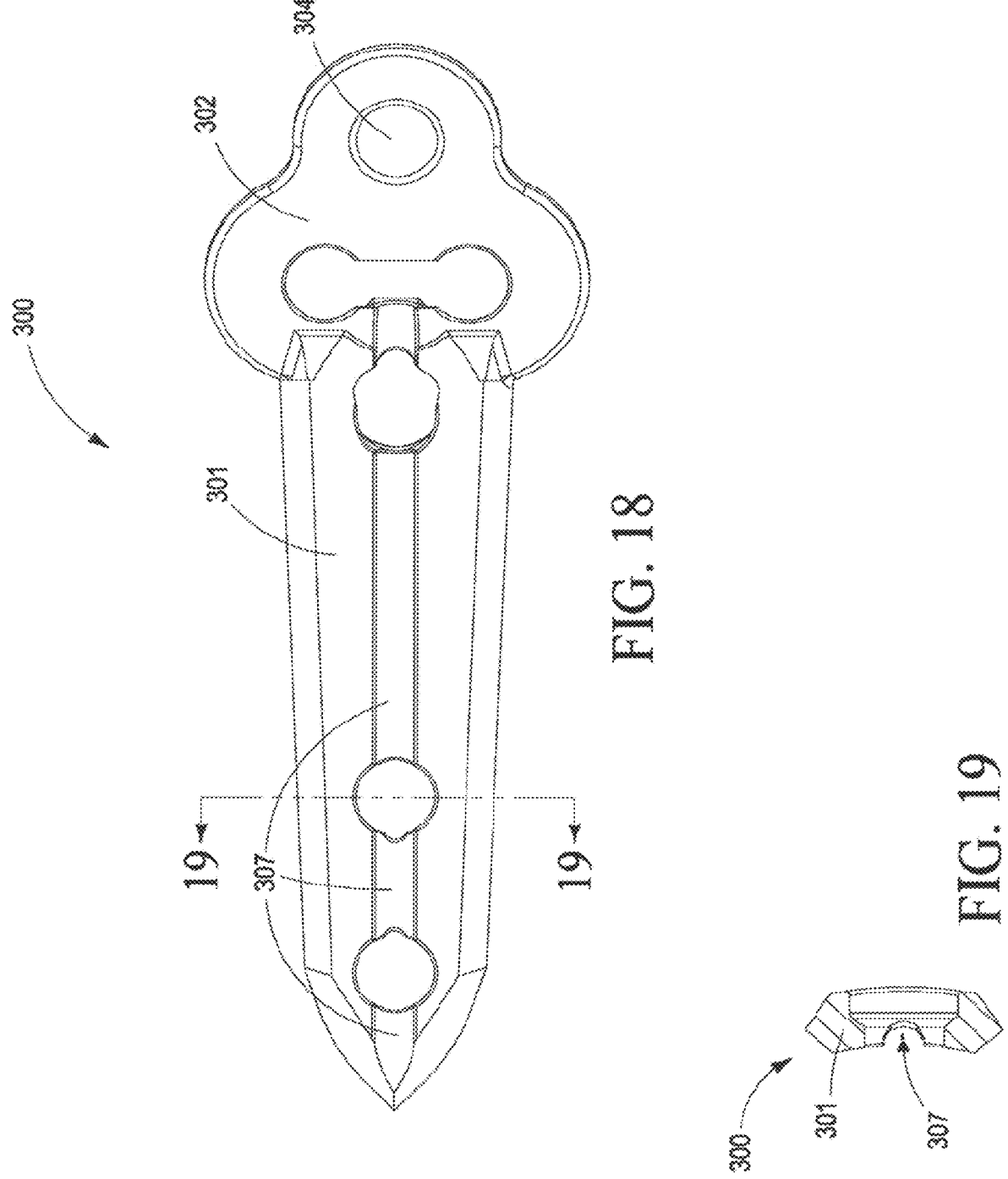
FIG. 18 is a bottom view of the example of the implant device illustrated in FIG. 14.
FIG. 19 is section view 19-19 from FIG. 18.

FIG. 18 is a bottom view of the example of the implant device 300 shown in FIG. 14, illustrating intramedullary portion 301, wire guide 307, extramedullary portion 302 and transverse fastener aperture 304 in the extramedullary portion 302. Like numbered items referenced in prior figures may not be repeated herein.

FIG. 19 is section view 19-19 from FIG. 18, illustrating the implant device 300 with wire guide aperture 307 and intramedullary portion 301.

Figure 20:
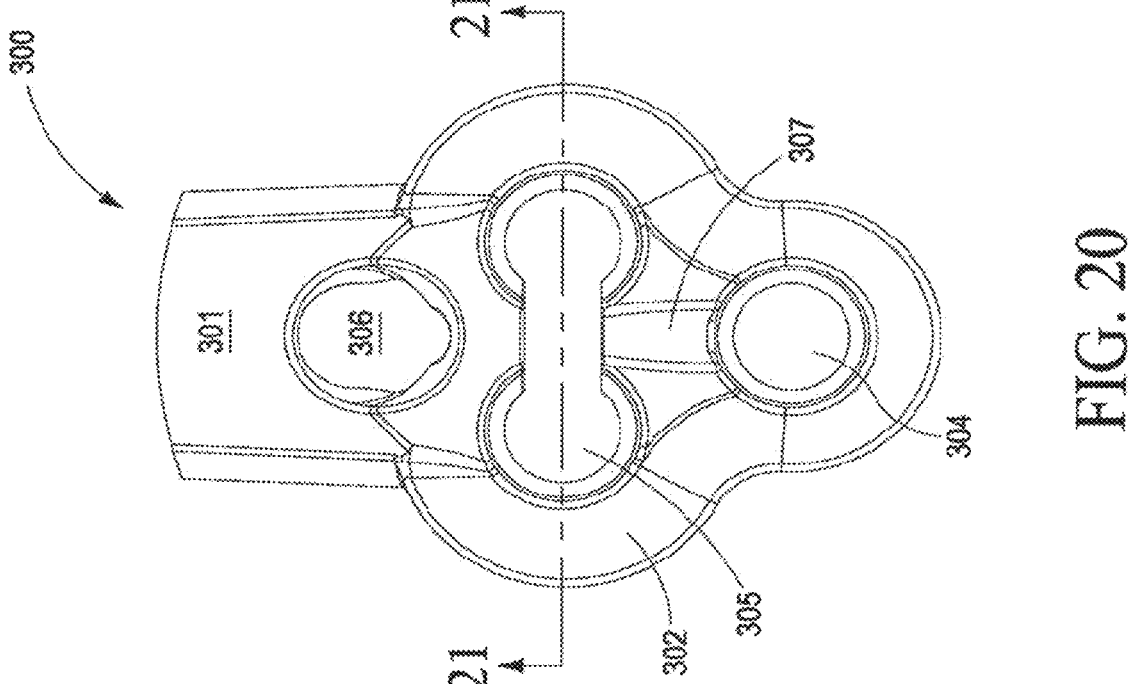
FIG. 20 is a top partial view of the implant device illustrated in FIG. 14.

FIG. 20 is a top partial view of the implant device 300 illustrated in FIG. 14, showing intramedullary portion 301, wire guide aperture 307, transverse fastener aperture 306, extramedullary portion 302, transverse fastener apertures 304 and 305 with extramedullary portion 302.

Figure 21:
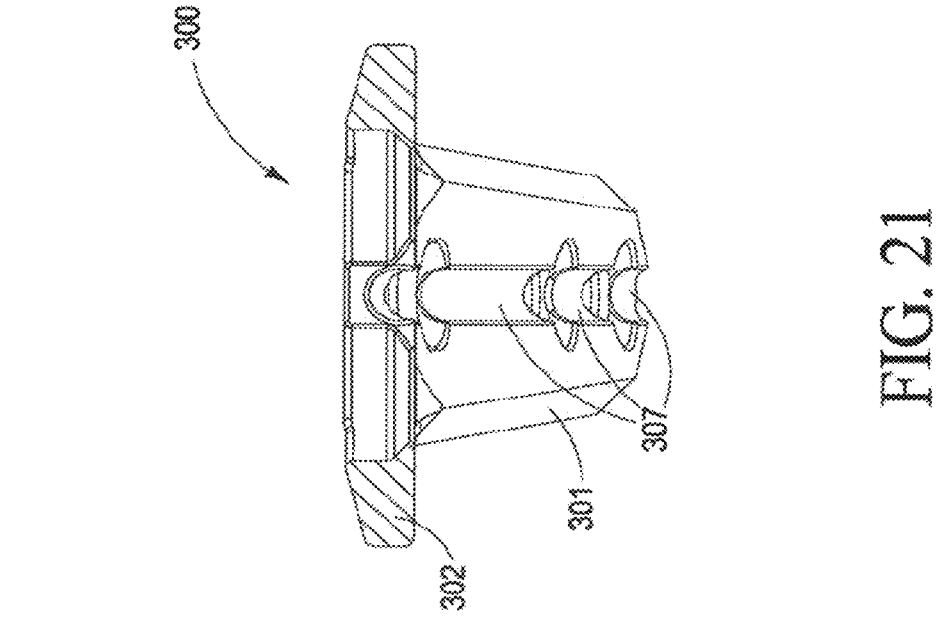
FIG. 21 is a section view 21-21 from FIG. 20.

FIG. 21 is a section view 21-21 from FIG. 20, illustrates implant device 300, extramedullary portion 302, intramedullary portion 301 and wire guide aperture 307.

Figure 22:
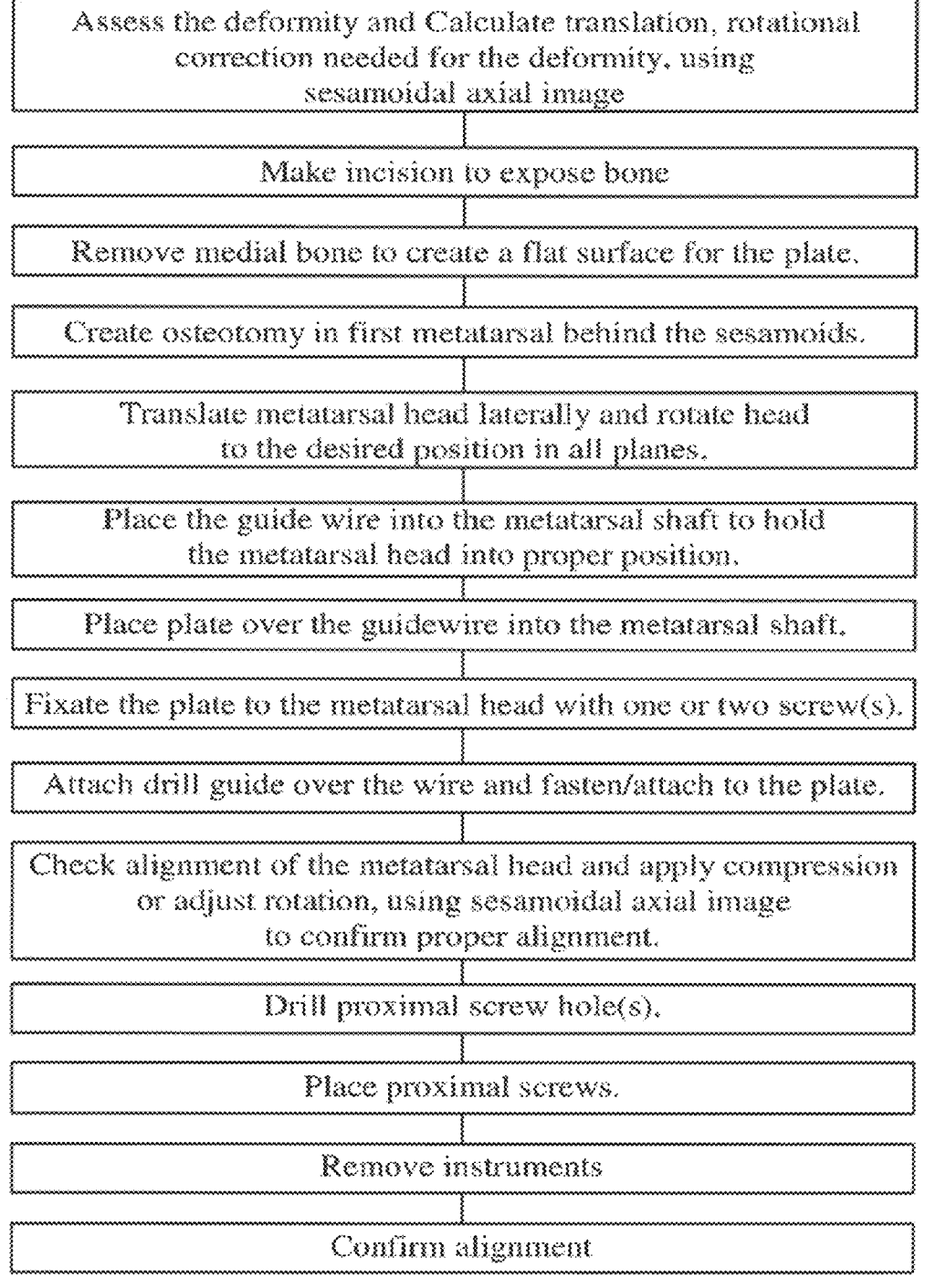
FIG. 22 is a box diagram flowchart of an example of a method contemplated by embodiments of this invention.

FIG. 22 is a box diagram flowchart of an example of an embodiment of a method contemplated by this invention. In the first step illustrated in FIG. 22, the deformity is assessed and the translation calculated, determining if and how much rotational correction may be needed for the deformity in question. Though this invention is not limited to it, a current tool in determining the translation and rotational correction is a sesamoidal axial image.

At that time an incision may be made to expose the bone which is to be operated on, and the medial bone is altered or a portion removed to create a surface (which may but need not be a flat surface) to prepare it for the fixation or attachment of the implant device. In embodiments of this invention, this would involve making a flat surface for the attachment of the plate portion of the implant device (the extramedullary portion).

A further step would be to then create an osteotomy in the first metatarsal behind the sesamoids, followed by the translation of the metatarsal head laterally and the rotation of the metatarsal head to the desired position in all planes.

Once the metatarsal head is in the desired position, the guide wire may be placed into the metatarsal shaft to hold the metatarsal head into proper position. Once the guide wire is placed and located as desired, the plate portion (extramedullary portion) may be placed over the guidewire into the metatarsal shaft.

At that stage the plate portion may be fixated to the metatarsal head with any one of a number of different fasteners, such as one or two screw(s).

The drill guide is preferably then attached over the guide wire and fastened/attached to the plate portion of the implant device.

Once the drill guide and other components are in place, an alignment check of the metatarsal head can be made and adjustments may be made for example by applying compression to move it to a more desired position, and/or a rotational force may be applied to rotationally adjust the position of the metatarsal head. During this process, known imaging equipment may be utilized to provide and use a sesamoidal axial image to confirm proper alignment.

An alignment tool may be utilized in embodiments of this invention to facilitate the compression and rotational adjustments. As described more fully below, the tool may be unitary or separate from the drill guide (preferably integral therewith), and would be attachable and detachable to the implant device already inserted in the metatarsal shaft to act as a targeting adjusting tool.

Once the final micro-adjustments have been made, the proximal screw holes may be drilled as desired and the proximal screws may be placed or inserted.

The instruments may then be removed, final alignment positioning confirmed and the incisions may then be closed.

Figure 23:
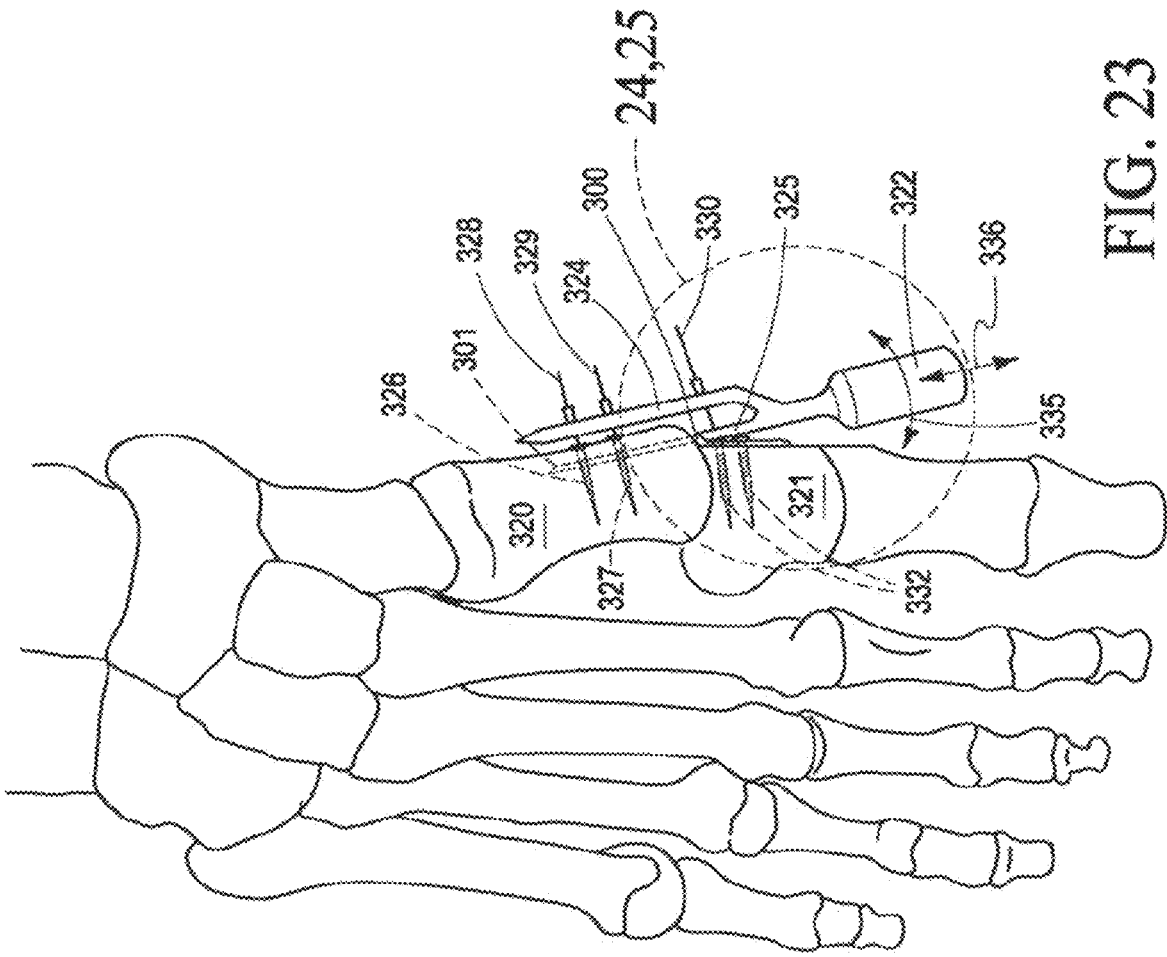
FIG. 23 is a top view of an example of the implanting of the implant device illustrated in FIG. 14, showing among other things, an alignment tool.

FIG. 23 is a top view of an example of the implanting of the implant device 300 illustrated in FIG. 14, showing among other things, an alignment tool comprised of handle 322, transverse or proximal screw guide portion 324 and implant device attachment portion 325. FIG. 23 shows the extramedullary portion of the implant device 300 fastened metatarsal head 321 via cannulated screws 332 with an exemplary guide wires 330 (for the extramedullary portion) and exemplary guide wires 328 & 329 for the intramedullary portion. FIG. 23 further shows how the proximal screw guide portion 324 is utilized with alignment guide wires 328 and 329, with cannulated screws 326 and 327 being placed or fastened into bone 320 once the proper positioning alignment has been achieved, as set forth and described elsewhere herein. Arrow 335 illustrates how the alignment tool may be rotated to place the implant device in the desired rotationally aligned position and arrow 336 illustrates how the alignment tool may be moved laterally or on a plane to place the implant device in the desired position.

Figure 24:
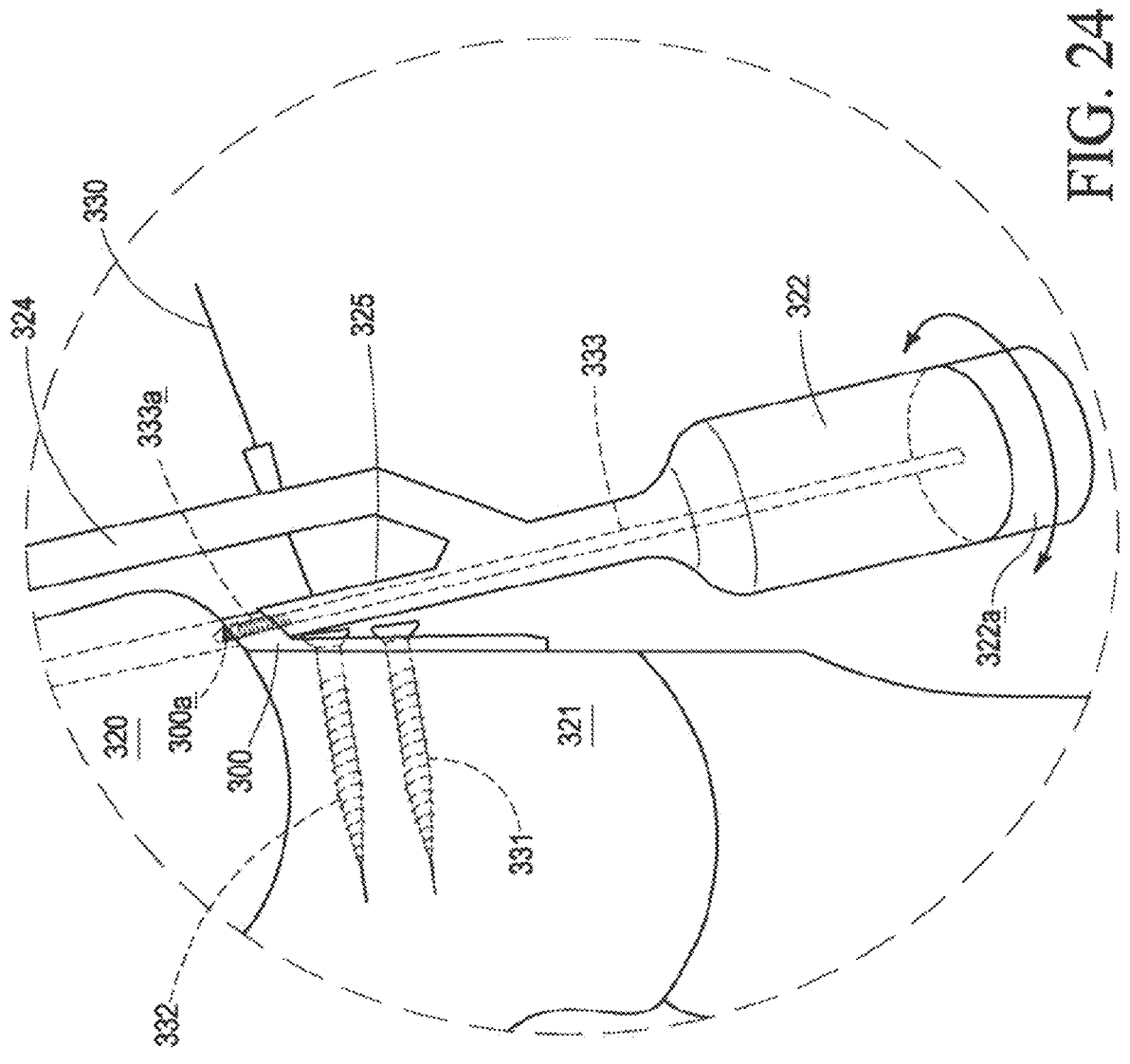
FIG. 24 is the referenced detail view from FIG. 23.

FIG. 24 is detail view from FIG. 23, and illustrates an example of one embodiment that may be utilized to practice this invention. FIG. 24 shows handle 322 with a shaft 333 extending there through, the shaft 333 being externally threaded at 333a and operably attached to a rotatable end 322a of handle 322. The surgeon can then rotate the rotatable end 322a to thereby cause the external threads 333a to engage in internally threaded aperture 300a in the implant device.

The configuration illustrated in FIG. 24 allows the surgeon to fix the handle to the implant device before the proximal screws are fixed and thereby manipulate the location and rotational angle of the implant device to the most desired location, as described more fully above. Although a threaded attachment and detachment mechanism or means is illustrated, it will be appreciated by those of ordinary skill in the art that any one of a number of attachable and detachable fastening mechanisms and means may be utilized, all within the contemplation of this invention, with no one being required to practice this invention. Aspects or embodiments of an implant alignment tool as shown in FIG. 24 may include an externally threaded shaft 333 configured to fasten to and unfasten from to an internally threaded aperture 300a in the implant device. One way to practice this embodiment of the invention is to further rotatably mount the shaft 333 relative to the handle 322 of the implant alignment tool such that it can be rotated (as shown by the arrow) to fasten it to the implant device and rotated an opposite direction to unfasten it from the implant device.

Figure 25:
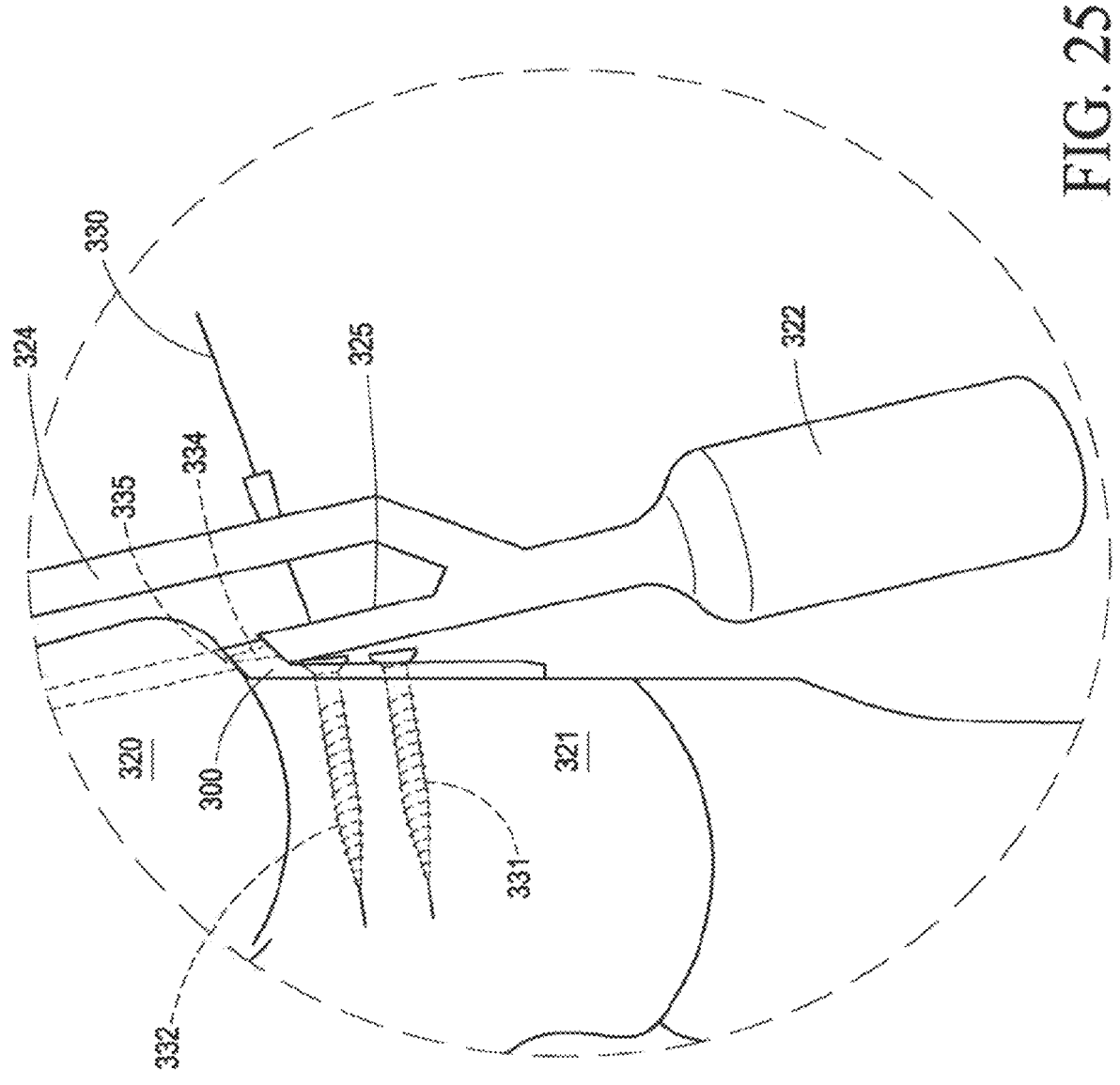
FIG. 25 is an alternative detail view from FIG. 23, which is another aspect or embodiment of that shown.

FIG. 25 is an alternative detail view from FIG. 23, which is an example of another way to practice an embodiment of this invention wherein the alignment tool is attachable and detachable to the implant device 300. In FIG. 25, the alignment tool aperture 335 in the implant device 300 receives attachment protrusion 334 which is part of the alignment tool, and the aperture 335 in the implant device is sized and/or shaped (such as by a truncated configuration— but not limited thereto) so that a solid fixed connection may occur to manipulate the implant device 300, before detaching it. In one aspect or example of this embodiment, a shaft 334 is sized relative to a shaft aperture 335 in the implant device such that the implant alignment tool may be fastened to and unfastened from the implant device via a friction fit.

FIG. 26 illustrates a skeletal foot image with the first metatarsal head 400 as part thereof. In embodiments of this invention, the patient would be positioned in a supine position and a longitudinal incision of approximately 1.5 cm to 2.0 cm would be made overlying the first metatarsal head, with the incision represented by line 401. The neurovascular bundle is isolated and protected and the first metatarsal-phalangeal joint capsule is incised according to the surgeon's preference to best expose the first metatarsal medial eminence.

Figure 27:
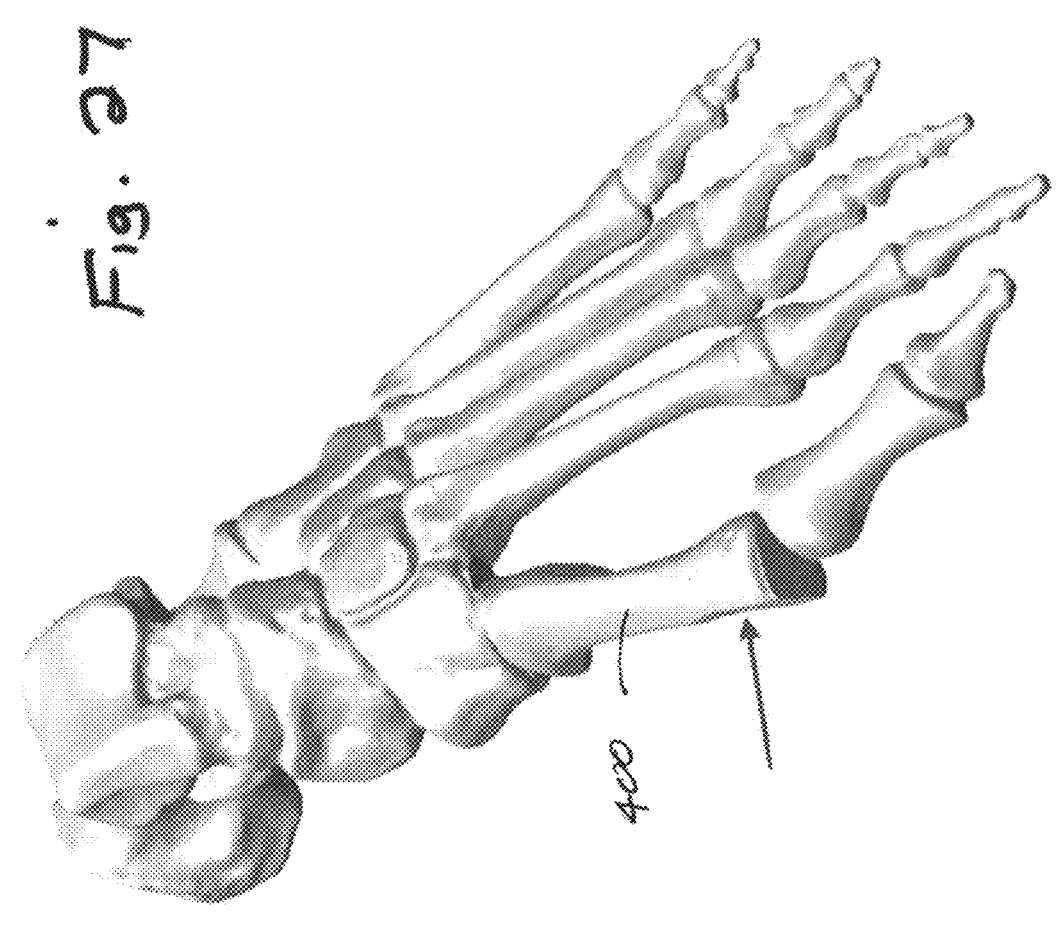

FIG. 27 illustrates a skeletal foot image with the first metatarsal head 400 as part thereof. In this step, the medial eminence resection and optional lateral release are performed. The medial eminence resection is an important procedural step as it will impact lateral translation and positioning or rotation of the metatarsal head in the transverse and frontal planes. A smaller resection of the medial eminence will result in a greater lateral translation of the metatarsal head in the corrected state, thereby reducing the enter metatarsal angle. In the step illustrated in FIG. 27, in the surgeon's discretion, a lateral soft-tissue release can be performed either percutaneously, through a second incision overlying the first metatarsal space, or through a medial trans articular approach. Transect horizontally the lateral metatarsal-sesamoid suspense a real ligament and release the lateral part of the cojoined abductor tendon. The lateral collateral ligament is respected to prevent the iatrogenic hallux varus.

FIG. 28 is more of a side elevation view of a skeletal foot image and this step illustrates template positioning. In the ideal situation, the osteotomy location is at the level of the surgical neck, at the metaphyseal-diaphyseal junction. Specifically, this is just proximal to the sesamoid's and the vascular bundle to the inferior metatarsal head. The face of the medial bunion template 402 is seated flush with the surface of the medial eminence resection. The proximal face of the medial bunion template is rotated such that it is oriented perpendicularly to the longitudinal axis of the metatarsal shaft. Note that the proximal face of the template represents the location of the cutting guide surface for the osteotomy. The template is then positioned superior/inferior to best fit in the area of the resected medial eminence. Perpendicular alignment lines 403 are also shown in FIG. 28.

In the next step shown in FIG. 29, the template fixation and Burr area demarcation are accomplished, as shown. The medial bunion template 402 is stabilized in the proper position by inserting a first 404 and a second 405 1.6 mm k-wire into each hole of the medial bunion template 402. The K-wire holes may be used for screw fixation in subsequent steps to fixate the plate to the metatarsal head. However, it will be noted by those of ordinary skill in the art that if other screw hole positions are later desired, those positions can be chosen despite this step in the procedure.

Figure 30:
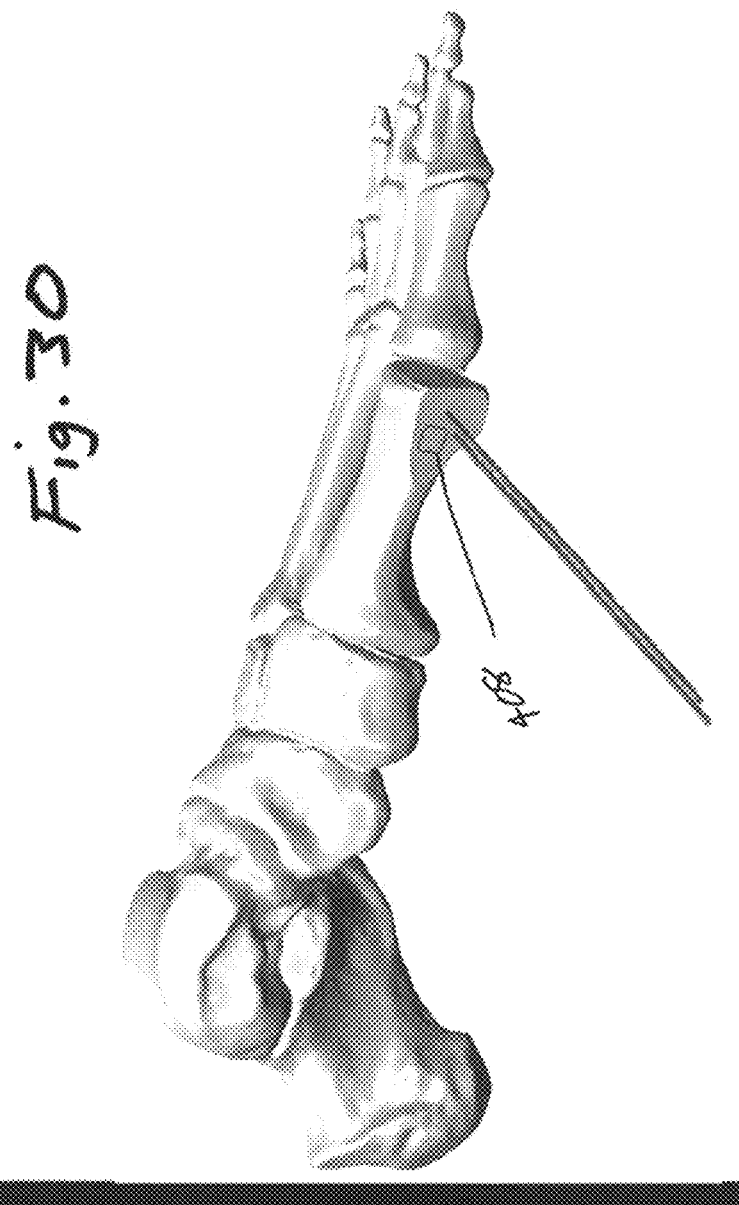

FIG. 30 illustrates a side view of a skeletal foot image and this step involves utilizing the template in place to use a surgical marker to outline or fill the square area 408 in the template, as shown. This area indicates where the metatarsal head needs to be notched to ensure flush placement of the plate to the metatarsal head. The notching of the square area 408 is illustrated in FIG. 31.

Figure 31:
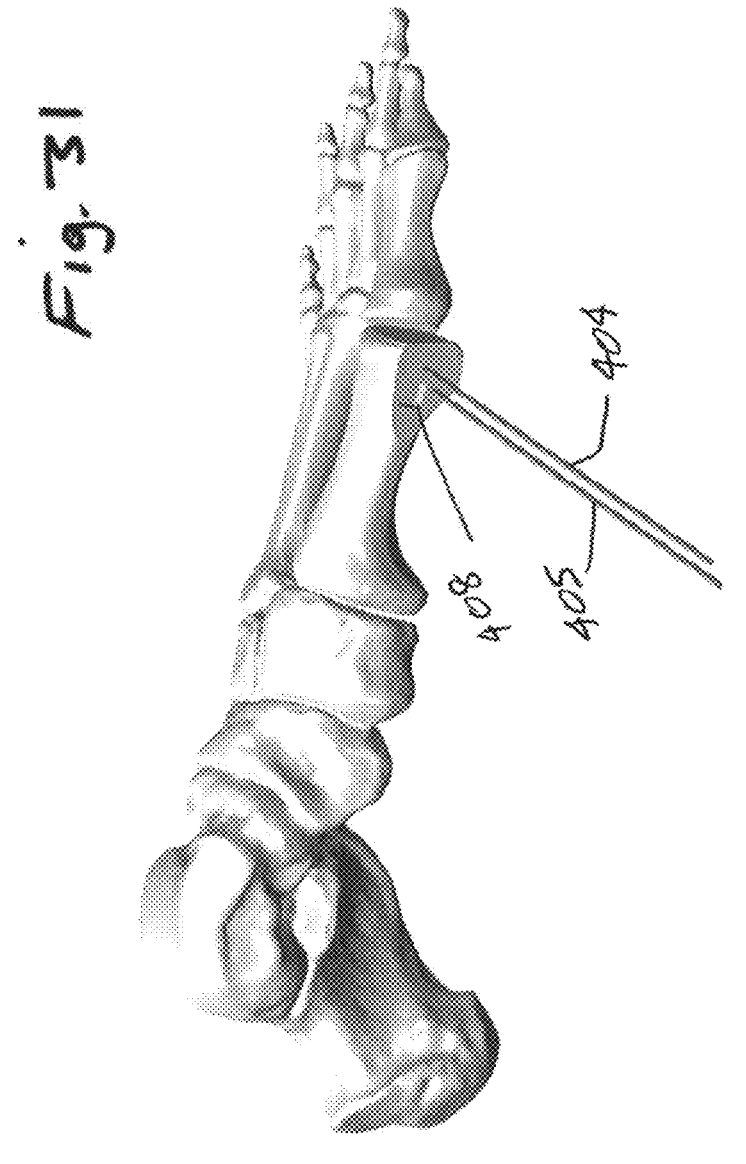

FIG. 31 illustrates that the use of a power Burr or rongeur may be utilized to remove approximately 5 mm×5 mm of bone in the area of the mark, i.e. the square area 408.

FIG. 32 is a top view of the skeletal foot image, illustrating K-wires 404 and 405 in the first metatarsal. In this step, the placement of the osteotomy guide is accomplished. The surgeon will use the osteotomy guide to assess if enough bone has been removed during the burring step. There is a prominence on the guide that mimics a similar feature that is on the plate implant. In this step, the surgeon will place or slide the osteotomy guide 410 over the K-wires 404 and 405 that were previously inserted, and then seat the osteotomy guide 410 over the K-wires 404 and 405 and up against the face of the resected medial eminence. If the osteotomy guide 410 can be seated flush with the resection, then the amount of bone removal during the burring step is adequate. If, however, the osteotomy guide 410 cannot be seated flush with the resection, then additional bone removal may be necessary. In this situation the surgeon will repeat the bone removal process from the prior steps to remove interferences until the osteotomy guide can be seated flush on the resection plane of the medial eminence.

Figure 33:
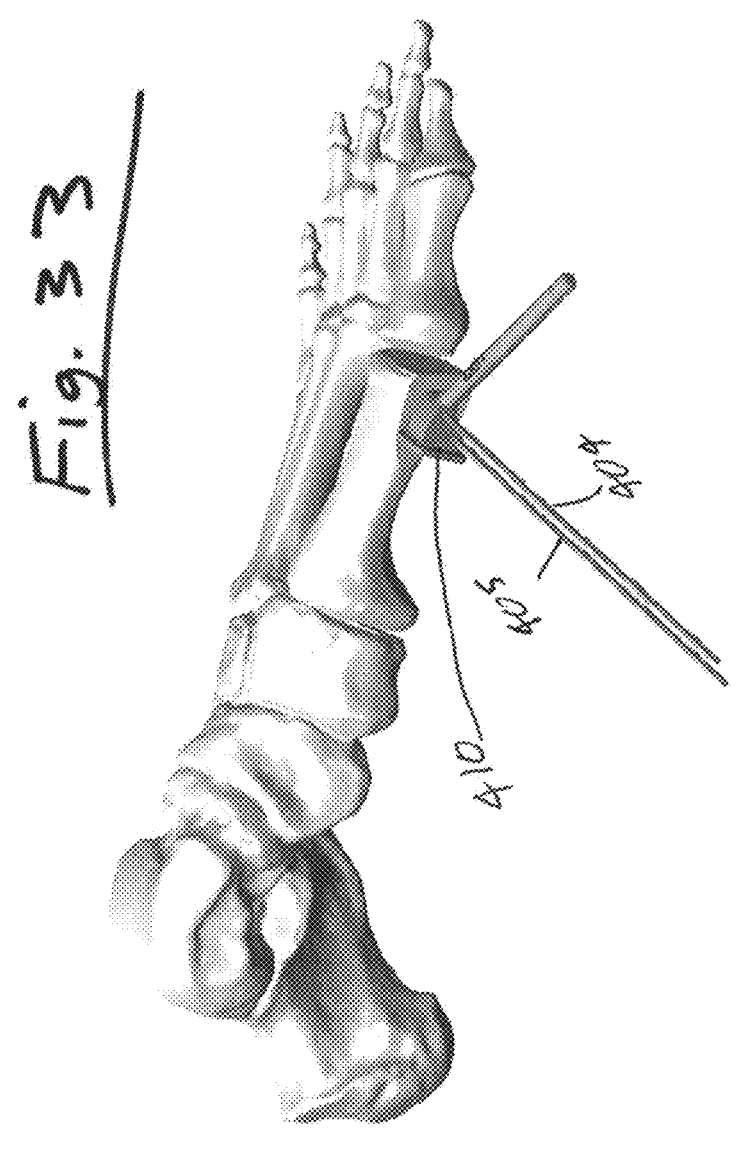

FIG. 33 is a side view of the skeletal foot image, illustrating K-wires 404 and 405 and the osteotomy guide 410 flush against the resection plane. When sufficient burring has been achieved and the osteotomy guide is seated flush with the resection plane of the medial eminence, it will appear as shown in FIG. 33. The large proximal face of the osteotomy guide 410 represents the osteotomy plane. The surgeon at this stage should verify via fluoroscopy that the level of the osteotomy plane is appropriate.

Figure 34:
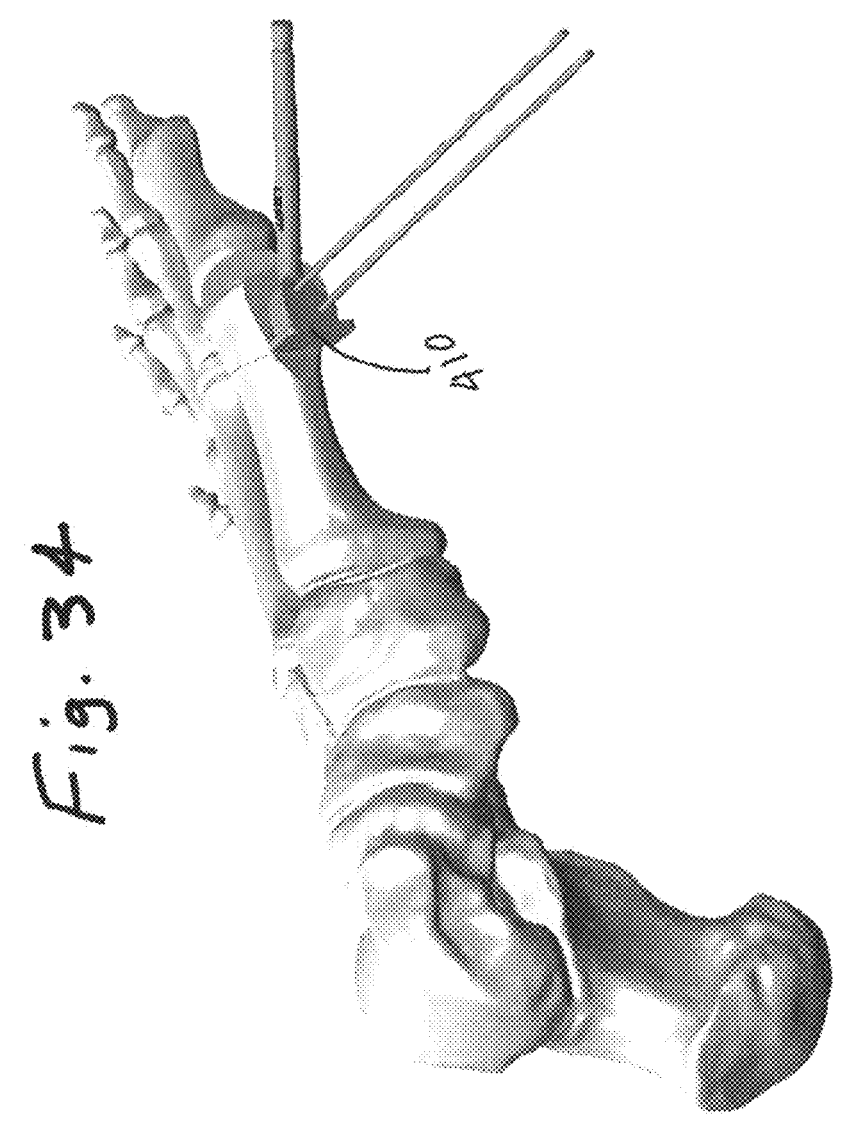

At the step represented by FIG. 34, the surgeon should perform the osteotomy with a sagittal blade using the proximal face as a guide. It should be ensured that proper retraction is used to protect the extensor tendons and soft tissue structures during the osteotomy. The obliquity of the osteotomy in the horizontal plane can have a lengthening or shortening effect. The osteotomy should be positioned to provide the correction necessary for the patient in the given situation. It will be appreciated by those of ordinary skill in the art that if the osteotomy is angled proximally, the result will be a shortened metatarsal.

Figure 35:
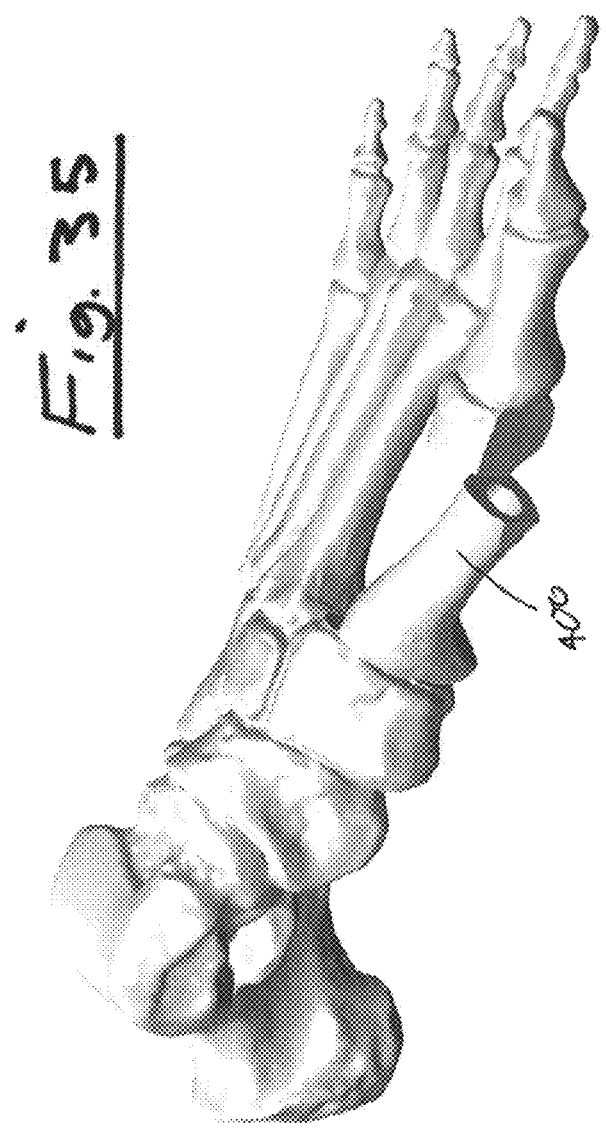

In the step represented by FIG. 35, preparation is made for broaching the first metatarsal canal. A wire driver will be used to remove the 1.6 mm K-wires from the metatarsal head and this will give clearance for the brooch to penetrate the canal of the first metatarsal 400.

Figure 36:
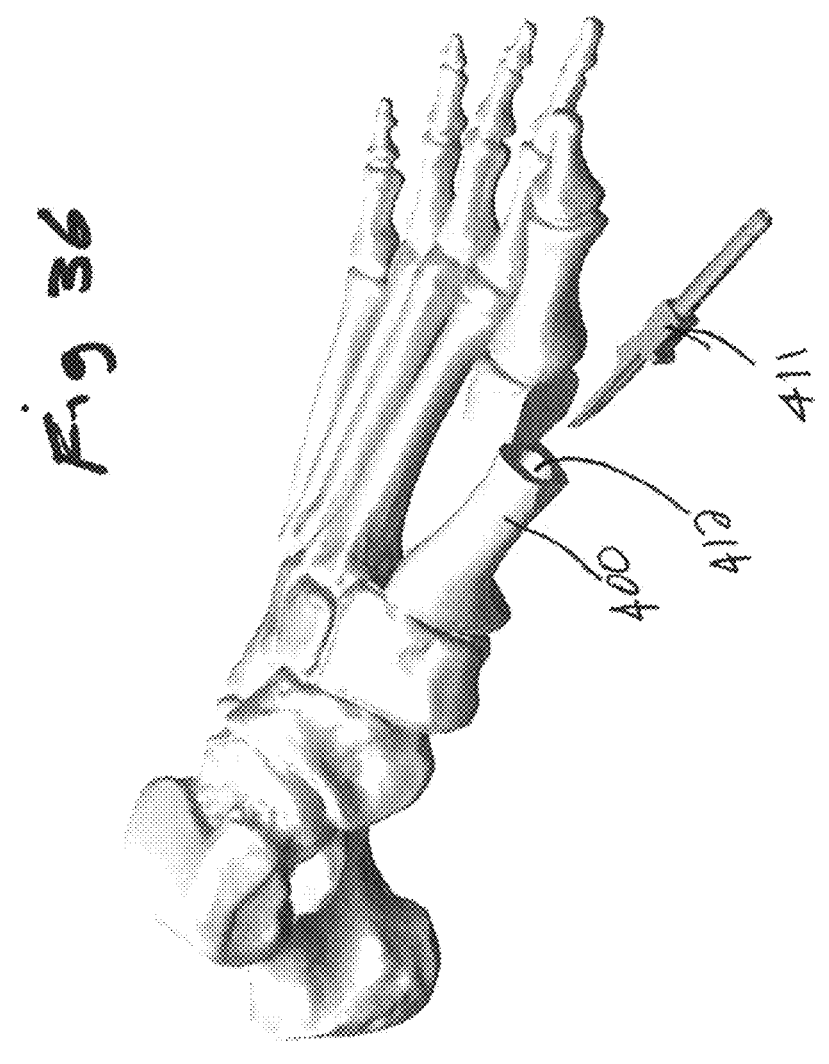

FIG. 36 illustrates a skeletal foot image and this step is wherein the broaching of the first metatarsal canal is accomplished. Using the broach to displace the metatarsal head laterally and insert the brooch into the metatarsal canal 412. The proper orientation of the brooch can be confirmed when the letter "M" marked on the brooch faces medially (cannot be seen from the view depicted in FIG. 36).

Figure 37:
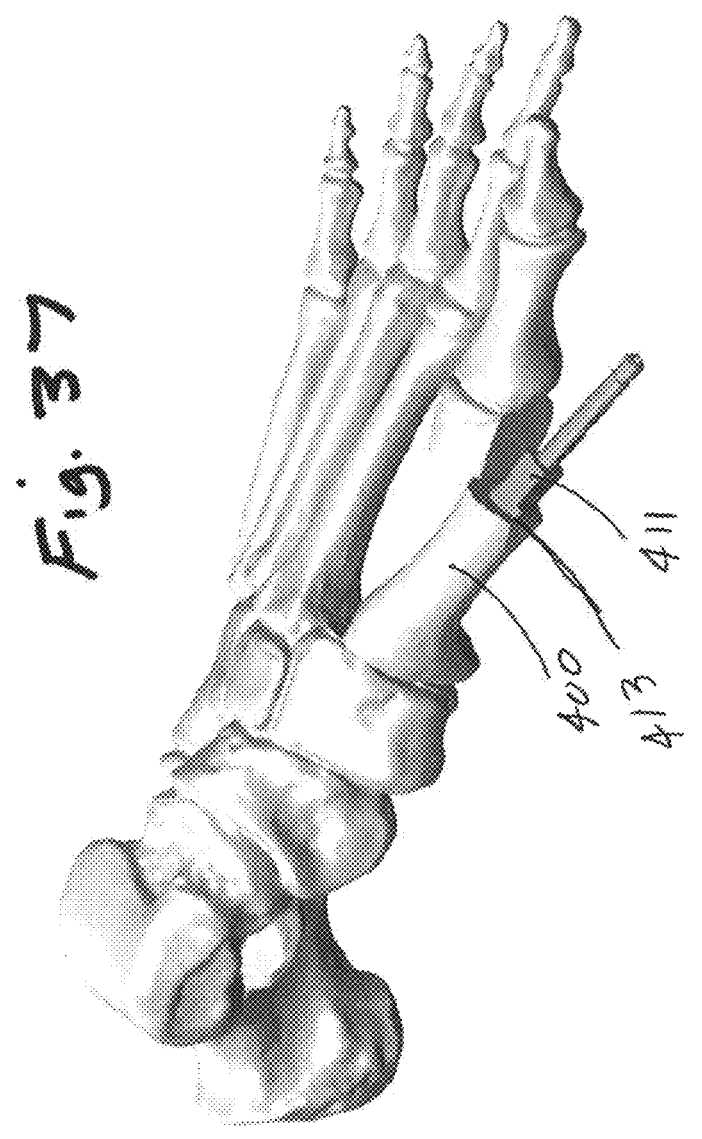

FIG. 37 depicts a skeletal foot image wherein the first metatarsal canal has been broached by placement of brooch 411 in the first metatarsal canal. The brooch is inserted into the canal until the positive stop 413 on the broach 411 contacts the level of the osteotomy, as can be seen. This will ensure that the plate can be fully inserted into the metatarsal canal without impedance once it gets to that step.

Figure 38:
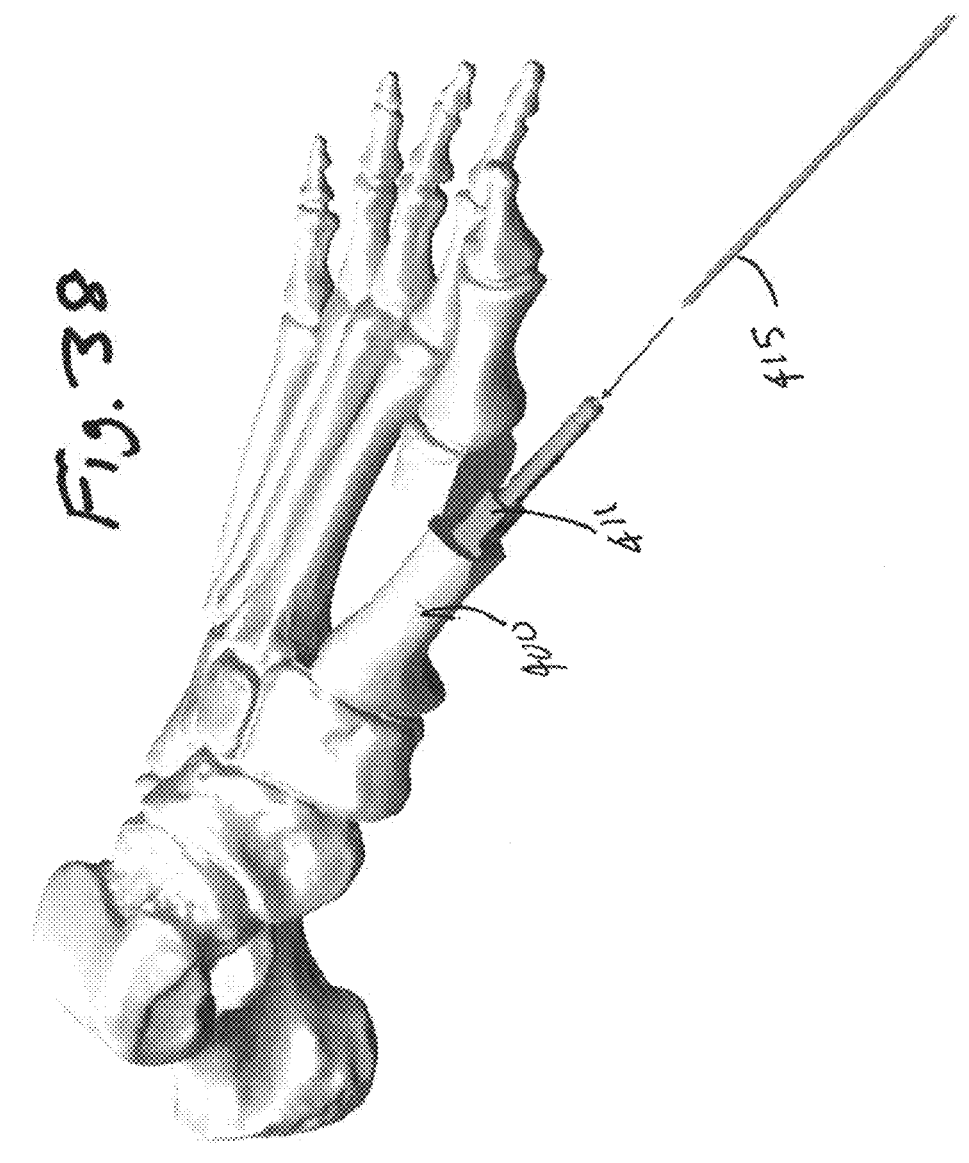

In the step represented by FIG. 38, a K-wire is placed or seated within the metatarsal canal. Once the brooch is fully seated, a 9 inch long space 1.6 mm K-wire is inserted through the cannulation of the handle and through the brooch. The K-wire 415 is inserted until cortical contact is made to anchor the K-wire 415 in place. It should be noted by those of ordinary skill in the art that care should be taken not to penetrate the k-wire 415 through the proximal end of the metatarsal and into the metatarso-cuneiform joint.

In the step represented by FIG. 39, the brooch is removed from the metatarsal canal 412, leaving the 1.6 mm K-wire 415 in place. With the wire in position, the shaft is now ready to receive the medial bunion plate.

FIG. 40 illustrates the assembly of the medial bunion plate 420 to the plate inserter 421. The medial plate has one size for each left and right cases and depending on the application, the proper medial plate should be selected. The surgeon then assembles the medial bunion inserter 421 to the plate by placing the proximal dome 421*b* of the plate, inserter 421 into the proximal oblique hole 420*a* of the medial plate 420. Then the distal tower 422 is threaded into the threaded hole 421*a* of the medial bunion inserter 421 until the threads at the tip of the distal tower 422 engage the threaded interior hole 421*a* of the medial bunion plate 420. This step essentially secures or securely fastens the medial bunion plate 420 two the medial bunion plate inserter 421, as shown in FIG. 40.

FIG. 41 illustrates the assembly of the medial bunion plate 420, the medial bunion plate inserter 421 and the tower construct 422, with the combination being ready for use to insert the plate into the metatarsal canal of the patient.

FIG. 42 illustrates the patient's first metatarsal bone 400, first metatarsal canal 412, K-wire 415, medial bunion plate 420, tower construct 422 and medial bunion plate inserter 421. The medial bunion plate 420, and medial bunion inserter 421, then placed over the central K-wire by inserting the exposed end of the K-wire 415 into the cannula of the tail of the medial bunion plate 420.

Figure 43:
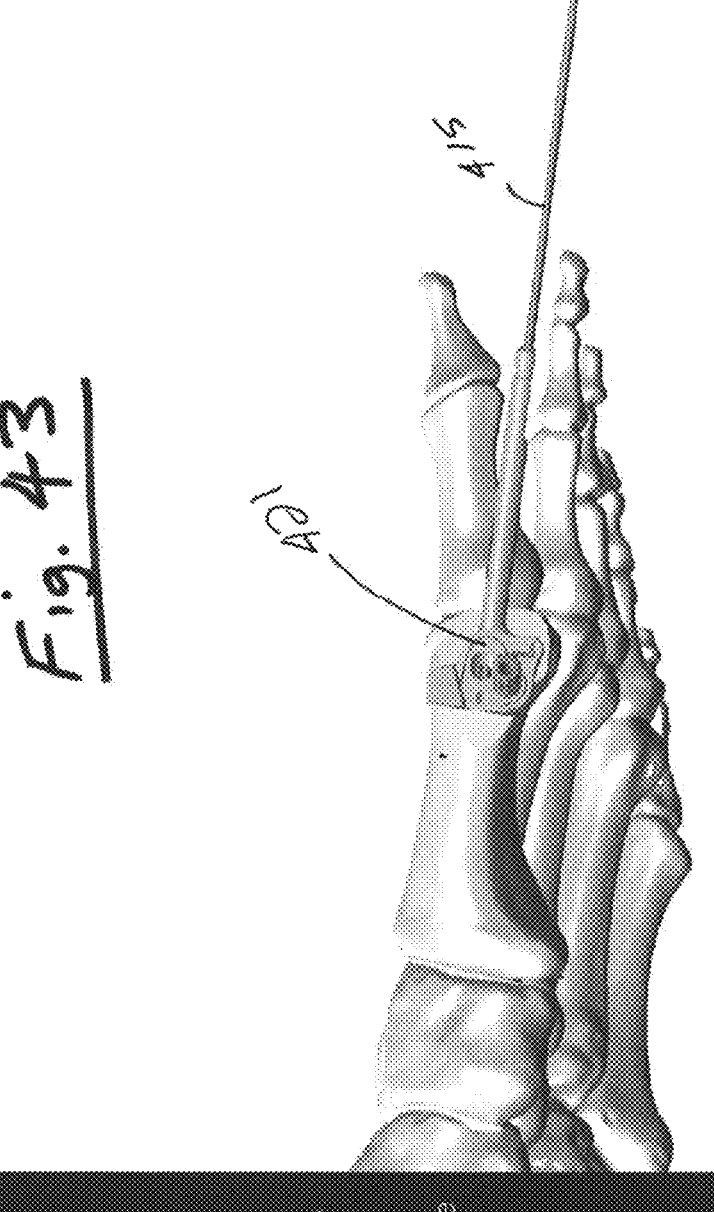

FIG. 43 helps illustrate the placement of the medial bunion plate utilizing the medial bunion plate inserter 421, utilizing the locating feature of the K-wire 415. The surgeon will insert the medial bunion plate, medial bunion plate inserter and tower construct over the K-wire and into the metatarsal canal until the medial bunion plate inserter 421 bottoms out on the plane of the osteotomy. The surgeon will then orient the tower construct such that the exposed lateral face of the medial bunion plate is in contact with the resection plane of the medial eminence of the metatarsal head.

FIG. 44 illustrates the preparation for placement of a distal inferior screw to secure the plate to the metatarsal bone. The optimal position of the medial bunion plate is achieved on the metatarsal head and confirmed under visualization and image intensification. The distal inferior hole 427 from prior steps can be aligned with the distal inferior plate hole and a 1.6 mm K-wire 426 is inserted. If there is a difficulty aligning the previously prepared hole or a different position is desired, the K-wire 426 can be placed in that new location.

In the step illustrated in FIG. 45, with the K-wire 426 in place through the distal tower 422, the medial bunion plate 420 and into the metatarsal head 400, a K-wire (1.66 mm) can be inserted through the inferior anti-rotation hole of the medial bunion plate inserter until contact with the dorsolateral cortex of the metatarsal head 400 is achieved. This will capture the metatarsal head 400 to the medial bunion plate/medial bunion plate inserter/and tower construct and then allow for translation and rotational correction of the metatarsal head 400 relative to the metatarsal shaft. This is where much directional alignment and adjustments can be made for optimal results for the patient.

Figure 46:
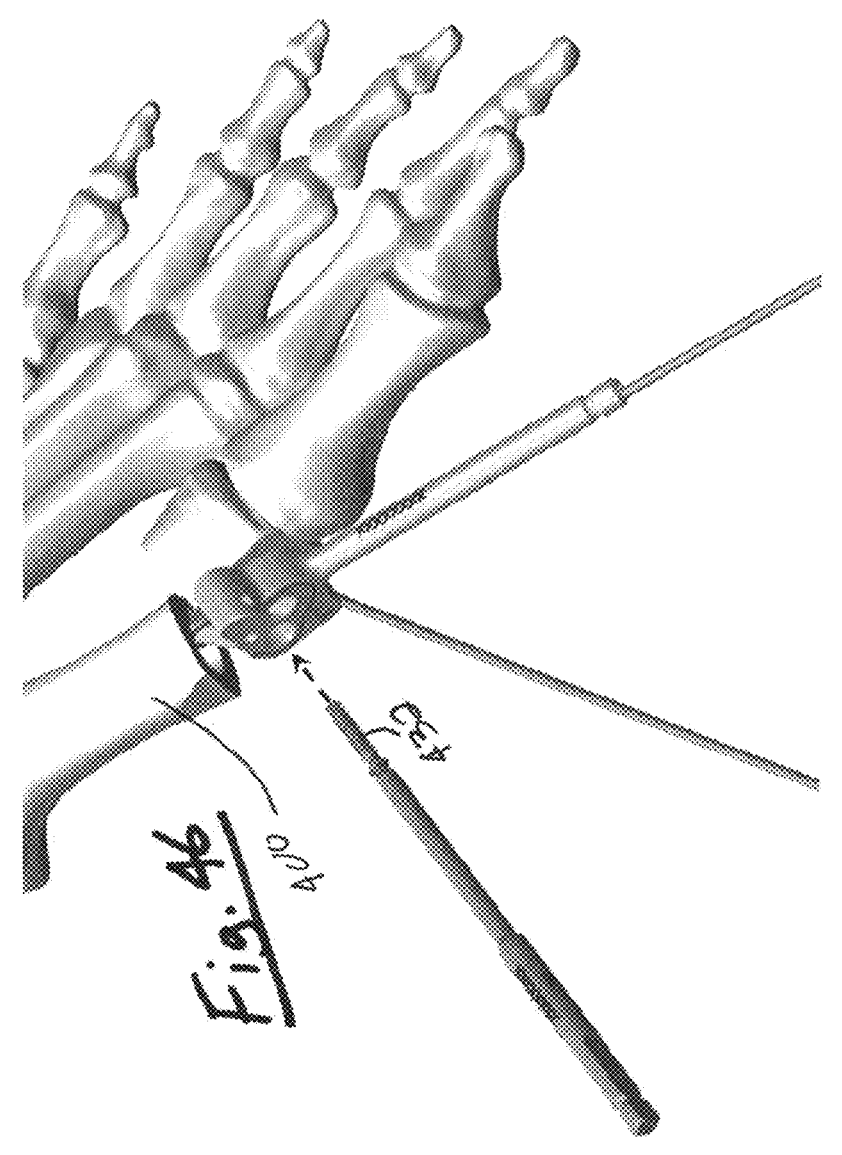

In the step illustrated in FIG. 46, the distal tower and the distal inferior K-wire can be removed. A depth gauge can be used through the threaded hole of the medial plate inserter and through the plate to measure the appropriate screw length. The surgeon then may select a 2.4 mm non-locking screw 432 of appropriate length. This should be a non-locking screw (an example of which is shown in later figures) for the first screw in the metatarsal head so that compression of the medial bunion plate to the metatarsal head 400 can be achieved. A screwdriver such as a T6 screwdriver may be utilized to drive the screw through the medial bunion plate inserter and through the medial bunion plate into the metatarsal head until the screw 432 is fully seated.

Figure 47:
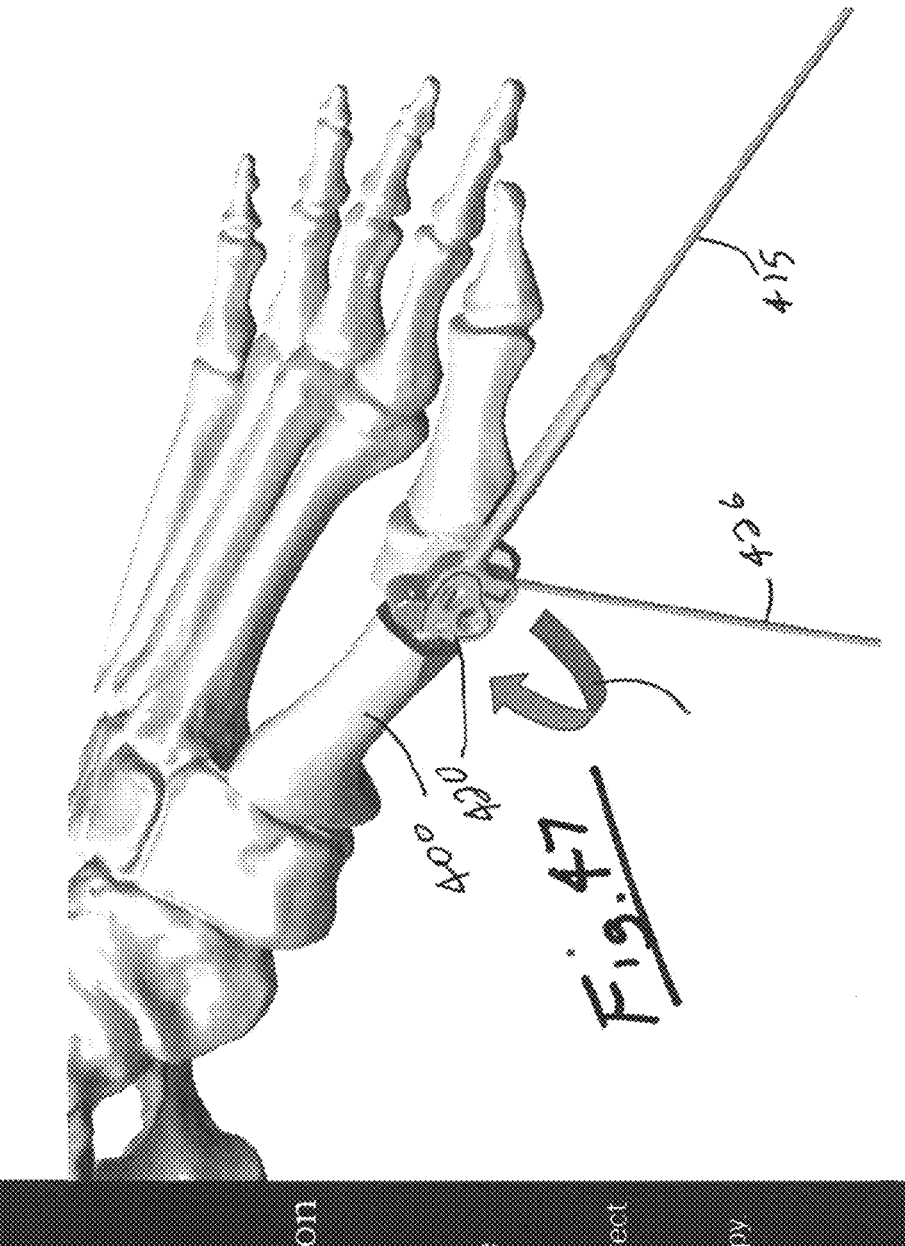
Figure 4A:
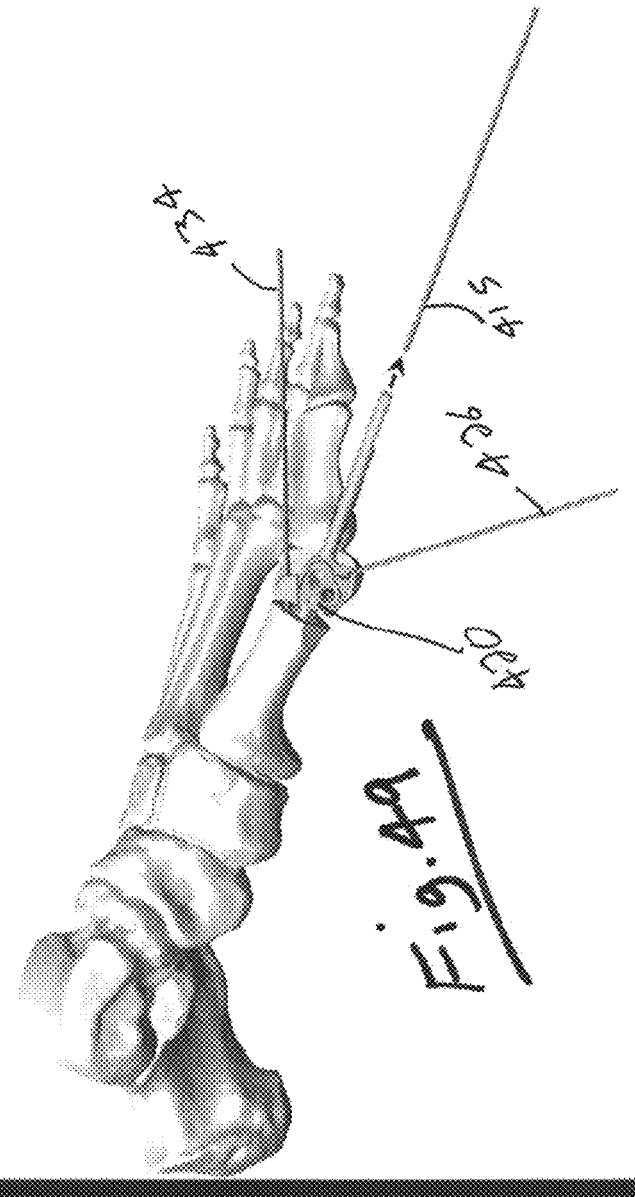

FIG. 47 illustrates that once the metatarsal head 400 is fixated to the medial bunion plate 420, medial bunion plate inserter, and construct, the position of the metatarsal head 400 can now be manipulated in all planes and dimensions. This is critical to achieving the optimum results for the patient. The plate inserter can be used to correct the rotational and the tri-plane components to the desired position. This can all be done under live fluoroscopy for better results.

FIG. 48 illustrates medial bunion plate 420, K-wire 426, K-wire 415 and the placement of an additional K-wire 434, through the bridging hole of the medial bunion plate inserter 421 and into the metatarsal shaft as shown in FIG. 48. In this illustration, the metatarsal head is now temporarily stabilized in the corrected position relative to the metatarsal shaft.

FIG. 49 illustrates the step wherein once the metatarsal head is stabilized in the corrected position, the K-wire 415 may be removed from the construct. The removal of the central K-wire provides access to place the distal oblique screw through the medial plate inserter and through the medial distal plate into the metatarsal shaft.

Figure 50:
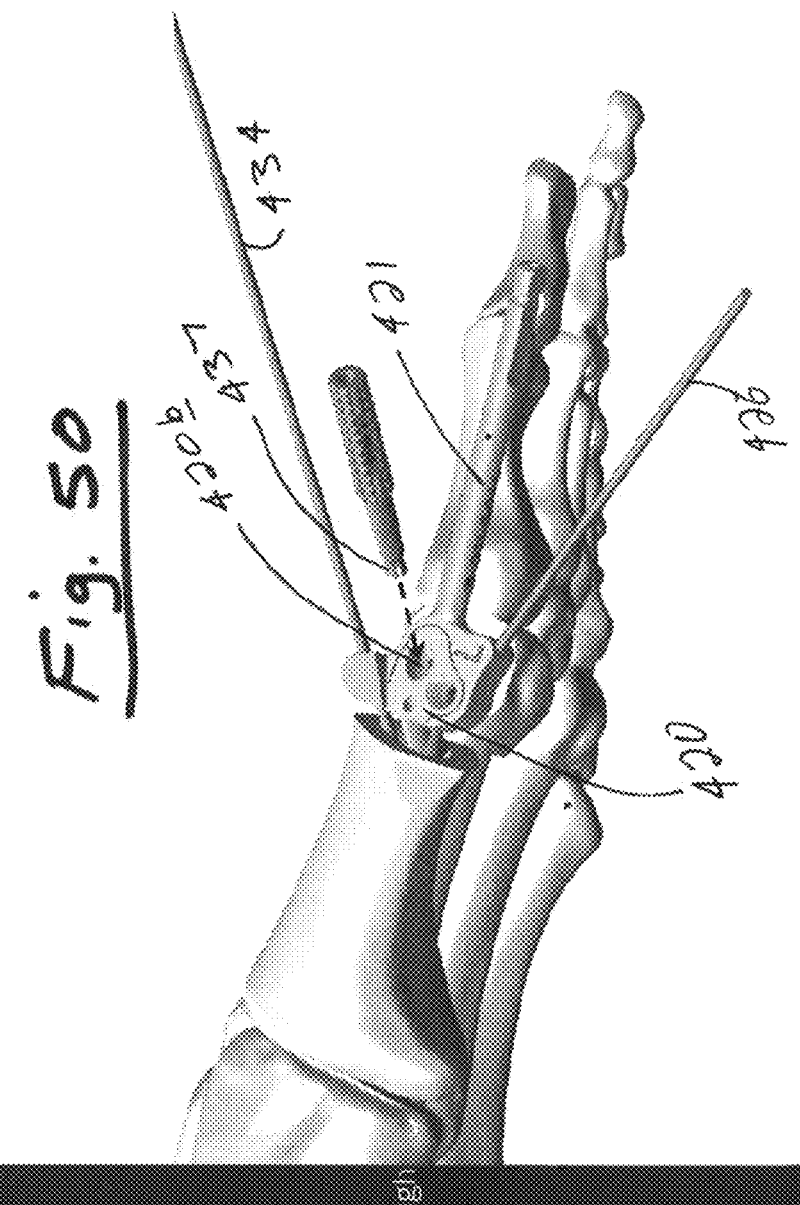

FIG. 50 illustrates K-wire 434, K-wire 426, medial bunion plate 420, medial bunion plate inserter 421, proximal tower 437 and screw aperture 420*b* in medial bunion plate 420. In this step, the proximal tower is inserted through the distal oblique hole 420*b* of the distal media plate inserter 421 and snapped into place.

Figure 51:
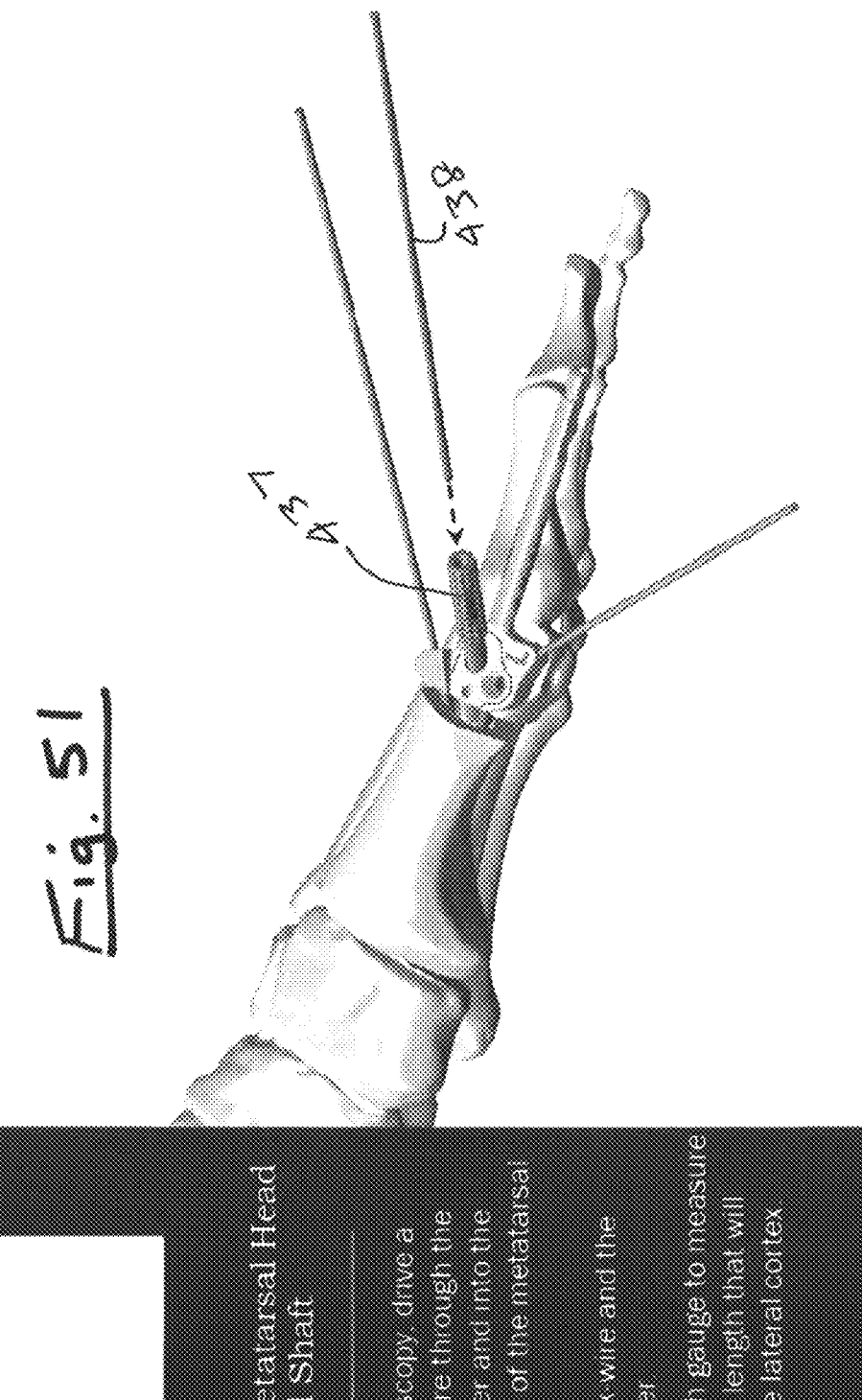

The step represented in FIG. 51 is preferably done under fluoroscopy, and a 1.6 mm K-wire is driven or placed through the proximal tower 437 and into the lateral cortex of the metatarsal shaft. The K-wire 438 is then removed as is the proximal tower 437 also removed. A depth gauge may then be used to measure the proper screw length that will sufficiently engage to the lateral cortex and through the aperture in the distal medial plate.

In the step illustrated in FIG. 52, the metatarsal head is compressed to the metatarsal shaft. In this case a diameter of 2.4 mm non-locking screw 440 of the appropriate length identified is utilized and is inserted via screwdriver 441 (preferably a T6 screwdriver). It is preferable in embodiments of this invention that only non-locking screws 440 are used with the oblique screw holes of the medial bunion plate 420. The non-locking screw 440 is driven through the medial bunion plate inserter and through the medial bunion plate, and into the cortex of the metatarsal shaft. However, at this step it is preferred not to fully seat and tighten the screw until a later step.

Figure 53:
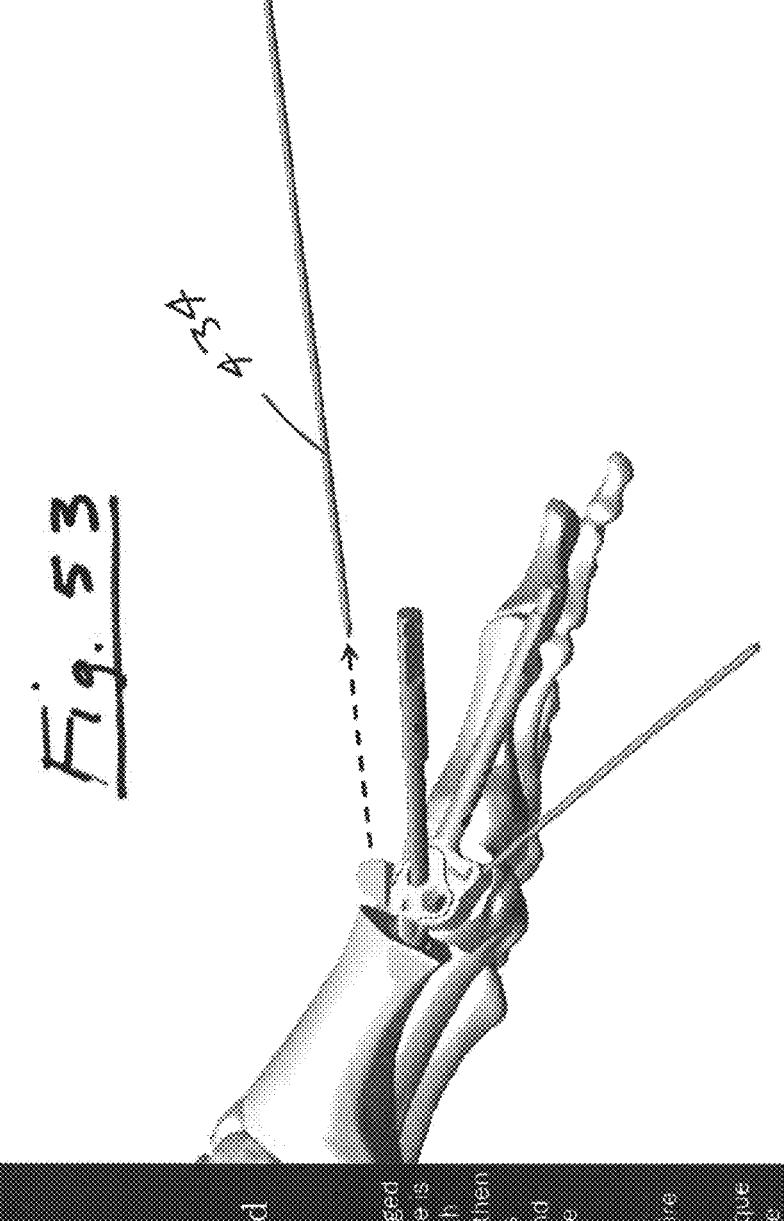

In the step represented by FIG. 53, the surgeon will ensure that the screw tip has engaged the cortex of the metatarsal. If there is a difficulty engaging the screw chip with the cortex of the metatarsal shaft, then a 2.0 mm drill may be used. In such event, the surgeon should preferably replace the proximal tower and use the drill to open the predrilled hole of the metatarsal cortex. Prior to fully seating the screw, the temporary stabilizing K-wire 434 that was inserted, should be removed. After K-wire 434 is removed, the distal oblique screw may be fully seated into place through the lateral cortex. The step therefore compresses the metatarsal head to the metatarsal shaft.

Figure 54:
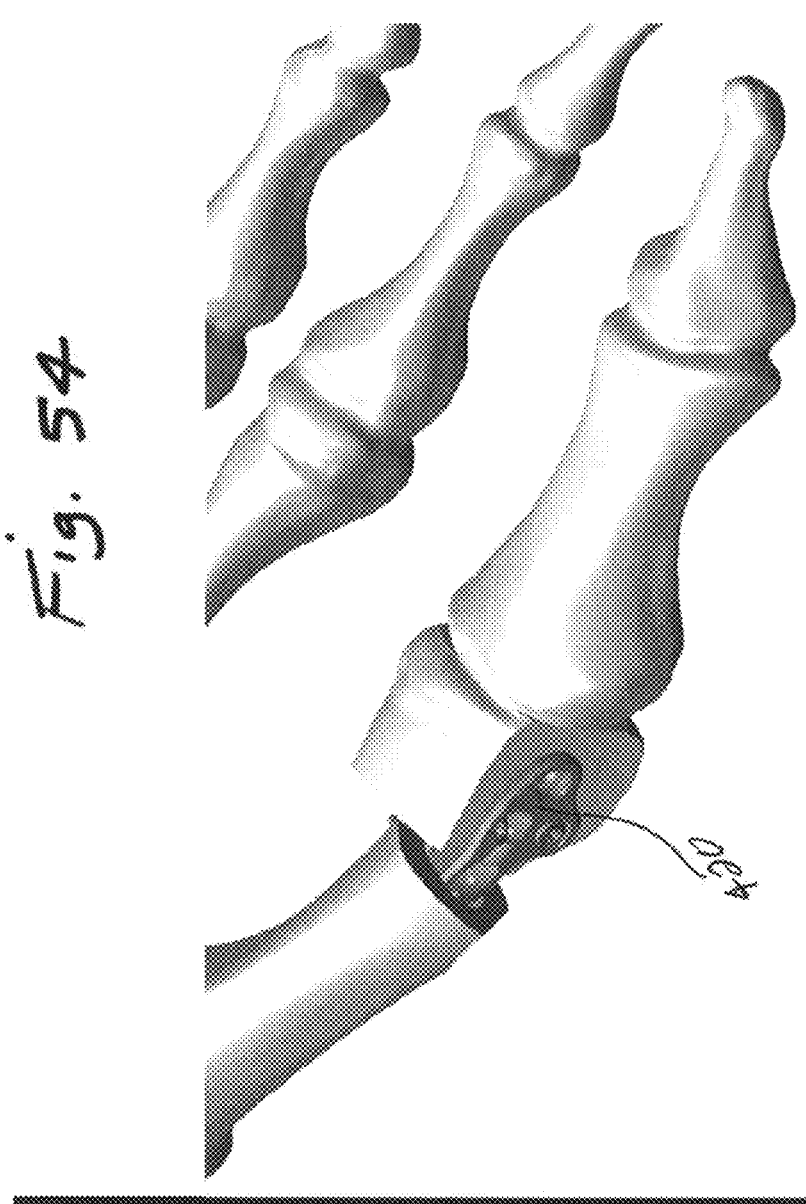

In the step represented by FIG. 54, the medial bunion plate inserter and accompanying K-wires are removed, thereby leaving the medial bunion plate 420 exposed. The remaining K-wires are removed and the medial bunion plate inserter is separated from the medial bunion plate 420. As shown in FIG. 54, the medial bunion plate 420 is now secured and compressed to the metatarsal head, which is now therefore compressed to the metatarsal shaft via the medial bunion plate and distal oblique screw in the corrected position.

Figure 55:
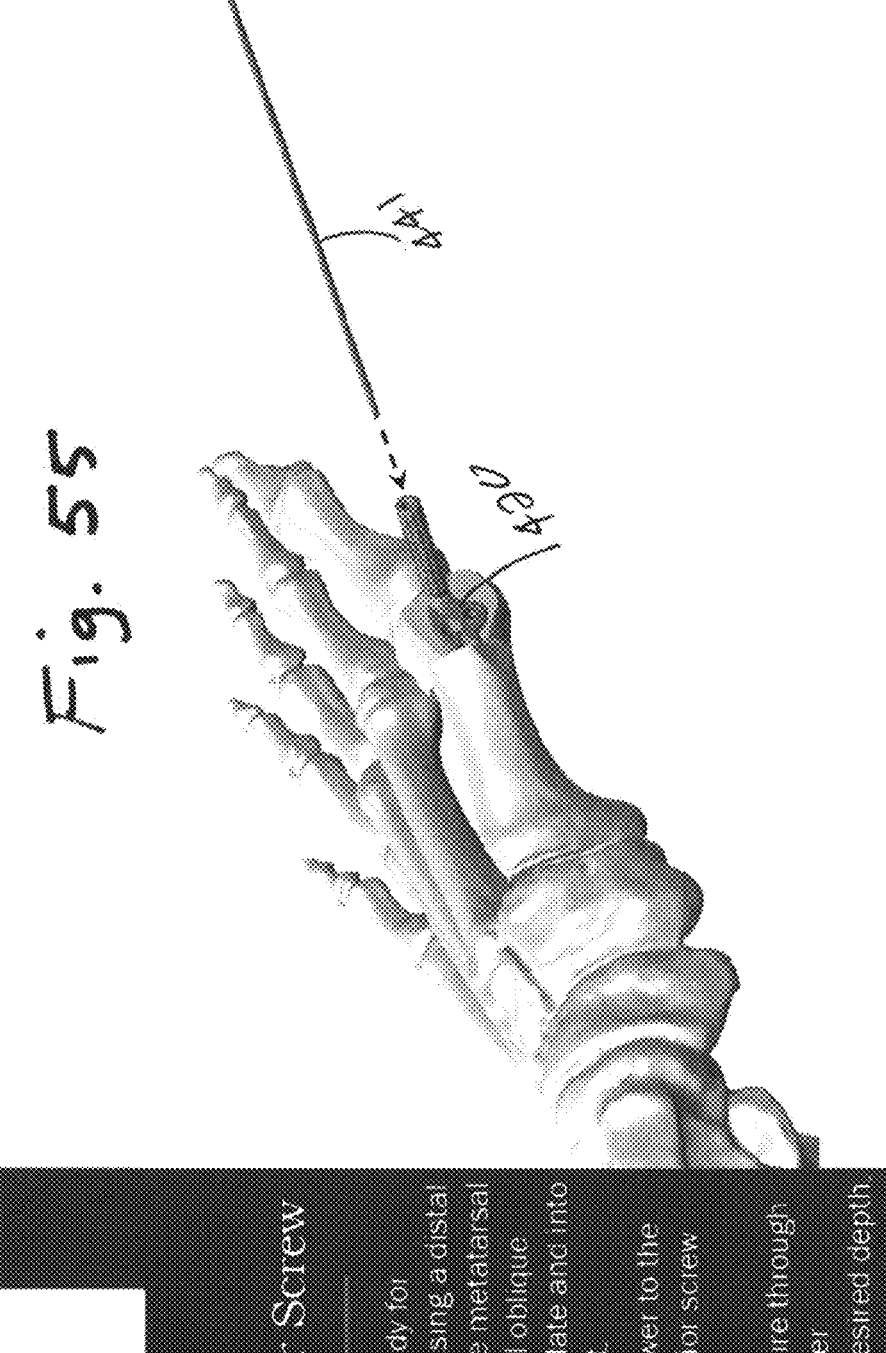

In FIG. 55, the medial bunion plate 420 is now ready for additional stability using a distal superior screw in the metatarsal head and a proximal oblique screw through the medial bunion plate and into the metatarsal shaft. The surgeon will thread the distal tower to the unused distal superior screw hole of the medial distal plate and drive a 1.6 mm K-wire 441 through the distal tower under fluoroscopy to the desired depth for the screw to be placed therein.

Figure 56:
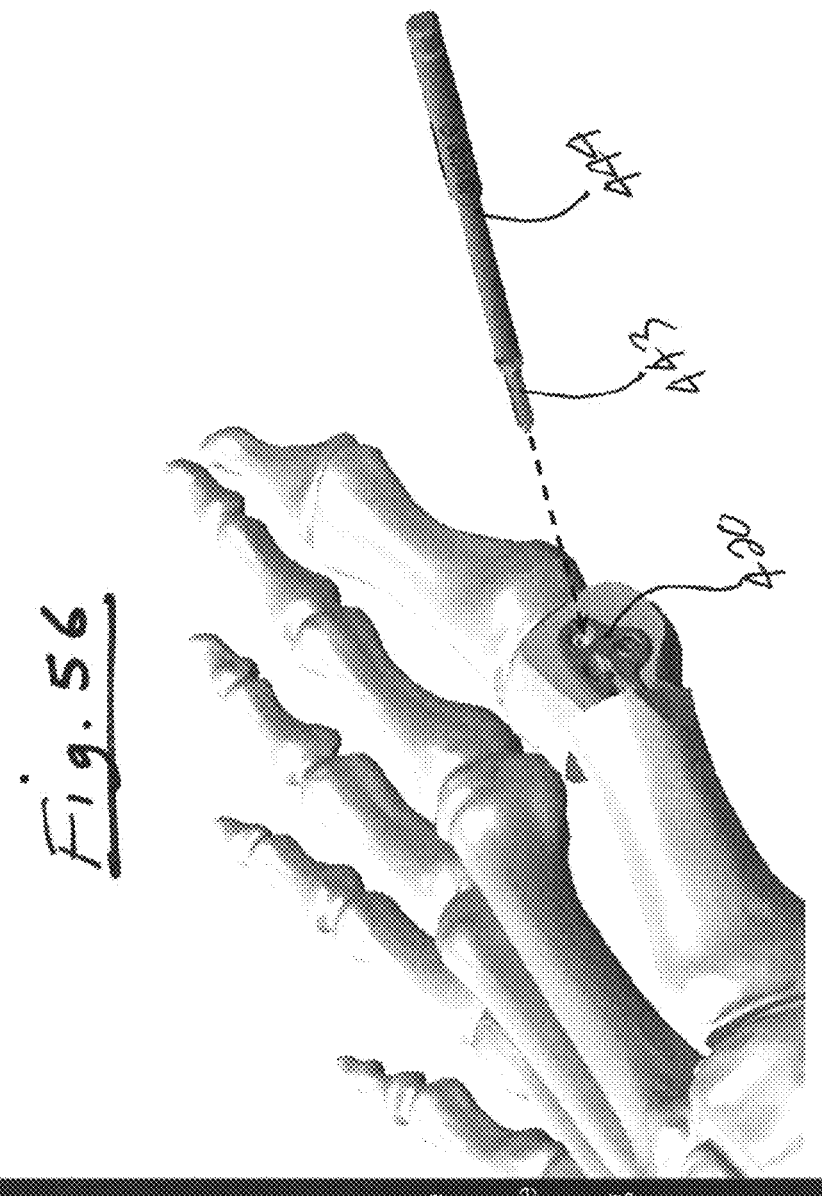

FIG. 56 illustrates that a distal superior screw is inserted. First however the K-wire 441 as shown in FIG. 55 is removed, a depth gauge is used to measure this desired screw length and a T6 screwdriver 444 is used to fully seat the distal superior screw 443.

Figure 57:
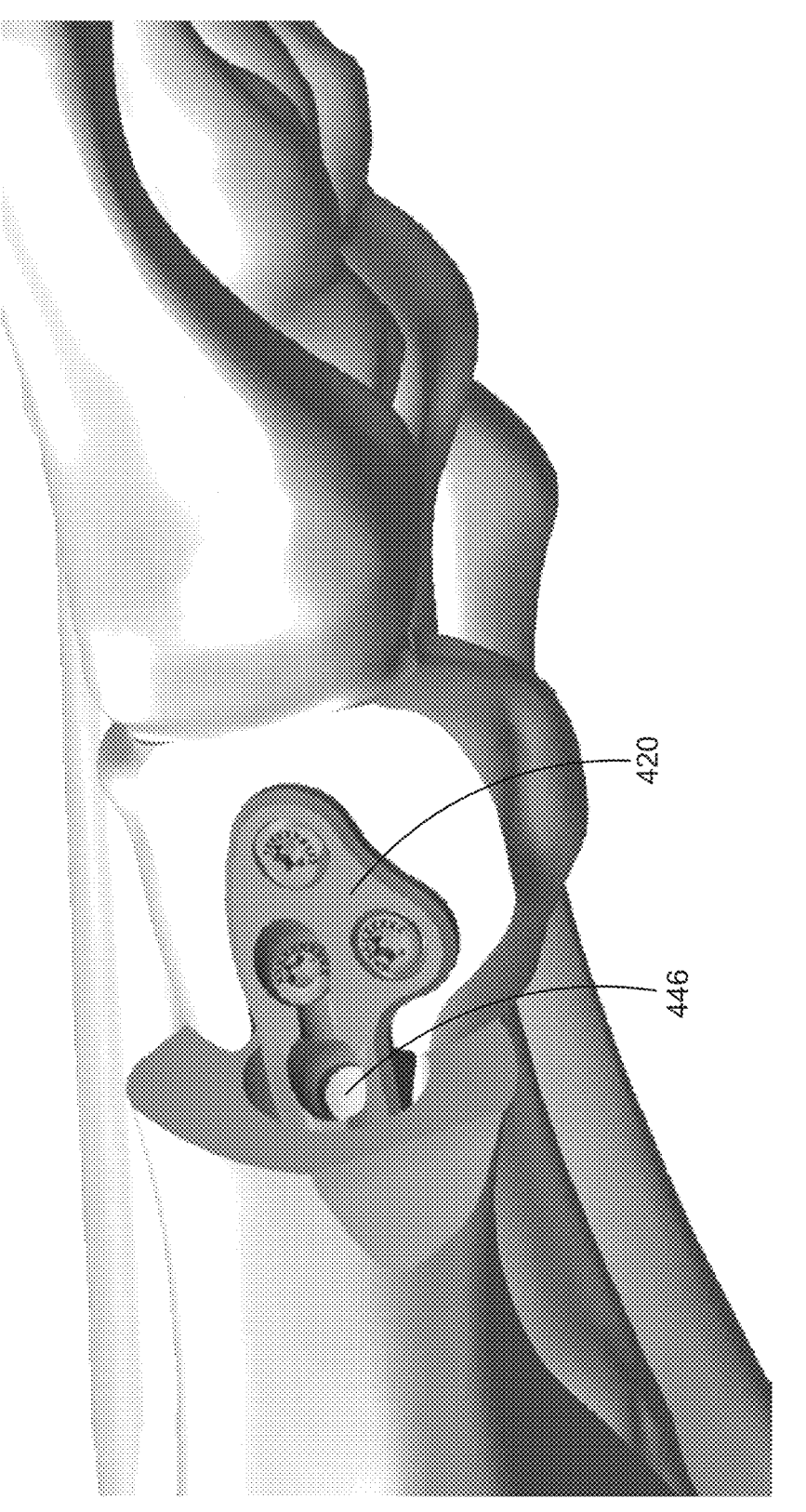

FIG. 57 illustrates that a single open screw hole 446 remains open. The surgeon will examine the prominent medial metatarsal shaft and if the prominence interferes with the trajectory of the remaining proximal oblique hole, then it will be removed until the interference is removed. The removal may be accomplished with a rongeur or a sagittal blade.

Figure 58:
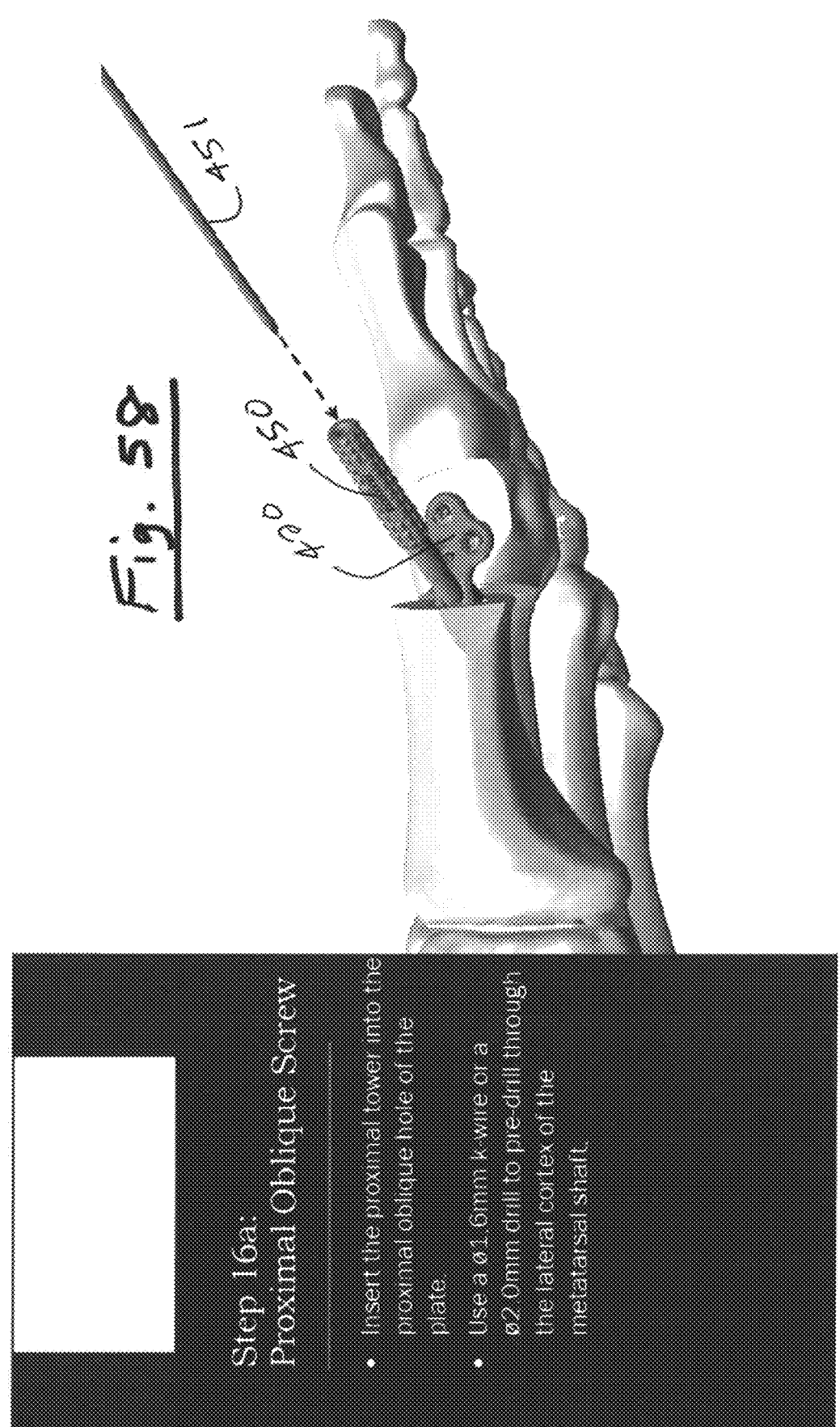

FIG. 58 illustrates the insertion of a proximal tower 450 into the proximal oblique hole of the distal medial plate 420, the use of a K-wire 451 to predrill through the lateral cortex of the metatarsal shaft. The proximal tower 450 is inserted into the proximal oblique hole of the medial bunion plate and then the K-wire or a drill is used to predrill through the lateral cortex of the metatarsal shaft.

FIG. 59 illustrates that, after the proximal tower and K-wire or drill are removed, and depth is determined for the screw length, the insertion of preferably a non-locking screw 452 through the plate and through the lateral cortex of the metatarsal shaft, is accomplished through use of a screwdriver.

Figure 60:
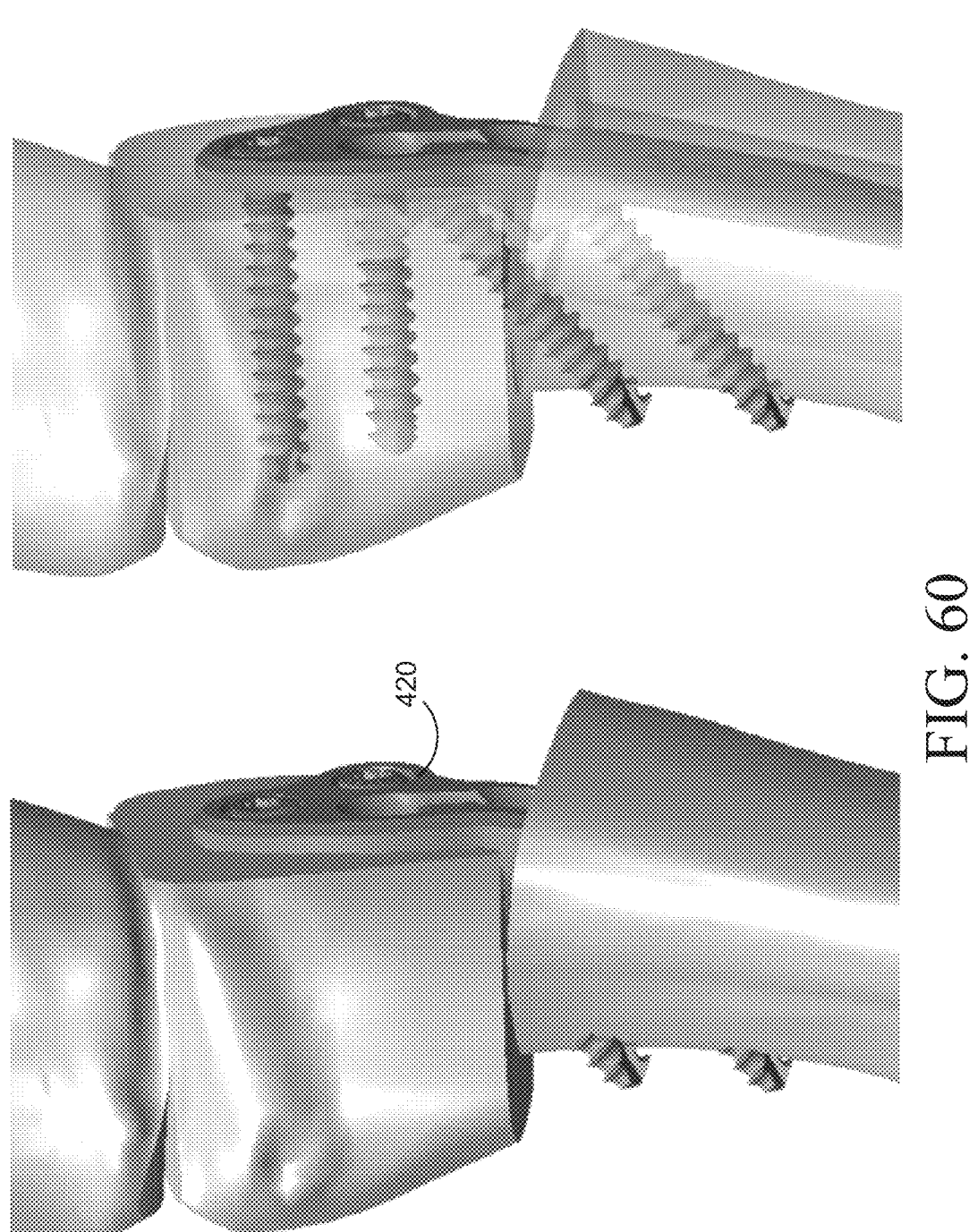

FIG. 60 illustrates that, under the discretion of the surgeon, the distal inferior non-locking screw may be explanted and replaced with a locking screw of the same length. This step is optional and not required. The surgeon will then check the final positioning of the medial distal plate and screws with A/P, Sesamoid Axial, and Lateral Fluroscopy. Once this is accomplished, the incisions can be closed with sutures of the surgeon's preference.

Figure 61:
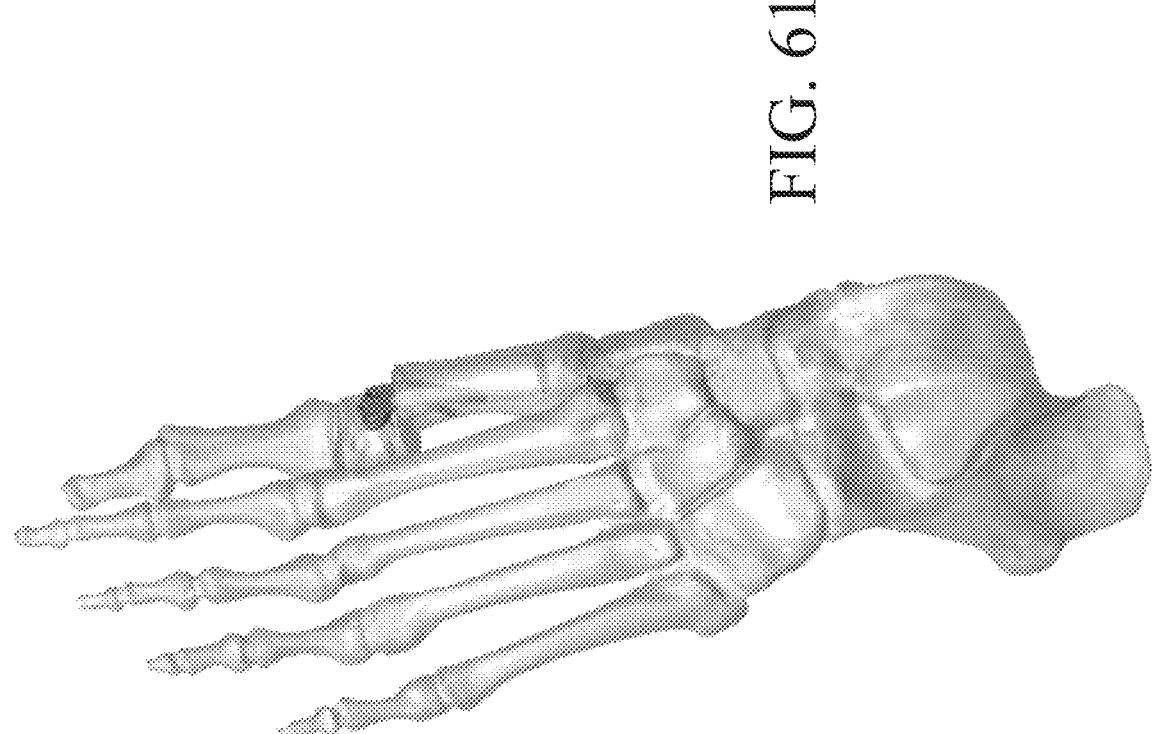

FIG. 61 shows the resulting skeletal foot image from the procedure described above.

Figure 62:
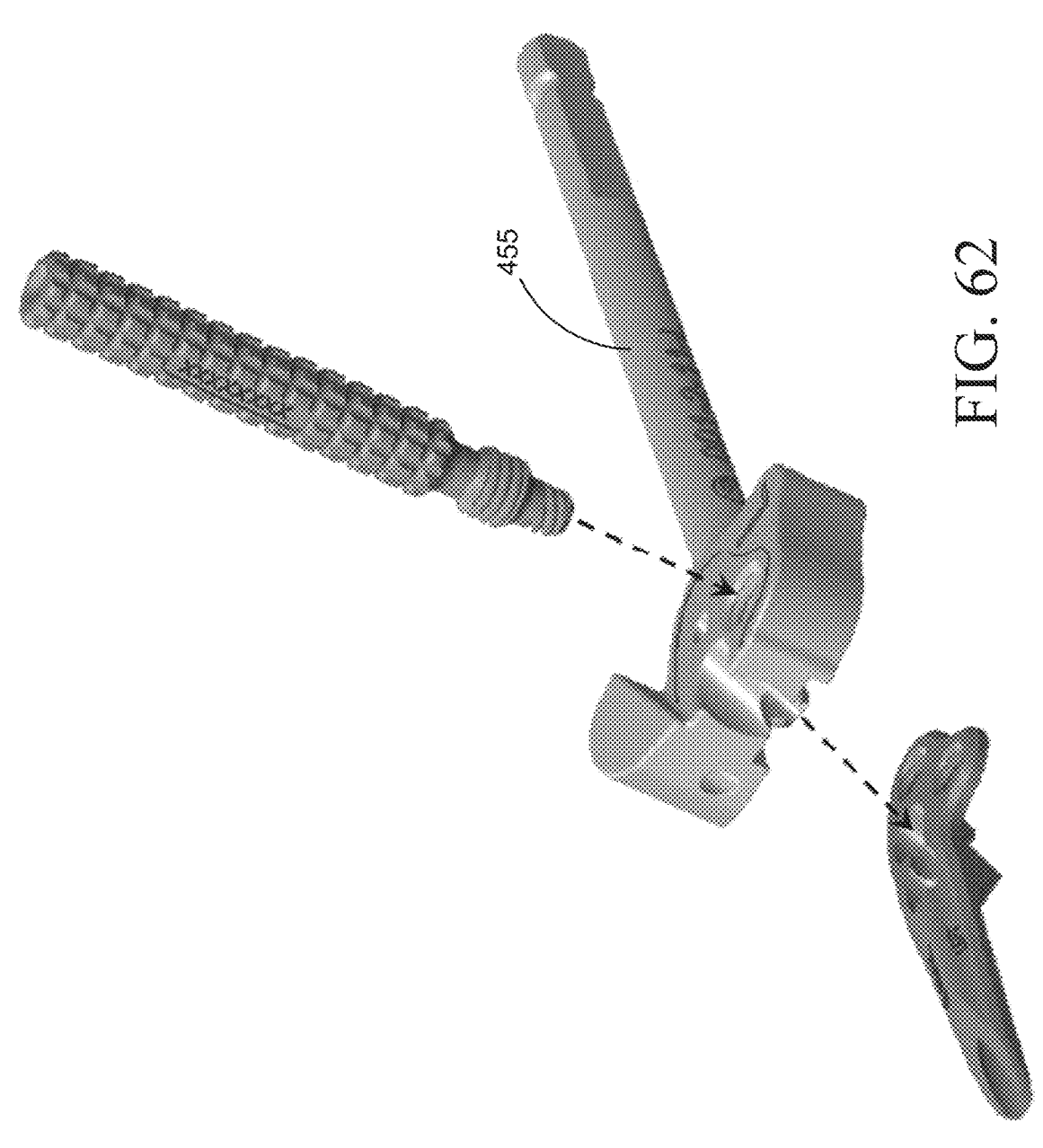

FIG. 62 shows an alternative methodology which may, but need not, be utilized. In cases of poor bone quality in the distal metatarsal shaft near the osteotomy, or if there is a surgical preference, the alternative medial bunion inserter 455 may be used instead of the standard medial bunion inserter shown and described above. The alternate medial bunion inserter 455. The alternate medial bunion inserter allows for placement of the proximal oblique screw, which engages further down the shaft of the metatarsal, prior to insertion of the distal oblique screw. The methodology of screw placement is the same with that chronological step being the only difference when using the alternate medial bunion inserter, as shown.

Figure 63:
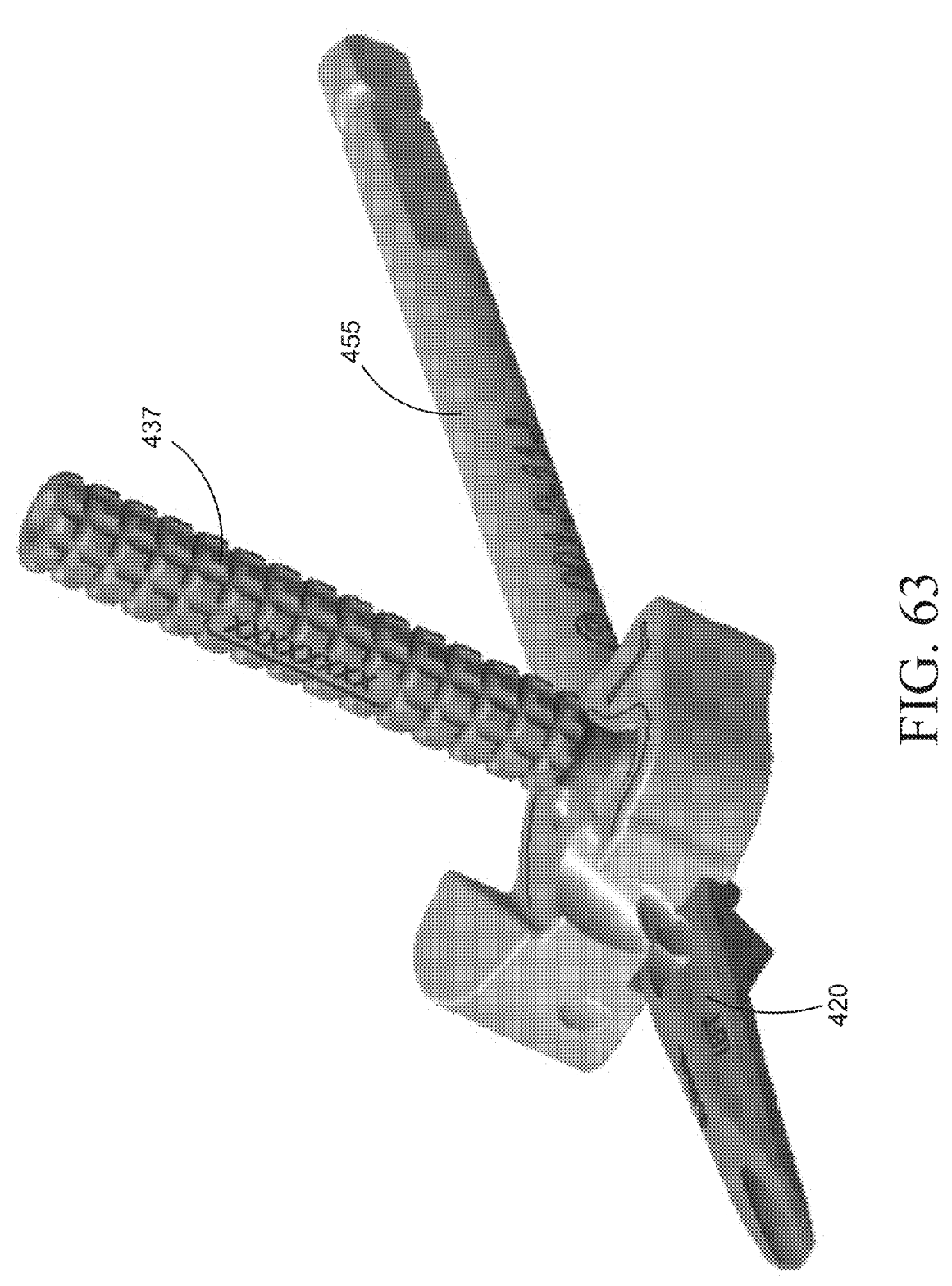
Figure 64:
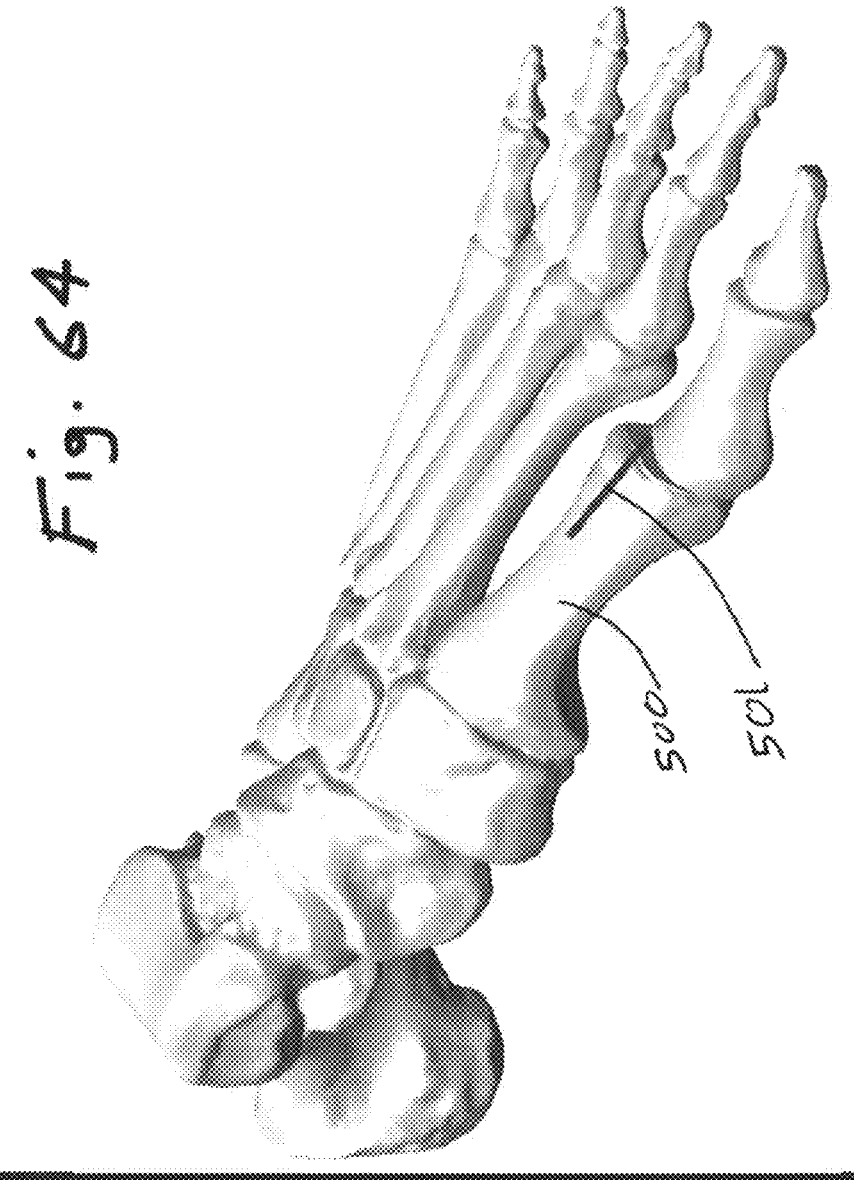
Figure 67:
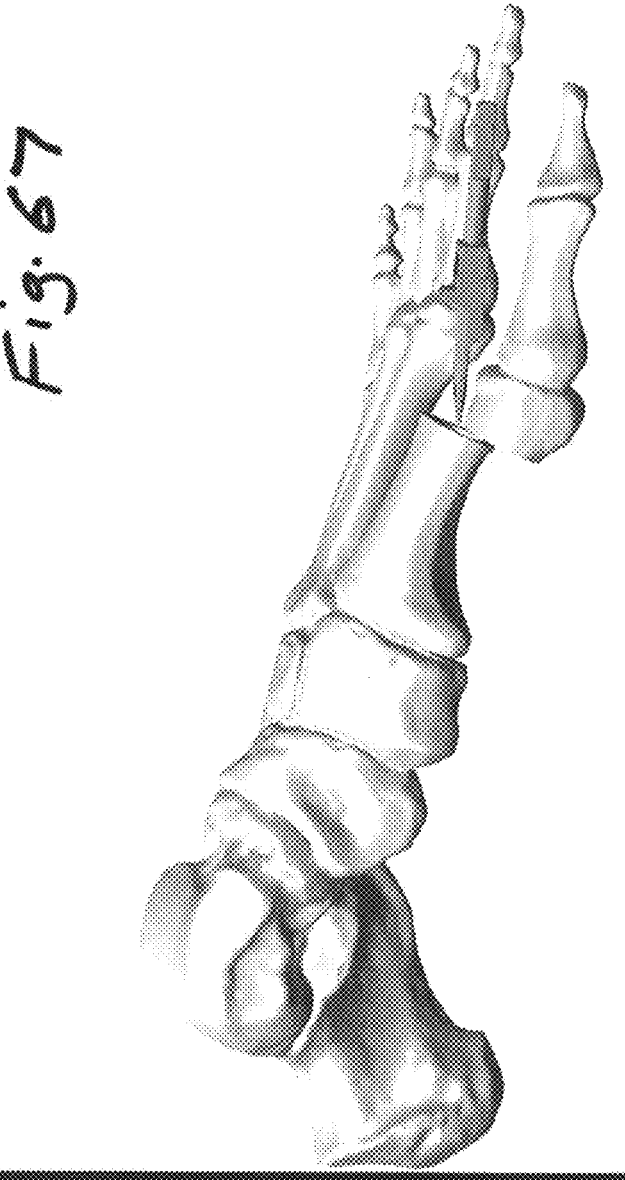
Figure 68:
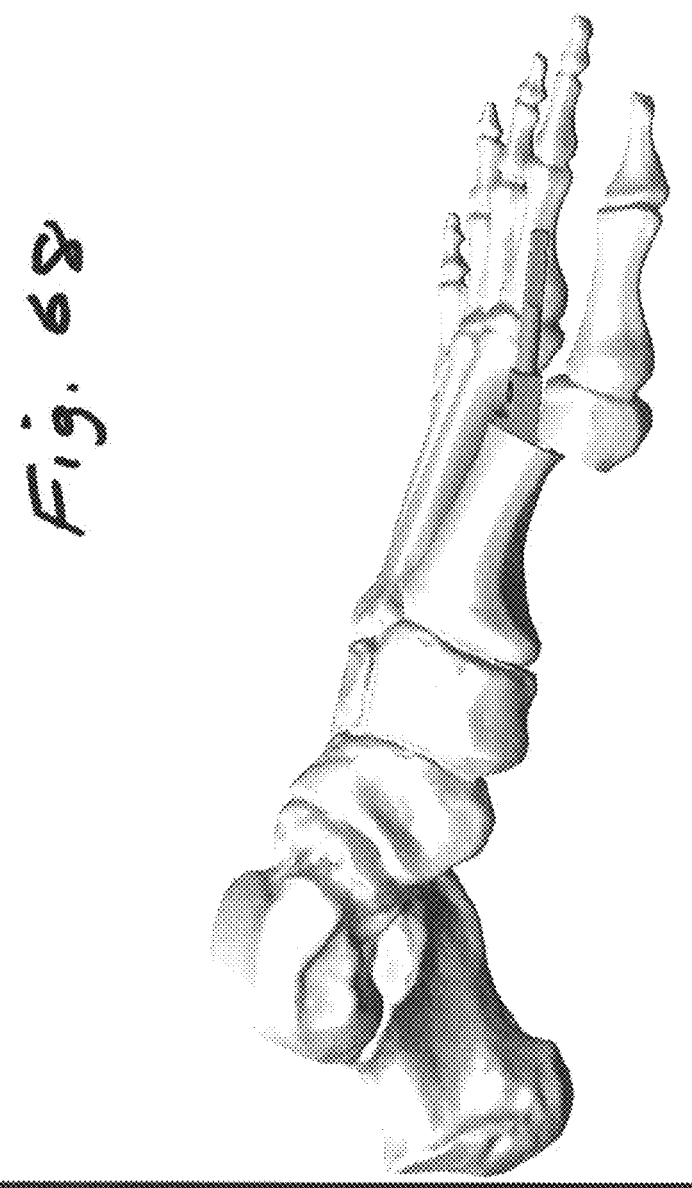
Figure 69:
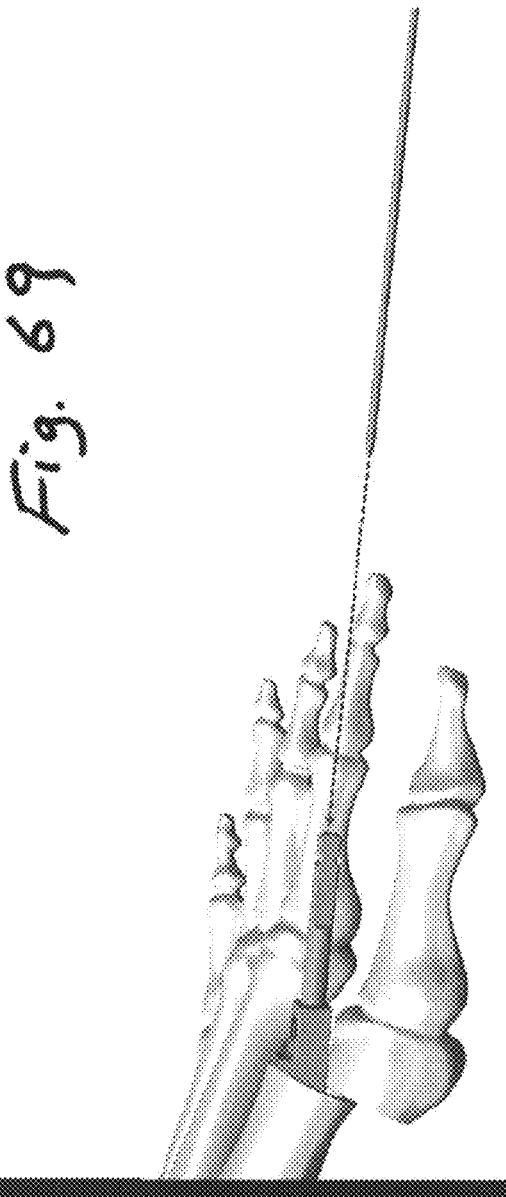
Figure 70:
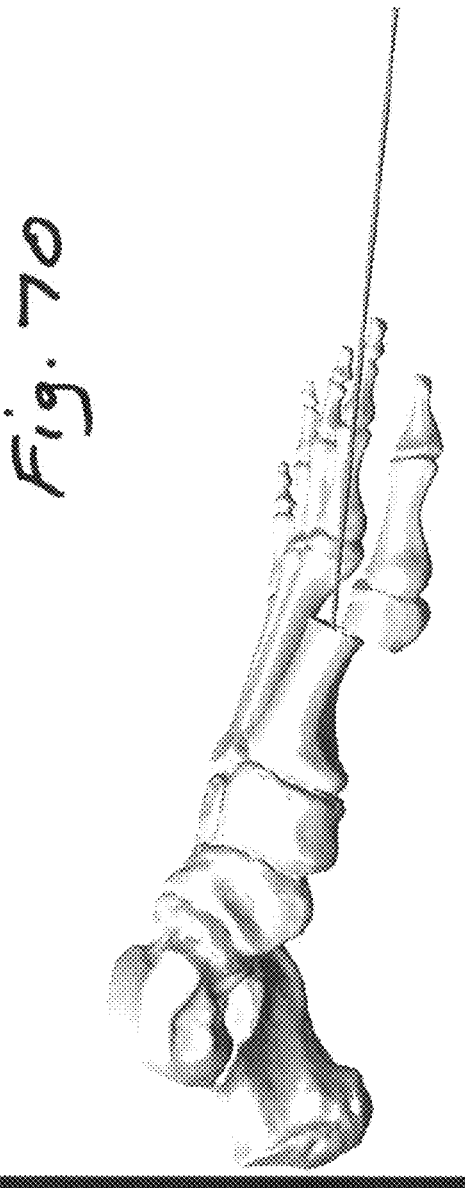
Figure 72:
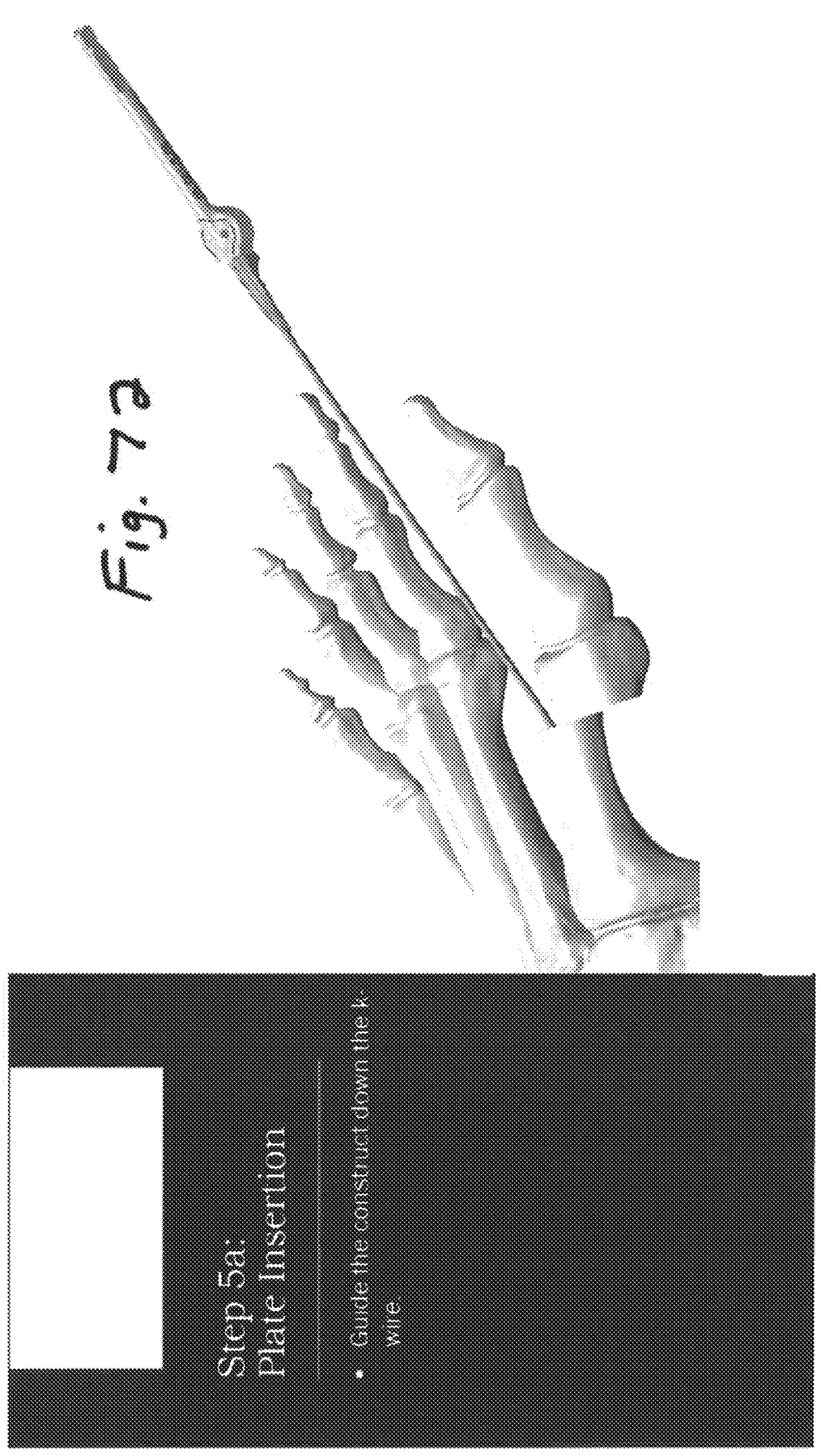
Figure 73:
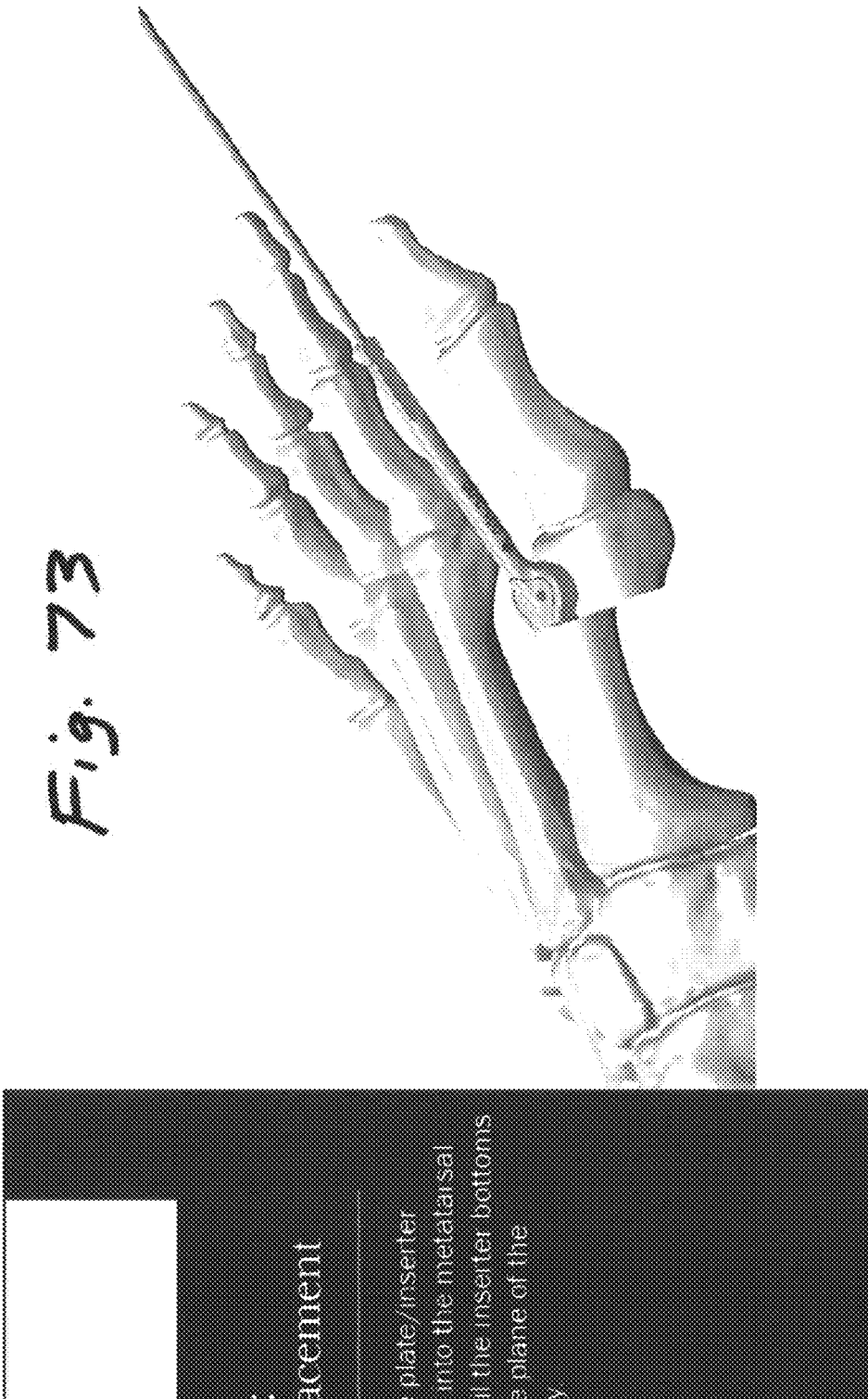
Figure 74:
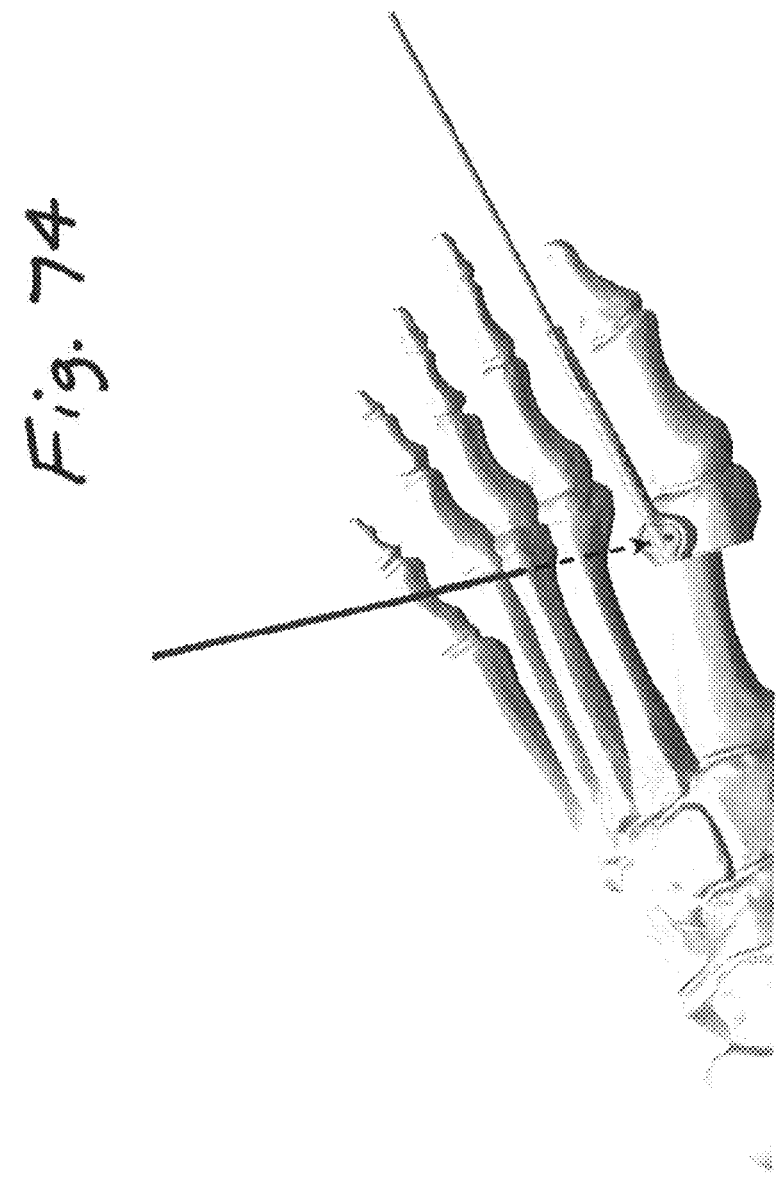
Figure 76:
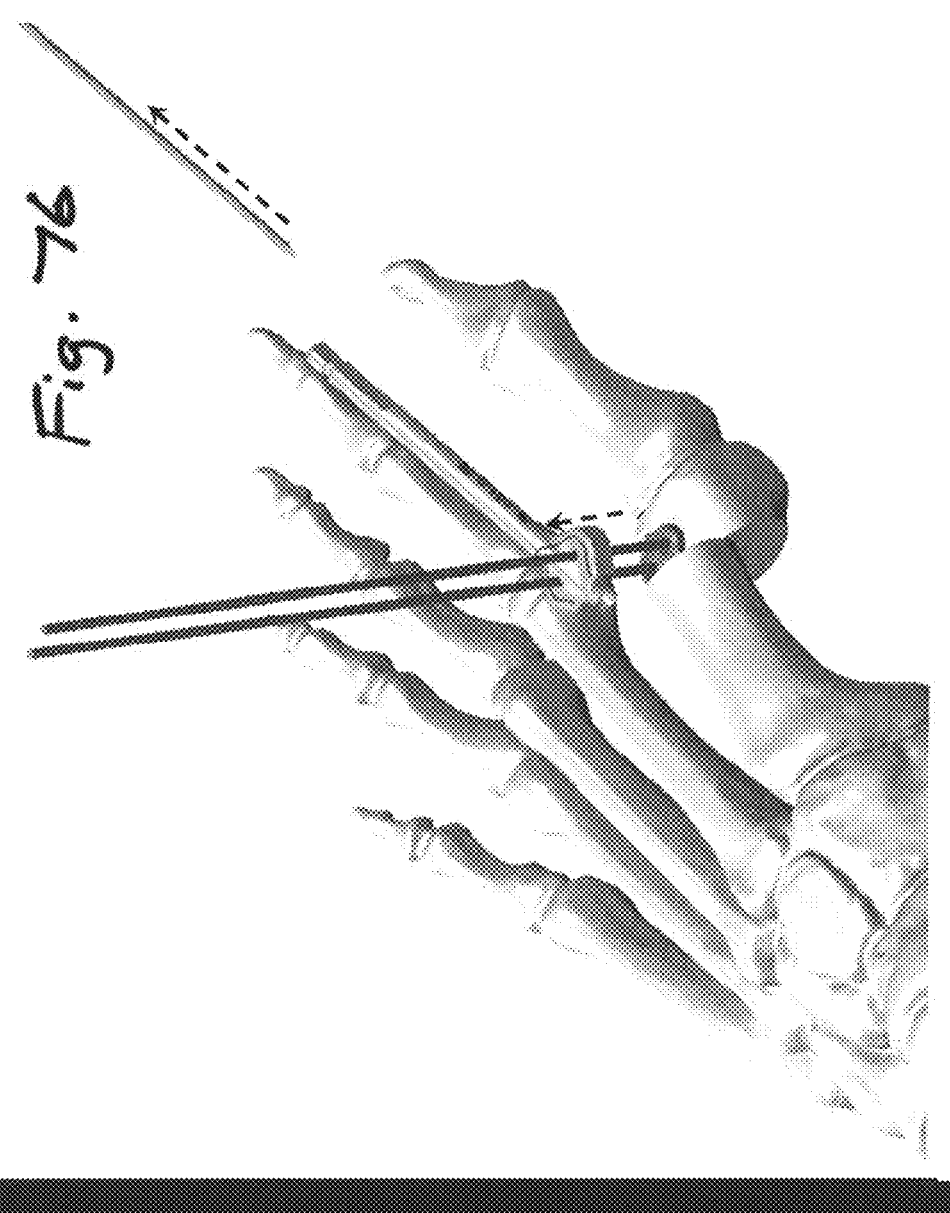
Figure 78:
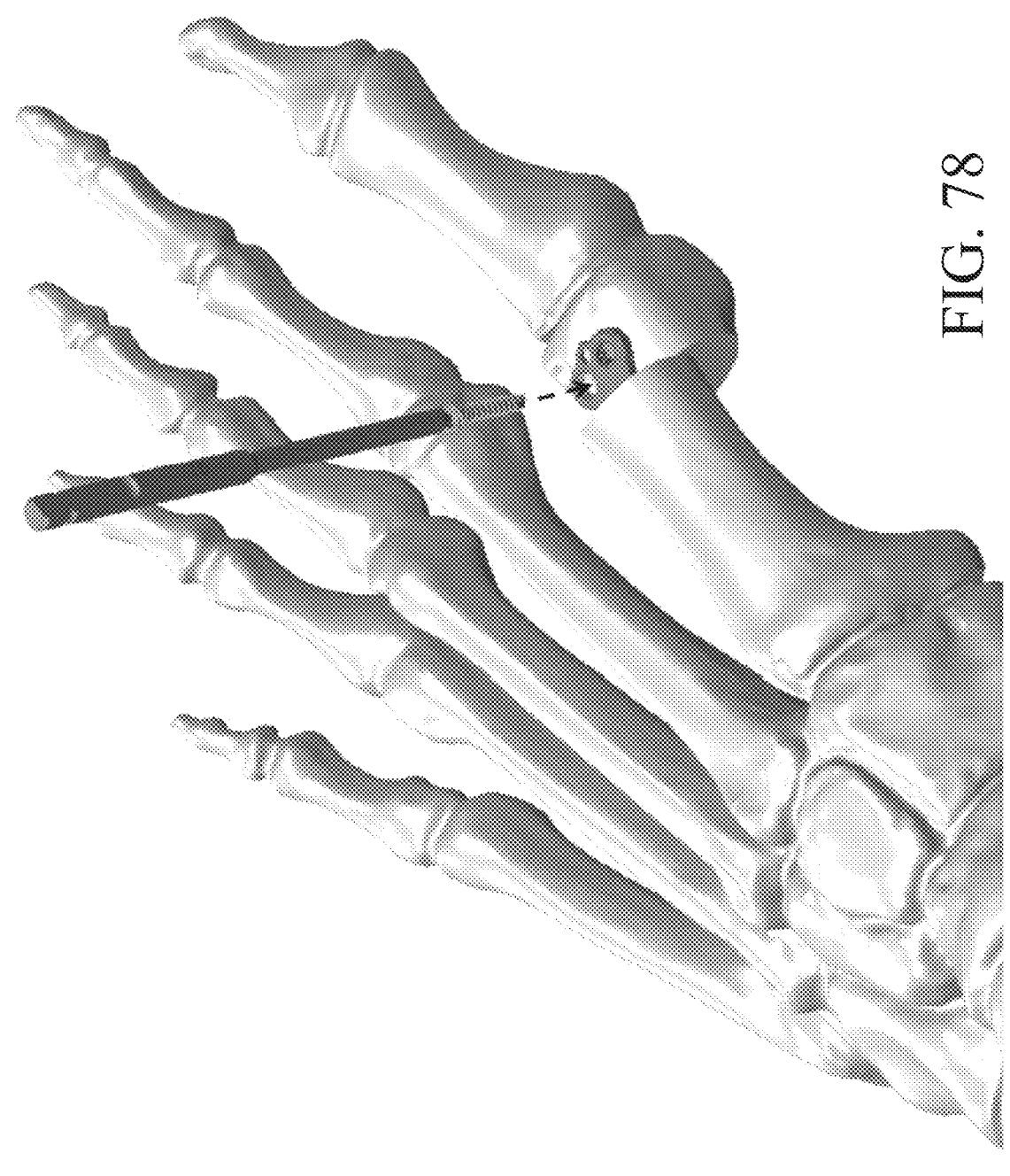
Figure 80:
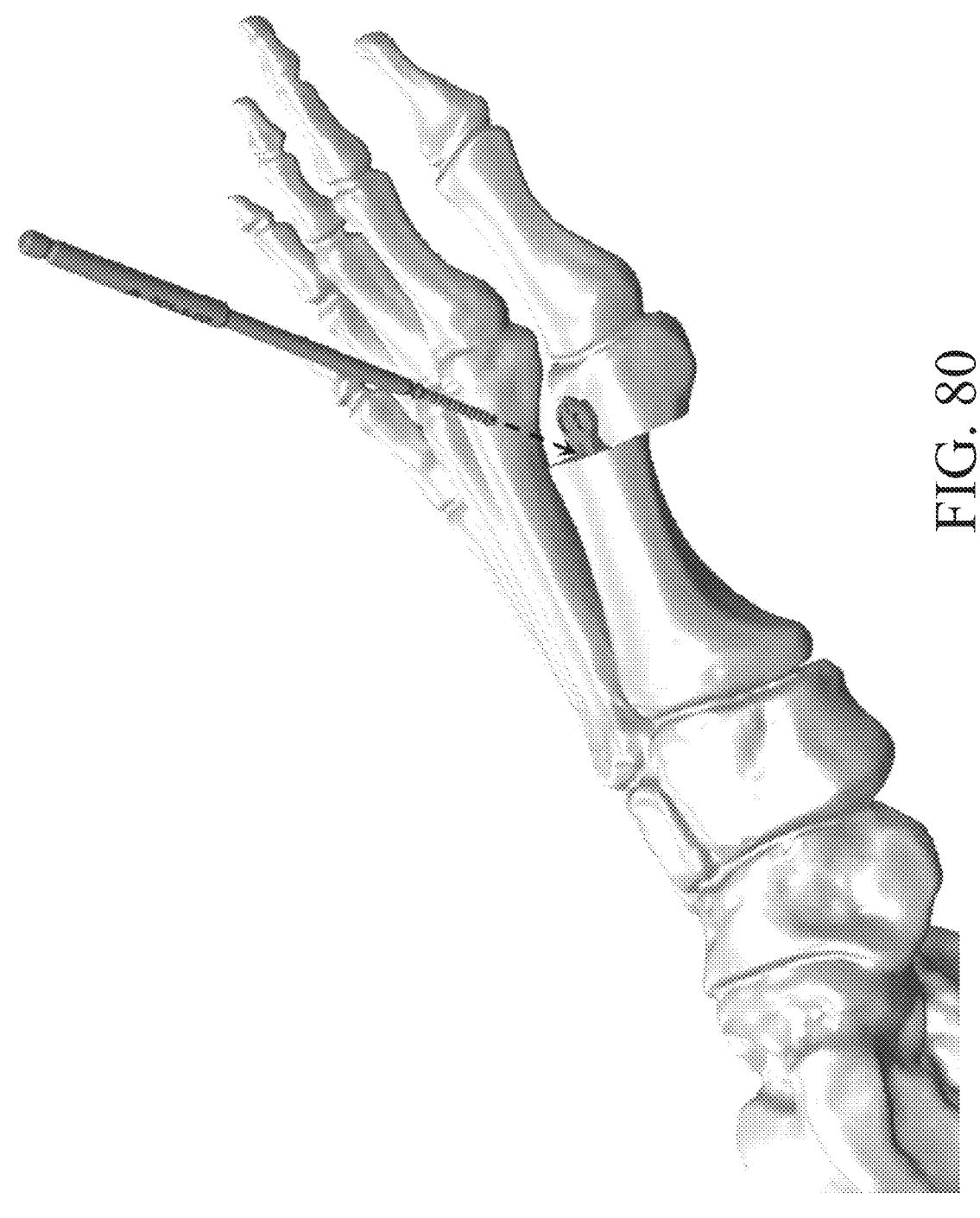
Figure 81:
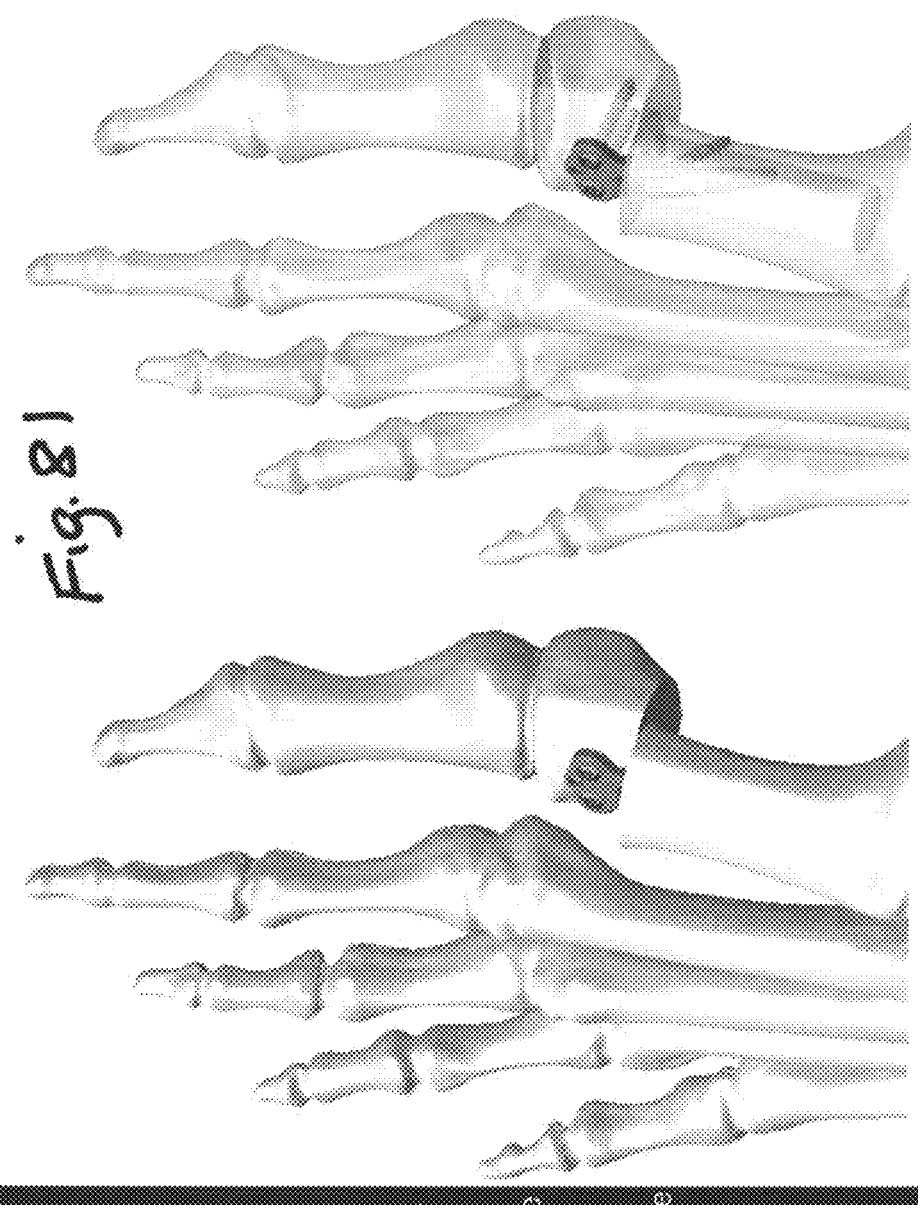
Figure 85:
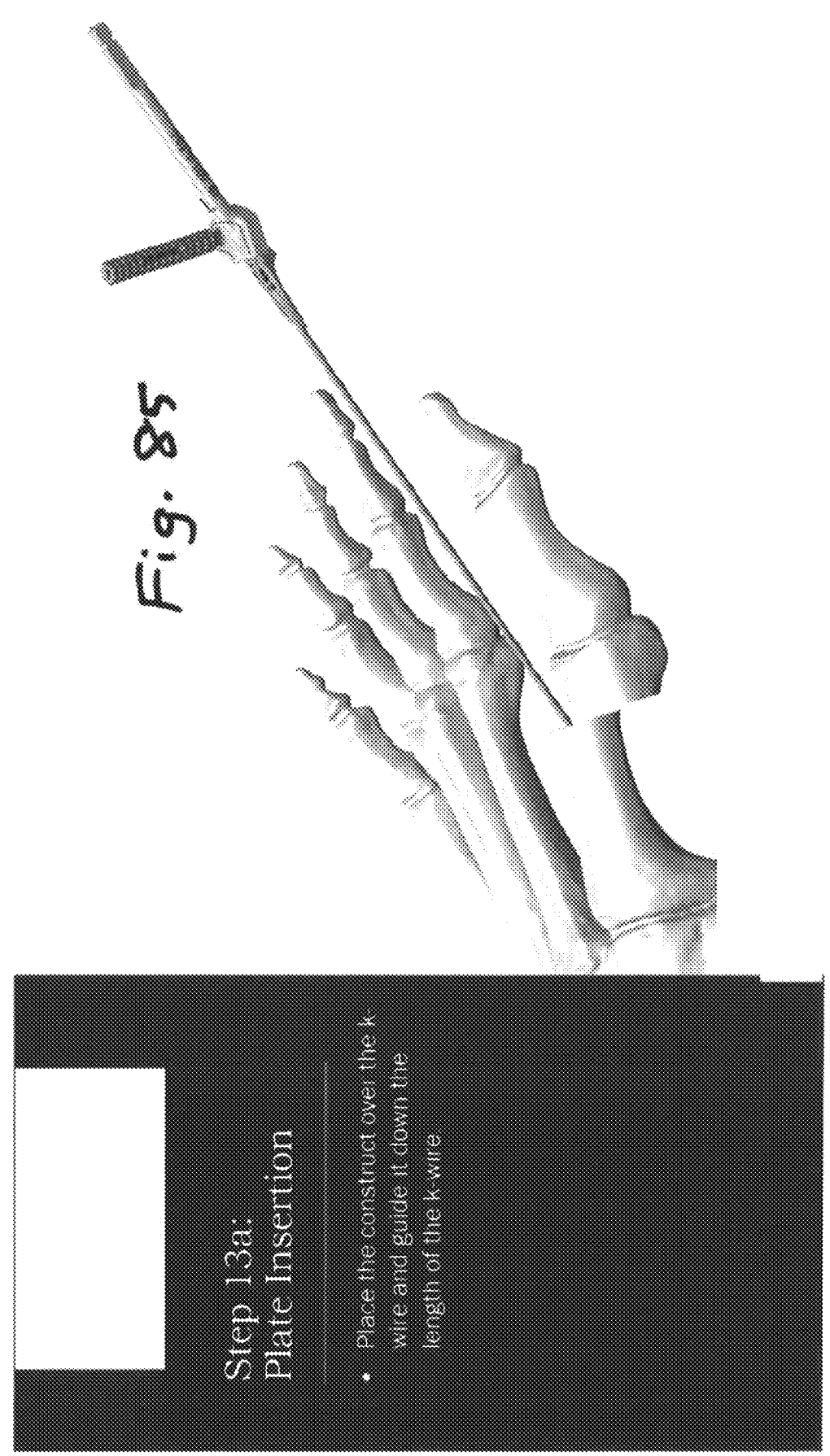
Figure 86:
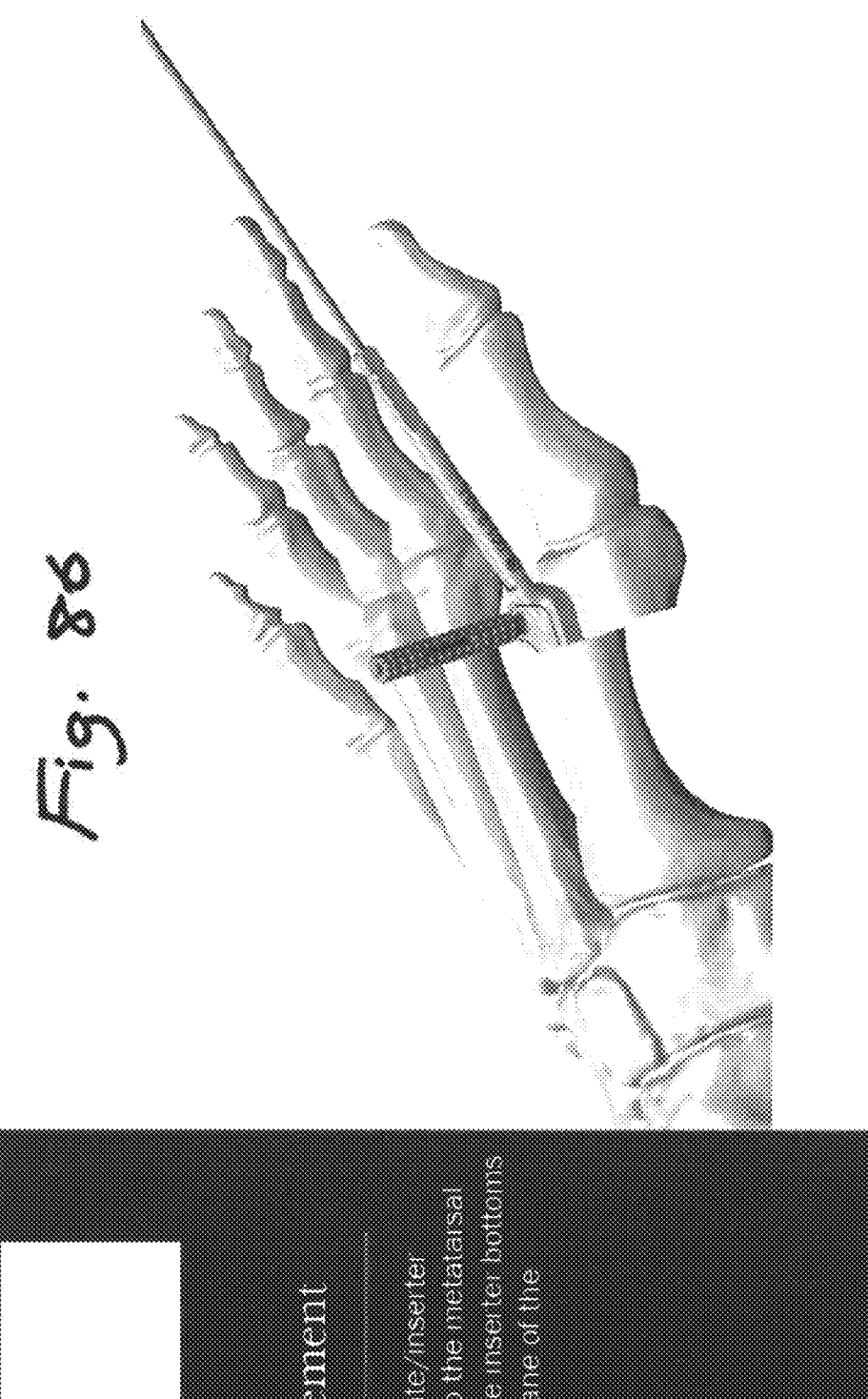
Figure 87:
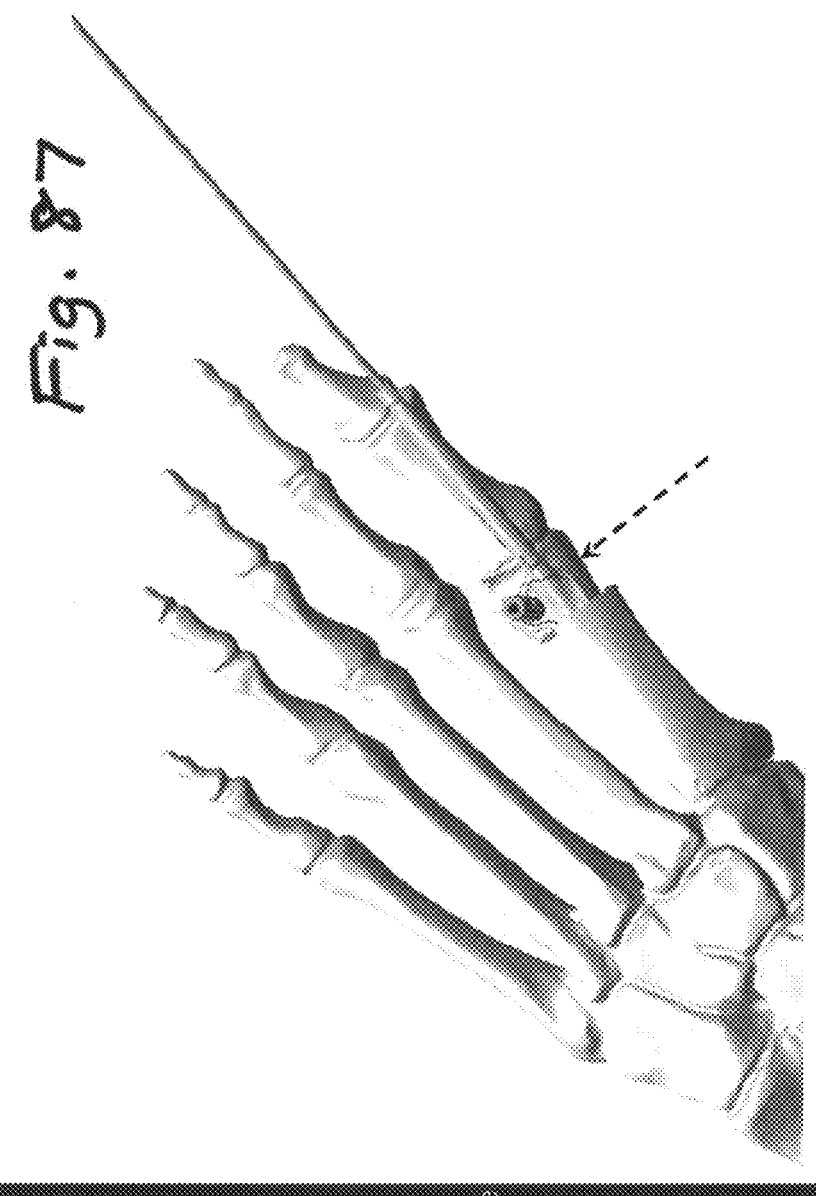
Figure 88:
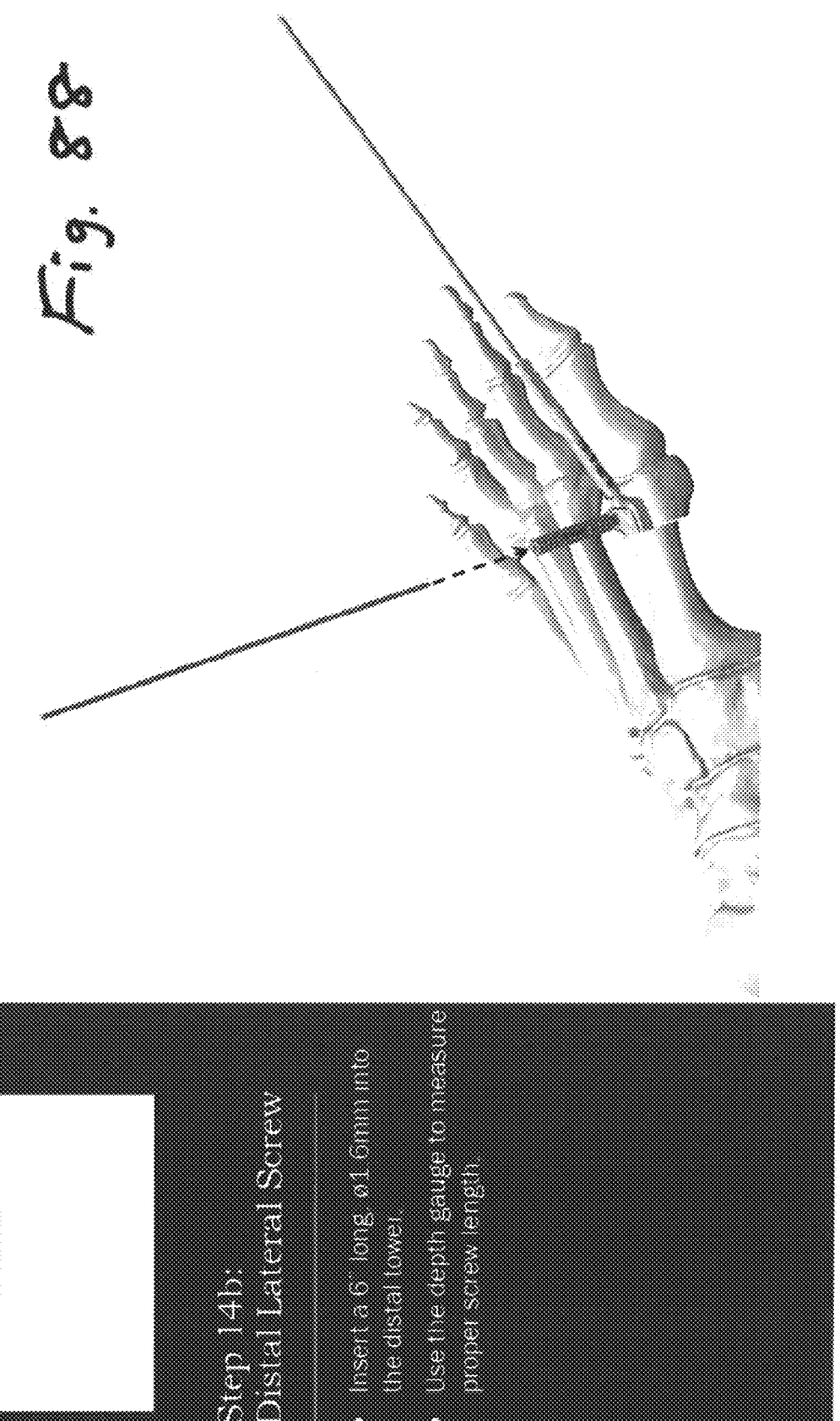
Figure 89:
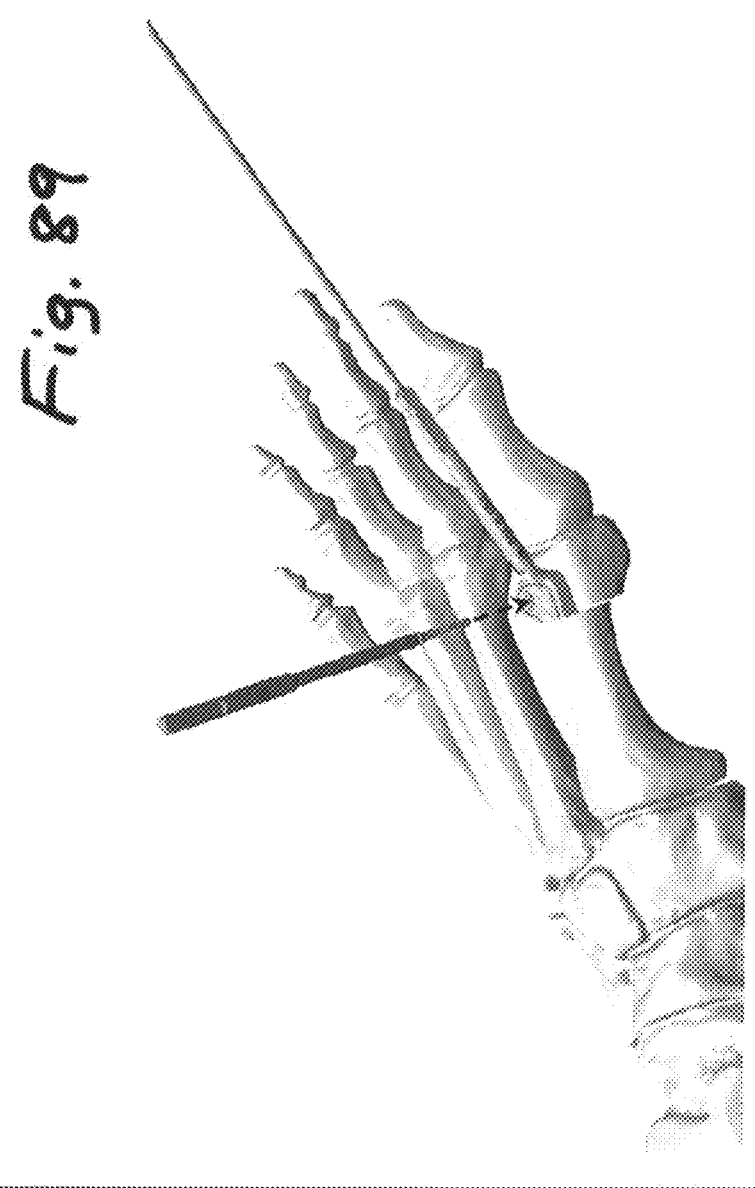
Figure 90:
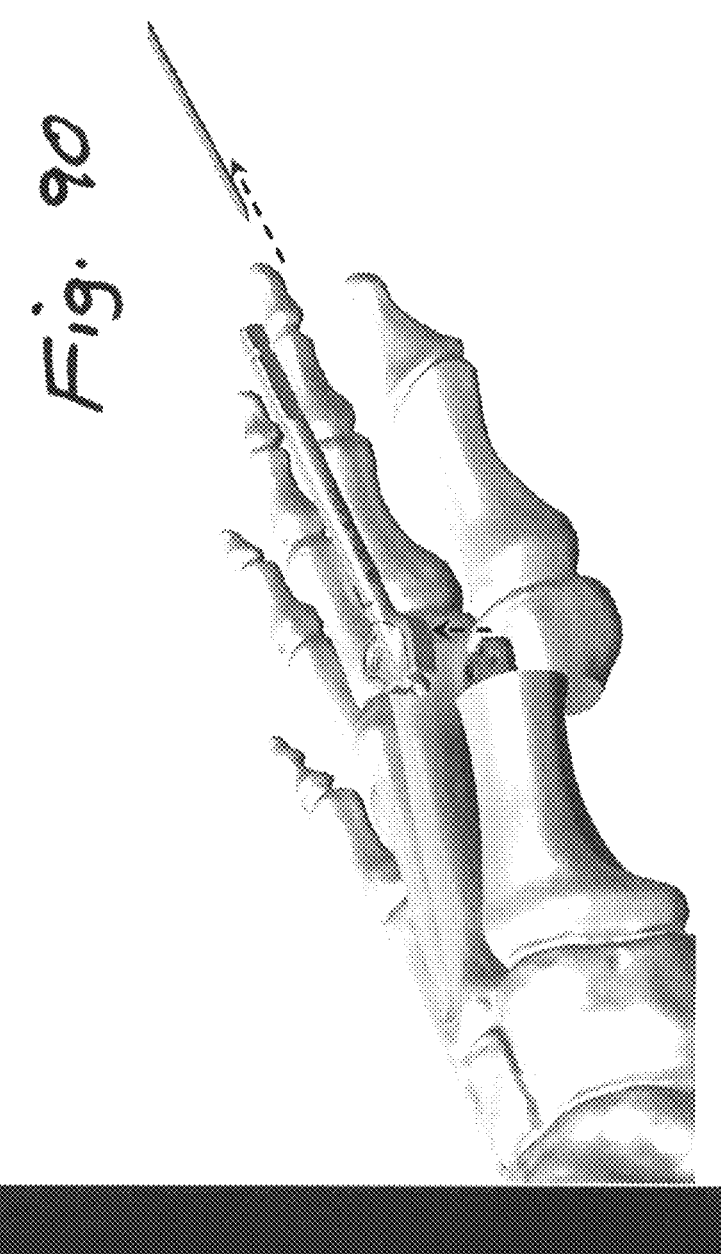
Figure 91:
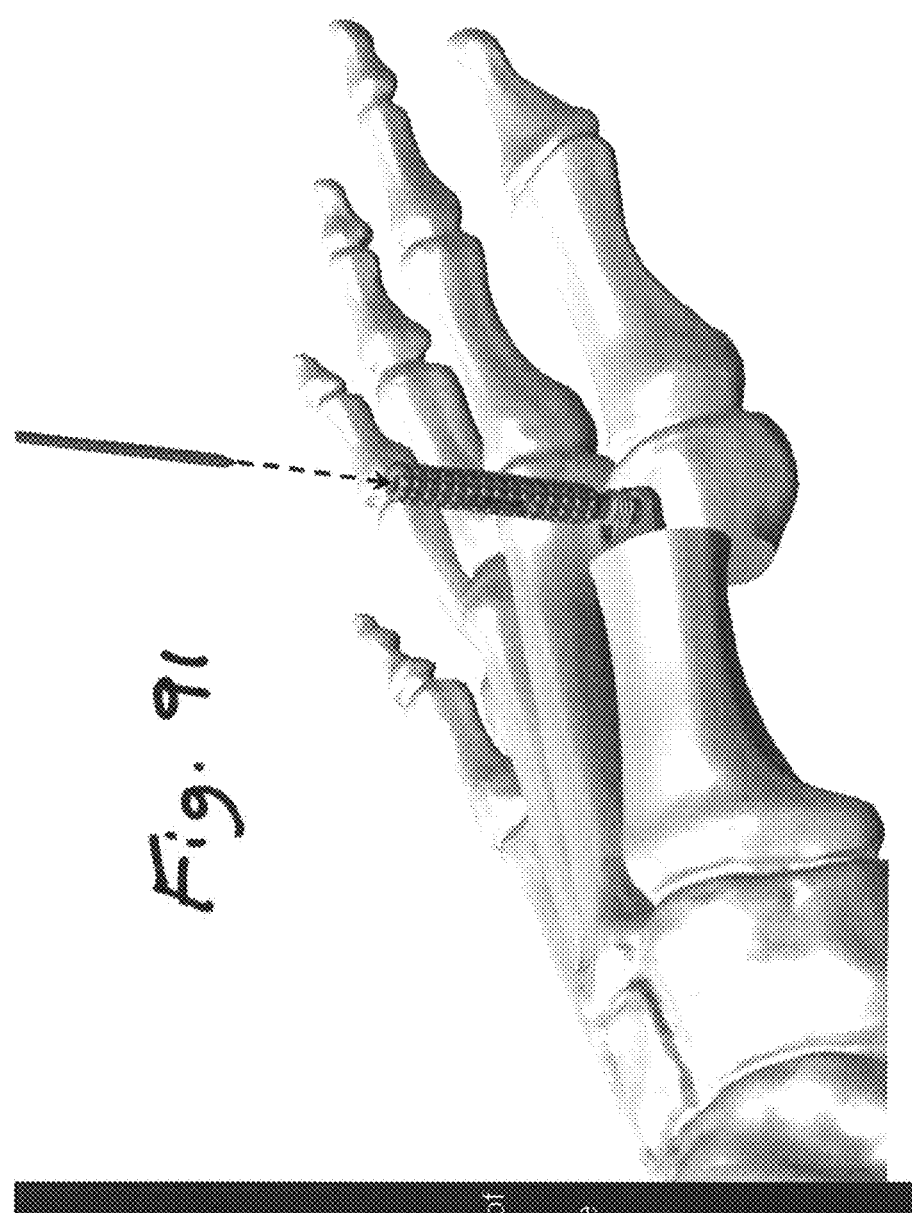
Figure 94:
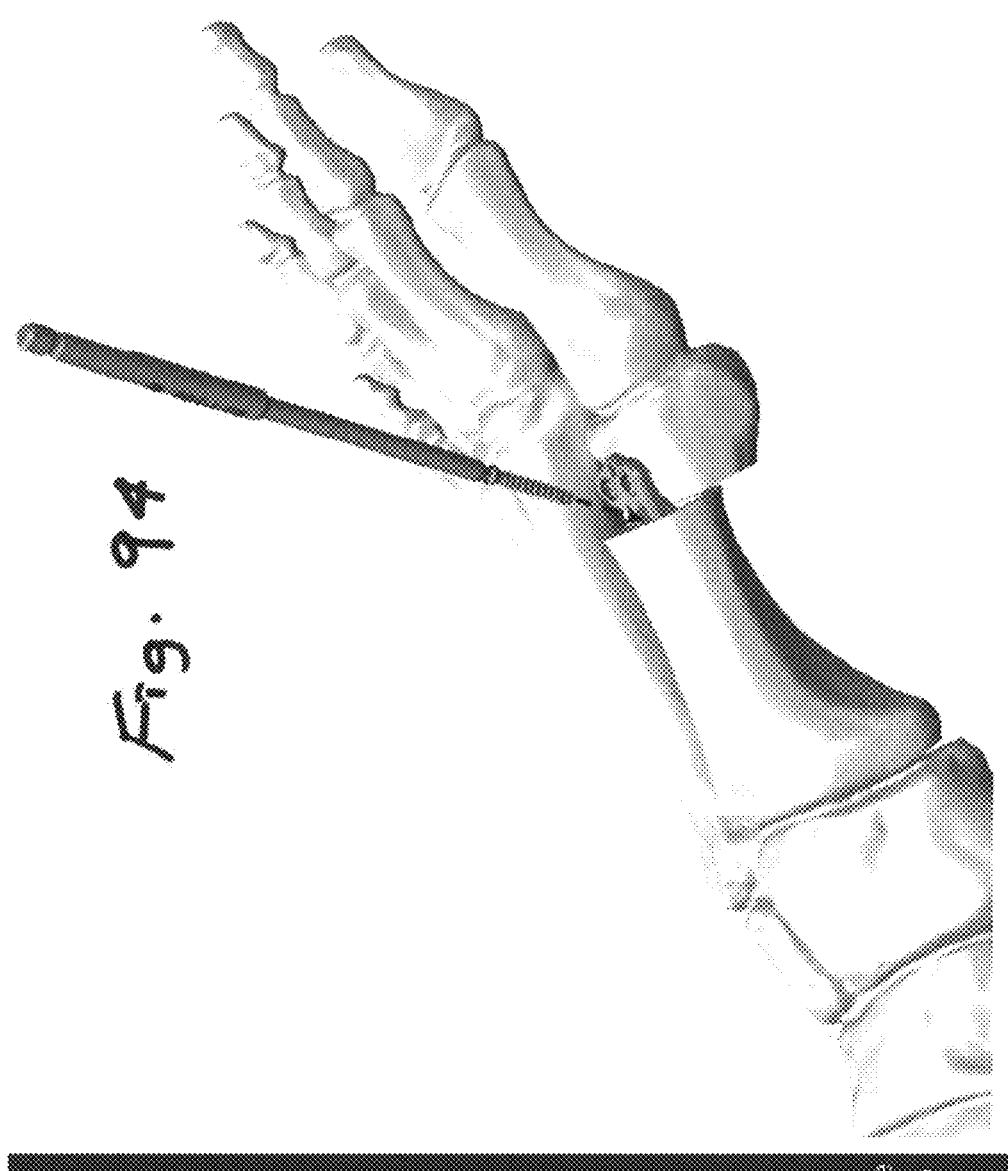
Figures 97, 98, 99, 100:
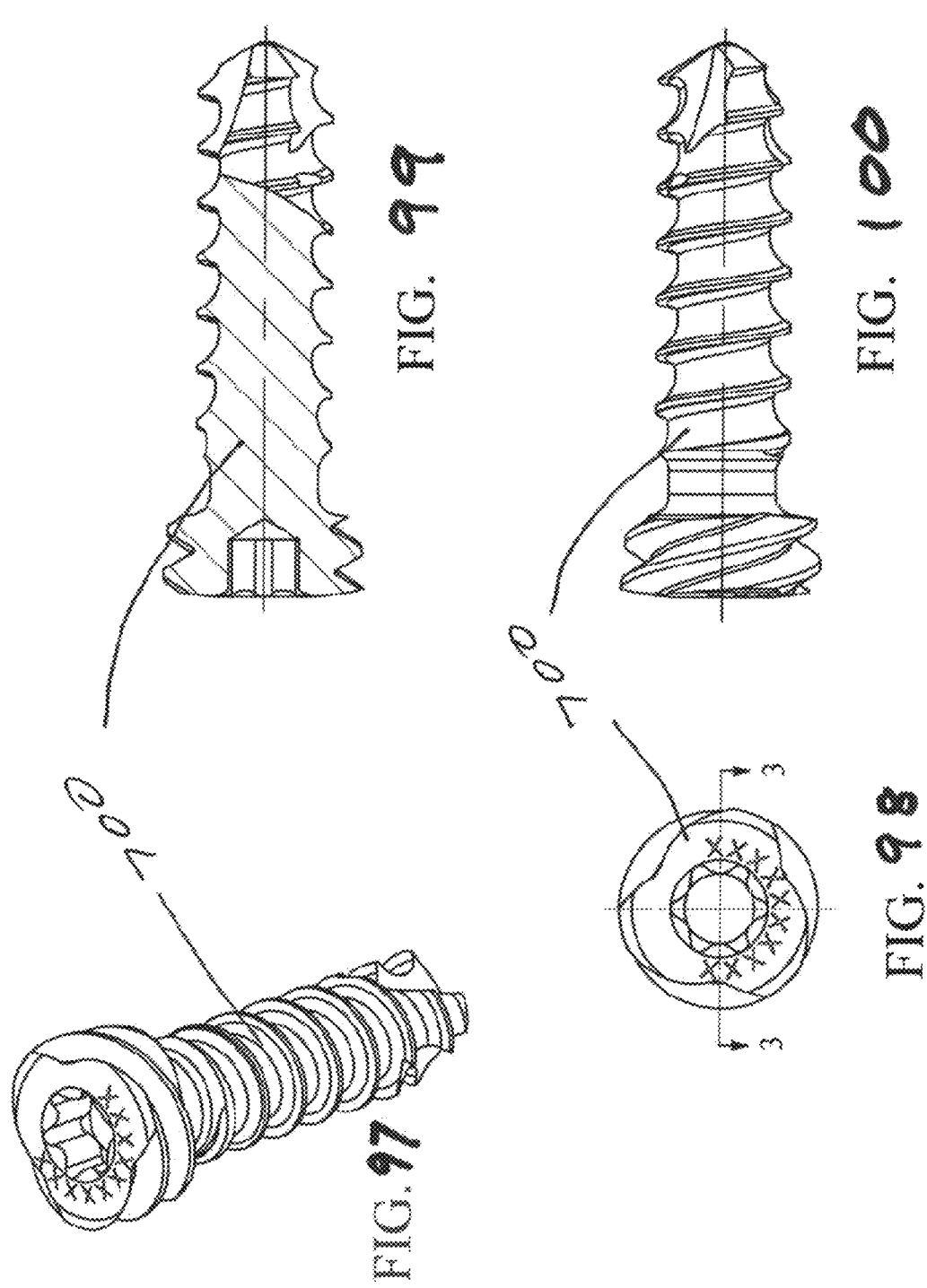

FIG. 63 further illustrates the alternative methodology where in the dome of the medial bunion inserter 455 is placed in the distal oblique hole of the medial bunion plate 420. The distal tower 437 of the medial bunion plate inserter is threaded through the inserter and the threads at the tip of the medial bunion inserter tower engaged the distal inferior hole of the medial bunion plate 420. The construct is now assembled in the plate can be inserted as previously described. The sequence of placing screws progresses from distal inferior to proximal oblique, to distal superior, and then to distal oblique, using this alternative methodology.

FIGS. 64-96 illustrate one example of an embodiment of this invention regarding a system applicable to a Hallux Limitus-Dorsal bunion apparatus and procedure, and the guidance and description on or within the drawings explain the general procedure and the apparatuses and devices used in connection therewith, in similar fashion that that above for the medial bunion apparatus and procedure.

FIGS. 97-100 show an example of an embodiment of a locking screw that may be utilized in combination with different embodiments of this invention, though no one embodiment is dependent upon a particular type of screw. FIGS. 97-100 show a perspective view, a top view, an elevation cross-sectional view and an elevation view of this particular type of screw 700, respectively. The uses and potential uses of screws, both locking and non-locking are described and shown more fully above.

FIGS. 101-104, show an example of an embodiment of a dorsal bunion plate that may be utilized in connection with embodiments of the inventions described herein. FIGS. 101-104 show a side elevation view, a first detail cross-sectional view of a top portion and screw aperture, a second detail cross-sectional view of the middle portion, a second detail cross-sectional view of the middle portion and a front elevation view of a portion of the dorsal bunion plate, respectively. The uses and potential uses of the dorsal bunion plate are described and shown more fully above.

FIG. 101 illustrates the dorsal bunion plate 710, lower cannulated portion 712 which becomes inserted into the metatarsal bone, upper screw aperture 711 and an exemplary angle 713 of the lower portion to the upper or extra intramedullary portion. The remaining figures show some additional detail, screw apertures and body characteristics, none of which are specifically or individually required to practice them all embodiments of this invention.

FIGS. 105-108 illustrate an example of an embodiment of a hallux limitus plate which may be utilized in connection with embodiments of the invention described herein. FIGS. 105-108 show a side elevation view, a first detail cross-sectional view of a top portion and screw aperture, a second detail cross-sectional view of the middle portion, a second detail cross-sectional view of the middle portion and a front elevation view of a portion of the hallux limitus plate, respectively. The uses and potential uses of the hallux limitus plate are described and shown more fully above.

Figures 105, 106, 107, 108:
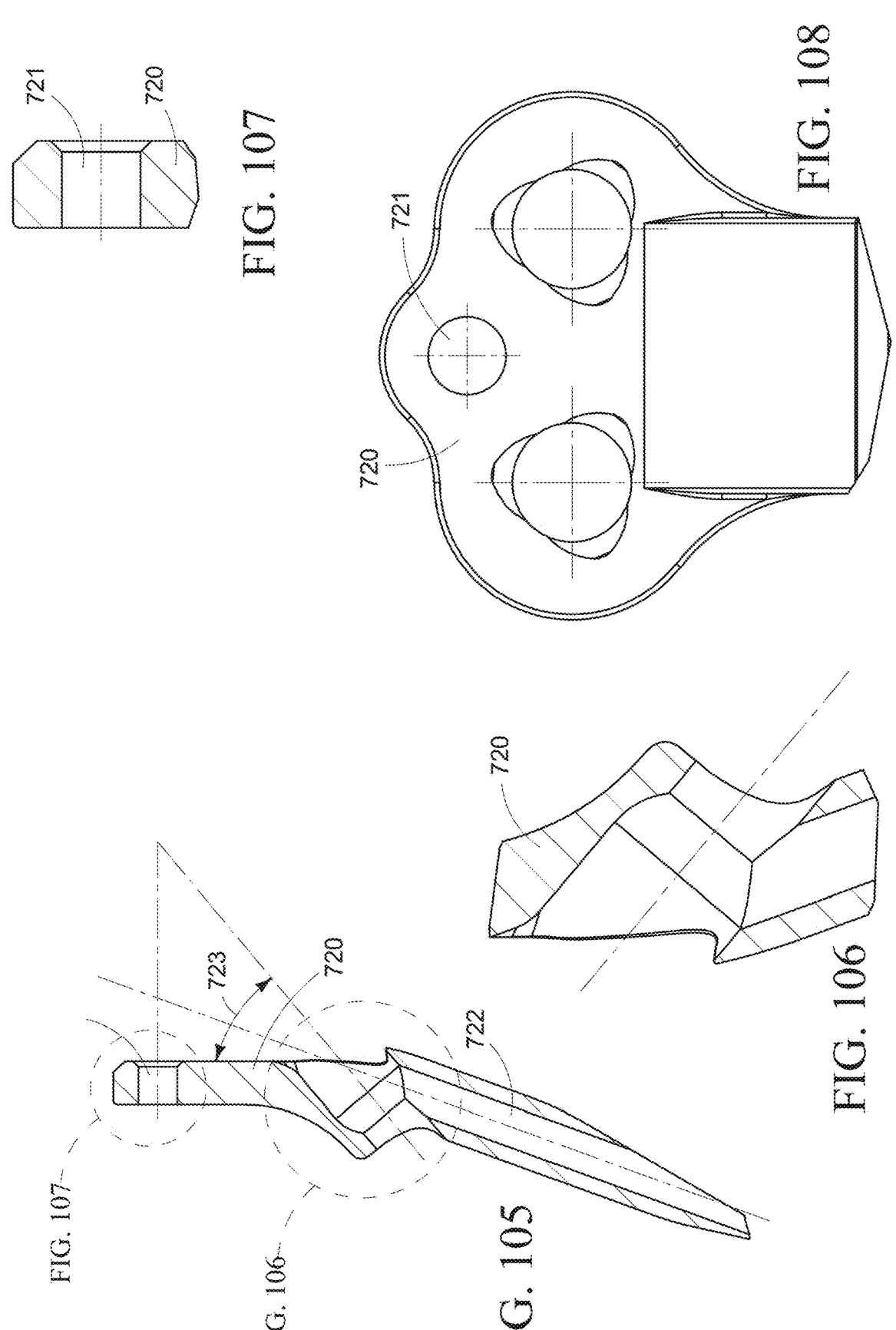
Figures 109, 110, 111, 112:
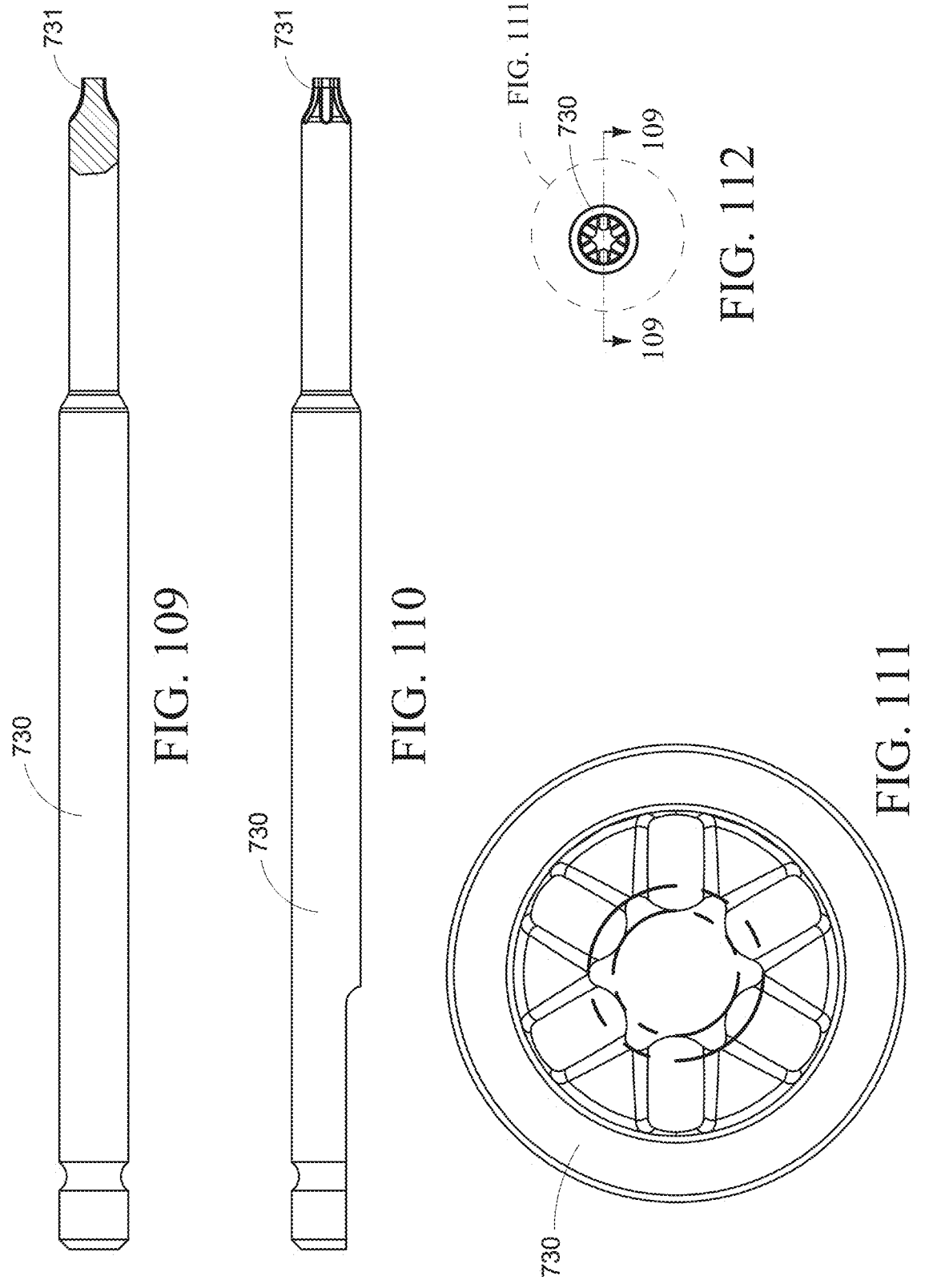
Figures 113, 114:
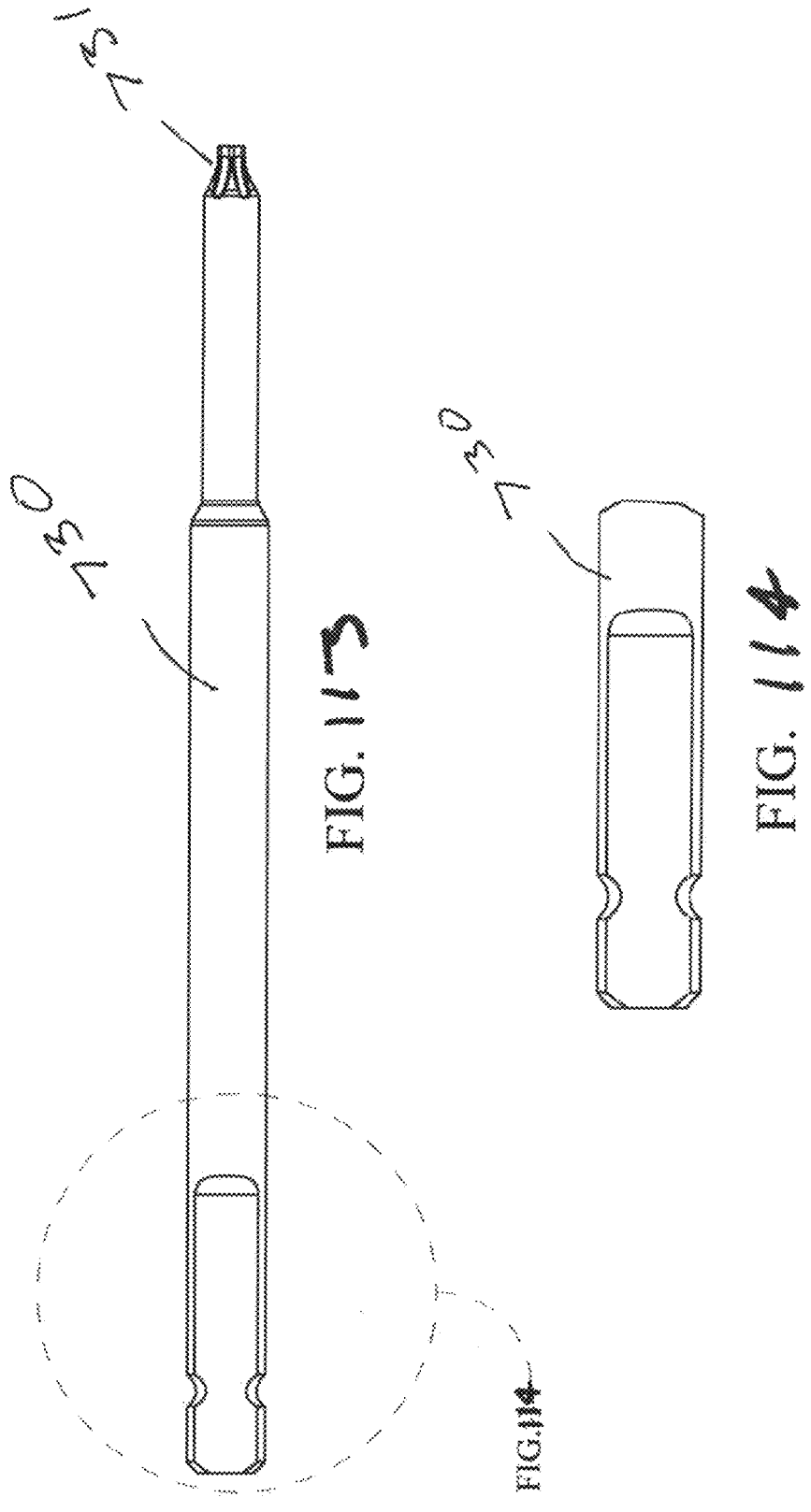
Figure 117:
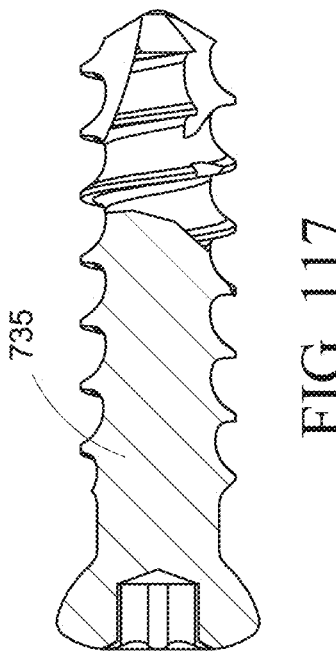
Figure 118:
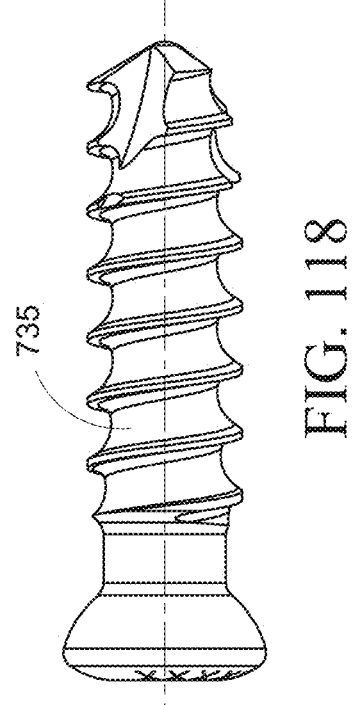
Figure 115:
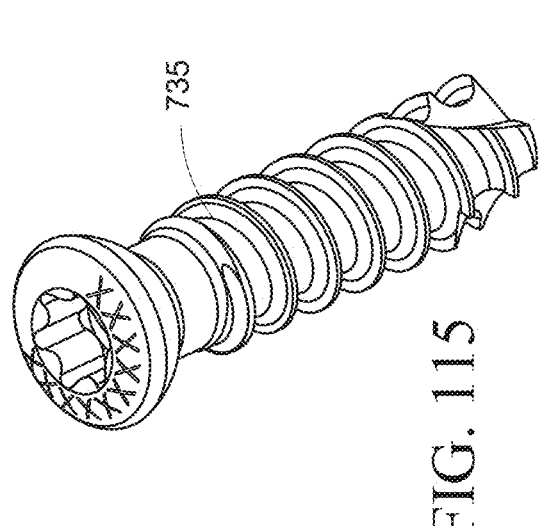
Figure 116:
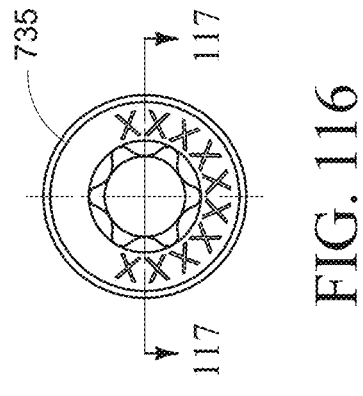

FIG. 105 illustrates the hallux limitus bunion plate 720, lower cannulated portion 722 which becomes inserted into the metatarsal bone, upper screw aperture 721 and an exemplary angle 723 between the lower portion (intramedullary portion) and the upper portion (extramedullary portion).

FIGS. 109-114 illustrate an example of a screwdriver-type device that may be utilized in combinations with embodiments invention. FIGS. 109-114 show a first side elevation view, a second side elevation view, a detail and view, and in view, a third elevation side view and a detail view. While no particular type of screwdriver is required to practice embodiments of this invention, FIGS. 109-114 illustrate a preferred screwdriver with an engaging pattern to engage the screws that may be utilized in connection with this invention.

FIGS. 109-114 illustrate screwdriver body 730 in screwdriver engagement and 731, which would be configured to engage in a aperture in a screw such as described elsewhere herein.

FIGS. 115-118 show an example of an embodiment of a non-locking screw that may be utilized in combination with different embodiments of this invention, though no one embodiment is dependent upon a particular type of screw. FIGS. 115-118 show a perspective view, a top view, an elevation cross-sectional view and an elevation view of this particular type of non-locking screw 735, respectively. The uses and potential uses of screws, both locking and non-locking are described and shown more fully above.

Figures 119, 120, 121:
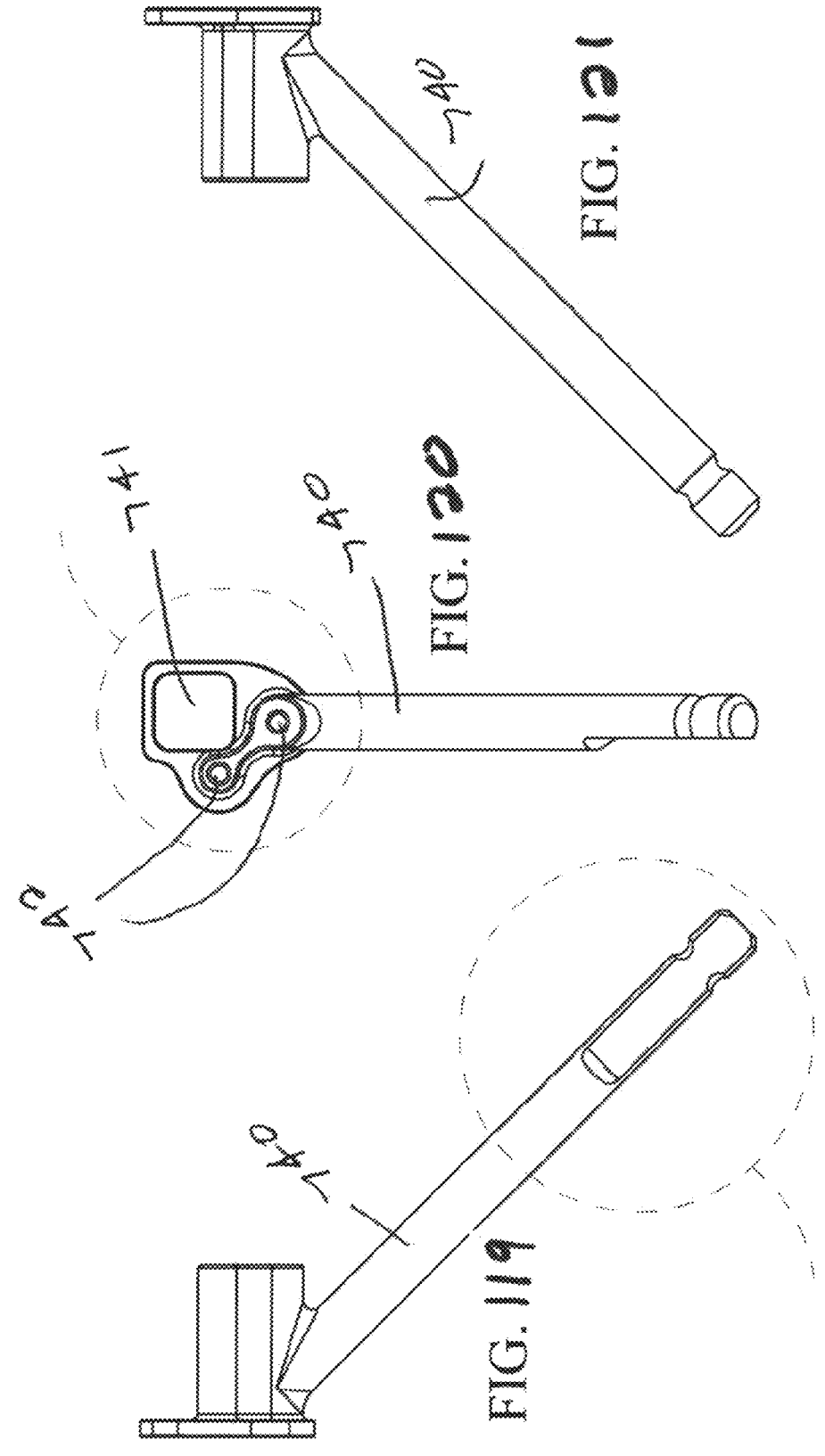

FIGS. 119-121 illustrate examples of a component that may be utilized connection with embodiments of this invention, namely illustrating a distal template for use as described more fully above. FIGS. 119-121 illustrate the distal template body 740 and aperture for imparting notched or indented box 408 or square area as illustrated above. Square area 741 or box can be utilized to create the indented box in the bone illustrated more fully above. Apertures 742 may be utilized in combination with K-wires to locate and secure the distal template while it is being used to create the shaped offset in the bone.

Figure 127:
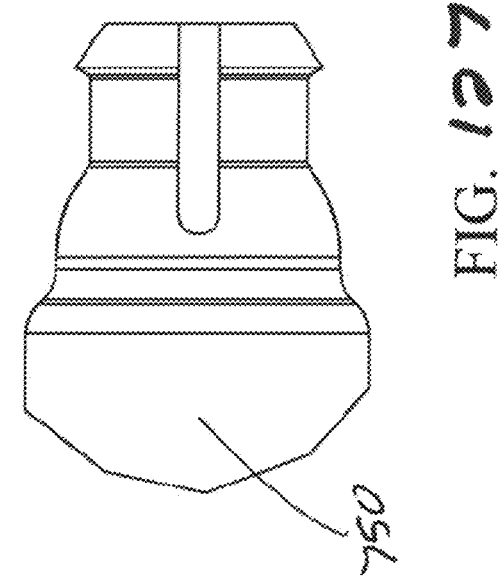
Figure 126:
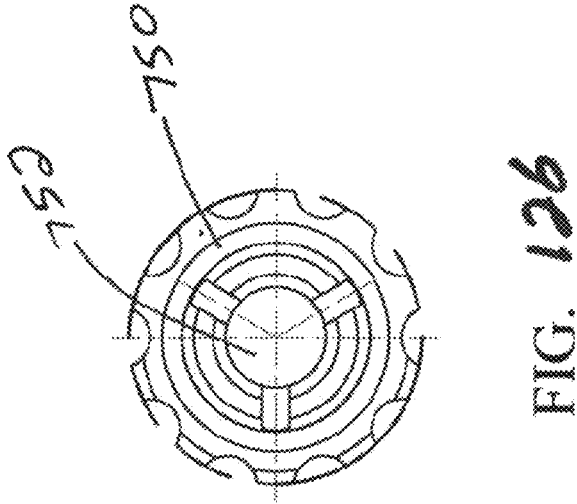

FIGS. 122-127 illustrate a drill tower for a distal application, the drill tower being used as set forth more fully herein. FIG. 122 illustrates a first side elevation view of the distal drill tower, FIG. 123 illustrates an elevation cross-sectional view (123-123) of the drill tower distal, FIG. 124 illustrates a second side elevational view and FIG. 127 illustrates detail end view of the drill tower distal. As will be noted by those of ordinary skill in the art, the distal drill tower 750 shows that it is a snap fit (see FIG. 127 detail) for connecting into aperture of a plate inserter and or a plate. FIGS. 122-127 further illustrate the cannulated nature of the distal drill tower, including its axially configured and located aperture 752 (which receives and guides K-wires). The distal drill tower and the proximal drill tower served to aid in the precise and/or desired alignment of K-wires and screws during the surgery.

Figures 128, 129, 130, 131:
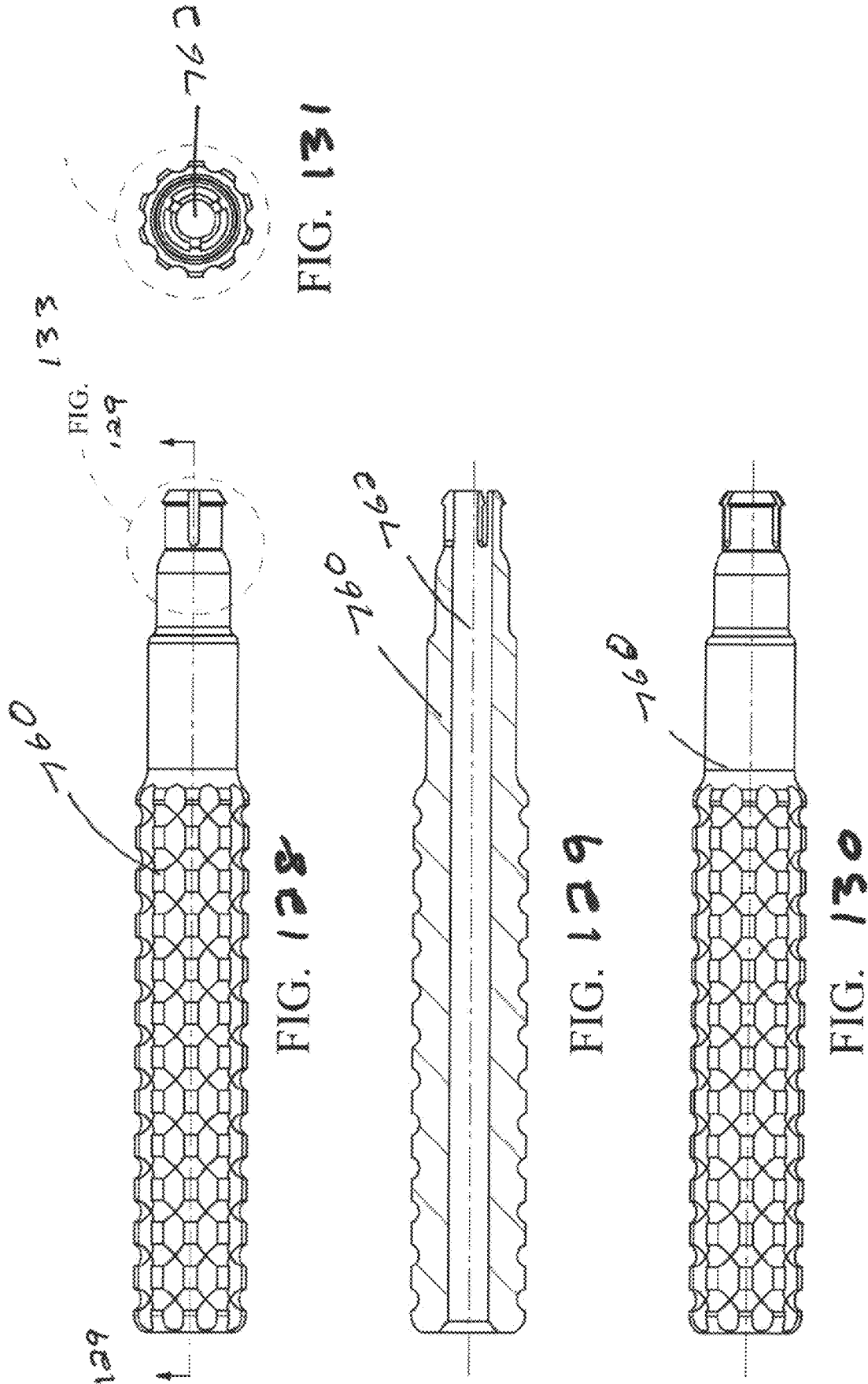
Figure 137:
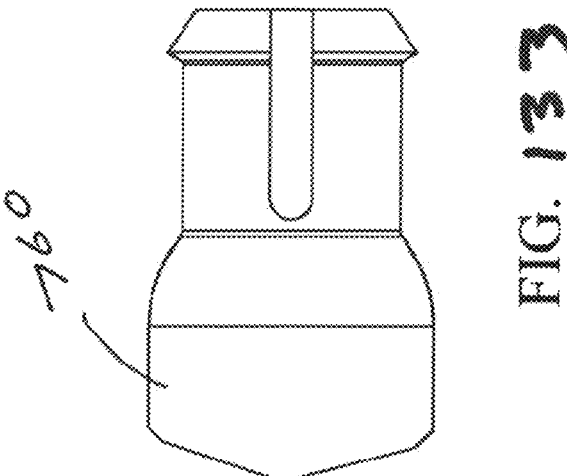
Figure 138:
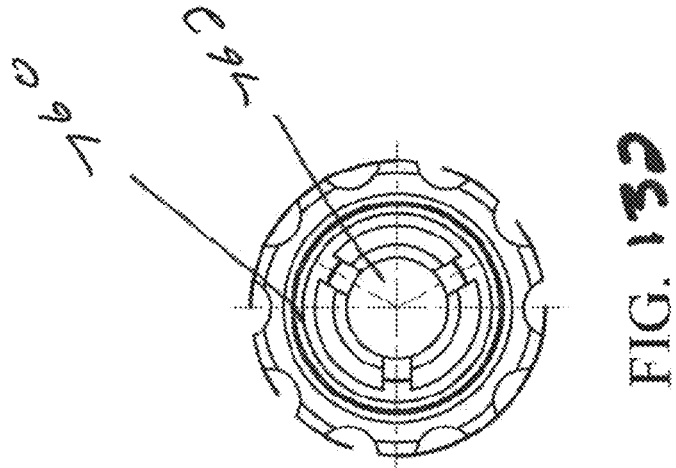
Figures 134, 135, 136, 137:
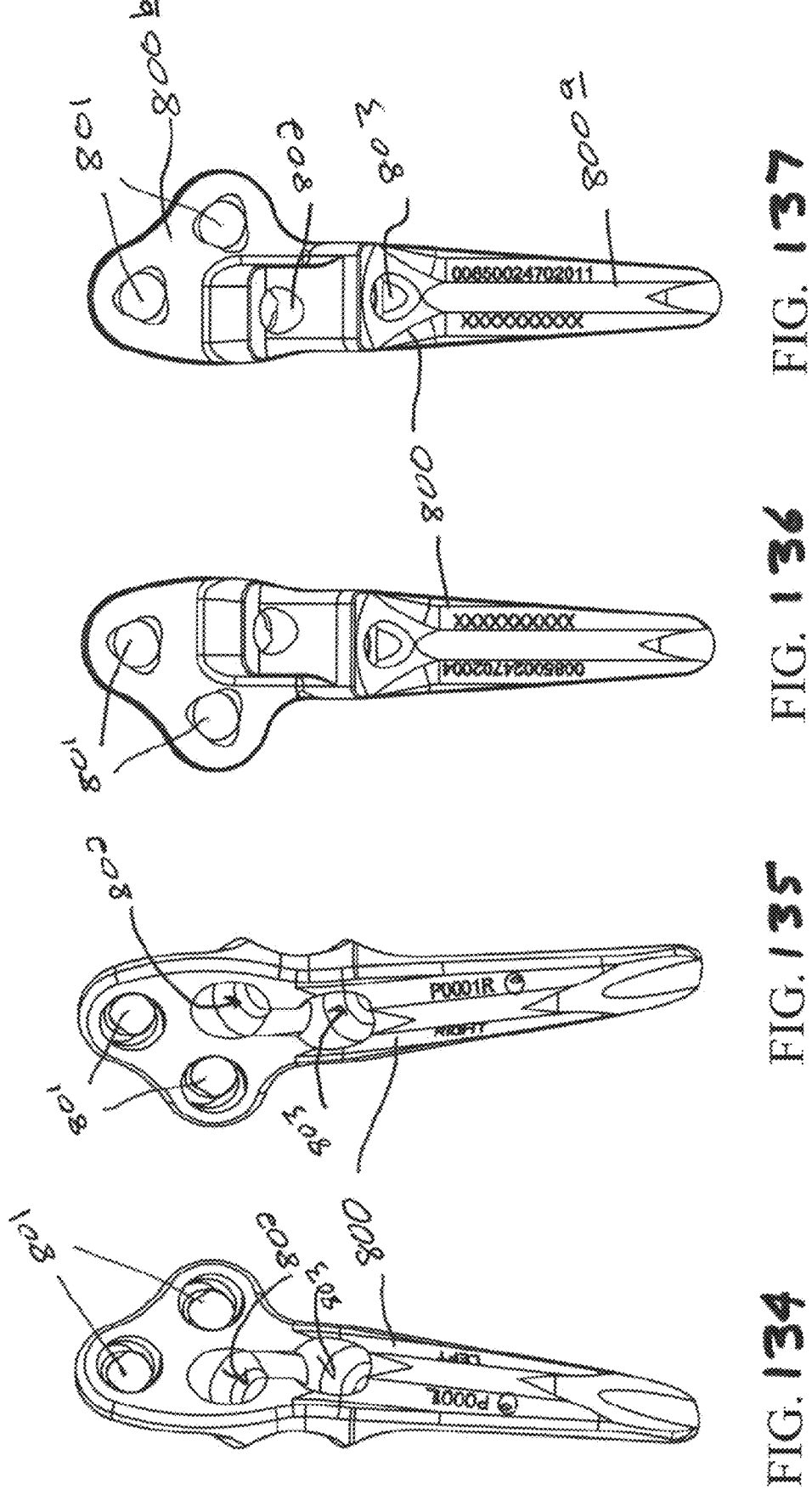
Figures 138, 139, 140, 141:
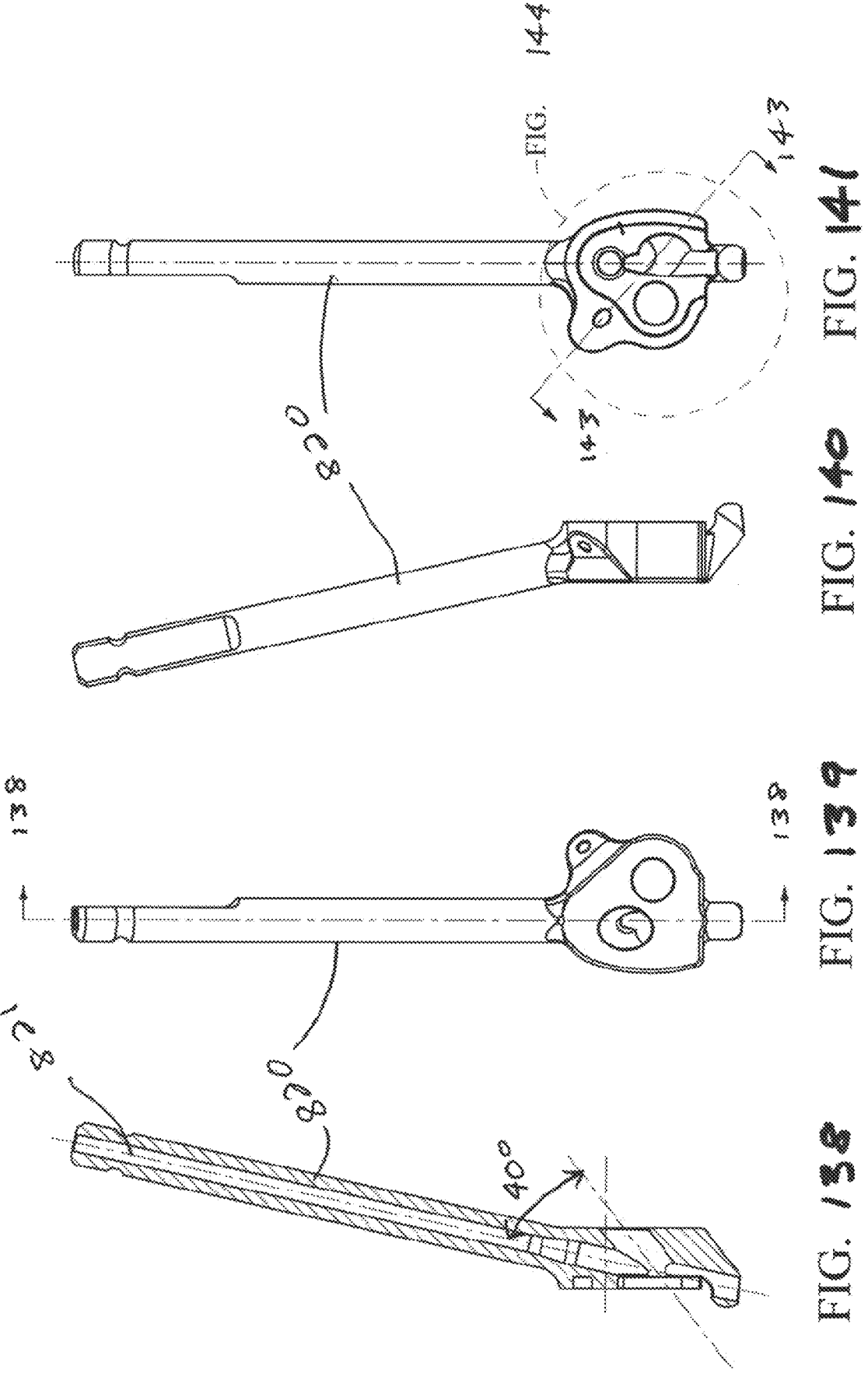
Figure 144:
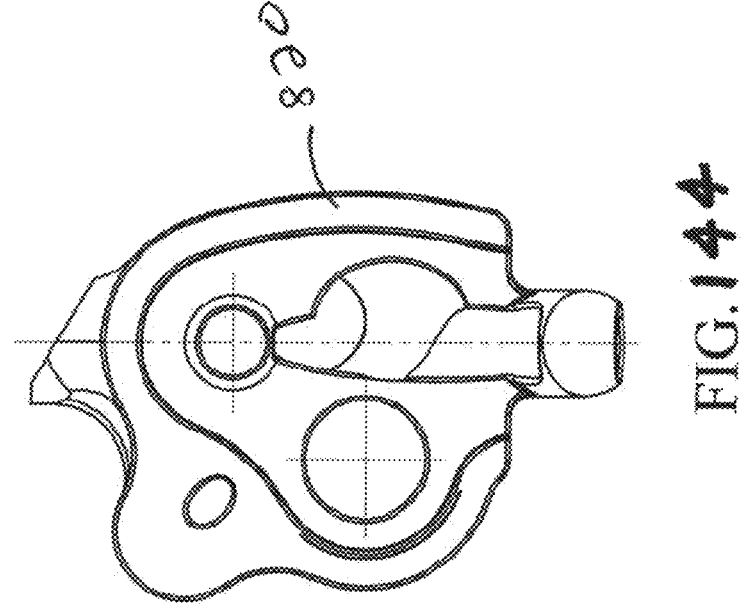
Figure 142:
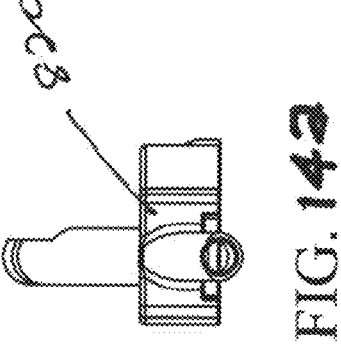
Figure 143:
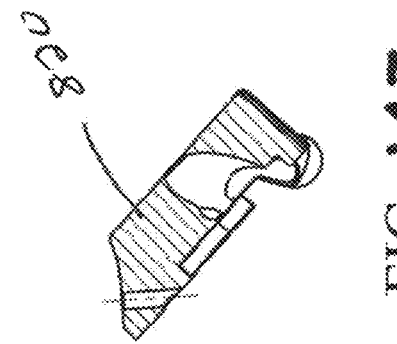

FIGS. 128-133 illustrate a drill tower for a proximal application, the drill tower being used as set forth more fully herein. FIG. 128 illustrates a first side elevation view of the distal drill tower, FIG. 128 illustrates an elevation cross-sectional view (123-123) of the drill tower distal, FIG. 130 illustrates a second side elevational view and FIG. 133 illustrates detail end view of the drill tower distal. As will be noted by those of ordinary skill in the art, the distal drill tower 760 shows that it is a snap fit (see FIG. 133 detail) for connecting into aperture of a plate inserter and or a plate. FIGS. 128-133 further illustrate the cannulated nature of the distal drill tower, including its axially configured and located aperture 762 (which receives and guides K-wires). The distal drill tower and the proximal drill tower served to aid in the precise and/or desired alignment of K-wires and screws during the surgery.

FIGS. 134-137 show an example of one embodiment of a medial bunion plate 800 which may be utilized in practicing aspects of this invention. FIGS. 134-137 show various aspects and components of the medial bunion plate 800, with an intramedullary portion 800*a* and an extramedullary portion 800. FIGS. 134-137 further show screw apertures 801, 802 and 803.

FIGS. 138-144 illustrate medial bunion plate inserter 820 with internal longitudinal aperture 821. The medial bunion plate inserter 820 is configured to interact with and complement a medial bunion plate to match its external dimensions to retain or fix it in place during part of the surgical procedure. It should be noted that no particular shape of the medial bunion plate or the medial bunion plate inserter is required to practice this invention but they must be correlated or matching to enable the inserter to attach to and retain the medial bunion plate during the surgery. The use of the various apertures in facets of the medial bunion plate inserter 820 are described more fully above and in the various figures detailing the process and illustrating the apparatus.

As will be appreciated by those of reasonable skill in the art, there are numerous embodiments to this invention, and variations of elements and components which may be used, all within the scope of this invention. In one embodiment for example, an implant device configured for implanting in a patient to align or stabilize a first bone section relative to a second bone section of a patient, the implant comprising: an elongated framework including an intramedullary portion integral with an extramedullary portion, configured to attach a first bone section to a second bone section; the intramedullary portion configured for insertion into the first bone section and including at least one fastener aperture configured to transversely receive a bone fastener there-through; the extramedullary portion configured to abut a surface of the second bone section and including at least one fastener aperture disposed to transversely receive a bone fastener inserted in the second bone section; a wire aperture through the intramedullary portion of the framework, disposed to receive and be guided by a wire inserted in the first bone section as the intramedullary portion is inserted into the first bone.

In addition to the embodiment disclosed in the preceding paragraph, further embodiments may be: further wherein the contiguous wire aperture is a slit in the framework; further wherein the contiguous wire aperture is a fully enclosed guide or cannula in the framework; further wherein the contiguous wire aperture is a continuous fully enclosed aperture in the framework; further wherein the intramedullary portion is generally circular or oval and the extramedullary portion is a plate; further wherein the at least one fastener aperture is comprised of a first fastener aperture and a second fastener aperture spaced apart on the extramedullary portion of the framework (further wherein the first and second fastener apertures are configured to combine with a first bone fastener inserted through the first fastener aperture and a second bone fastener inserted through the second fastener aperture, to secure the extramedullary portion of the framework to the first bone of the patient); further wherein the first bone of the patient is a first piece of the first metatarsal bone and the second bone of the patient is a second piece of the first metatarsal bone; further wherein the extramedullary portion includes a wire aperture also disposed to receive and be guided by the wire inserted in the first bone section as the intramedullary portion is inserted into the first bone section, the wire aperture in the extramedullary portion being contiguous with the wire aperture in the intramedullary portion; further wherein the extramedullary portion is bent at an angle relative to the intramedullary portion such that it is disposed to affix to a surface of the second bone section; further wherein the extramedullary portion is bent at a transverse angle relative to the intramedullary portion such that it is disposed to affix to a surface of the second bone section; and/or further wherein the wire is a k-wire.

In another embodiment, a method embodiment, a method to re-align and stabilize a patient's metatarsal bone may be provided which comprises: transversely severing the first metatarsal bone at a desired location, resulting in a first piece and a second piece of the first metatarsal bone; placing the second piece of the first metatarsal bone in the desired alignment with the first piece; inserting a first end of a wire into the first piece of the first metatarsal bone at a desired angle and such that a second end of the wire is substantially aligned alongside the second piece; providing an implant device comprised of: an elongated framework including an intramedullary portion and an extramedullary portion, the extramedullary portion including at least one fastener aperture disposed to transversely receive a bone fastener to affix the extramedullary portion to the second piece of the first metatarsal bone; and a contiguous wire aperture axially through the intramedullary portion; sliding the wire aperture of the intramedullary portion over the second end of the wire and sliding the implant device over the wire until the intramedullary portion of the implant device is implanted into the first piece of the metatarsal bone; and fastening the extramedullary portion of the implant device to the second piece of the first metatarsal bone by inserting a fastener through the at least one fastener aperture and into the second piece of the first metatarsal bone; and fastening the intramedullary portion of the implant device to the first piece of the first metatarsal bone by inserting a fastener through the at least one fastener aperture and into the first piece of the first metatarsal bone.

In addition to the embodiment disclosed in the preceding paragraph, further embodiments may be: further comprising the step of reforming the first piece of the metatarsal bone to provide a surface which disposes it to better attach to the extramedullary portion of the implant device; further wherein the reforming of the first piece of the metatarsal bone includes cutting a substantially planar surface disposed for abutment to the extramedullary portion of the implant device; further comprising bending the extramedullary portion relative to the intramedullary portion such that the extramedullary portion more desirably abuts substantially planar surface on the second piece of the patient's metatarsal bone; further comprising the step of using the wire alignment angle to align the insertion of the intramedullary portion into the first piece of the metatarsal bone; further comprising the step of using the wire alignment angle to align the position of the extramedullary portion of the implant device relative to the mounting location on the second piece of the metatarsal bone; further wherein the bone fastener is a bone screw; further wherein the step of fastening the intramedullary portion of the implant device to the first piece of the first metatarsal bone by inserting a fastener through the at least one fastener aperture and into the first piece of the first metatarsal bone, is performed before the step of fastening the extramedullary portion of the implant device to the second piece of the first metatarsal bone by inserting a fastener through the at least one fastener aperture and into the second piece of the first metatarsal bone; and/or further wherein the step of fastening the intramedullary portion of the implant device to the first piece of the first metatarsal bone by inserting a fastener through the at least one fastener aperture and into the first piece of the first metatarsal bone, further comprises: fixing a drill guide to the extramedullary portion, the drill guide including a drill aperture which is thereby fixed and aligned relative to the transverse fastener aperture in the intramedullary portion such that a pilot hole may be drilled through a portion of the first bone piece and through the transverse fastener aperture in the intramedullary portion, thereby furthering the securement of the intramedullary portion to the first bone piece.

In yet a more general method embodiment, a method to re-align and stabilize a patient's bone may be provided which comprises: transversely severing the patient's bone at a desired location, resulting in a first piece and a second piece of the patient's bone; placing the second piece of the patient's bone in the desired alignment with the first piece; inserting a first end of a wire into the first piece of the patient's bone at a desired angle and such that a second end of the wire is substantially aligned alongside the second piece; providing an implant device comprised of: an elongated framework including an intramedullary portion and an extramedullary portion, the extramedullary portion including at least one fastener aperture disposed to transversely receive a bone fastener to affix the extramedullary portion to the second piece of the patient's bone; and a contiguous wire aperture axially through the intramedullary portion; sliding the wire aperture of the intramedullary portion over the second end of the wire and sliding the implant device over the wire until the intramedullary portion of the implant device is implanted into the first piece of the patient's bone; and fastening the extramedullary portion of the implant device to the second piece of the patient's bone by inserting a fastener through the at least one fastener aperture and into the second piece of the patient's bone; and fastening the intramedullary portion of the implant device to the first piece of the patient's bone by inserting a fastener through the at least one fastener aperture and into the first piece of the patient's bone.

In another embodiment, an implant alignment tool may be provided for use in combination with an implant device, configured for aligning an implant device in a patient being implanted to stabilize a first bone section relative to a second bone section of a patient, the implant alignment tool comprising: a handle; a proximal screw guide portion extending from said handle; and an implant device attachment portion.

Additional embodiments from those in the preceding paragraph may include such an implant alignment tool: wherein the implant device attachment portion is further comprised of an externally threaded shaft configured to fasten to and unfasten from to an internally threaded aperture in the implant device, and optionally further wherein the shaft is rotatably mounted relative to the handle of the implant alignment tool such that it can be rotated to fasten it to the implant device and rotated an opposite direction to unfasten it from the implant device.

An additional embodiment from that described in the second preceding paragraph may be further wherein the shaft is sized relative to a shaft aperture in the implant device such that the implant alignment tool may be fastened to and unfastened from the implant device via a friction fit.

Another method embodiment may include a method to re-align and stabilize a patient's metatarsal bone comprising: assessment of a deformity to be remedied, including the desired translational and rotational correction; make incision to expose the metatarsal bone; remove a medial bone to create an appropriate surface for receiving a portion of an implant device; create an osteotomy in a first metatarsal bone behind the sesamoids; translate the metatarsal head laterally and rotate head to the desired position in all planes; place a guide wire into a shaft of the metatarsal bone to locate the metatarsal head into a desired position; providing an implant device comprised of: an elongated framework including an intramedullary portion and an extramedullary portion, the extramedullary portion including at least one fastener aperture disposed to transversely receive a bone fastener to affix the extramedullary portion to the second piece of the first metatarsal bone; and a contiguous wire aperture axially through the intramedullary portion; place the extramedullary portion over the guide wire and into the shaft of the metatarsal; fixate the extramedullary portion to the metatarsal head with one or more fasteners; attach a drill guide over the wire and fast the drill guide to the extramedullary portion; evaluate and adjust the alignment of the metatarsal head utilizing the implant adjustment tool; drill proximal fastener apertures in the metatarsal bone; and place proximal fasteners into the metatarsal bone.

In compliance with the statute, the invention has been described in language more or less specific as to structural and methodical features. It is to be understood, however, that the invention is not limited to the specific features shown and described, since the means herein disclosed comprise preferred forms of putting the invention into effect. The invention is, therefore, claimed in any of its forms or modifications within the proper scope of the appended claims appropriately interpreted in accordance with the doctrine of equivalents.

We claim:

1. A surgical assembly comprising: an implant alignment tool and an implant device, said implant alignment tool configured for aligning the implant device for use as a medial bunion plate or a Hallux Limitus/Dorsal Bunion Plate, in a patient being implanted to stabilize a first bone section of a metatarsal relative to a second bone section of the metatarsal of the patient, the implant alignment tool comprising:
a handle;
a proximal screw guide portion extending from said handle; and
an implant device attachment portion configured to secure the implant alignment tool to the implant device, the implant device comprises:
an elongated framework including an intramedullary portion integral with an extramedullary portion, configured to attach a first section of the first metatarsal bone to the second section of the first metatarsal bone;
the intramedullary portion configured for longitudinal insertion into the first section of the first metatarsal bone and including at least one fastener aperture disposed to receive a bone fastener there-through transverse to the longitudinally inserted intramedullary portion;
the extramedullary portion configured to abut a prepared external surface of the second section of the first metatarsal bone and including at least one fastener aperture disposed to receive a bone fastener inserted in the second section of the first metatarsal bone transverse to the extramedullary portion; and a wire aperture extending longitudinally through the intramedullary portion of the framework, disposed to receive and be guided by a guide wire inserted in the first section of the first metatarsal bone as the intramedullary portion is inserted into the first section of the first metatarsal bone over the guidewire, thereby aligning the extramedullary portion with the prepared external surface of the second section of the first metatarsal bone with the guide wire.

2. An implant alignment tool as recited in claim 1, and wherein the implant device attachment portion is further comprised of an externally threaded shaft configured to fasten to and unfasten from an internally threaded aperture in the implant device.

3. An implant alignment tool as recited in claim 2, and further wherein the shaft is rotatably mounted relative to the handle of the implant alignment tool such that it can be rotated to fasten it to the implant device and rotated an opposite direction to unfasten it from the implant device.

4. An implant alignment tool as recited in claim 1, and further wherein the shaft is sized relative to a shaft aperture in the implant device such that the implant alignment tool may be fastened to and unfastened from the implant device via a friction fit.

* * * * *